(12) United States Patent
Jain et al.

(10) Patent No.: US 11,098,051 B2
(45) Date of Patent: *Aug. 24, 2021

(54) FUSED TRICYCLIC PYRIDAZINONE COMPOUNDS USEFUL TO TREAT ORTHOMYXOVIRUS INFECTIONS

(71) Applicant: Novartis AG, Basel (CH)

(72) Inventors: Rama Jain, Fremont, CA (US); Dennis Christofer Koester, Emeryville, CA (US); James R. Manning, Pleasant Hill, CA (US); Vanessa Marx, Richmond, CA (US); Daniel Poon, Piedmont, CA (US); James Clifford Sutton, Pleasanton, CA (US); Benjamin Robert Taft, Lafayette, CA (US); Lifeng Wan, Union City, CA (US); Aregahegn Yifru, Benicia, CA (US); Qian Zhao, Louisville, CO (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/328,616

(22) PCT Filed: Aug. 25, 2017

(86) PCT No.: PCT/IB2017/055137
§ 371 (c)(1),
(2) Date: Feb. 26, 2019

(87) PCT Pub. No.: WO2018/042303
PCT Pub. Date: Mar. 8, 2018

(65) Prior Publication Data
US 2020/0123167 A1 Apr. 23, 2020

Related U.S. Application Data

(60) Provisional application No. 62/380,712, filed on Aug. 29, 2016.

(51) Int. Cl.
| | |
|---|---|
| *C07D 487/14* | (2006.01) |
| *C07D 471/14* | (2006.01) |
| *C07D 498/14* | (2006.01) |
| *A61P 31/16* | (2006.01) |
| *A61K 31/16* | (2006.01) |
| *A61K 31/5025* | (2006.01) |
| *A61K 31/53* | (2006.01) |
| *A61K 31/5365* | (2006.01) |
| *A61K 31/5383* | (2006.01) |
| *A61K 31/551* | (2006.01) |

(52) U.S. Cl.
CPC ........ *C07D 487/14* (2013.01); *A61K 31/5025* (2013.01); *A61K 31/53* (2013.01); *A61K 31/5365* (2013.01); *A61K 31/5383* (2013.01); *A61K 31/551* (2013.01); *A61P 31/16* (2018.01); *C07D 471/14* (2013.01); *C07D 498/14* (2013.01)

(58) Field of Classification Search
CPC ............... A61K 31/5025; A61K 31/53; A61K 31/5365; A61K 31/5383; A61K 31/551; A61P 31/14; A61P 31/16; C07D 471/14; C07D 487/14; C07D 498/14
See application file for complete search history.

(56) References Cited

U.S. PATENT DOCUMENTS

| | | | |
|---|---|---|---|
| 7,211,572 B2 | 5/2007 | Miyazaki | |
| 8,927,710 B2 | 1/2015 | Akiyama | |
| 8,987,441 B2 | 3/2015 | Takahashi | |
| 9,469,638 B2 | 10/2016 | Akiyama | |
| 10,160,764 B2 * | 12/2018 | Jain ........................ | A61K 31/53 |
| 2011/0190254 A1 | 8/2011 | Nishitani | |
| 2011/0245236 A1 | 10/2011 | Ali et al. | |
| 2012/0022251 A1 | 1/2012 | Sumino | |
| 2012/0195857 A1 | 8/2012 | Belema | |
| 2013/0197219 A1 | 8/2013 | Takahashi | |

(Continued)

FOREIGN PATENT DOCUMENTS

| | | |
|---|---|---|
| CN | 102803260 A | 11/2012 |
| EP | 2444400 | 4/2012 |

(Continued)

OTHER PUBLICATIONS

Baughman et al., "Identification of Influenza Endonuclease Inhibitors Using a Novel Fluorescence Polarization Assay" *ACS Med. Chem. Bio* 7(3):526-534, 2012.

(Continued)

*Primary Examiner* — Erich A Leeser

(74) *Attorney, Agent, or Firm* — Barnes & Thornburg LLP

(57) ABSTRACT

The invention provides compounds of Formula (I):

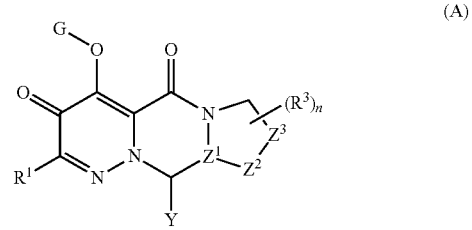

as further described herein, as well as pharmaceutical compositions comprising such compounds, and methods to use the compounds and pharmaceutical compositions for treatment of certain viral disorders, including influenza.

19 Claims, No Drawings

(56) References Cited

U.S. PATENT DOCUMENTS

| | | |
|---|---|---|
| 2014/0256937 A1 | 9/2014 | Akiyama |
| 2015/0031876 A1 | 1/2015 | Sumino |
| 2015/0072982 A1 | 3/2015 | Hendricks |
| 2015/0202208 A1 | 7/2015 | Kiyama et al. |
| 2016/0002227 A1 | 1/2016 | Schulz-Gasch |

FOREIGN PATENT DOCUMENTS

| | | | |
|---|---|---|---|
| EP | 2620436 | | 7/2013 |
| EP | 2774928 | | 9/2014 |
| GB | 2158440 | A1 | 11/1985 |
| JP | A-S61-167687 | A | 7/1986 |
| WO | 200316275 | A1 | 2/2003 |
| WO | WO 2004/078163 | | 9/2004 |
| WO | 200561490 | A1 | 7/2005 |
| WO | WO 2005/087766 | | 9/2005 |
| WO | 2007138081 | A1 | 12/2007 |
| WO | 2010110231 | A1 | 9/2010 |
| WO | 2010110409 | A1 | 9/2010 |
| WO | WO 2010/147068 | | 12/2010 |
| WO | 2012151567 | A1 | 11/2012 |
| WO | WO 2014/046441 | | 3/2014 |
| WO | 2014108406 | A1 | 7/2014 |
| WO | WO 2015/026792 | | 2/2015 |
| WO | 2015038665 | A1 | 3/2015 |
| WO | WO 2015/038655 | * | 3/2015 ........... C07D 487/04 |
| WO | WO 2015/038660 | | 3/2015 |
| WO | WO 2016/145103 | | 9/2016 |
| WO | 2017153919 | A1 | 9/2017 |
| WO | 2018030463 | A1 | 2/2018 |
| WO | 2018042303 | A1 | 3/2018 |
| WO | 2019166950 | A1 | 9/2019 |

OTHER PUBLICATIONS

Chen et al., "Computation-Guided Discovery of Influenza Endonuclease Inhibitors" *ACS Med. Chem. Letters* 5:61-64, 2014.

Liu et al., "Total Synthesis of the *Securinega* Alkaloid (—)-Secu'amamine A" *J. Am. Chem. Soc.* 130:7562-7563, 2008.

Handbook of Pharmaceutical Salts: Properties, Selection, and Use by Stahl and Wermuth (Wiley-VCH, Weinheim, Germany, 2002).

Houben-Weyl 4th Ed. 1952, Methods of Organic Synthesis, Thieme, vol. 21.

Remington's Pharmaceutical Sciences, 20th ed., Mack Publishing Company, Easton, Pa., (1985).

Remington: The Science and Practice of Pharmacy, $22^{nd}$ ed.

Rodriguez et al.. "Palau'chlor: A Practical and Reactive Chlorinating Reagent" J. Am. Chem. Soc., vol. 136, No. 19, (2014), pp. 6908-6911.

Zhang, "Discovery of Novel Trisubstituted Asymmetric Derivatives of (2S,4R,5R)-2-benzhydryl-5-benzylaminotetrahydropyran-4-ol, Exhibiting High Affinity for Serotonin and Norepinephrine Transporters in a Stereospecific Manner," J. Med. Chem., vol. 48, (2005), pp. 4962-4971.

International Search Report, issued in PCT/IB2017/055137, dated Oct. 30, 2017.

International Search Report, issued in PCT/IB2017/051338, dated May 10, 2017.

International Search Report, issued in PCT/IB2019/051549, dated May 21, 2019.

* cited by examiner

FUSED TRICYCLIC PYRIDAZINONE COMPOUNDS USEFUL TO TREAT ORTHOMYXOVIRUS INFECTIONS

CROSS-REFERENCE TO RELATED APPLICATION

This application is U.S. national stage of International Application No. PCT/IB2017/055137, filed 25 Aug. 2017, which claims the benefit of priority to U.S. Provisional Application No. 62/380,712, filed 29 Aug. 2016, the content of which is incorporated herein by reference.

FIELD OF THE INVENTION

The invention provides compounds that inhibit orthomyxovirus replication, and are accordingly useful for treatment of viral infections caused by orthomyxoviruses. The invention further provides pharmaceutical compositions containing these compounds and methods of using these compounds to treat or prevent viral infections caused by orthomyxovirus.

BACKGROUND

Orthomyxoviruses have negative-sense single stranded RNA genomes, and replicate in the nucleus of infected cells, as they lack the machinery to generate the cap structure to produce their own mRNA. Members of the Orthomyxovirus family have an RNA-dependent RNA polymerase with endonuclease activity that cleaves a section of the capped 5'-end of cellular mRNA; the RNA polymerase then uses the cleavage product as a primer for synthesis of viral mRNA. This process is known as cap-snatching. This endonuclease has been recognized as a promising target for development of antivirals effective against orthomyxoviruses. *ACS Med. Chem. Letters,* 2014, vol. 5, 61-64. Inhibitors of this endonuclease have been disclosed, for example, in WO2015/038660, U.S. Pat. No. 8,987,441, WO2010/147068, and U.S. patent applications US2012/022251, US2013/0197219, US2014/256937, and US2015/0072982, which report that such inhibitors are useful to treat influenza infections in mammals.

The orthomyxovirus family includes influenza A, influenza B and influenza C, all of which can infect humans, as well as several other genera of viruses that generally do not infect humans. Influenza A is the most virulent of these pathogens in humans, often accounting for the majority of serious cases of influenza during a typical flu season. It is estimated that influenza kills as many as 40,000 people per year in the U.S., in spite of the widespread use of vaccines to reduce the incidence of influenza; thus there is a great need for antiviral therapeutics effective to treat influenza, especially influenza A. The present invention provides compounds that inhibit replication of orthomyxoviruses, including influenza A, influenza B and influenza C. Without being bound by theory, it is believed these compounds achieve their antiviral effects by inhibiting the endonuclease function of the viral polymerase. Because this endonuclease is highly conserved across influenza A viruses (id.), the compounds are especially useful for treatment of influenza A.

SUMMARY OF THE INVENTION

In one aspect, the invention provides a compound of Formula (A):

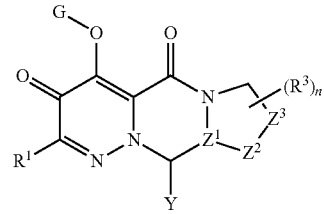

as further described herein.

In another aspect, the invention provides a compound of formula (I):

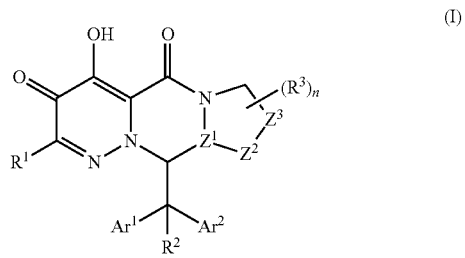

(I)

or a pharmaceutically acceptable salt thereof, wherein:
  $R^1$ is H, halo, CN, COOR*, —CONR*$_2$, or $C_1$-$C_6$ alkyl optionally substituted with one or two groups selected from —OR* and —NR*$_2$, $C_1$-$C_4$ haloalkyl;
  R* is independently at each occurrence H or $C_1$-$C_6$ alkyl optionally substituted with —OR or —NR$_2$;
  $Z^1$ is N, and $Z^2$ is C(R)$_2$;
  or $Z^1$ is CH, and $Z^2$ is NR, O, S, or CH$_2$;
  $Z^3$ is CH$_2$, Q, —CH$_2$—CH$_2$—, -Q-CH$_2$—, —CH$_2$-Q-, —CH$_2$-Q-CH$_2$— or —CH$_2$—CH$_2$—CH$_2$—;
  Q is selected from —NR—, O, S, SO, and SO$_2$;
  $R^2$ is selected from H, halo, CN, $C_{1-4}$ alkyl optionally substituted with up to three groups independently selected from halo, CN, $C_{1-4}$ alkyl, —OR, $C_{1-4}$ haloalkoxy, —NR$_2$, and $C_{1-4}$ haloalkyl, OR, and $C_1$-$C_4$ haloalkyl;
  each $R^3$ is a substituent optionally present on any carbon atom of the ring containing $Z^2$ and $Z^3$, and is independently selected from —OR, $C_{1-4}$ haloalkyl, $C_{1-4}$ haloalkoxy, oxo, CN, —NR$_2$, and $C_{1-4}$ alkyl optionally substituted with up to three groups independently selected from halo, CN, $C_{1-4}$ alkyl, —OR, $C_{1-4}$ haloalkoxy, —NR$_2$, and $C_{1-4}$ haloalkyl;
  n is 0-2;
  $Ar^1$ and $Ar^2$ each independently represent phenyl or a 5-6 membered heteroaryl ring containing 1-3 heteroatoms selected from N, O and S as ring members, and are each independently substituted with up to three groups selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;
    and $Ar^1$ and $Ar^2$ are optionally linked together by a bridge of the formula —C(R$^L$)$_2$-L- to form a tricyclic group, wherein $Ar^1$ and $Ar^2$ are each optionally substituted by up to two groups independently selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;

R is independently at each occurrence H or $C_1$-$C_4$ alkyl optionally substituted with up to three groups independently selected from halo, OH, oxo, $C_{1-4}$ alkyl, $C_{1-4}$ alkoxy, $C_{1-4}$ haloalkoxy, and $C_{1-4}$ haloalkyl;

L is selected from S, S=O, $SO_2$, O, NR, $C(R^L)_2$ and $CF_2$; and and each $R^L$ is independently H or $C_{1-2}$ alkyl;

as further described herein.

The invention includes these compounds, their pharmaceutically acceptable salts, and compositions and combinations comprising these compounds (including pharmaceutically acceptable salts), and methods of using the same as further described herein.

The compounds of Formula (A) are inhibitors of the endonuclease function of influenza viruses as shown by the data provided herein, and they inhibit replication of influenza viruses. Accordingly, these compounds are useful to treat or prevent orthomyxovirus infections in mammals susceptible to such infections, and are particularly useful to treat influenza virus infections in humans. They are also useful to inhibit replication of orthomyxoviruses, including influenza viruses, in cells.

In another aspect, the invention provides pharmaceutical compositions comprising a compound of Formula (A) admixed with at least one pharmaceutically acceptable carrier or excipient, optionally admixed with two or more pharmaceutically acceptable carriers or excipients. The compounds may be used as pharmaceutically acceptable salts.

In another aspect, the invention provides a method to treat a subject infected with influenza A, B or C, which comprises administering to a subject in need of such treatment an effective amount of a compound of Formula (A) or any subgenus or species thereof as described herein, or a pharmaceutical composition comprising such compound. The subject can be a mammal, and is preferably a human, although the compounds and methods of the invention are suitable for treatment of other species that contract Influenza A, Influenza B, or influenza C, as well as other orthomyxoviruses. The invention includes compounds of Formula (A) and the subgenera of Formula (I) described herein, and all stereoisomers (including diastereoisomers and enantiomers) except where a specific isomer is expressly described, as well as tautomers and isotopically enriched versions thereof (including deuterium substitutions) as well as pharmaceutically acceptable salts of these compounds. Compounds of the present invention also comprise polymorphs of compounds of formula (A) (or subformulae thereof) and salts thereof.

DETAILED DESCRIPTION

The following definitions apply unless otherwise expressly provided:

As used herein, the term "halogen" or "halo" refers to fluorine, bromine, chlorine or iodine, in particular it typically refers to fluorine or chlorine when attached to an alkyl group, and further includes bromine or iodine when on an aryl or heteroaryl group.

As used herein, unless otherwise specified, the term "heteroatom" refers to a nitrogen (N), oxygen (O) or sulfur (S) atom.

As used herein, the term "alkyl" refers to a fully saturated branched or unbranched hydrocarbon moiety having up to 10 carbon atoms. Unless otherwise provided, alkyl refers to hydrocarbon moieties having 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more substituents in place of hydrogen, such as one, two, or three substituents, up to the number of hydrogens present on the unsubstituted alkyl group. Suitable substituents for alkyl groups, if not otherwise specified, may be selected from halogen, CN, oxo, hydroxy, $C_{1-4}$ alkoxy, substituted or unsubstituted $C_{3-6}$ cycloalkyl, substituted or unsubstituted phenyl, amino, ($C_{1-4}$ alkyl)amino, di($C_{1-4}$ alkyl)amino, $C_{1-4}$ alkylthio, $C_{1-4}$ alkylsulfonyl, —C(=O)—$C_{1-4}$ alkyl, COOH, COO($C_{1-4}$ alkyl), —C(C=O)— $C_{1-4}$ alkyl, —NHC(=O)$C_{1-4}$ alkyl and —NHC(=O)$CO_{1-4}$ alkyl groups, where substituents for the substituted cycloalkyl or phenyl are up to three groups selected from Me, Et, —OMe, —OEt, $CF_3$, halo, CN, OH, and $NH_2$.

As used herein, the term "alkylene" refers to a divalent alkyl group having 1 to 10 carbon atoms, and two open valences to attach to other features. Unless otherwise provided, alkylene refers to moieties having 1 to 6 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 2,2-dimethylbutylene, and the like. A substituted alkylene is an alkylene group containing one or more, such as one, two or three substituents; unless otherwise specified, suitable substituents for an alkylene group are selected from the substituents listed above for alkyl groups.

As used herein, the term "haloalkyl" refers to an alkyl as defined herein, which is substituted by one or more halo groups. The haloalkyl can be monohaloalkyl, dihaloalkyl, trihaloalkyl, or polyhaloalkyl including perhaloalkyl. A monohaloalkyl can have one chloro or fluoro within the alkyl group. Chloro and fluoro are commonly present as substituents on alkyl or cycloalkyl groups; fluoro, chloro and bromo are often present on aryl or heteroaryl groups. Dihaloalkyl and polyhaloalkyl groups can have two or more of the same halo atoms or a combination of different halo groups on the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, 2,2,2-trifluoroethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable substituents are selected from the substituents listed above for alkyl groups, except that hydroxyl and amino are not normally present on the carbon that is directly attached to the oxygen of the substituted 'alkyl-0' group.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are those named above for alkyl groups unless, otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

As used herein, the term "cycloalkyl" refers to saturated or unsaturated non-aromatic monocyclic, bicyclic, tricyclic or spirocyclic hydrocarbon groups of 3-12 carbon atoms: the cycloalkyl group may be unsaturated, and may be fused to another ring that can be saturated, unsaturated or aromatic, provided the ring atom of the cycloalkyl group that is connected to the molecular formula of interest is not an aromatic ring carbon. Unless otherwise provided, cycloalkyl refers to cyclic hydrocarbon groups having between 3 and 9 ring carbon atoms or between 3 and 7 ring carbon atoms. Preferably, cycloalkyl groups are saturated monocyclic rings having 3-7 ring atoms, such as cyclopropyl, cyclobutyl, cyclopentyl and cyclohexyl, unless otherwise specified.

A substituted cycloalkyl is a cycloalkyl group substituted by one, or two, or three, or more than three substituents, up to the number of hydrogens on the unsubstituted group. Typically, a substituted cycloalkyl will have 1-4 substituents unless otherwise specified. Suitable substituents, unless otherwise specified, are independently selected from the group consisting of halogen, hydroxyl, thiol, cyano, nitro, oxo, C1-C4-alkylimino, C1-C4-alkoximino, hydroxyimino, C1-C4-alkyl, C2-C4-alkenyl, C2-C4-alkynyl, C1-C4-alkoxy, C1-C4-thioalkyl, C2-C4-alkenyloxy, C2-C4-alkynyloxy, C1-C4-alkylcarbonyl, carboxy, C1-C4-alkoxycarbonyl, amino, C1-C4-alkylamino, di-C1-C4-alkylamino, C1-C4-alkylaminocarbonyl, di-C1-C4-alkylaminocarbonyl, C1-C4-alkylcarbonylamino, C1-C4-alkylcarbonyl(C1-C4-alkyl)amino, C1-C4-alkylsulfonyl, C1-C4-alkylsulfamoyl, and C1-C4-alkylaminosulfonyl, where each of the aforementioned hydrocarbon groups (e.g., alkyl, alkenyl, alkynyl, alkoxy residues) may be further substituted by one or more groups independently selected at each occurrence from the list of substituents for 'alkyl' groups herein. Preferred substituents for a cycloalkyl group include C1-C4 alkyl and the substituent groups listed above as suitable substituents for alkyl groups.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "cycloalkyl". When used in these terms, the cycloalkyl is typically a monocyclic 3-7 carbon ring, that is unsubstituted or substituted with 1-2 groups. When optionally substituted, the substituents are typically selected from C1-C4 alkyl and those set forth above as suitable for alkyl groups.

As used herein, the term "aryl" refers to an aromatic hydrocarbon group having 6-14 carbon atoms in the ring portion. Typically, aryl is monocyclic, bicyclic or tricyclic aryl having 6-14 carbon atoms, often 6-10 carbon atoms, e.g., phenyl or naphthyl. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group. Unless otherwise indicated, a preferred aryl group is phenyl.

A substituted aryl is an aryl group substituted by 1-5 (such as one, or two, or three) substituents independently selected from the group consisting of hydroxyl, thiol, cyano, nitro, $C_1$-$C_4$-alkyl, $C_2$-$C_4$-alkenyl, $C_2$-$C_4$-alkynyl, $C_1$-$C_4$-alkoxy, $C_1$-$C_4$-thioalkyl, $C_2$-$C_4$-alkenyloxy, $C_2$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, $C_1$-$C_4$-alkylsulfonyl, sulfamoyl, $C_1$-$C_4$-alkylsulfamoyl, and $C_1$-$C_4$-alkylaminosulfonyl where each of the aforementioned hydrocarbon groups (e.g., alkyl, alkenyl, alkynyl, alkoxy residues) may be further substituted by one or more groups independently selected at each occurrence from the groups listed above as suitable substituents for alkyl groups. Preferred substituents for a substituted aryl group are $C_{1-4}$ alkyl and those groups named above as suitable substituents for alkyl groups, excluding divalent groups such as oxo.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" refers to a heterocyclic radical that is saturated or partially unsaturated but not aromatic, and can be a monocyclic or a polycyclic ring (in case of a polycyclic ring particularly a bicyclic, tricyclic or spirocyclic ring); and has 3 to 14, more commonly 4 to 10, and most preferably 5 or 6 ring atoms; wherein one or more, preferably one to four, especially one or two ring atoms are heteroatoms independently selected from O, S and N (the remaining ring atoms therefore being carbon). Even if it is described as, e.g., a C5-6 atom ring, a heterocycle contains at least one heteroatom as a ring atom with the other ring atoms being carbon, and has the number of ring atoms stated, e.g. 5-6 in this example. Preferably, a heterocyclyl group has one or two such heteroatoms as ring atoms, and preferably the heteroatoms are not directly connected to each other. The bonding ring (i.e. the ring connecting to the Formula of interest) preferably has 4 to 12, especially 5 to 7 ring atoms unless otherwise specified. The heterocyclic group can be fused to an aromatic ring, provided the atom of the heterocyclic group attached to the Formula of interest is not aromatic. The heterocyclic group can be attached to the Formula of interest via a heteroatom (typically nitrogen) or a carbon atom of the heterocyclic group. The heterocyclyl can include fused or bridged rings as well as spirocyclic rings, and only one ring of a polycyclic heterocyclic group needs to contain a heteroatom as a ring atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-5 (such as one, or two, or three) substituents selected from the substituents described above for a cycloalkyl group.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms as ring members, with the remaining ring atoms being carbon, and the heteroatoms are selected from N, O and S. Typically, the heteroaryl is a 5-10 membered ring system, especially a 5-6 membered monocyclic or an 8-10 membered bicyclic group. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2, 3-triazolyl, 1- or 2-tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloalkyl, or heterocyclyl rings. Non-limiting examples include 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents, typically one or two substituents, selected from the substituents described above as suitable for an aryl group.

Similarly, each heteroaryl part of other groups like "heteroaryloxy", "heteroaryloxyalkyl", "heteroaryloxycarbonyl" shall have the same meaning as described in the above-mentioned definition of "heteroaryl".

Various embodiments of the invention are described herein. It will be recognized that features specified in each embodiment may be combined with other specified features to provide further embodiments of the present invention. The following enumerated embodiments are representative of aspects of the invention:

In one embodiment, the invention provides compounds of Formula (A):

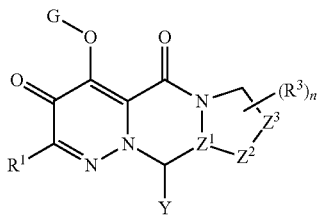

(A)

or a pharmaceutically acceptable salt thereof, wherein:
Y is a group of the formula

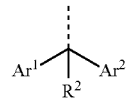

wherein the dashed line represents a bond connecting Y to the tricyclic core of Formula (A);

G is H or a group selected from —C(O)R$^0$, —C(O)—OR$^0$, —C(R$^G$)$_2$—O—C(O)R$^0$, —C(R$^G$)$_2$—O—C(O)—OR$^0$, —C(O)—N(R$^0$)$_2$, and —C(R$^G$)$_2$—O—C(O)N(R$^0$)$_2$, where each R$^0$ is independently H or a group selected from $C_1$-$C_6$ alkyl, phenyl, pyridyl, $C_3$-$C_7$ cycloalkyl, and a 3-6 membered heterocyclic ring containing one or two heteroatoms selected from N, O and S as ring members; and each R$^0$ that is not H is optionally substituted with one or two groups selected from halo, CN, —OH, amino, $C_{1-4}$ alkyl, phenyl, $C_{1-4}$ alkoxy, $C_{1-4}$ haloalkyl, and $C_{1-4}$ haloalkoxy;
and each R$^G$ is independently selected from H and $C_{1-4}$ alkyl;
R$^1$ is H, halo, CN, COOR*, —CONR*$_2$, or $C_1$-$C_6$ alkyl optionally substituted with one or two groups selected from —OR* and —NR*$_2$, $C_1$-$C_4$ haloalkyl;
R* is independently at each occurrence H or $C_1$-$C_6$ alkyl optionally substituted with —OR or —NR$_2$;
$Z^1$ is N, and $Z^2$ is C(R)$_2$;
or $Z^1$ is CH, and $Z^2$ is NR, O, S, or CH$_2$;
$Z^3$ is CH$_2$, Q, —CH$_2$—CH$_2$—, -Q-CH$_2$—, —CH$_2$-Q-, —CH$_2$-Q-CH$_2$— or —CH$_2$—CH$_2$—CH$_2$—;
Q is selected from —NR—, O, S, SO, and SO$_2$;
R$^2$ is selected from H, halo, CN, $C_{1-4}$ alkyl optionally substituted with up to three groups independently selected from halo, CN, $C_{1-4}$ alkyl, —OR, $C_{1-4}$ haloalkoxy, —NR$_2$, and $C_{1-4}$ haloalkyl, OR, and $C_1$-$C_4$ haloalkyl;
each R$^3$ is a substituent optionally present on any carbon atom of the ring containing $Z^2$ and $Z^3$, and is independently selected from —OR, $C_{1-4}$ haloalkyl, $C_{1-4}$ haloalkoxy, oxo, CN, —NR$_2$, and $C_{1-4}$ alkyl optionally substituted with up to three groups independently selected from halo, CN, $C_{1-4}$ alkyl, —OR, $C_{1-4}$ haloalkoxy, —NR$_2$, and $C_{1-4}$ haloalkyl;
n is 0-2;
Ar$^1$ and Ar$^2$ each independently represent phenyl or a 5-6 membered heteroaryl ring containing 1-3 heteroatoms selected from N, O and S as ring members, and are each independently substituted with up to three groups selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;
and Ar$^1$ and Ar$^2$ are optionally linked together by a bridge of the formula —C(R$^L$)$_2$-L- to form a tricyclic group, wherein Ar$^1$ and Ar$^2$ are each optionally substituted by up to two groups independently selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;
R is independently at each occurrence H or $C_1$-$C_4$ alkyl optionally substituted with up to three groups independently selected from halo, OH, oxo, $C_{1-4}$ alkyl, $C_{1-4}$ alkoxy, $C_{1-4}$ haloalkoxy, and $C_{1-4}$ haloalkyl;
L is selected from S, S═O, SO$_2$, O, NR, C(R$^L$)$_2$ and CF$_2$; and
and each R$^L$ is independently H or $C_{1-2}$ alkyl.

Compounds of Formula (A) where G is not H can act as pro-drugs that are readily converted in vivo into compounds where G is H.

In one embodiment of the compounds of Formula (A), G is H.

In another embodiment of the compounds of Formula (A), G is selected from —C(O)R$^0$, —C(O)—OR$^0$, —C(R$^G$)$_2$—O—C(O)R$^0$, —C(R$^G$)$_2$—O—C(O)—OR$^0$, —C(O)—N(R$^0$)$_2$, and —C(R$^G$)$_2$—O—C(O)N(R$^0$)$_2$, where each R$^0$ is independently H or a group selected from $C_1$-$C_4$ alkyl, phenyl, pyridyl, $C_3$-$C_7$ cycloalkyl, and a 3-6 membered heterocyclic ring containing one or two heteroatoms selected from N, O and S as ring members; and each R that is not H is optionally substituted with one or two groups selected from halo, CN, —OH, amino, $C_{1-4}$ alkyl, phenyl, $C_{1-4}$ alkoxy, $C_{1-4}$ haloalkyl, and $C_{1-4}$ haloalkoxy.

In certain of the preceding embodiments, G is selected from —C(O)R$^0$, —C(O)—OR$^0$, —C(R$^G$)$_2$—O—C(O)R$^0$, and —C(R$^G$)$_2$—O—C(O)—OR$^0$, where each R$^0$ is independently H or $C_1$-$C_4$ alkyl, and each R$^G$ is H or $C_1$-$C_4$ alkyl. In some of these embodiments, each R$^G$ is H and R$^0$ is $C_1$-$C_4$ alkyl.

In certain of the preceding embodiments, the compound of Formula (A) is of the formula:

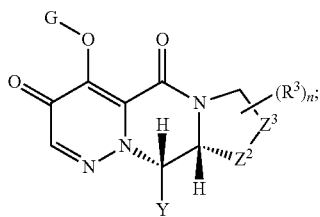

or a pharmaceutically acceptable salt thereof.

In certain compounds of this formula, $Z^2$ is $CH_2$, $Z^3$ is $CH_2$, n is 0, 1 or 2, and each R$^3$ is Me.

In another embodiment (Embodiment 1), the invention provides compounds of Formula

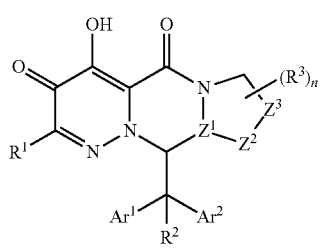

or a pharmaceutically acceptable salt thereof, wherein:

R$^1$ is H, halo, CN, COOR*, —CONR*$_2$, or $C_1$-$C_6$ alkyl optionally substituted with one or two groups selected from —OR* and —NR$_2$, $C_{1-4}$ haloalkyl;

R* is independently at each occurrence H or $C_1$-$C_6$ alkyl optionally substituted with —OR or —NR$_2$;

$Z^1$ is N, and $Z^2$ is C(R)$_2$;

or $Z^1$ is CH, and $Z^2$ is NR, O, S, or $CH_2$;

$Z^3$ is $CH_2$, Q, —$CH_2$—$CH_2$—, -Q-$CH_2$—, —$CH_2$-Q-, —$CH_2$-Q-$CH_2$— or —$CH_2$—$CH_2$—$CH_2$—;

Q is selected from —NR—, O, S, SO, and SO$_2$;

R$^2$ is selected from H, halo, CN, $C_{1-4}$ alkyl optionally substituted with up to three groups independently selected from halo, CN, $C_{1-4}$ alkyl, —OR, $C_{1-4}$ haloalkoxy, —NR$_2$, and $C_{1-4}$ haloalkyl, OR, and $C_1$-$C_4$ haloalkyl;

each R$^3$ is a substituent optionally present on any carbon atom of the ring containing $Z^2$ and $Z^3$, and is independently selected from —OR, $C_{1-4}$ haloalkyl, $C_{1-4}$ haloalkoxy, oxo, CN, —NR$_2$, and $C_{1-4}$ alkyl optionally substituted with up to three groups independently selected from halo, CN, $C_{1-4}$ alkyl, —OR, $C_{1-4}$ haloalkoxy, —NR$_2$, and $C_{1-4}$ haloalkyl;

n is 0-2;

Ar$^1$ and Ar$^2$ each independently represent phenyl or a 5-6 membered heteroaryl ring containing 1-3 heteroatoms selected from N, O and S as ring members, and are each independently substituted with up to three groups selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;

and Ar$^1$ and Ar$^2$ are optionally linked together by a bridge of the formula —C(R$^L$)$_2$-L- to form a tricyclic group, wherein Ar$^1$ and Ar$^2$ are each optionally substituted by up to two groups independently selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;

R is independently at each occurrence H or $C_1$-$C_4$ alkyl optionally substituted with up to three groups independently selected from halo, OH, oxo, $C_{1-4}$ alkyl, $C_{1-4}$ alkoxy, $C_{1-4}$ haloalkoxy, and $C_{1-4}$ haloalkyl;

L is selected from S, S=O, SO$_2$, O, NR, C(R$^L$)$_2$ and CF$_2$; and and each R$^L$ is independently H or $C_{1-2}$ alkyl.

In a preferred embodiment of any of the compounds of Formula (G) or Formula (I) in the preceding embodiments, if $Z^2$ is NR, O or S, then $Z^3$ is $CH_2$, $CH_2CH_2$, or $CH_2CH_2CH_2$.

The following enumerated embodiments describe and illustrate certain aspects of the invention.

2. A compound according to embodiment 1, or any of the embodiments of Formula (A), or a pharmaceutically acceptable salt thereof, wherein $Z^1$ is CH.

3. A compound according to embodiment 1 or embodiment 2, or any of the embodiments of Formula (A), or a pharmaceutically acceptable salt thereof, wherein $Z^1$ is N.

4. A compound according to any one of embodiments 1 to 3, or any of the embodiments of Formula (A), or a pharmaceutically acceptable salt thereof, wherein $Z^2$ is $CH_2$ or —$CH_2$—$CH_2$—.

5. A compound according to any of the preceding embodiments or a pharmaceutically acceptable salt thereof, wherein $Z^3$ is $CH_2$, —$CH_2$—$CH_2$—, —$CH_2$—$CH_2$—$CH_2$—, —$CH_2$—O—, or O.

6. A compound according to any of the preceding embodiments or a pharmaceutically acceptable salt thereof, wherein R$^1$ is H.

7. A compound according to any of the preceding embodiments or a pharmaceutically acceptable salt thereof, wherein R$^2$ is H.

8. A compound according to any of the preceding embodiments or a pharmaceutically acceptable salt thereof, wherein Ar$^1$ and Ar$^2$ are both phenyl and are each independently substituted with up to two groups selected from halo, $C_{1-4}$ alkyl, $C_{1-4}$ haloalkyl, $C_1$-4 alkoxy, $C_{1-4}$ haloalkoxy, $C_{2-4}$ alkyne, and CN.

9. A compound of any of the preceding embodiments, which is of the formula:

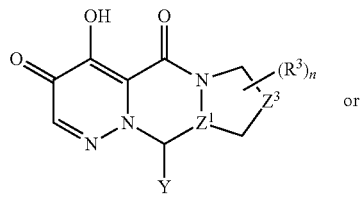

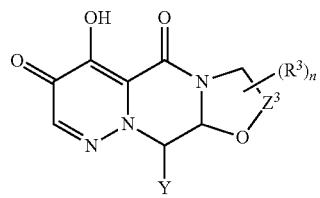

wherein Y represents a group selected from

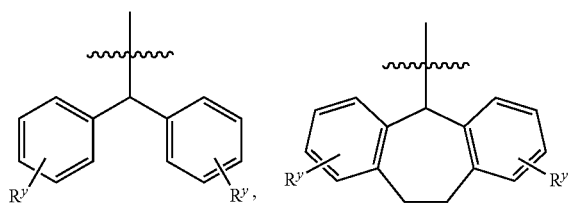

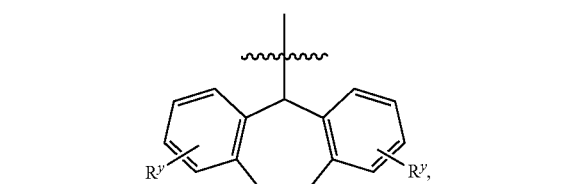

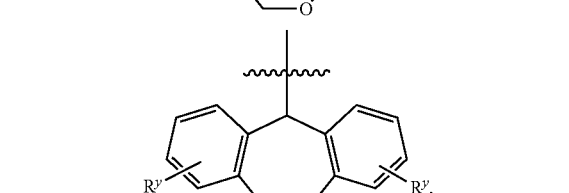

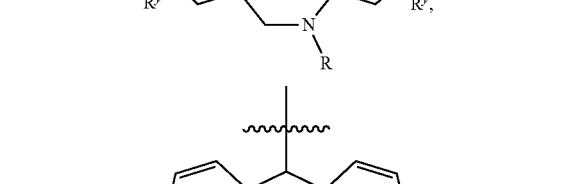

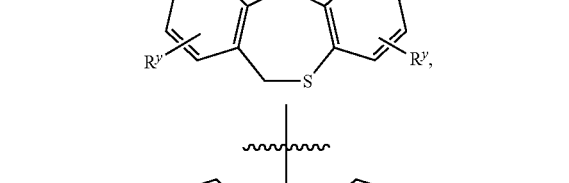

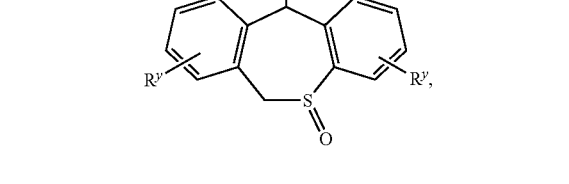

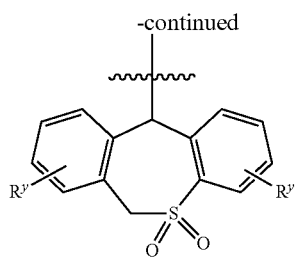

and

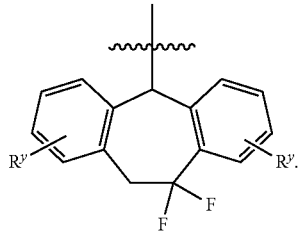

wherein each $R^y$ is independently selected from H, halo, $C_{1-4}$ alkyl, $C_{1-4}$ haloalkyl, $C_{1-4}$ alkoxy, $C_{1-4}$ haloalkoxy, $C_{2-4}$ alkyne, and CN, or a pharmaceutically acceptable salt thereof.

10. A compound of embodiment 9, or a pharmaceutically acceptable salt thereof, which is of the formula

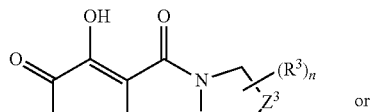

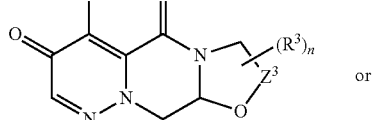

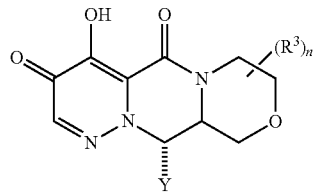

wherein $Z^1$ is N or CH; and
$Z^3$ is $CH_2$ or —$CH_2$—$CH_2$—.

11. A compound of embodiment 1, or any of the embodiments of Formula (A), which is selected from the group consisting of Examples 1-149, or a pharmaceutically acceptable salt thereof. Each of the compounds of the examples is a specific embodiment of the invention, thus the invention provides a compound selected from:

1    12-benzhydryl-4-hydroxy-7,8,9,10-tetrahydro-12H-dipyridazino[1,2-a:1',6'-d][1,2,4]triazine-3,5-dione;

2    12-(bis(3-fluorophenyl)methyl)-4-hydroxy-7,8,9,10-tetrahydro-12H-dipyridazino[1,2-a:1',6'-d][1,2,4]triazine-3,5-dione;

3    12-(bis(4-chlorophenyl)methyl)-4-hydroxy-7,8,9,10-tetrahydro-12H-dipyridazino[1,2-a:1',6'-d][1,2,4]triazine-3,5-dione;

4  12-(bis(3-chlorophenyl)methyl)-4-hydroxy-7,8,9,10-tetrahydro-12H-dipyridazino[1,2-a:1',6'-d][1,2,4]triazine-3,5-dione;
5  12-(bis(4-fluorophenyl)methyl)-4-hydroxy-7,8,9,10-tetrahydro-12H-dipyridazino[1,2-a:1',6'-d][1,2,4]triazine-3,5-dione;
6  13-benzhydryl-4-hydroxy-8,9,10,11-tetrahydro-7H,13H-pyridazino[1',6':4,5][1,2,4]triazino[1,2-a][1,2]diazepine-3,5-dione;
7  13-(bis(3-fluorophenyl)methyl)-4-hydroxy-8,9,10,11-tetrahydro-7H,13H-pyridazino[1',6':4,5][1,2,4]triazino[1,2-a][1,2]diazepine-3,5-dione;
8  (R)-12-(bis(3-fluorophenyl)methyl)-4-hydroxy-7,8,9,10-tetrahydro-12H-dipyridazino[1,2-a:1',6'-d][1,2,4]triazine-3,5-dione;
9  (S)-12-(bis(3-fluorophenyl)methyl)-4-hydroxy-7,8,9,10-tetrahydro-12H-dipyridazino[1,2-a:1',6'-d][1,2,4]triazine-3,5-dione;
10  (9aR,10S)-10-benzhydryl-4-hydroxy-8,9,9a,10-tetrahydro-7H-pyrrolo[1',2':4,5]pyrazino[1,2-b]pyridazine-3,5-dione;
11  (9aR,10R)-10-benzhydryl-4-hydroxy-8,9,9a,10-tetrahydro-7H-pyrrolo[1',2':4,5]pyrazino[1,2-b]pyridazine-3,5-dione;
12  (9aS,10R)-10-benzhydryl-4-hydroxy-8,9,9a,10-tetrahydro-7H-pyrrolo[1',2':4,5]pyrazino[1,2-b]pyridazine-3,5-dione;
13  (9aS,10S)-10-benzhydryl-4-hydroxy-8,9,9a,10-tetrahydro-7H-pyrrolo[1',2':4,5]pyrazino[1,2-b]pyridazine-3,5-dione;
14  (9aR,10S)-10-((R)-(3-fluorophenyl)(phenyl)methyl)-4-hydroxy-8,9,9a,10-tetrahydro-7H-pyrrolo[1',2':4,5]pyrazino[1,2-b]pyridazine-3,5-dione;
15  (9aR,10R)-10-(bis(3-fluorophenyl)methyl)-4-hydroxy-8,9,9a,10-tetrahydro-7H-pyrrolo[1',2':4,5]pyrazino[1,2-b]pyridazine-3,5-dione;
16  (9aR,10S)-10-(bis(3-fluorophenyl)methyl)-4-hydroxy-8,9,9a,10-tetrahydro-7H-pyrrolo[1',2':4,5]pyrazino[1,2-b]pyridazine-3,5-dione;
17  (9aS,10R)-10-((S)-(3-chlorophenyl)(phenyl)methyl)-4-hydroxy-8,9,9a,10-tetrahydro-7H-pyrrolo[1',2':4,5]pyrazino[1,2-b]pyridazine-3,5-dione;
18  (10aS,11R)-11-benzhydryl-4-hydroxy-7,8,10a,11-tetrahydro-10H-pyridazino[1',6':4,5]pyrazino[2,1-c][1,4]oxazine-3,5-dione;
19A  12-benzhydryl-7-hydroxy-3,4,12,12a-tetrahydro-2H-pyridazino[1',6':4,5]pyrazino[2,1-b][1,3]oxazine-6,8-dione;
19B  12-benzhydryl-7-hydroxy-3,4,12,12a-tetrahydro-2H-pyridazino[1',6':4,5]pyrazino[2,1-b][1,3]oxazine-6,8-dione;
11-(bis(3-fluorophenyl)methyl)-4-hydroxy-8,9-dihydro-7H,11H-pyrazolo[1,2-a]pyridazino[1,6-d][1,2,4]triazine-3,5-dione;
12-(1,1-diphenylethyl)-4-hydroxy-7,8,9,10-tetrahydro-12H-dipyridazino[1,2-a:1',6'-d][1,2,4]triazine-3,5-dione;
12-(bis(2-fluorophenyl)methyl)-4-hydroxy-7,8,9,10-tetrahydro-12H-dipyridazino[1,2-a:1',6'-d][1,2,4]triazine-3,5-dione;
23A  12-benzhydryl-4-hydroxy-10-methyl-7,8,9,10-tetrahydro-12H-dipyridazino[1,2-a:1',6'-d][1,2,4]triazine-3,5-dione;
23B  12-benzhydryl-4-hydroxy-10-methyl-7,8,9,10-tetrahydro-12H-dipyridazino[1,2-a:1',6'-d][1,2,4]triazine-3,5-dione;
12-benzhydryl-4-hydroxy-7-methyl-7,8,9,10-tetrahydro-12H-dipyridazino[1,2-a:1',6'-d][1,2,4]triazine-3,5-dione;
25A  12-benzhydryl-4-hydroxy-7,10-dimethyl-7,8,9,10-tetrahydro-12H-dipyridazino[1,2-a:1',6'-d][1,2,4]triazine-3,5-dione;
25B  12-benzhydryl-4-hydroxy-7,10-dimethyl-7,8,9,10-tetrahydro-12H-dipyridazino[1,2-a:1',6'-d][1,2,4]triazine-3,5-dione;
26A  12-(6,11-dihydrodibenzo[b,e]thiepin-11-yl)-4-hydroxy-7,8,9,10-tetrahydro-12H-dipyridazino[1,2-a:1',6'-d][1,2,4]triazine-3,5-dione;
26B  12-(6,11-dihydrodibenzo[b,e]thiepin-11-yl)-4-hydroxy-7,8,9,10-tetrahydro-12H-dipyridazino[1,2-a:1',6'-d][1,2,4]triazine-3,5-dione;
27A  12-(6,11-dihydrodibenzo[b,e]oxepin-11-yl)-4-hydroxy-7,8,9,10-tetrahydro-12H-dipyridazino[1,2-a:1',6'-d][1,2,4]triazine-3,5-dione;
27B  12-(6,11-dihydrodibenzo[b,e]oxepin-11-yl)-4-hydroxy-7,8,9,10-tetrahydro-12H-dipyridazino[1,2-a:1',6'-d][1,2,4]triazine-3,5-dione;
28A  12-(7,8-difluoro-6,11-dihydrodibenzo[b,e]thiepin-11-yl)-4-hydroxy-7,8,9,10-tetrahydro-12H-dipyridazino[1,2-a:1',6'-d][1,2,4]triazine-3,5-dione;
28B  12-(7,8-difluoro-6,11-dihydrodibenzo[b,e]thiepin-11-yl)-4-hydroxy-7,8,9,10-tetrahydro-12H-dipyridazino[1,2-a:1',6'-d][1,2,4]triazine-3,5-dione;
29  (S)-12-benzhydryl-4-hydroxy-7,8,9,10-tetrahydro-12H-dipyridazino[1,2-a:1',6'-d][1,2,4]triazine-3,5-dione;
30  (S)-12-(bis(4-fluorophenyl)methyl)-4-hydroxy-7,8,9,10-tetrahydro-12H-dipyridazino[1,2-a:1',6'-d][1,2,4]triazine-3,5-dione;
31  (R)-12-(bis(4-fluorophenyl)methyl)-4-hydroxy-7,8,9,10-tetrahydro-12H-dipyridazino[1,2-a:1',6'-d][1,2,4]triazine-3,5-dione;
32  (9aR,10S)-10-((R)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione;
33  (9aR,10S)-10-((R)-(3,4-difluorophenyl)(2-fluorophenyl)methyl)-4-hydroxy-8,9,9a,10-tetrahydro-7H-pyrrolo[1',2':4,5]pyrazino[1,2-b]pyridazine-3,5-dione;
34  (9aR,10S)-10-((S)-(3,4-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;
35  (9aR,10S)-10-((R)-(2-fluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;
36  (9aR,10S)-10-((S)-(3,5-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;
37  (9aR,10S)-10-((S)-(4-fluoro-2-methylphenyl)(3-fluorophenyl)methyl)-4-hydroxy-8,9,9a,10-tetrahydro-7H-pyrrolo[1',2':4,5]pyrazino[1,2-b]pyridazine-3,5-dione;
38  (9aR,10S)-10-((S)-(3,4-difluorophenyl)(phenyl)methyl)-4-hydroxy-8,9,9a,10-tetrahydro-7H-pyrrolo[1',2':4,5]pyrazino[1,2-b]pyridazine-3,5-dione;
39  (9aR,10S)-10-((R)-(2-fluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;
40  (9aR,10S)-10-((R)-(3,5-difluorophenyl)(2-fluorophenyl)methyl)-4-hydroxy-8,9,9a,10-tetrahydro-7H-pyrrolo[1',2':4,5]pyrazino[1,2-b]pyridazine-3,5-dione;
41  (9aR,10S)-10-((R)-(4-fluoro-2-methylphenyl)(2-fluorophenyl)methyl)-4-hydroxy-8,9,9a,10-tetrahydro-7H-pyrrolo[1',2':4,5]pyrazino[1,2-b]pyridazine-3,5-dione;
42  (9aR,10S)-10-((R)-(2-fluorophenyl)(2-methoxyphenyl)methyl)-4-hydroxy-8,9,9a,10-tetrahydro-7H-pyrrolo[1',2':4,5]pyrazino[1,2-b]pyridazine-3,5-dione;

43 (9aR,10S)-10-((R)-(2-fluorophenyl)(o-tolyl)methyl)-4-hydroxy-8,9,9a,10-tetrahydro-7H-pyrrolo[1',2':4,5]pyrazino[1,2-b]pyridazine-3,5-dione;

44 (9aR,10S)-10-(bis(2-fluorophenyl)methyl)-4-hydroxy-8,9,9a,10-tetrahydro-7H-pyrrolo[1',2':4,5]pyrazino[1,2-b]pyridazine-3,5-dione;

45 (9aR,10S)-10-((R)-(3,5-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

46 (9aR,10S)-10-((R)-(2,6-difluorophenyl)(phenyl)methyl)-4-hydroxy-8,9,9a,10-tetrahydro-7H-pyrrolo[1',2':4,5]pyrazino[1,2-b]pyridazine-3,5-dione;

47 (9aR,10S)-10-((R)-(3-fluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

48 (9aR,10S)-10-((R)-(2,6-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

49 (9aR,10S)-10-((R)-(2,6-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

50 (9aR,10S)-10-((S)-(3-fluorophenyl)(3,4,5-trifluorophenyl)methyl)-4-hydroxy-8,9,9a,10-tetrahydro-7H-pyrrolo[1',2':4,5]pyrazino[1,2-b]pyridazine-3,5-dione;

51 (9aR,10S)-10-((S)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione;

52 (9aR,10S)-10-((R)-(3,4-difluorophenyl)(phenyl)methyl)-4-hydroxy-8,9,9a,10-tetrahydro-7H-pyrrolo[1',2':4,5]pyrazino[1,2-b]pyridazine-3,5-dione;

53 (9aR,10S)-10-((S)-(3,4-difluorophenyl)(2-fluorophenyl)methyl)-4-hydroxy-8,9,9a,10-tetrahydro-7H-pyrrolo[1',2':4,5]pyrazino[1,2-b]pyridazine-3,5-dione;

54 (9aR,10S)-10-((S)-(3,5-difluorophenyl)(2-fluorophenyl)methyl)-4-hydroxy-8,9,9a,10-tetrahydro-7H-pyrrolo[1',2':4,5]pyrazino[1,2-b]pyridazine-3,5-dione;

55 (9aR,10S)-10-((S)-(2-fluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

56 (9aR,10S)-10-((S)-(4-fluoro-2-methylphenyl)(2-fluorophenyl)methyl)-4-hydroxy-8,9,9a,10-tetrahydro-7H-pyrrolo[1',2':4,5]pyrazino[1,2-b]pyridazine-3,5-dione;

57 (9aR,10S)-10-((S)-(2-fluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

58 (9aR,10S)-10-((S)-(4-fluorophenyl)(phenyl)methyl)-4-hydroxy-8,9,9a,10-tetrahydro-7H-pyrrolo[1',2':4,5]pyrazino[1,2-b]pyridazine-3,5-dione;

59 (9aR,10S)-10-((S)-(3-fluorophenyl)(phenyl)methyl)-4-hydroxy-8,9,9a,10-tetrahydro-7H-pyrrolo[1',2':4,5]pyrazino[1,2-b]pyridazine-3,5-dione;

60 (9aR,10S)-10-((S)-(3-fluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

61 (9aR,10S)-10-((S)-(2,6-difluorophenyl)(phenyl)methyl)-4-hydroxy-8,9,9a,10-tetrahydro-7H-pyrrolo[1',2':4,5]pyrazino[1,2-b]pyridazine-3,5-dione;

62 (9aR,10S)-10-((S)-(2,6-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

63 (9aR,10S)-10-((S)-(2,6-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

64 (9aR,10S)-10-((R)-(3-fluorophenyl)(3,4,5-trifluorophenyl)methyl)-4-hydroxy-8,9,9a,10-tetrahydro-7H-pyrrolo[1',2':4,5]pyrazino[1,2-b]pyridazine-3,5-dione;

65 (9aR,10S)-10-((R)-(2,3-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

66 (9aR,10S)-10-((R)-(4-fluorophenyl)(o-tolyl)methyl)-4-hydroxy-8,9,9a,10-tetrahydro-7H-pyrrolo[1',2':4,5]pyrazino[1,2-b]pyridazine-3,5-dione;

67 (9aR,10R)-10-((S)-(4-fluorophenyl)(o-tolyl)methyl)-4-hydroxy-8,9,9a,10-tetrahydro-7H-pyrrolo[1',2':4,5]pyrazino[1,2-b]pyridazine-3,5-dione;

68 (9aR,10S)-10-((R)-(4-fluorophenyl)(phenyl)methyl)-4-hydroxy-8,9,9a,10-tetrahydro-7H-pyrrolo[1',2':4,5]pyrazino[1,2-b]pyridazine-3,5-dione;

69 (9aR,10S)-10-(bis(4-fluorophenyl)methyl)-4-hydroxy-8,9,9a,10-tetrahydro-7H-pyrrolo[1',2':4,5]pyrazino[1,2-b]pyridazine-3,5-dione;

70 (9aR,10S)-10-((S)-(3,4-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

71 (9aR,10S)-10-((S)-(4-fluoro-2-methylphenyl)(4-fluorophenyl)methyl)-4-hydroxy-8,9,9a,10-tetrahydro-7H-pyrrolo[1',2':4,5]pyrazino[1,2-b]pyridazine-3,5-dione;

72 (9aR,10S)-10-((R)-(2,3-difluorophenyl)(2,4-difluorophenyl)methyl)-4-hydroxy-8,9,9a,10-tetrahydro-7H-pyrrolo[1',2':4,5]pyrazino[1,2-b]pyridazine-3,5-dione;

73 (9aR,10R)-10-(bis(4-fluorophenyl)methyl)-4-hydroxy-8,9,9a,10-tetrahydro-7H-pyrrolo[1',2':4,5]pyrazino[1,2-b]pyridazine-3,5-dione;

74 (9aR,10S)-10-((R)-(2,3-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

75 (9aR,10S)-10-((S)-(3,5-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

76 (9aR,10S)-10-((S)-(3,4-difluorophenyl)(3,5-difluorophenyl)methyl)-4-hydroxy-8,9,9a,10-tetrahydro-7H-pyrrolo[1',2':4,5]pyrazino[1,2-b]pyridazine-3,5-dione;

77 (9aR,10S)-10-((R)-(3,4-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

78 (9aR,10S)-10-(bis(3,4-difluorophenyl)methyl)-4-hydroxy-8,9,9a,10-tetrahydro-7H-pyrrolo[1',2':4,5]pyrazino[1,2-b]pyridazine-3,5-dione;

79 (9aR,10S)-10-(bis(2,4-difluorophenyl)methyl)-4-hydroxy-8,9,9a,10-tetrahydro-7H-pyrrolo[1',2':4,5]pyrazino[1,2-b]pyridazine-3,5-dione;

80 (9aR,10S)-10-((R)-(2,5-difluorophenyl)(phenyl)methyl)-4-hydroxy-8,9,9a,10-tetrahydro-7H-pyrrolo[1',2':4,5]pyrazino[1,2-b]pyridazine-3,5-dione;

81 (9aR,10S)-10-((R)-(2,5-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

82 (9aR,10S)-10-((R)-(2,5-difluorophenyl)(3,4-difluorophenyl)methyl)-4-hydroxy-8,9,9a,10-tetrahydro-7H-pyrrolo[1',2':4,5]pyrazino[1,2-b]pyridazine-3,5-dione;

83 (9aR,10S)-10-((S)-(3,5-difluorophenyl)(phenyl)methyl)-4-hydroxy-8,9,9a,10-tetrahydro-7H-pyrrolo[1',2':4,5]pyrazino[1,2-b]pyridazine-3,5-dione;

84 (9aR,10S)-10-((R)-(2,5-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

85 (9aR,10S)-10-((R)-(2,4-difluorophenyl)(3,4-difluorophenyl)methyl)-4-hydroxy-8,9,9a,10-tetrahydro-7H-pyrrolo[1',2':4,5]pyrazino[1,2-b]pyridazine-3,5-dione;

86 (9aR,10S)-10-((S)-(4-fluorophenyl)(o-tolyl)methyl)-4-hydroxy-8,9,9a,10-tetrahydro-7H-pyrrolo[1',2':4,5]pyrazino[1,2-b]pyridazine-3,5-dione;

87 (9aR,10S)-10-((R)-(2,4-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

88 (9aR,10S)-10-((R)-(2,4-difluorophenyl)(phenyl)methyl)-4-hydroxy-8,9,9a,10-tetrahydro-7H-pyrrolo[1',2':4,5]pyrazino[1,2-b]pyridazine-3,5-dione;

89 (9aR,10S)-10-((R)-(2,4-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

90 (9aR,10S)-10-((R)-(2,3-difluorophenyl)(phenyl)methyl)-4-hydroxy-8,9,9a,10-tetrahydro-7H-pyrrolo[1',2':4,5]pyrazino[1,2-b]pyridazine-3,5-dione;

91 (9aR,10S)-10-((S)-(2,3-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

92 (9aR,10S)-10-((R)-(4-fluoro-2-methylphenyl)(4-fluorophenyl)methyl)-4-hydroxy-8,9,9a,10-tetrahydro-7H-pyrrolo[1',2':4,5]pyrazino[1,2-b]pyridazine-3,5-dione;

93 (9aR,10S)-10-((R)-(3,4-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

94 (9aR,10S)-10-((R)-(3,4-difluorophenyl)(4-fluorophenyl)methyl)-4-hydroxy-2-(hydroxymethyl)-8,9,9a,10-tetrahydro-7H-pyrrolo[1',2':4,5]pyrazino[1,2-b]pyridazine-3,5-dione;

95 (9aR,10S)-10-((S)-(2,3-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

96 (9aR,10S)-10-((R)-(3,4-difluorophenyl)(3,5-difluorophenyl)methyl)-4-hydroxy-8,9,9a,10-tetrahydro-7H-pyrrolo[1',2':4,5]pyrazino[1,2-b]pyridazine-3,5-dione;

97 (9aR,10S)-10-((R)-(3,5-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

98 (9aR,10S)-10-((S)-(2,5-difluorophenyl)(phenyl)methyl)-4-hydroxy-8,9,9a,10-tetrahydro-7H-pyrrolo[1',2':4,5]pyrazino[1,2-b]pyridazine-3,5-dione;

99 (9aR,10S)-10-((S)-(2,5-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

100 (9aR,10S)-10-((S)-(2,5-difluorophenyl)(3,4-difluorophenyl)methyl)-4-hydroxy-8,9,9a,10-tetrahydro-7H-pyrrolo[1',2':4,5]pyrazino[1,2-b]pyridazine-3,5-dione;

101 (9aR,10S)-10-((R)-(3,5-difluorophenyl)(phenyl)methyl)-4-hydroxy-8,9,9a,10-tetrahydro-7H-pyrrolo[1',2':4,5]pyrazino[1,2-b]pyridazine-3,5-dione;

102 (9aR,10S)-10-((S)-(2,4-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

103 (9aR,10S)-10-((S)-(2,4-difluorophenyl)(phenyl)methyl)-4-hydroxy-8,9,9a,10-tetrahydro-7H-pyrrolo[1',2':4,5]pyrazino[1,2-b]pyridazine-3,5-dione;

104 (9aR,10S)-10-((S)-(2,4-difluorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

105 (9aR,10S)-10-((S)-(2,4-difluorophenyl)(3,4-difluorophenyl)methyl)-4-hydroxy-8,9,9a,10-tetrahydro-7H-pyrrolo[1',2':4,5]pyrazino[1,2-b]pyridazine-3,5-dione;

106 10-(bis(3-fluorophenyl)methyl)-4-hydroxy-8,9,9a,10-tetrahydro-7H-pyrrolo[1',2':4,5]pyrazino[1,2-b]pyridazine-3,5-dione;

107 4-((R)-(3-fluorophenyl)((9aR,10S)-hydroxy-3,5-dioxo-3,5,8,9,9a,10-hexahydro-7H-pyrrolo[1',2':4,5]pyrazino[1,2-b]pyridazin-10-yl)methyl)benzonitrile;

108 (9aR,10S)-10-((S)-(4-chlorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

109 (9aR,10S)-10-((R)-(3-chlorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

110 (9aR,10S)-10-((S)-(2-bromophenyl)(4-fluorophenyl)methyl)-4-hydroxy-8,9,9a,10-tetrahydro-7H-pyrrolo[1',2':4,5]pyrazino[1,2-b]pyridazine-3,5-dione;

111 (9aR,10S)-10-((R)-(2-bromophenyl)(4-fluorophenyl)methyl)-4-hydroxy-8,9,9a,10-tetrahydro-7H-pyrrolo[1',2':4,5]pyrazino[1,2-b]pyridazine-3,5-dione;

112 (9aR,10S)-10-((S)-(3-fluorophenyl)(o-tolyl)methyl)-4-hydroxy-8,9,9a,10-tetrahydro-7H-pyrrolo[1',2':4,5]pyrazino[1,2-b]pyridazine-3,5-dione;

113 (9aR,10S)-10-((S)-(3-chlorophenyl)(3-fluorophenyl)methyl)-4-hydroxy-8,9,9a,10-tetrahydro-7H-pyrrolo[1',2':4,5]pyrazino[1,2-b]pyridazine-3,5-dione;

114 (9aR,10S)-10-((R)-(3-chlorophenyl)(4-fluorophenyl)methyl)-4-hydroxy-8,9,9a,10-tetrahydro-7H-pyrrolo[1',2':4,5]pyrazino[1,2-b]pyridazine-3,5-dione;

115 (9aR,10S)-10-((R)-(3-fluorophenyl)(4-fluorophenyl)methyl)-4-hydroxy-7,7-dimethyl-8,9,9a,10-tetrahydro-7H-pyrrolo[1',2':4,5]pyrazino[1,2-b]pyridazine-3,5-dione;

116 (9aR,10R)-10-((S)-(3-fluorophenyl)(4-fluorophenyl)methyl)-4-hydroxy-7,7-dimethyl-8,9,9a,10-tetrahydro-7H-pyrrolo[1',2':4,5]pyrazino[1,2-b]pyridazine-3,5-dione;

117 (7S,9aR,10S)-10-((R)-(3-fluorophenyl)(4-fluorophenyl)methyl)-4-hydroxy-7-methyl-8,9,9a,10-tetrahydro-7H-pyrrolo[1',2':4,5]pyrazino[1,2-b]pyridazine-3,5-dione;

118 (7S,9aR,10R)-10-((S)-(3-fluorophenyl)(4-fluorophenyl)methyl)-4-hydroxy-7-methyl-8,9,9a,10-tetrahydro-7H-pyrrolo[1',2':4,5]pyrazino[1,2-b]pyridazine-3,5-dione;

119 (7R,9aR,10S)-10-((R)-(3-fluorophenyl)(4-fluorophenyl)methyl)-4-hydroxy-7-methyl-8,9,9a,10-tetrahydro-7H-pyrrolo[1',2':4,5]pyrazino[1,2-b]pyridazine-3,5-dione;

120 (7R,9aR,10R)-10-((S)-(3-fluorophenyl)(4-fluorophenyl)methyl)-4-hydroxy-7-methyl-8,9,9a,10-tetrahydro-7H-pyrrolo[1',2':4,5]pyrazino[1,2-b]pyridazine-3,5-dione;

121 (8S,9aR,10S)-10-(bis(3-fluorophenyl)methyl)-4-hydroxy-8-methoxy-8,9,9a,10-tetrahydro-7H-pyrrolo[1',2':4,5]pyrazino[1,2-b]pyridazine-3,5-dione;

122 (8R,9aR,10S)-10-(bis(3-fluorophenyl)methyl)-4-hydroxy-8-methoxy-8,9,9a,10-tetrahydro-7H-pyrrolo[1',2':4,5]pyrazino[1,2-b]pyridazine-3,5-dione;

123 (10aR,11S)-11-benzhydryl-4-hydroxy-7,8,10a,11-tetrahydro-10H-pyridazino[1',6':4,5]pyrazino[2,1-c][1,4]oxazine-3,5-dione;

124A 11-benzhydryl-4-hydroxy-7,8,9,10,10a,11-hexahydropyrido[1',2':4,5]pyrazino[1,2-b]pyridazine-3,5-dione;

124B 11-benzhydryl-4-hydroxy-7,8,9,10,10a,11-hexahydropyrido[1',2':4,5]pyrazino[1,2-b]pyridazine-3,5-dione;

125A 11-(bis(3-fluorophenyl)methyl)-4-hydroxy-7,8,9,10,10a,11-hexahydropyrido[1',2':4,5]pyrazino[1,2-b]pyridazine-3,5-dione;

125B 11-(bis(3-fluorophenyl)methyl)-4-hydroxy-7,8,9,10,10a,11-hexahydropyrido[1',2':4,5]pyrazino[1,2-b]pyridazine-3,5-dione;

126 11-benzhydryl-4-hydroxy-7,8,10a,11-tetrahydro-10H-pyridazino[1',6':4,5]pyrazino[2,1-c][1,4]oxazine-3,5-dione;

127 11-benzhydryl-4-hydroxy-7-methyl-7,8,9,10,10a,11-hexahydropyrido[1',2':4,5]pyrazino[1,2-b]pyridazine-3,5-dione;

128 (9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl 3-methylbutanoate;
129 (9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl3-methylbutanoate;
130 (9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl acetate;
131 (9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl isobutyrate;
132 (9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl isopropyl carbonate;
133 1-(((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)ethyl ethyl carbonate;
134 (S)-((12-(bis(3-fluorophenyl)methyl)-3,5-dioxo-3,5,7,8,9,10-hexahydro-12H-dipyridazino[1,2-a:1',6'-d][1,2,4]triazin-4-yl)oxy)methyl ethyl carbonate;
135 (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl (2-methoxyethyl) carbonate;
136 1-(((9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl)oxy)ethyl ethyl carbonate;
137 (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl methyl carbonate;
138 (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl ethyl carbonate;
139 (((9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl methyl carbonate;
140 (((9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl ethyl carbonate;
141 (((9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl isopropyl carbonate;
142 (((9aR,10S)-10-((R)-(4-fluorophenyl)(phenyl)methyl)-3,5-dioxo-3,5,8,9,9a,10-hexahydro-7H-pyrrolo[1',2':4,5]pyrazino[1,2-b]pyridazin-4-yl)oxy)methyl methyl carbonate;
143 (((9aR,10S)-10-(bis(3-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl pivalate;
144 (S)-((12-(bis(3-fluorophenyl)methyl)-3,5-dioxo-3,5,7,8,9,10-hexahydro-12H-dipyridazino[1,2-a:1',6'-d][1,2,4]triazin-4-yl)oxy)methyl methyl carbonate;
145 (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl L-valinate;
146 (9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl dimethylcarbamate;
147 (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl ethyl(methyl)carbamate;
148 methyl 2-(((((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)(ethoxy)phosphoryl)oxy)acetate;

and 149 methyl 2-((((((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methoxy)carbonyl)oxy)-2-methylpropanoate;

and the pharmaceutically acceptable salts of these compounds.

12. A pharmaceutical composition comprising a compound of any of the preceding embodiments or a pharmaceutically acceptable salt thereof and one or more pharmaceutically acceptable carriers.

13. A combination comprising a therapeutically effective amount of a compound according to any one of embodiments 1 to 11, or any of the embodiments of Formula (A), or a pharmaceutically acceptable salt thereof and one or more therapeutically active co-agents.

14. A method of treating influenza, comprising administering to a subject in need thereof a therapeutically effective amount of a compound of any of embodiments 1-11, or any of the embodiments of Formula (A), or a pharmaceutically acceptable salt thereof.

15. A compound according to any one of embodiments 1 to 11, or any of the embodiments of Formula (A), or a pharmaceutically acceptable salt thereof, for use as a medicament.

16. A compound according to any one of embodiments 1 to 11, or any of the embodiments of Formula (A), or a pharmaceutically acceptable salt thereof, for use in the treatment of influenza.

17. Use of a compound according to any one of embodiments 1 to 11, or any of the embodiments of Formula (A), or a pharmaceutically acceptable salt thereof in the manufacture of a medicament for the treatment of influenza.

In some embodiments, the compound of Formula (A) is a compound of one of the following formulas:

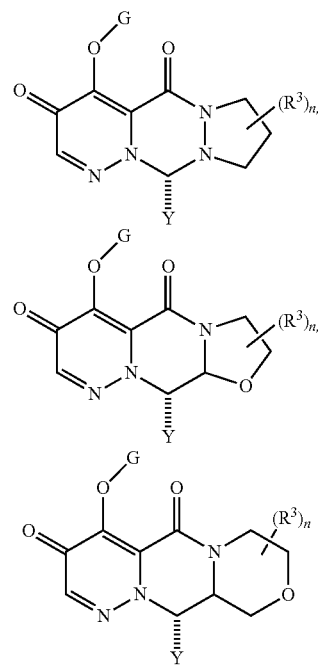

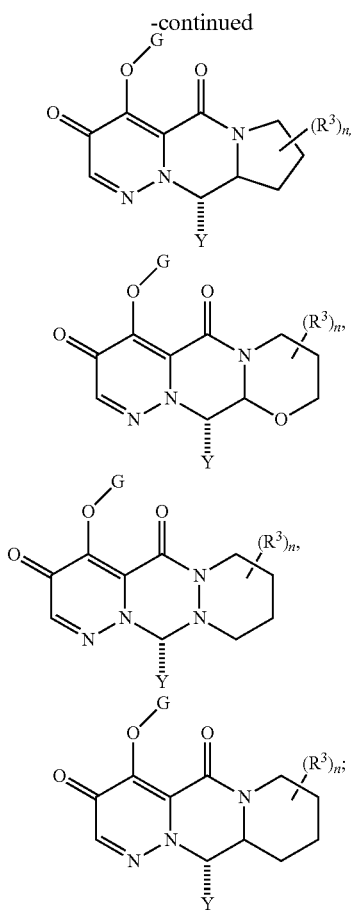

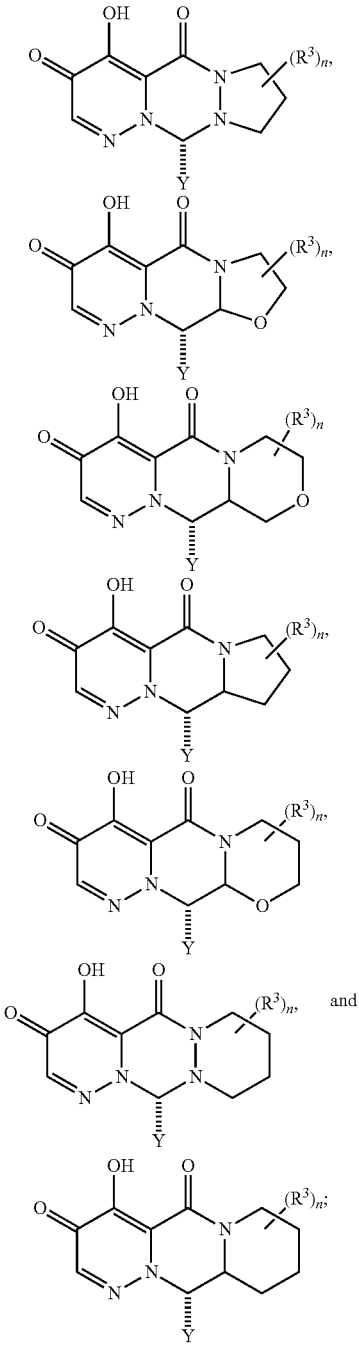

wherein G is H, or G is selected from —C(O)R$^o$, —C(O)—OR$^o$, —C(R$^G$)$_2$—O—C(O)R$^o$, and —C(R$^G$)$_2$—O—C(O)—OR$^o$, where each R$^o$ is independently H or C$_1$-C$_4$ alkyl, and each R$^G$ is H or C$_1$-C$_4$ alkyl. In some of these embodiments, each R$^G$ is H and R$^o$ is C$_1$-C$_4$ alkyl;

n is 0, 1 or 2;

each R$^3$ represents Me, OH, OMe, or halo; and Y represents

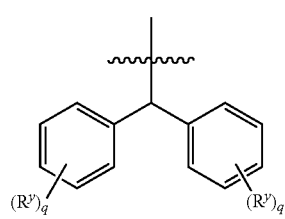

or

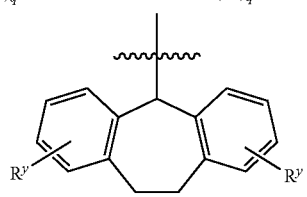

wherein each R$^y$ is independently selected from F, Cl, Me, OMe, CF$_3$, OCF$_3$, and CN; and each q is independently 0, 1, or 2.

In some embodiments, the compound of Formula (I) is a compound of one of the following formulas:

wherein n is 0, 1 or 2;

each R$^3$ represents Me, OH, OMe, or halo; and Y represents

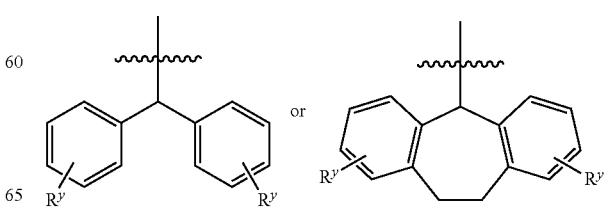

wherein each $R^y$ is independently selected from H, F, Cl, Me, OMe, $CF_3$, $OCF_3$, and CN.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R—S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)—.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a di-substituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as 2H, 3H, 11C, $^{13}O$, $^{14}O$, $^{15}N$, $^{18}F$, $^{31}F$, $^{32}F$, $^{35}S$, $^{36}Cl$, and $^{125}I$. The invention includes various isotopically labeled compounds as defined herein, for example those in which radioactive isotopes, such as $^3H$ and $^{14}C$, or those in which non-radioactive isotopes, such as $^2H$ and $^{13}C$, are present at levels significantly above the natural abundance for these isotopes. These isotopically labeled compounds are useful in metabolic studies (e.g., with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagent in place of the non-labeled reagent otherwise employed.

Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. D2O, d6-acetone, d6-DMSO, as well as solvates with non-enriched solvents.

Compounds of the invention, i.e., compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art for use in a pharmaceutical composition for administration to a human subject (see, for example, Remington: The Science and Practice of Pharmacy, 22nd ed.). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response in a subject, for example, an amount sufficient to reduce of one or more symptoms, alleviate conditions, slow or delay disease progression, or prevent a disease, etc. In one non-limiting embodiment, the term "a therapeutically effective amount" refers to the amount of a compound of the present invention that, when administered to a subject, is effective to reduce one or more symptoms associated with an influenza virus infection, or to shorten the duration of the symptomatic stage of an influenza virus infection, or to slow the progression of an influenza virus infection, or to reduce or stop the exacerbation of an underlying condition by an influenza virus infection.

In another non-limiting embodiment, the term "a therapeutically effective amount" refers to the amount of the compound of the present invention that, when administered to a cell, or a tissue, or a non-cellular biological material, or a medium, is effective to cause a statistically significant reduction in rate of replication or proliferation of a strain of orthomyxovirus.

As used herein, the term "subject" refers to an animal. Typically, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer, so typically an enantiomeric purity of at least 95% is preferred. Substituents at atoms with unsaturated double bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Resulting mixtures of isomers can typically be separated on the basis of the physicochemical differences of the constituents, into the pure or substantially pure geometric or optical isomers, diastereomers, racemates, for example, by chromatography and/or fractional crystallization.

Racemates of final products or intermediates can typically be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral stationary phase.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

In another aspect, the present invention provides a pharmaceutical composition comprising a compound of the present invention, or a pharmaceutically acceptable salt thereof, and at least one pharmaceutically acceptable carrier. In some embodiments, the pharmaceutical composition comprises at least two pharmaceutically acceptable excipients or carriers. Pharmaceutically acceptable carriers and other excipients are known to those of skill in the art, and may be selected, for example, from carriers and excipients used in approved (registered) formulated therapeutic agents that are administered via similar routes of administration. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

In one embodiment, the compounds of the invention are formulated for oral delivery. Typically, these pharmaceutical compositions are tablets or gelatin capsules comprising the active ingredient (at least one compound of Formula (I)) together with one or more excipients selected from:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems may pertain to an inhalation or to an intranasal application that may be suitable for use to treat influenza, for example, and may contain solubilizers, stabilizers, tonicity enhancing agents, buffers and preservatives. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula (I), in free form or in salt form, exhibit valuable pharmacological properties, e.g. they inhibit or prevent replication of orthomyxovirus, as indicated by test data provided in the next sections, and are therefore indicated for therapy or for use as research chemicals, e.g. as tool compounds such as for the study of replication of an orthomyxovirus, particularly Influenza A, Influenza B or Influenza C. Accordingly, compounds of the invention are useful in the treatment of an infection caused by an orthymyxovirus, particularly Influenza A, Influenza B or Influenza C, especially in human subjects. In some embodiments, the subject to be treated is a human having or at risk of contracting an influenza viral infection. For example, subjects having pre-existing conditions such as asthma or COPD that can be greatly exacerbated by an influenza infection may be treated with the methods or compounds of the invention before exhibiting symptoms of an influenza infection, especially if they are at risk of contracting influenza due to close proximity to persons such as family members who have or appear to have influenza. In other embodiments, the subject for treatment by the methods and compositions of the invention is one diagnosed as having symptoms consistent with an influenza infection. In other embodiments, the subject may be a human who has been tested with known diagnostic methods such as a Rapid Influenza Diagnostic Test (RIDT) or Reverse Transcriptase PCT (RT-PCR) methods to detect the presence of influenza virus, and found to be infected with influenza, regardless of the presence of typical influenza symptoms.

As a further embodiment, the present invention provides the use of a compound of formula (I) or any of the embodiments within the scope of Formula (I) as described herein, in therapy. In particular, the compounds are suitable for use to treat a subject having or at particularly high risk for an orthomyxovirus viral infection, especially Influenza A, Influenza B, or Influenza C.

In another embodiment, the invention provides a method of treating a disease which is caused by an orthomyxovirus, comprising administration of a therapeutically effective amount of a compound of formula (I) or any of the embodiments within the scope of Formula (I) as described herein to a subject in need of such treatment. In some embodiments, the compound of formula (I) is administered orally. In a further embodiment, the disease is selected from Influenza A, Influenza B, and Influenza C. The method typically comprises administering an effective amount of a compound as described herein, or a pharmaceutical composition comprising an effective amount of such compound, to a subject in need of such treatment. The compound may be administered by any suitable method such as those described herein, and the administration may be repeated at intervals which may be selected by a treating physician. In some embodiments, the compound or pharmaceutical composition is administered orally.

Thus, as a further embodiment, the present invention provides the use of a compound of formula (I) or any of the embodiments of such compounds described herein for the manufacture of a medicament. In a particular embodiment, the medicament is for treatment of an orthomyxovirus infection, especially Influenza A, Influenza B, or Influenza C.

The compound of the present invention may be administered either simultaneously with, or before or after, one or more therapeutic co-agent(s). The compound of the present invention may be administered separately, by the same or different route of administration, or together in the same pharmaceutical composition as the co-agent(s). Suitable co-agents for use with the compounds of the invention include antivirals active on influenza viruses, such as neuraminidase inhibitors including oseltamivir, peramivir, zanamivir and laninamivir, laninamivir octanoate, and adamantanes such as amantadine and rimantadine. Additional co-agents for use in these methods include an M2 protein inhibitor, a polymerase inhibitor, a PB2 inhibitor, favipiravir, fludase, ADS-8902, beraprost, Neugene®, ribavirin, CAS Reg. No. 1422050-75-6, VX-787, Flu Mist Quadrivalent®, Fluarix® Quadrivalent, Fluzone® Quadrivalent, Flucelvax® and FluBlok®.

In one embodiment, the invention provides a product comprising a compound of formula (I) and at least one other therapeutic co-agent as a combined preparation for simultaneous, separate or sequential use in therapy. In one embodiment, the therapy is the treatment of a viral infection caused by an orthomyxovirus, particularly Influenza A, Influenza B or Influenza C. Products provided as a combined preparation include a composition comprising a compound of formula (I) and at least one of the other therapeutic co-agent(s) together in the same pharmaceutical composition, or the compound of formula (I) and at least one other therapeutic co-agent(s) in separate form, e.g. in the form of a kit for use to treat a subject by the methods described herein.

In one embodiment, the invention provides a pharmaceutical composition comprising a compound of formula (I) and another therapeutic co-agent(s). Suitable co-agents include antivirals active on influenza viruses, such as neuraminidase inhibitors including oseltamivir, peramivir, zanamivir and laninamivir, and adamantanes such as amantadine and rimantadine. Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). The other pharmaceutical composition may contain one of the suitable co-agents. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the therapeutic co-agent may be manufactured and/or formulated by the same or different manufacturers. Moreover, the compound of the invention and the therapeutic co-agent may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the therapeutic co-agent.

Accordingly, the invention provides the use of a compound of formula (I) for treating a viral infection caused by an orthomyxovirus, particularly influenza, which may be Influenza A, Influenza B or Influenza C, wherein the medicament is prepared for administration with a therapeutic co-agent. Typically in the methods of using the compounds of the invention, the serotype of influenza is not identified before treatment. The invention also provides the use of therapeutic co-agent for treating a disease or condition, wherein the medicament is administered with a compound of formula (I).

The invention also provides a compound of formula (I) for use in a method of treating a viral infection caused by an orthomyxovirus, particularly Influenza A, Influenza B or Influenza C, wherein the compound of formula (I) is prepared for administration with a therapeutic co-agent. The invention also provides another therapeutic co-agent for use in a method of treating a viral infection caused by an orthomyxovirus, particularly influenza, e.g., Influenza A, Influenza B or Influenza C, wherein the therapeutic co-agent is prepared for administration with a compound of formula (I). The invention also provides a compound of formula (I) for use in a method of treating a viral infection caused by an orthomyxovirus, particularly Influenza A, Influenza B or Influenza C, wherein the compound of formula (I) is administered with a therapeutic co-agent. The invention also provides a therapeutic co-agent for use in a method of treating a viral infection caused by an orthomyxovirus, particularly Influenza A, Influenza B or Influenza C, wherein the a therapeutic co-agent is administered with a compound of formula (I).

The invention also provides the use of a compound of formula (I) for treating a viral infection caused by an orthomyxovirus, particularly influenza, e.g., Influenza A, Influenza B or Influenza C, wherein the patient has previously (e.g. within 24 hours) been treated with another therapeutic agent. The invention also provides the use of another therapeutic agent for treating a viral infection caused by an orthomyxovirus, particularly Influenza A, Influenza B or Influenza C, wherein the patient has previously (e.g. within 24 hours) been treated with a compound of formula (I).

In one embodiment, the therapeutic co-agent is selected from antivirals purported to be useful for treating infections caused by influenza viruses, such as neuraminidase inhibitors including oseltamivir, peramivir, zanamivir and laninamivir, and adamantanes such as amantadine and rimantadine.

The pharmaceutical composition or combination of the present invention can be in unit dosage containing about 1-1000 mg of active ingredient(s) for a human subject of about 50-70 kg, or about 1-500 mg, or about 1-250 mg, or about 1-150 mg, or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 0.1-50 mg/kg.

The invention further includes processes to make the compounds of Formula (I) as disclosed herein, and any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

Methods to synthesize compounds of Formula (I) are depicted in Schemes A-C and are illustrated by the Examples herein. Scheme A depicts a way to prepare compounds wherein $Z^1$ is N, $Z^2$ is C(R)2, and $Z^3$ is —CR2-CR2-, and should also enable synthesis of compounds with other $Z^3$ linkages. It begins with a 5-hydroxypyridazine-4-one-3-carboxylic acid compound, where both the 5-hydroxy and the ring NH are protected with a suitable protecting group that can readily be removed. The carboxylic acid is condensed with a cyclic hydrazine linkage to provide the two outer rings. After deprotection of the ring nitrogen, the center ring is formed by condensation with an aldehyde.

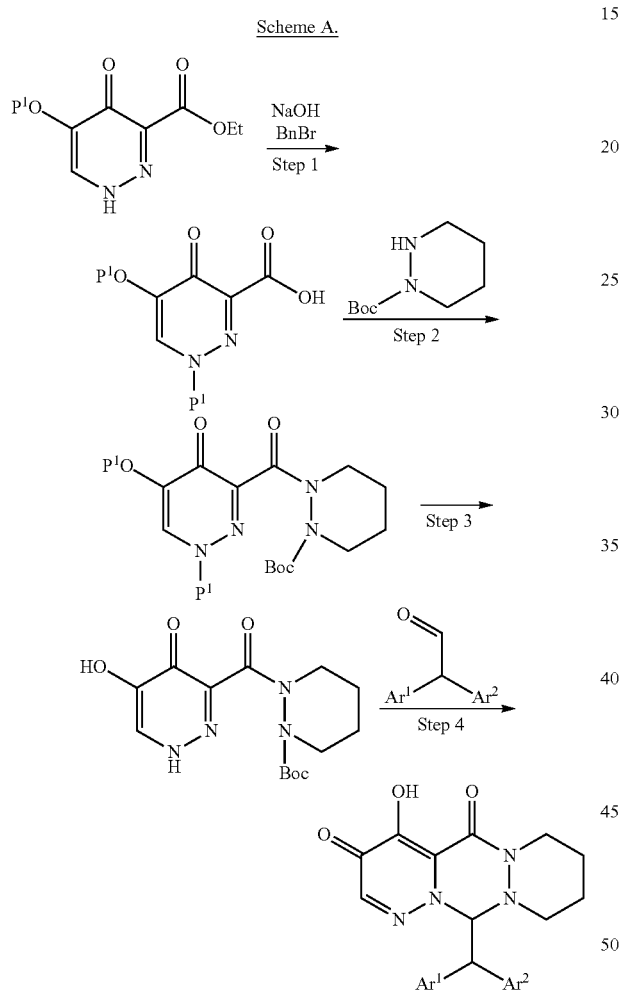

Schemes B and C depict methods to make compounds of Formula (I) wherein $Z^1$ is CR, $Z^2$ is $CR_2$, and $Z^3$ is $CR_2$.

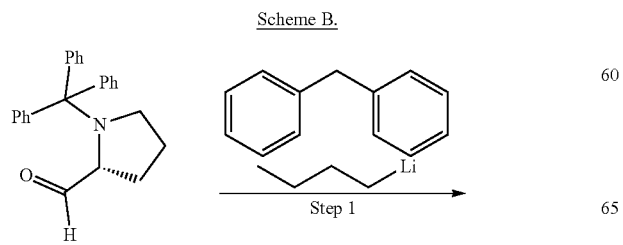

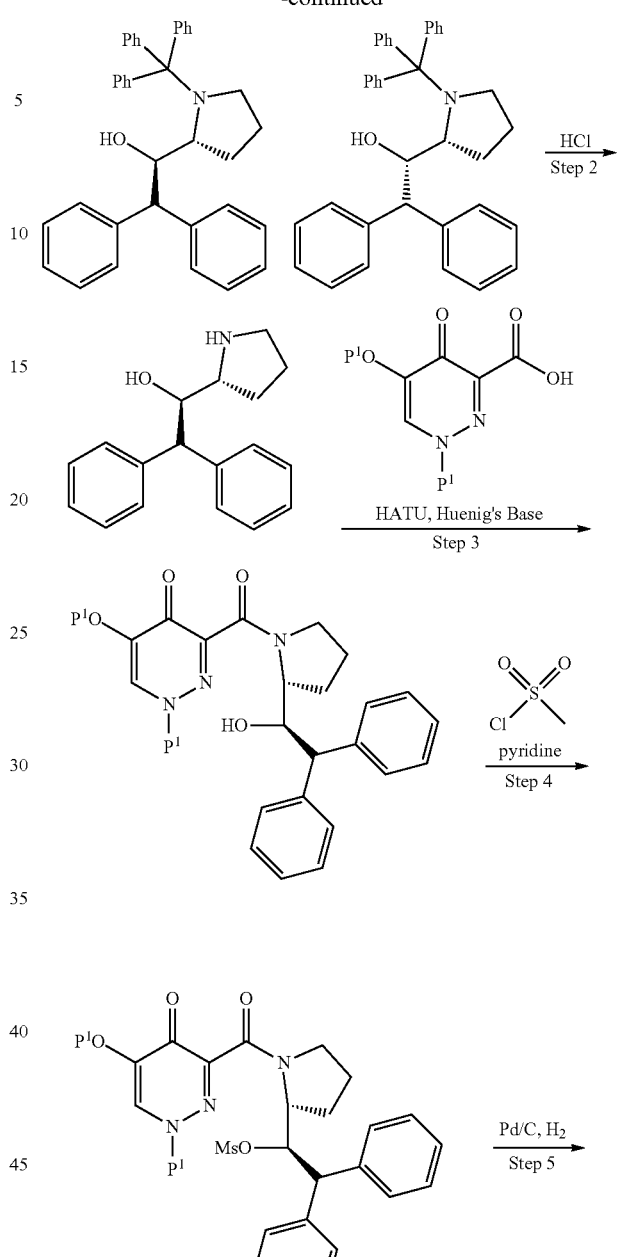

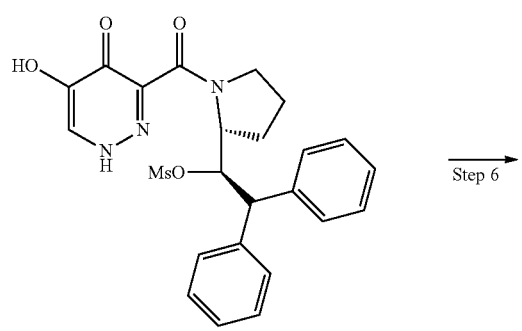

-continued
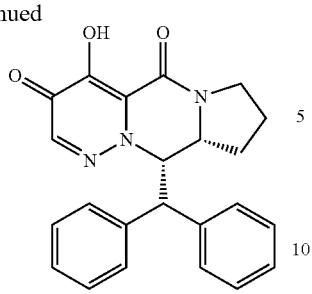
Scheme C.
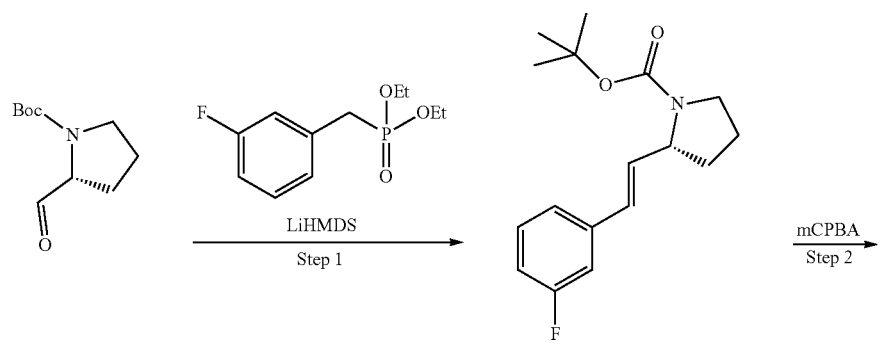
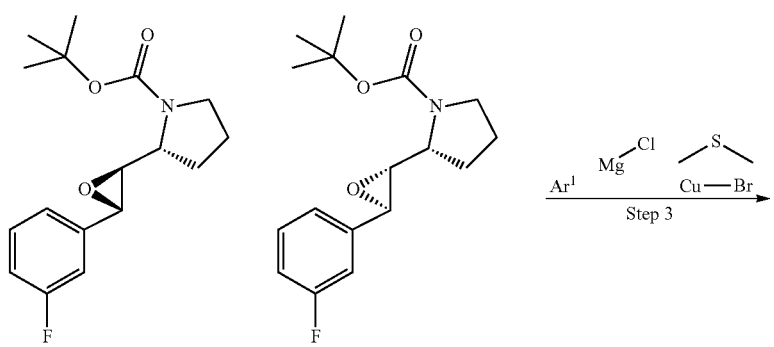
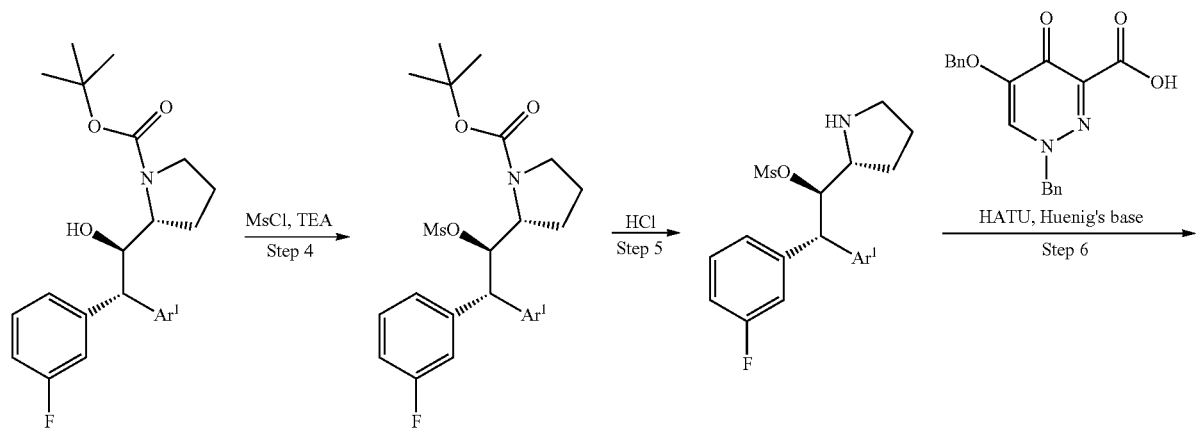

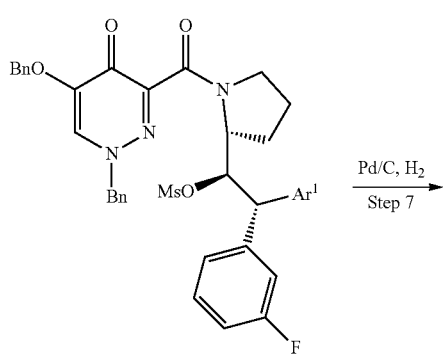
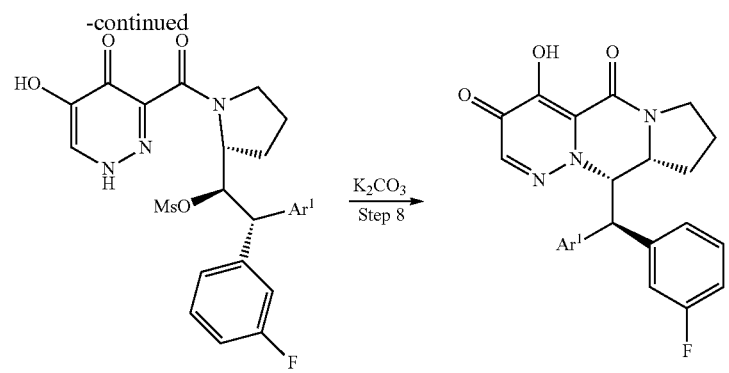

Using these synthesis schemes and the examples provided, the skilled person can prepare the compounds of Formula (I).

EXAMPLES

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (about 20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

ABBREVIATIONS

ATP adenosine 5'-triphosphate
Bn benzyl
BOC tertiary butyl carboxy
br broad
BSA bovine serum albumin
d doublet
dd doublet of doublets
DCM dichloromethane
DEAD diethyl azodicarboxylate
DBAD di-tert-butyl azodicarboxylate
DIBAL-H diisobutylaluminum hydride
DIEA diethylisopropylamine
DME 1,4-dimethoxyethane
DMF N,N-dimethylformamide
DMSO dimethylsulfoxide
DTT dithiothreitol
EDTA ethylenediamine tetraacetic acid
ESI electrospray ionization
EtOAc ethyl acetate
FCC flash column chromatography
h hour(s)
HBTU 1-[bis(dimethylamino)methylene]-1H-benzotriazolium hexafluorophosphate(1-) 3-oxide
HOBt 1-hydroxy-7-azabenzotriazole
HPLC high pressure liquid chromatography
IR infrared spectroscopy
LCMS liquid chromatography and mass spectrometry
MeOH methanol
MS mass spectrometry
MW microwave
m multiplet
min minutes
mL milliliter(s)
m/z mass to charge ratio
NBS N-bromosuccinimide
NCS N-chlorosuccinimide
NMP N-methyl pyrrolidinone
NMR nuclear magnetic resonance
ppm parts per million
PyBOP benzotriazol-1-yloxytripyrrolidinophosphonium hexafluorophosphate
rac racemic
rt room temperature
s singlet
SEM (2-(trimethylsilyl)ethoxy)methyl
t triplet
TBDMS t-butyldimethylsilyl
TBDPS t-butyldiphenylsilyl
TFA trifluoroacetic acid
THF tetrahydrofuran
Tris.HCl aminotris(hydroxymethyl)methane hydrochloride Example 1: 12-benzhydryl-4-hydroxy-7,8,9,10-tetrahydro-3H-dipyridazino[1,2-a:1',6'-d][1,2,4]triazine-3,5(12H)-dione Intermediate 1.1: 1-benzyl-5-(benzyloxy)-4-oxo-1,4-dihydropyridazine-3-carboxylic acid To a suspension of ethyl 5-(benzyloxy)-4-oxo-1,4-dihydropyridazine-3-carboxylate hydrochloride (1.5 g, 4.83 mmol) in MeOH at RT was added NaOH (0.792 g, 19.79 mmol). Stirred at rt for 2 h. Benzyl bromide (2.067 ml, 17.38 mmol) was added and the mixture stirred for 2 hours. The reaction was concentrated on the rotovap, then added EtOAc and water. The mixture was then acidified with 1 M HCl to pH 3. solid crashed out while adding HCl. filtered. The white solid was washed with a small amount of EtOAc and water. The white solid collected on the filter was dried in vacuo to give 1-benzyl-5-(benzyloxy)-4-oxo-1,4-dihydropyridazine-3-carboxylic acid (1.1 g, 3.27 mmol, 67.7% yield), which was used without further purification. MS m/z 337.3 (M+1).

Intermediate 1.2: tert-butyl 2-(1-benzyl-5-(benzyloxy)-4-oxo-1,4-dihydropyridazine-3-carbonyl)tetrahydropyridazine-1(2H)-carboxylate

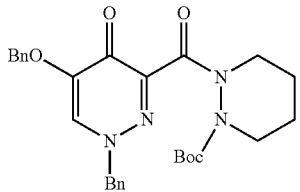 [SMILES: CC(C)(C)OC(=O)N1CCCCN1C(=O)c1nn(Cc2ccccc2)cc(OCc2ccccc2)c1=O]

To a solution of 1-benzyl-5-(benzyloxy)-4-oxo-1,4-dihydropyridazine-3-carboxylic acid (850 mg, 2.53 mmol) in DCM (Volume: 12.600 mL) at RT was added Huenig's Base (1.170 mL, 6.70 mmol) and HATU (1249 mg, 3.29 mmol). The mixture was stirred at RT for 30 min, then added tert-butyl tetrahydropyridazine-1(2H)-carboxylate (518 mg, 2.78 mmol). The mixture was stirred at RT for 16 h, diluted with DCM (10 mL) and washed with water (10 mL), then brine (10 mL). The organic layer was dried over Na$_2$SO$_4$, filtered and concentrated on the rotovap. The residue was purified by ISCO (40 g silica gel column, 40-100% EtOAc in heptane) to give tert-butyl 2-(1-benzyl-5-(benzyloxy)-4-oxo-1,4-dihydropyridazine-3-carbonyl)tetrahydropyridazine-1(2H)-carboxylate (1.22 g, 2.418 mmol, 96% yield) as a white foam. MS m/z 505.4 (M+1).

Intermediate 1.3: tert-butyl 2-(5-hydroxy-4-oxo-1,4-dihydropyridazine-3-carbonyl)tetrahydropyridazine-1(2H)-carboxylate

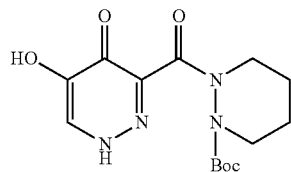 [SMILES: CC(C)(C)OC(=O)N1CCCCN1C(=O)c1n[nH]cc(O)c1=O]

A solution of tert-butyl 2-(1-benzyl-5-(benzyloxy)-4-oxo-1,4-dihydropyridazine-3-carbonyl)tetrahydropyridazine-1 (2H)-carboxylate (220 mg, 0.436 mmol) in MeOH (Volume: 21.800 mL) was purged with nitrogen. Added a spatula tip of Pd—C (10%) (46.4 mg, 0.044 mmol) and attached a hydrogen balloon. The flask was evacuated and refilled with hydrogen (3 times) and then stirred vigorously at RT under a balloon of hydrogen. After 30 min, the reaction was purged with nitrogen and then filtered through a plug of celite, using MeOH to wash through. The filtrate was concentrated in vacuo and used without further purification. MS m/z 325.3 (M+1).

Example 1: 12-benzhydryl-4-hydroxy-7,8,9,10-tetrahydro-3H-dipyridazino[1,2-a:1',6'-d][1,2,4]triazine-3,5(12H)-dione

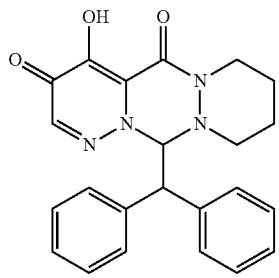 [SMILES: O=C1c2c(O)c(=O)cnn2C(C(c2ccccc2)c2ccccc2)N2CCCCN12]

Added 2,2-diphenylacetaldehyde (77 mg, 0.392 mmol) to a vial containing crude tert-butyl 2-(5-hydroxy-4-oxo-1,4-dihydropyridazine-3-carbonyl)tetrahydropyridazine-1(2H)-carboxylate (141 mg, 0.436 mmol) and a stir bar. TFA (Volume: 2 mL) was added and the mixture was stirred at RT for 30 min. The reaction was concentrated in vacuo. The residue was purified by reverse-phase HPLC (MeCN/water with 0.1% TFA). The fractions containing product were combined, frozen and lyophilized to give 12-benzhydryl-4-hydroxy-7,8,9,10-tetrahydro-3H-dipyridazino[1,2-a:1',6'-d][1,2,4]triazine-3,5(12H)-dione (19 mg, 0.036 mmol, 8.27% yield) as a yellow solid. $^1$H NMR (400 MHz, DMSO-d6) δ 7.55-7.46 (m, 2H), 7.34 (s, 1H), 7.30 (dd, J=8.1, 1.6 Hz, 4H), 7.25-7.10 (m, 4H), 6.33 (d, J=10.5 Hz, 1H), 4.62 (d, J=10.5 Hz, 1H), 4.36-4.25 (m, 1H), 3.29-3.21 (m, 1H), 2.86 (td, J=11.1, 2.6 Hz, 1H), 2.46-2.38 (m, 1H), 1.70-1.39 (m, 4H). MS m/z 403.4 (M+1).

Example 2. 12-(bis(3-fluorophenyl)methyl)-4-hydroxy-7,8,9,10-tetrahydro-3H-dipyridazino[1,2-a:1',6'-d][1,2,4]triazine-3,5(12H)-dione

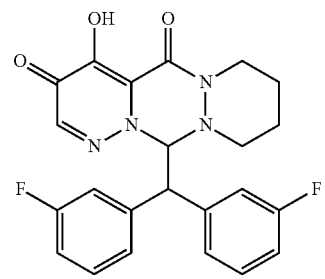 [SMILES: O=C1c2c(O)c(=O)cnn2C(C(c2cccc(F)c2)c2cccc(F)c2)N2CCCCN12]

This compound was made by the same process used to make Example 1. 1H NMR (400 MHz, DMSO-d6) δ 7.50-7.45 (m, 1H), 7.39 (s, 1H), 7.39-7.33 (m, 2H), 7.32-7.13 (m, 3H), 7.12-6.94 (m, 2H), 6.41 (d, J=10.8 Hz, 1H), 4.82 (d, J=10.7 Hz, 1H), 4.36-4.26 (m, 1H), 3.28-3.18 (m, 1H), 2.88 (td, J=11.0, 2.5 Hz, 1H), 2.39 (td, J=12.5, 3.1 Hz, 1H), 1.73-1.64 (m, 1H), 1.51 (dddd, J=30.2, 15.0, 6.1, 3.3 Hz, 3H). MS m/z 439.3 (M+1).

Example 3. 12-(bis(4-chlorophenyl)methyl)-4-hydroxy-7,8,9,10-tetrahydro-3H-dipyridazino[1,2-a:1',6'-d][1,2,4]triazine-3,5(12H)-dione

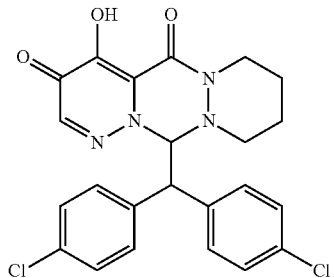 [SMILES: O=C1c2c(O)c(=O)cnn2C(C(c2ccc(Cl)cc2)c2ccc(Cl)cc2)N2CCCCN12]

This compound was made by the same process used to make Example 1. 1H NMR (400 MHz, DMSO-d6) δ 7.54 (d, J=8.5 Hz, 2H), 7.43-7.31 (m, 5H), 7.30-7.23 (m, 2H), 6.36 (d, J=10.7 Hz, 1H), 4.78 (d, J=10.7 Hz, 1H), 4.36-4.24 (m, 1H), 3.27-3.19 (m, 1H), 2.87 (td, J=11.1, 2.7 Hz, 1H), 2.40 (td, J=12.5, 2.9 Hz, 1H), 1.72-1.62 (m, 1H), 1.62-1.38 (m, 3H). MS m/z 471.2 (M+1).

Example 4. 12-(bis(3-chlorophenyl)methyl)-4-hydroxy-7,8,9,10-tetrahydro-3H-dipyridazino[1,2-a:1',6'-d][1,2,4]triazine-3,5(12H)-dione

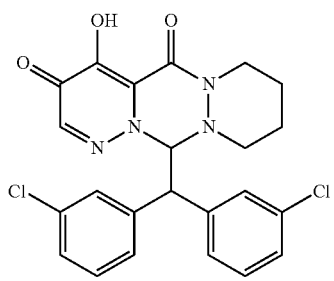 [SMILES: O=C1c2c(O)c(=O)cnn2C(C(c2cccc(Cl)c2)c2cccc(Cl)c2)N2CCCCN12]

This compound was made by the same process used to make Example 1. 1H NMR (400 MHz, DMSO-d6) δ 7.64 (t, J=1.8 Hz, 1H), 7.52 (dt, J=7.8, 1.3 Hz, 1H), 7.47 (q, J=1.4 Hz, 1H), 7.40 (d, J=3.1 Hz, 1H), 7.37 (m, 5H), 6.44 (d, J=10.7 Hz, 1H), 4.83 (d, J=10.7 Hz, 1H), 4.37-4.25 (m, 1H), 3.29-3.16 (m, 1H), 2.88 (td, J=11.2, 2.6 Hz, 1H), 2.44-2.29 (m, 1H), 1.73-1.62 (m, 1H), 1.61-1.37 (m, 3H). MS m/z 471.2 (M+1).

Example 5. 12-(bis(4-fluorophenyl)methyl)-4-hydroxy-7,8,9,10-tetrahydro-3H-dipyridazino[1,2-a:1',6'-d][1,2,4]triazine-3,5(12H)-dione

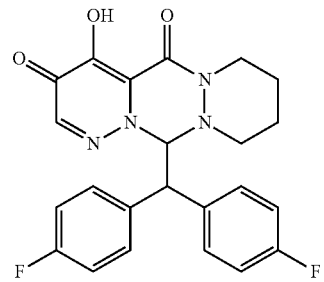 [SMILES: O=C1c2c(O)c(=O)cnn2C(C(c2ccc(F)cc2)c2ccc(F)cc2)N2CCCCN12]

This compound was made by the same process used to make Example 1. 1H NMR (400 MHz, Solvent) δ ppm 7.52 (s, 1H) 7.43-7.49 (m, 2H) 7.21-7.28 (m, 2H) 7.04-7.13 (m, 2H) 6.88-6.95 (m, 2H) 6.12 (d, J=10.32 Hz, 1H) 4.65 (d, J=10.37 Hz, 1H) 4.38-4.52 (m, 1H) 3.23 (dt, J=10.99, 3.26 Hz, 1H) 2.88-2.99 (m, 1H) 2.68 (td, J=12.18, 4.16 Hz, 1H) 1.72-1.83 (m, 2H) 1.56-1.70 (m, 2H). MS m/z 439.3 (M+1).

Example 6. 13-benzhydryl-4-hydroxy-8,9,10,11-tetrahydropyridazino[1',6':4,5][1,2,4]triazino[1,2-a][1,2]diazepine-3,5(7H,13H)-dione

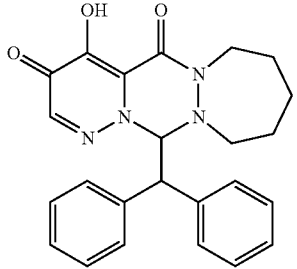

This compound was made by the same process used to make Example 1. 1H NMR (400 MHz, DMSO-d6) δ 7.62-7.54 (m, 2H), 7.37 (s, 1H), 7.33 (dd, J=8.3, 7.0 Hz, 2H), 7.30-7.09 (m, 6H), 6.39 (d, J=10.8 Hz, 1H), 4.44 (d, J=10.8 Hz, 1H), 4.00 (ddd, J=13.4, 8.8, 4.9 Hz, 1H), 3.31 (dt, J=10.9, 5.0 Hz, 1H), 2.70 (dq, J=12.6, 3.7 Hz, 2H), 1.63-1.41 (m, 4H), 1.32-1.18 (m, 1H), 1.14-1.00 (m, 1H). MS m/z 417.4 (M+1).

Example 7. 13-(bis(3-fluorophenyl)methyl)-4-hydroxy-8,9,10,11-tetrahydropyridazino[1',6':4,5][1,2,4]triazino[1,2-a][1,2]diazepine-3,5(7H,13H)-dione

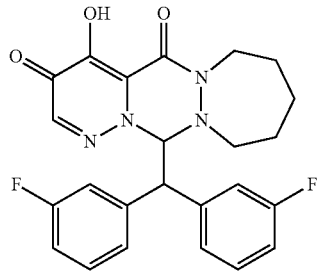

This compound was made by the same process used to make Example 1. 1H NMR (400 MHz, DMSO-d6) δ 7.63-7.54 (m, 1H), 7.46-7.33 (m, 3H), 7.29-7.20 (m, 2H), 7.15 (dt, J=7.8, 1.2 Hz, 1H), 7.11-7.03 (m, 1H), 7.03-6.94 (m, 1H), 6.46 (d, J=10.9 Hz, 1H), 4.67 (d, J=10.9 Hz, 1H), 4.02 (ddd, J=13.3, 8.8, 4.8 Hz, 1H), 3.29 (dt, J=10.9, 5.0 Hz, 1H), 2.71 (dddd, J=18.7, 10.9, 7.1, 2.9 Hz, 2H), 1.66-1.41 (m, 4H), 1.26 (q, J=9.4, 8.9 Hz, 1H), 1.15-1.00 (m, 1H). MS m/z 453.3 (M+1).

Example 8. (R)-12-(bis(3-fluorophenyl)methyl)-4-hydroxy-7,8,9,10-tetrahydro-3H-dipyridazino[1,2-a:1',6'-d][1,2,4]triazine-3,5(12H)-dione

Intermediate 8.1. (R)-12-(bis(3-fluorophenyl)methyl)-3,5-dioxo-3,5,7,8,9,10-hexahydro-12H-dipyridazino[1,2-a:1',6'-d][1,2,4]triazin-4-yl (S)-3,3,3-trifluoro-2-methoxy-2-phenylpropanoate and (S)-12-(bis(3-fluorophenyl)methyl)-3,5-dioxo-3,5,7,8,9,10-hexahydro-12H-dipyridazino[1,2-a:1',6'-d][1,2,4]triazin-4-yl (S)-3,3,3-trifluoro-2-methoxy-2-phenylpropanoate

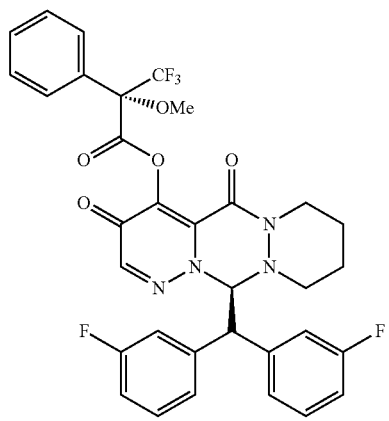

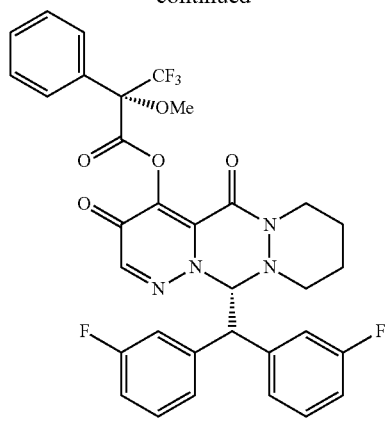

12-(bis(3-fluorophenyl)methyl)-4-hydroxy-7,8,9,10-tetrahydro-3H-dipyridazino[1,2-a:1',6'-d][1,2,4]triazine-3,5(12H)-dione (127 mg, 0.290 mmol) was dissolved with stirring under N2 in dry THF (Volume: 4 mL) before the addition of TEA (0.081 mL, 0.579 mmol). (R)-3,3,3-trifluoro-2-methoxy-2-phenylpropanoyl chloride (73.2 mg, 0.290 mmol) was added dropwise. The reaction was stirred at room temperature for 90 minutes before being partitioned between EtOAc (10 mL) and water (10 mL). The phases were separated and the organic layer was washed with brine, dried over Na₂SO₄ and concentrated. The residue was purified by ISCO (24 g silica gel column, 0-100% EtOAc in heptane). The diastereomers were then separated via chiral HPLC (IC column, heptanes/EtOH=80/20) to yield:

(R)-12-(bis(3-fluorophenyl)methyl)-3,5-dioxo-3,5,7,8,9,10-hexahydro-12H-dipyridazino[1,2-a:1',6'-d][1,2,4]triazin-4-yl (S)-3,3,3-trifluoro-2-methoxy-2-phenylpropanoate (63 mg, 0.096 mmol, 33% yield, 99% ee). ¹H NMR (400 MHz, Chloroform-d) δ 7.90 (d, J=7.5 Hz, 2H), 7.62 (s, 1H), 7.54-7.29 (m, 4H), 7.19 (q, J=7.8 Hz, 1H), 7.07-6.81 (m, 6H), 5.57 (d, J=10.2 Hz, 1H), 4.68-4.43 (m, 2H), 3.83 (s, 3H), 3.08 (d, J=10.5 Hz, 1H), 3.03-2.87 (m, 1H), 2.66 (t, J=11.5 Hz, 1H), 1.93-1.46 (m, 4H). MS m/z 655.3 (M+1).

(S)-12-(bis(3-fluorophenyl)methyl)-3,5-dioxo-3,5,7,8,9,10-hexahydro-12H-dipyridazino[1,2-a:1',6'-d][1,2,4]triazin-4-yl (S)-3,3,3-trifluoro-2-methoxy-2-phenylpropanoate (57 mg, 0.087 mmol, 30% yield, 99% ee). 1H NMR (400 MHz, Chloroform-d) δ 7.94 (s, 2H), 7.64 (s, 1H), 7.50-7.41 (m, 3H), 7.35 (q, J=7.5 Hz, 1H), 7.19 (q, J=7.6 Hz, 1H), 7.02 (dd, J=14.8, 8.4 Hz, 3H), 6.96-6.88 (m, 2H), 6.85 (d, J=7.6 Hz, 1H), 5.57 (d, J=9.9 Hz, 1H), 4.62 (s, 1H), 4.49 (s, 1H), 3.84 (s, 3H), 3.09 (d, J=10.8 Hz, 1H), 2.93 (s, 1H), 2.66 (td, J=12.5, 3.3 Hz, 1H), 1.82 (s, 2H), 1.58 (s, 1H), 1.27 (s, 1H). MS m/z 655.3 (M+1).

Example 8. (R)-12-(bis(3-fluorophenyl)methyl)-4-hydroxy-7,8,9,10-tetrahydro-3H-dipyridazino[1,2-a:1',6'-d][1,2,4]triazine-3,5(12H)-dione

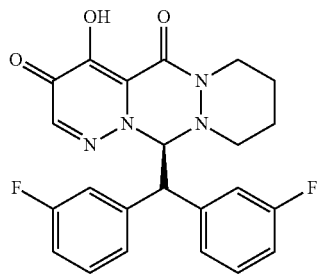 [SMILES: O=C1c2c(O)c(=O)cnn2[C@H](C(c2cccc(F)c2)c2cccc(F)c2)N2CCCCN12]

To a solution of (R)-12-(bis(3-fluorophenyl)methyl)-3,5-dioxo-3,5,7,8,9,10-hexahydro-12H-dipyridazino[1,2-a:1',6'-d][1,2,4]triazin-4-yl (S)-3,3,3-trifluoro-2-methoxy-2-phenylpropanoate (50 mg, 0.076 mmol) dissolved in MeOH (Volume: 382 µl, Ratio: 1.000) and H$_2$O (Volume: 382 µl, Ratio: 1.000) was added LiOH.H$_2$O (32.1 mg, 0.764 mmol. The mixture was stirred at rt for 1 h, then diluted with EtOAc, washed with 1N HCl, brine and dried over Na$_2$SO$_4$ filtered and concentrated. The crude was purification by reverse-phase HPLC (MeCN/water with 0.1% TFA). The fractions containing product were combined, frozen and lyophilized to give (R)-12-(bis(3-fluorophenyl)methyl)-4-hydroxy-7,8,9,10-tetrahydro-3H-dipyridazino[1,2-a:1',6'-d][1,2,4]triazine-3,5(12H)-dione (3.7 mg, 0.006 mmol, 8.33% yield). 1H NMR (400 MHz, DMSO-d6) δ 7.45 (d, J=10.1 Hz, 1H), 7.39-7.30 (m, 3H), 7.20 (ddd, J=24.4, 19.0, 9.8 Hz, 3H), 7.09-6.92 (m, 2H), 6.39 (d, J=10.8 Hz, 1H), 4.80 (d, J=10.7 Hz, 1H), 4.29 (d, J=11.9 Hz, 1H), 3.20 (d, J=9.7 Hz, 1H), 2.86 (t, J=11.1 Hz, 1H), 2.43-2.27 (m, 1H), 1.72-1.33 (m, 4H). MS m/z 439.1 (M+1).

Example 9. (S)-12-(bis(3-fluorophenyl)methyl)-4-hydroxy-7,8,9,10-tetrahydro-12H-dipyridazino[1,2-a:1',6'-d][1,2,4]triazine-3,5-dione

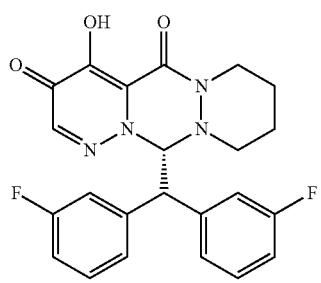 [SMILES: O=C1c2c(O)c(=O)cnn2[C@@H](C(c2cccc(F)c2)c2cccc(F)c2)N2CCCCN12]

This compound was made by the same process used to make Example 8. 1H NMR (400 MHz, DMSO-d6) δ 7.45 (d, J=11.7 Hz, 1H), 7.39-7.29 (m, 3H), 7.29-7.11 (m, 3H), 7.08-6.92 (m, 2H), 6.39 (d, J=10.7 Hz, 1H), 4.80 (d, J=10.8 Hz, 1H), 4.29 (d, J=11.2 Hz, 1H), 3.20 (d, J=10.1 Hz, 1H), 2.86 (t, J=11.1 Hz, 1H), 2.42-2.28 (m, 1H), 1.70-1.35 (m, 4H). MS m/z 439.1 (M+1).

Example 10. (9aR,10S)-10-benzhydryl-4-hydroxy-8,9,9a,10-tetrahydro-3H-pyrrolo[1',2':4,5]pyrazino[1,2-b]pyridazine-3,5(7H)-dione Intermediate 10.1. (R)-2,2-diphenyl-1-((R)-1-tritylpyrrolidin-2-yl)ethan-1-ol and (S)-2,2-diphenyl-1-((R)-1-tritylpyrrolidin-2-yl)ethan-1-ol

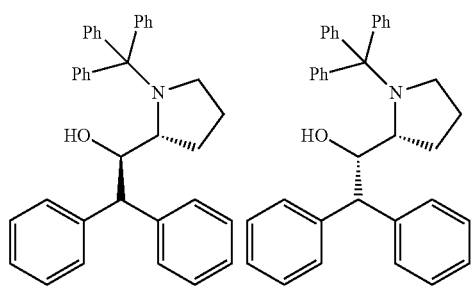

To a solution of diphenylmethane (2.155 ml, 12.89 mmol) in THF (Volume: 58.6 ml) at RT was added a solution of n-butyllithium (2.5 M in hexane) (4.69 ml, 11.71 mmol). After 10 minutes, the mixture was added a solution of (R)-1-tritylpyrrolidine-2-carbaldehyde (2 g, 5.86 mmol: see J. Am. Chem. Soc., 2008, 130, 7562-7563) in THF (6 mL). After 15 minutes, the reaction mixture was quenched with saturated aqueous NH4Cl and extracted with EtOAc (twice). The combined organic extracts were washed with brine, dried over Na$_2$SO$_4$, filtered and concentrated in vacuo. The residue was purified by ISCO (220 g silica gel column, 0-40% EtOAc in heptane) to give (R)-2,2-diphenyl-1-((R)-1-tritylpyrrolidin-2-yl)ethan-1-ol (1.64 g, 3.22 mmol, 54.9% yield) (Peak 1) as a sticky white solid (1H NMR (400 MHz, Chloroform-d) δ 7.50-7.43 (m, 6H), 7.41-7.36 (m, 2H), 7.36-7.09 (m, 17H), 5.90 (s, 1H), 3.96-3.79 (m, 2H), 3.62 (t, J=6.8 Hz, 1H), 3.18 (ddd, J=12.9, 9.3, 6.9 Hz, 1H), 3.04 (ddd, J=13.3, 8.9, 4.9 Hz, 1H), 1.45-1.35 (m, 1H), 0.76 (ddd, J=12.1, 8.9, 2.8 Hz, 1H), 0.65 (ddd, J=13.0, 5.9, 2.6 Hz, 1H), 0.59-0.46 (m, 1H)) and (S)-2,2-diphenyl-1-((R)-1-tritylpyrrolidin-2-yl)ethan-1-ol (0.62 g, 1.216 mmol, 20.77% yield) (Peak 2) as a white solid (1H NMR (400 MHz, Chloroform-d) δ 7.41 (dt, J=6.2, 1.6 Hz, 6H), 7.30-7.01 (m, 17H), 6.67-6.61 (m, 2H), 4.81 (dd, J=10.9, 2.4 Hz, 1H), 3.64 (d, J=10.9 Hz, 1H), 3.32 (ddd, J=8.9, 6.8, 2.4 Hz, 1H), 3.16 (ddd, J=12.1, 10.4, 6.3 Hz, 1H), 2.96 (ddd, J=11.6, 7.8, 2.5 Hz, 1H), 2.65 (s, 1H), 1.82 (dddd, J=12.4, 10.0, 8.0, 6.6 Hz, 1H), 1.23 (ddp, J=14.9, 8.8, 3.2 Hz, 1H), 1.17-1.03 (m, 1H), −0.01--0.15 (m, 1H)).

Intermediate 10.2. (R)-2,2-diphenyl-1-((R)-pyrrolidin-2-yl)ethanol

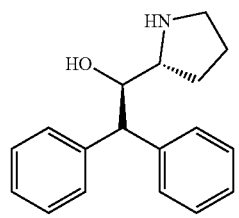 [SMILES: O[C@H](C(c1ccccc1)c1ccccc1)[C@H]1CCCN1]

Added HCl (3.0 M in water) (683 µl, 2.048 mmol) to a suspension of (R)-2,2-diphenyl-1-((R)-1-tritylpyrrolidin-2-yl)ethan-1-ol (348 mg, 0.683 mmol) in MeOH (Volume: 6828 µl) at RT. The white suspension eventually became clear and then later precipitate formed again. After 1 hour, the mixture was then concentrated on the rotovap to give a yellow oil. Toluene was added and the mixture was concentrated again on the rotovap again to an oily white solid. Used without further purification. MS m/z 268.2 (M+1).

Intermediate 10.3. 1-benzyl-5-(benzyloxy)-3-((R)-2-((R)-1-hydroxy-2,2-diphenylethyl)pyrrolidine-1-carbonyl)pyridazin-4(1H)-one

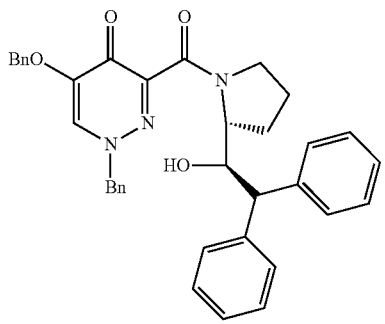

To a solution of 1-benzyl-5-(benzyloxy)-4-oxo-1,4-dihydropyridazine-3-carboxylic acid (253 mg, 0.751 mmol) in DCM (4 ML) at RT was added Huenig's Base (477 µl, 2.73 mmol) and HATU (338 mg, 0.888 mmol). Stirred at RT for 15 min, then added a solution of crude (R)-2,2-diphenyl-1-((R)-pyrrolidin-2-yl)ethanol (208 mg, 0.683 mmol) and Huenig's base (0.4 mL) in DCM (4 mL). The mixture was stirred at RT for 1 h, diluted with DCM and washed with water and brine. The organic layer was dried over Na₂SO₄, filtered and concentrated on the rotovap. The residue was purified by ISCO (40 g silica gel column, 5-100% EtOAc (containing 10% MeOH) in heptane) to give 1-benzyl-5-(benzyloxy)-3-((R)-2-((R)-1-hydroxy-2,2-diphenylethyl)pyrrolidine-1-carbonyl)pyridazin-4(1H)-one (315 mg, 0.538 mmol, 79% yield) as an oil. MS m/z 586.4 (M+1).

Intermediate 10.4. (R)-1-((R)-1-(1-benzyl-5-(benzyloxy)-4-oxo-1,4-dihydropyridazine-3-carbonyl)pyrrolidin-2-yl)-2,2-diphenylethyl methanesulfonate

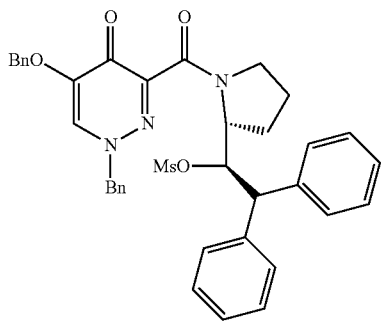 [SMILES: CS(=O)(=O)O[C@H](C(c1ccccc1)c1ccccc1)[C@H]1CCCN1C(=O)c1nn(Cc2ccccc2)cc(OCc2ccccc2)c1=O]

To a solution of 1-benzyl-5-(benzyloxy)-3-((R)-2-((R)-1-hydroxy-2,2-diphenylethyl)pyrrolidine-1-carbonyl)pyridazin-4(1H)-one (315 mg, 0.538 mmol) in pyridine (Volume: 5378 µl) at 0° C. was added MsCl (168 µl, 2.151 mmol). The ice bath was removed and the mixture stirred at RT for 1 hour. Added another 100 uL of mesyl chloride. Stirred 30 minutes longer. The reaction mixture was diluted with DCM and washed with water, then 0.5 N aqueous HCl (2 times), and water again. The organic layer was dried over Na₂SO₄, filtered and concentrated in vacuo. The residue was purified by ISCO (80 g silica gel column, 5-100% EtOAc (containing 10% MeOH) in heptane) to give (R)-1-((R)-1-(1-benzyl-5-(benzyloxy)-4-oxo-1,4-dihydropyridazine-3-carbonyl)pyrrolidin-2-yl)-2,2-diphenylethyl methanesulfonate (120 mg, 0.181 mmol, 33.6% yield) as a yellow solid. MS m/z 664.3 (M+1).

Intermediate 10.5. (R)-1-((R)-1-(5-hydroxy-4-oxo-1,4-dihydropyridazine-3-carbonyl)pyrrolidin-2-yl)-2,2-diphenylethyl methanesulfonate

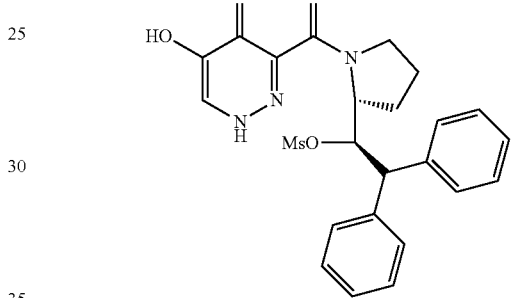

A solution of (R)-1-((R)-1-(1-benzyl-5-(benzyloxy)-4-oxo-1,4-dihydropyridazine-3-carbonyl)pyrrolidin-2-yl)-2,2-diphenylethyl methanesulfonate (102 mg, 0.154 mmol) in MeOH (Volume: 5 mL) was purged with nitrogen. Added a spatula tip of 10% Pd/C (32.7 mg, 0.031 mmol) and attached a hydrogen balloon. The flask was evacuated and refilled with hydrogen (3 times) and then stirred vigorously at RT under a balloon of hydrogen. After 30 min, the reaction was purged with nitrogen and then filtered through a plug of celite, using MeOH to wash through. The filtrate was concentrated in vacuo, azeotroped from toluene and used without further purification. MS m/z 484.3 (M+1).

Example 10. (9aR,10S)-10-benzhydryl-4-hydroxy-8,9,9a,10-tetrahydro-3H-pyrrolo[1',2':4,5]pyrazino[1,2-b]pyridazine-3,5(7H)-dione

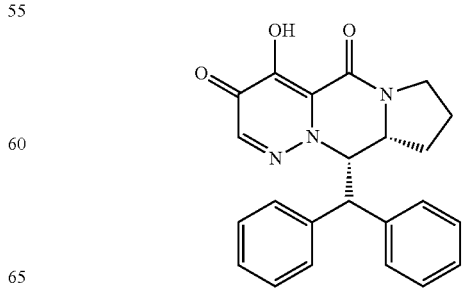

To a solution of crude (R)-1-((R)-1-(5-hydroxy-4-oxo-1,4-dihydropyridazine-3-carbonyl)pyrrolidin-2-yl)-2,2-diphenylethyl methanesulfonate (61.4 mg, 0.127 mmol) in DMF (Volume: 2 mL) at RT was added potassium carbonate (52.7 mg, 0.381 mmol). After overnight at RT, The reaction mixture was filtered through a 1 micron filter and purified in 2 batches directly on the reverse-phase prep HPLC (MeCN/H2O with 0.1% TFA eluent) to give (9aR,10S)-10-benzhydryl-4-hydroxy-8,9,9a,10-tetrahydro-3H-pyrrolo[1',2':4,5]pyrazino[1,2-b]pyridazine-3,5(7H)-dione (18 mg, 0.036 mmol, 28.0% yield) as a grey solid. 1H NMR (400 MHz, DMSO-d6) δ 7.63-7.57 (m, 2H), 7.38 (t, J=7.6 Hz, 2H), 7.29-7.23 (m, 1H), 7.22 (s, 1H), 7.04 (td, J=4.9, 2.3 Hz, 3H), 6.95 (dd, J=7.6, 2.0 Hz, 2H), 5.68 (dd, J=9.6, 3.6 Hz, 1H), 4.55 (d, J=9.5 Hz, 1H), 4.48 (ddd, J=10.1, 5.9, 4.0 Hz, 1H), 3.76-3.58 (m, 2H), 1.91 (tdd, J=9.5, 5.0, 3.0 Hz, 1H), 1.82-1.63 (m, 2H), 1.51-1.40 (m, 1H). MS m/z 388.3 (M+1).

Example 11. (9aR,10R)-10-benzhydryl-4-hydroxy-8,9,9a,10-tetrahydro-3H-pyrrolo[1',2':4,5]pyrazino[1,2-b]pyridazine-3,5(7H)-dione

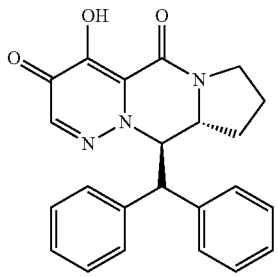 [SMILES: O=C1c2c(O)c(=O)cnn2[C@H](C(c2ccccc2)c2ccccc2)[C@H]2CCCN12]

This compound was made by the same process used to make Example 10. 1H NMR (400 MHz, DMSO-d6) δ 7.45 (s, 1H), 7.37-7.32 (m, 2H), 7.32-7.17 (m, 8H), 5.45 (dd, J=10.4, 6.1 Hz, 1H), 5.08 (d, J=6.1 Hz, 1H), 4.04 (td, J=10.5, 5.7 Hz, 1H), 3.55-3.42 (m, 2H), 1.89 (dt, J=12.6, 7.4 Hz, 1H), 1.74-1.59 (m, 1H), 1.55-1.38 (m, 2H). MS m/z 388.3 (M+1).

Example 12. (9aS,10R)-10-benzhydryl-4-hydroxy-8,9,9a,10-tetrahydro-3H-pyrrolo[1',2':4,5]pyrazino[1,2-b]pyridazine-3,5(7H)-dione

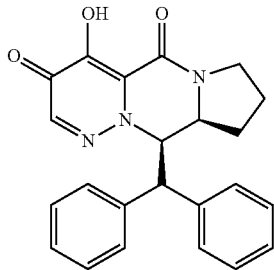 [SMILES: O=C1c2c(O)c(=O)cnn2[C@H](C(c2ccccc2)c2ccccc2)[C@@H]2CCCN12]

This compound was made by the same process used to make Example 10. 1H NMR (400 MHz, DMSO-d6) δ 7.66-7.55 (m, 2H), 7.38 (t, J=7.6 Hz, 2H), 7.29-7.23 (m, 1H), 7.21 (s, 1H), 7.08-7.01 (m, 3H), 6.96 (dd, J=7.6, 2.0 Hz, 2H), 5.68 (dd, J=9.6, 3.6 Hz, 1H), 4.55 (d, J=9.6 Hz, 1H), 4.48 (ddd, J=10.3, 6.1, 4.0 Hz, 1H), 3.78-3.68 (m, 1H), 3.62 (td, J=11.7, 11.0, 7.2 Hz, 1H), 1.91 (tdd, J=9.1, 5.7, 1.7 Hz, 1H), 1.82-1.64 (m, 2H), 1.53-1.37 (m, 1H). MS m/z 388.3 (M+1).

Example 13. (9aR,10R)-10-benzhydryl-4-hydroxy-8,9,9a,10-tetrahydro-3H-pyrrolo[1',2':4,5]pyrazino[1,2-b]pyridazine-3,5(7H)-dione

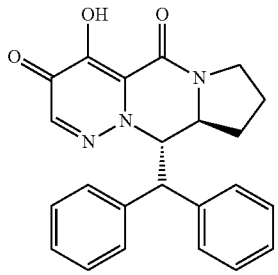 [SMILES: O=C1c2c(O)c(=O)cnn2[C@@H](C(c2ccccc2)c2ccccc2)[C@@H]2CCCN12]

This compound was made by the same process used to make Example 10. 1H NMR (400 MHz, DMSO-d6) δ 7.45 (s, 1H), 7.37-7.32 (m, 2H), 7.29 (dd, J=5.8, 3.5 Hz, 6H), 7.21 (dtd, J=7.1, 4.5, 2.1 Hz, 2H), 5.45 (dd, J=10.4, 6.1 Hz, 1H), 5.08 (d, J=6.0 Hz, 1H), 4.04 (td, J=10.4, 5.6 Hz, 1H), 3.61-3.52 (m, 1H), 3.46 (ddd, J=12.2, 10.0, 7.7 Hz, 1H), 1.96-1.84 (m, 1H), 1.75-1.58 (m, 1H), 1.56-1.37 (m, 2H). MS m/z 388.3 (M+1).

Example 14. (9aR,10S)-10-((R)-(3-fluorophenyl)(phenyl)methyl)-4-hydroxy-8,9,9a,10-tetrahydro-3H-pyrrolo[1',2':4,5]pyrazino[1,2-b]pyridazine-3,5(7H)-dione Intermediate 14.1. (R,E)-tert-butyl 2-(3-fluorostyryl)pyrrolidine-1-carboxylate

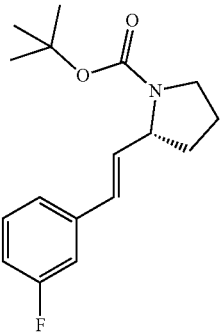 [SMILES: CC(C)(C)OC(=O)N1CCC[C@@H]1/C=C/c1cccc(F)c1]

To a solution of diethyl 3-fluorobenzylphosphonate (2.60 g, 10.54 mmol) in THF (Volume: 30 mL) at 0° C. was added a solution of LHMDS (1.0 M in THF) (10.44 mL, 10.44 mmol) dropwise. The reaction mixture was stirred at 0° C. for 20 minutes, then added a solution of (R)-tert-butyl 2-formylpyrrolidine-1-carboxylate (2 g, 10.04 mmol) in THF (10 mL) dropwise. The reaction mixture was slowly warm to RT in 1 h and then stirred additional 1 h at RT. The reaction was quenched with water and extracted with EtOAc (twice). The combined organic extracts were washed with brine, dried over Na2SO4, filtered and concentrated in vacuo. The residue was purified by ISCO (80 g silica gel column, 0-40% EtOAc in heptane) to give (R,E)-tert-butyl 2-(3-fluorostyryl)pyrrolidine-1-carboxylate (2.15 g, 7.23 mmol, 72.0% yield) as a white solid. MS m/z 292.0 (M+1).

Intermediate 14.2. (R)-tert-butyl 2-((2S,3S)-3-(3-fluorophenyl)oxiran-2-yl)pyrrolidine-1-carboxylate and (R)-tert-butyl 2-((2R,3R)-3-(3-fluorophenyl)oxiran-2-yl)pyrrolidine-1-carboxylate

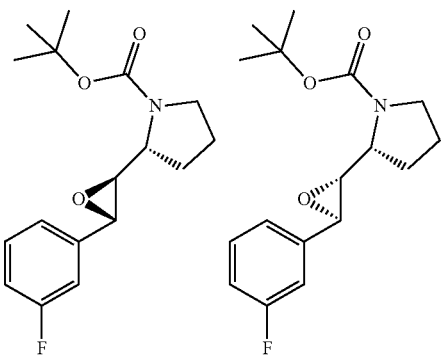

Added mCPBA (1327 mg, 7.69 mmol) to a solution of (R,E)-tert-butyl 2-(3-fluorostyryl)pyrrolidine-1-carboxylate (640 mg, 2.197 mmol) in DCM (Volume: 20 mL) at RT. Reaction mixture was stirred at RT overnight. The reaction was quenched with water and extracted with DCM. The combined organic extracts were washed with Sat. sodium thiosulfate, sodium bicarbonate and brine. The organics was dried over Na$_2$SO$_4$, filtered and concentrated in vacuo. The residue was purified by ISCO (40 g silica gel column, 0-40% EtOAc in heptane) to give a mixture of (R)-tert-butyl 2-((2S,3S)-3-(3-fluorophenyl)oxiran-2-yl)pyrrolidine-1-carboxylate and (R)-tert-butyl 2-((2R,3R)-3-(3-fluorophenyl)oxiran-2-yl)pyrrolidine-1-carboxylate (0.35 g, 1.025 mmol, 46.7% yield). MS m/z 308.3 (M+1).

Intermediate 14.3. (R)-tert-butyl 2-((1R,2R)-2-(3-fluorophenyl)-1-hydroxy-2-phenylethyl)pyrrolidine-1-carboxylate and (R)-tert-butyl 2-((1S,2S)-2-(3-fluorophenyl)-1-hydroxy-2-phenylethyl)pyrrolidine-1-carboxylate

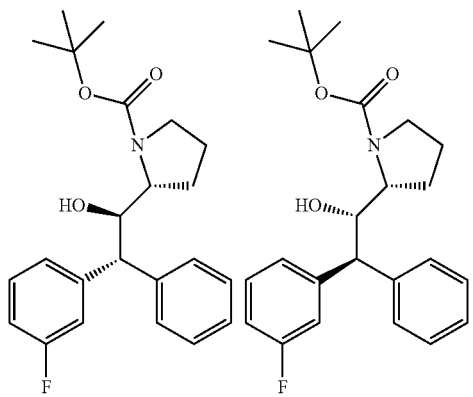

A mixture of (R)-tert-butyl 2-((2S,3S)-3-(3-fluorophenyl)oxiran-2-yl)pyrrolidine-1-carboxylate and (R)-tert-butyl 2-((2R,3R)-3-(3-fluorophenyl)oxiran-2-yl)pyrrolidine-1-carboxylate (220 mg, 0.716 mmol) and copper(I) bromide-dimethyl sulfide complex (169 mg, 0.823 mmol) in THF (Volume: 4 mL) was cooled to between −20 and −30° C. in an acetone bath with periodic dry ice additions. A solution of phenylmagnesium chloride (2.0 M in THF) (2.86 mL, 5.73 mmol) was added dropwise. After 40 min at this temperature, the reaction mixture was slowly warm to 0° C. in 30 min and kept at 0° C. for additional 60 min. The reaction was quenched with saturated aqueous NH$_4$Cl solution and extracted with EtOAc (2 times). The combined organic extracts were dried over Na$_2$SO$_4$, filtered and concentrated in vacuo. The residue was purified by ISCO (12 g silica gel column, 0-40% EtOAc in heptane) to yield (R)-tert-butyl 2-((1R,2R)-2-(3-fluorophenyl)-1-hydroxy-2-phenylethyl)pyrrolidine-1-carboxylate (40 mg, 0.104 mmol, 14.50% yield, $^1$H NMR (400 MHz, CDCl$_3$) δ ppm 7.39 (d, J=7.73 Hz, 2H), 7.27-7.36 (m, 2H), 7.14-7.26 (m, 4H), 6.91 (td, J=8.84, 2.62 Hz, 1H), 4.09-4.25 (m, 1H), 4.01 (d, J=2.89 Hz, 1H), 3.73-3.87 (m, 1H), 3.50 (br d, J=4.84 Hz, 1H), 3.19-3.34 (m, 1H), 1.80-1.99 (m, 2H), 1.68-1.80 (m, 2H), 1.37-1.49 (m, 9H)) and (R)-tert-butyl 2-((1S,2S)-2-(3-fluorophenyl)-1-hydroxy-2-phenylethyl)pyrrolidine-1-carboxylate (85 mg, 0.221 mmol, 30.8% yield, 1H NMR (400 MHz, CDCl3) δ ppm 7.31 (dt, J=14.71, 7.44 Hz, 4H), 7.06-7.25 (m, 4H), 6.77-6.96 (m, 1H), 4.96 (br d, J=10.03 Hz, 1H), 3.84 (d, J=10.32 Hz, 1H), 3.74 (br s, 1H), 3.55 (br s, 1H), 3.20 (dt, J=10.66, 7.46 Hz, 1H), 2.00-2.20 (m, 1H), 1.72-1.93 (m, 3H), 1.57-1.68 (m, 1H), 1.49 (s, 9H)). MS m/z 386.3 (M+1).

Intermediate 14.4. (R)-tert-butyl 2-((1R,2R)-2-(3-fluorophenyl)-1-((methylsulfonyl)oxy)-2-phenylethyl)pyrrolidine-1-carboxylate

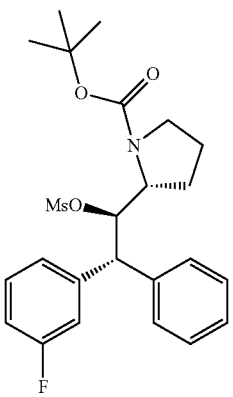 [SMILES: CC(C)(C)OC(=O)N1CCC[C@@H]1[C@H](OS(C)(=O)=O)[C@H](c1ccccc1)c1cccc(F)c1]

To a solution of (R)-tert-butyl 2-((1R,2R)-2-(3-fluorophenyl)-1-hydroxy-2-phenylethyl)pyrrolidine-1-carboxylate (85 mg, 0.221 mmol) in DCM (Volume: 2 mL) at 0° C. was added TEA (0.154 mL, 1.103 mmol) and MsCl (0.052 mL, 0.662 mmol). After 10 min at this temperature, the reaction mixture was took out from ice bath and stirred 1H at RT. Additional MsCl (0.052 mL, 0.662 mmol) was added. After another 2 h at rt, the reaction was diluted with DCM and washed with water and brine. The DCM layer was dried over Na$_2$SO$_4$, filtered and concentrated in vacuo. The residue was purified by ISCO (12 g silica gel column, 0-50% EtOAc in heptane) to give (R)-tert-butyl 2-((1R,2R)-2-(3-fluorophenyl)-1-((methylsulfonyl)oxy)-2-phenylethyl)pyrrolidine-1-carboxylate (10.2 mg, 0.022 mmol, 9.98% yield). MS m/z 464.2 (M+1).

Intermediate 14.5. (1R,2R)-2-(3-fluorophenyl)-2-phenyl-1-((R)-pyrrolidin-2-yl)ethyl methanesulfonate

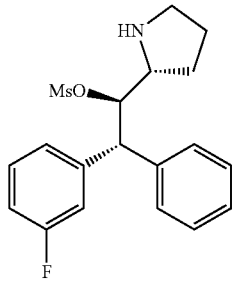 [SMILES: CS(=O)(=O)O[C@H]([C@H](c1ccccc1)c1cccc(F)c1)[C@H]1CCCN1]

Added HCl (1 mL, 4.0 mmol, 4.0 M in dioxane) to (R)-tert-butyl 2-((1R,2R)-2-(3-fluorophenyl)-1-((methylsulfonyl)oxy)-2-phenylethyl)pyrrolidine-1-carboxylate (10.2 mg, 0.022 mmol) at RT. After 1H at RT, the mixture was concentrated in vacuo and proceed for next step. MS m/z 364.3 (M+1).

Intermediate 14.6. (1R,2R)-1-((R)-1-(1-benzyl-5-(benzyloxy)-4-oxo-1,4-dihydropyridazine-3-carbonyl)pyrrolidin-2-yl)-2-(3-fluorophenyl)-2-phenylethyl methanesulfonate

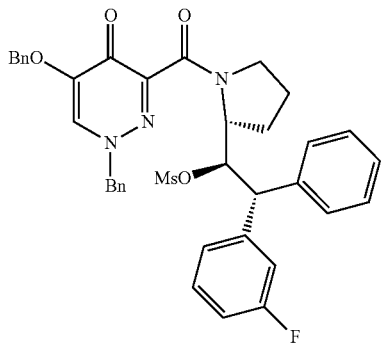 [SMILES: CS(=O)(=O)O[C@H]([C@H](c1ccccc1)c1cccc(F)c1)[C@H]1CCCN1C(=O)c1nn(Cc2ccccc2)cc(OCc2ccccc2)c1=O]

Added Huenig's Base (0.019 mL, 0.110 mmol) and HATU (10.88 mg, 0.029 mmol) to a solution of 1-benzyl-5-(benzyloxy)-4-oxo-1,4-dihydropyridazine-3-carboxylic acid (8.14 mg, 0.024 mmol) in DCM (Volume: 1 mL) at RT. After 15 min, the mixture was added a solution of crude (1R,2R)-2-(3-fluorophenyl)-2-phenyl-1-((R)-pyrrolidin-2-yl)ethyl methanesulfonate (8 mg, 0.022 mmol) and Huenig's base (0.05 mL) in DCM (0.5 mL). The mixture was stirred at RT for 1 h, diluted with DCM and washed with water and brine. The organic layer was dried over Na$_2$SO$_4$, filtered and concentrated on the rotovap. The residue was purified by ISCO (4 g silica gel column, 0-100% EtOAc (containing 10% MeOH) in heptane) to give (1R,2R)-1-((R)-1-(1-benzyl-5-(benzyloxy)-4-oxo-1,4-dihydropyridazine-3-carbonyl)pyrrolidin-2-yl)-2-(3-fluorophenyl)-2-phenylethyl methanesulfonate (14.2 mg, 0.021 mmol, 95% yield). MS m/z 682.1 (M+1).

Intermediate 14.7. (1R,2R)-2-(3-fluorophenyl)-1-((R)-1-(5-hydroxy-4-oxo-1,4-dihydropyridazine-3-carbonyl)pyrrolidin-2-yl)-2-phenylethyl methanesulfonate

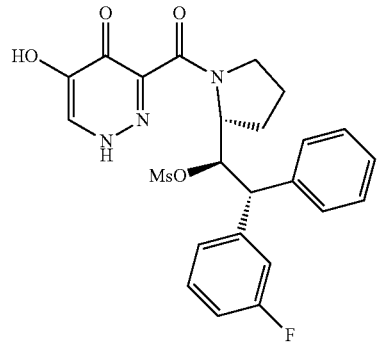 [SMILES: CS(=O)(=O)O[C@H]([C@H](c1ccccc1)c1cccc(F)c1)[C@H]1CCCN1C(=O)c1n[nH]cc(O)c1=O]

A solution of (1R,2R)-1-((R)-1-(1-benzyl-5-(benzyloxy)-4-oxo-1,4-dihydropyridazine-3-carbonyl)pyrrolidin-2-yl)-2-(3-fluorophenyl)-2-phenylethyl methanesulfonate (14.5 mg, 0.021 mmol) in MeOH (Volume: 5 mL) was purged with nitrogen. Added a spatula tip of 10% Pd/C (4.53 mg, 4.25 μmol) and attached a hydrogen balloon. The flask was evacuated and refilled with hydrogen (3 times) and then stirred vigorously at RT under a balloon of hydrogen. After 1H, the reaction mixture was filtered through celite, washed with MeOH. Filtered and evaporated. Proceed for next step without further purification. MS m/z 502.3 (M+1).

Example 14. (9aR,10S)-10-((R)-(3-fluorophenyl)(phenyl)methyl)-4-hydroxy-8,9,9a,10-tetrahydro-3H-pyrrolo[1',2':4,5]pyrazino[1,2-b]pyridazine-3,5(7H)-dione

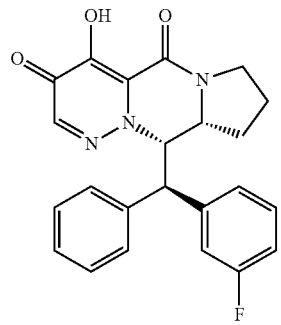 [SMILES: O=C1c2c(O)c(=O)cnn2[C@@H]([C@H](c2ccccc2)c2cccc(F)c2)[C@H]2CCCN12]

Added potassium carbonate (8.76 mg, 0.063 mmol) to a solution of crude (1R,2R)-2-(3-fluorophenyl)-1-((R)-1-(5-hydroxy-4-oxo-1,4-dihydropyridazine-3-carbonyl)pyrrolidin-2-yl)-2-phenylethyl methanesulfonate (10.6 mg, 0.021 mmol) in DMF (Volume: 1 mL) at RT. The mixture was stirred at RT for 4H, filtered through a 1 micron filter and purified in 2 batches directly on the reverse-phase prep HPLC (MeCN/H2O with 0.1% TFA eluent). Fractions contains product were combined and lyophilyzed to give (9aR,10S)-10-((R)-(3-fluorophenyl)(phenyl)methyl)-4-hydroxy-8,9,9a,10-tetrahydro-3H-pyrrolo[1',2':4,5]pyrazino[1,2-b]pyridazine-3,5(7H)-dione (3.9 mg, 7.36 μmol, 34.8% yield) as an off white solid. 1H NMR (400 MHz, DMSO-d6) δ 7.50

(d, J=10.5 Hz, 1H), 7.46-7.35 (m, 2H), 7.18 (s, 1H), 7.11-6.99 (m, 4H), 6.97-6.90 (m, 2H), 5.70 (dd, J=9.6, 3.5 Hz, 1H), 4.60 (d, J=9.6 Hz, 1H), 4.45 (dt, J=10.1, 5.5 Hz, 1H), 3.78-3.66 (m, 1H), 3.66-3.53 (m, 1H), 1.91 (dt, J=12.6, 6.7 Hz, 1H), 1.85-1.60 (m, 2H), 1.40 (qd, J=11.5, 6.9 Hz, 1H). MS m/z 406.2 (M+1).

Example 15. (9aR,10R)-10-(bis(3-fluorophenyl)methyl)-4-hydroxy-8,9,9a,10-tetrahydro-3H-pyrrolo[1',2':4,5]pyrazino[1,2-b]pyridazine-3,5(7H)-dione

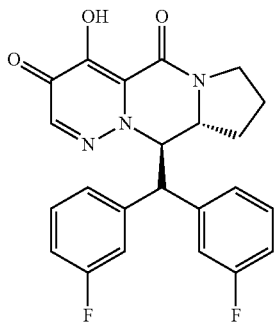 [SMILES: O=C1c2c(O)c(=O)cnn2[C@H](C(c2cccc(F)c2)c2cccc(F)c2)[C@H]2CCCN12]

This compound was made by the same process used to make Example 14. 1H NMR (400 MHz, MeOD) δ ppm 7.64 (s, 1H), 7.26-7.40 (m, 2H), 7.08-7.22 (m, 3H), 6.94-7.07 (m, 3H), 5.40 (dd, J=10.78, 6.09 Hz, 1H), 5.15 (d, J=6.06 Hz, 1H), 4.09 (td, J=10.51, 5.87 Hz, 1H), 3.67-3.77 (m, 1H), 3.53-3.65 (m, 1H), 1.99-2.09 (m, 1H), 1.58-1.85 (m, 3H). MS m/z 424.3 (M+1).

Example 16. (9aR,10S)-10-(bis(3-fluorophenyl)methyl)-4-hydroxy-8,9,9a,10-tetrahydro-3H-pyrrolo[1',2':4,5]pyrazino[1,2-b]pyridazine-3,5(7H)-dione

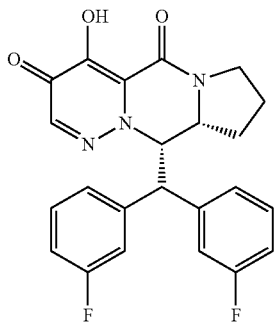

This compound was made by the same process used to make Example 14. 1H NMR (400 MHz, MeOD) δ ppm 7.29-7.52 (m, 4H), 7.01-7.12 (m, 2H), 6.70-6.86 (m, 3H), 5.76 (dd, J=9.59, 3.62 Hz, 1H), 4.61 (d, J=9.63 Hz, 1H), 4.51 (dt, J=10.20, 5.12 Hz, 1H), 3.82-3.93 (m, 1H), 3.67 (td, J=11.16, 7.56 Hz, 1H), 2.01-2.10 (m, 1H), 1.78-1.97 (m, 2H), 1.54-1.67 (m, 1H). MS m/z 424.3 (M+1).

Example 17. (9aS,10R)-10-((S)-(3-chlorophenyl)(phenyl)methyl)-4-hydroxy-8,9,9a,10-tetrahydro-3H-pyrrolo[1',2':4,5]pyrazino[1,2-b]pyridazine-3,5(7H)-dione

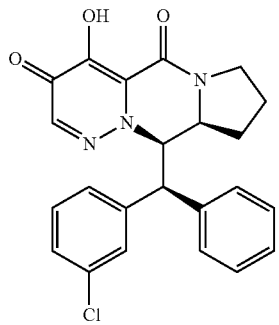 [SMILES: O=C1c2c(O)c(=O)cnn2[C@H]([C@@H](c2ccccc2)c2cccc(Cl)c2)[C@@H]2CCCN12]

This compound was made by the same process used to make Example 14. ¹H NMR (400 MHz, DMSO-d6) δ 7.69 (t, J=1.9 Hz, 1H), 7.42 (t, J=7.9 Hz, 1H), 7.66-7.60 (m, 1H), 7.36-7.29 (m, 1H), 7.22 (s, 1H), 7.12-7.00 (m, 3H), 6.94 (dd, J=7.6, 1.9 Hz, 2H), 5.73 (dd, J=9.5, 3.6 Hz, 1H), 4.63 (d, J=9.5 Hz, 1H), 4.47 (ddd, J=10.2, 5.4, 3.4 Hz, 1H), 3.78-3.68 (m, 1H), 3.62 (td, J=11.7, 11.0, 7.2 Hz, 1H), 2.01-1.89 (m, 1H), 1.87-1.78 (m, 1H), 1.75-1.65 (m, 1H), 1.44 (qd, J=11.6, 6.8 Hz, 1H). MS m/z 422.3 (M+1).

Example 18. (10aS)-11-benzhydryl-4-hydroxy-7,8,10a,11-tetrahydro-10H-pyridazino[1',6':4,5]pyrazino[2,1-c][1,4]oxazine-3,5-dione

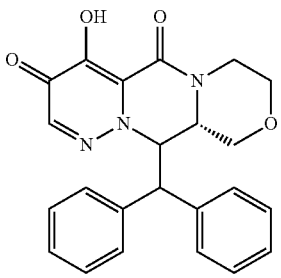 [SMILES: O=C1c2c(O)c(=O)cnn2C(C(c2ccccc2)c2ccccc2)[C@H]2COCCN12]

This compound was made by the same process used to make Example 14 except starting with tert-butyl (R)-3-formylmorpholine-4-carboxylate. 1H NMR (500 MHz, DMSO-d6) δ 7.58 (d, J=7.5 Hz, 2H), 7.39 (t, J=7.6 Hz, 2H), 7.29 (t, J=7.3 Hz, 1H), 7.21 (d, J=6.6 Hz, 2H), 7.17 (s, 1H), 7.14 (q, J=6.1 Hz, 3H), 5.51 (d, J=11.2 Hz, 1H), 4.58 (d, J=11.1 Hz, 1H), 4.36 (d, J=11.4 Hz, 1H), 3.98 (d, J=8.5 Hz, 1H), 3.75-3.67 (m, 4H), 3.04-2.95 (m, 1H). MS m/z 404.3 (M+1).

Examples 19A and 19B

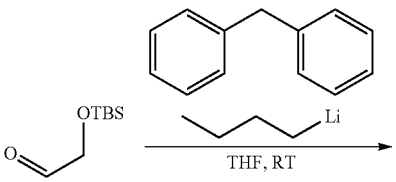

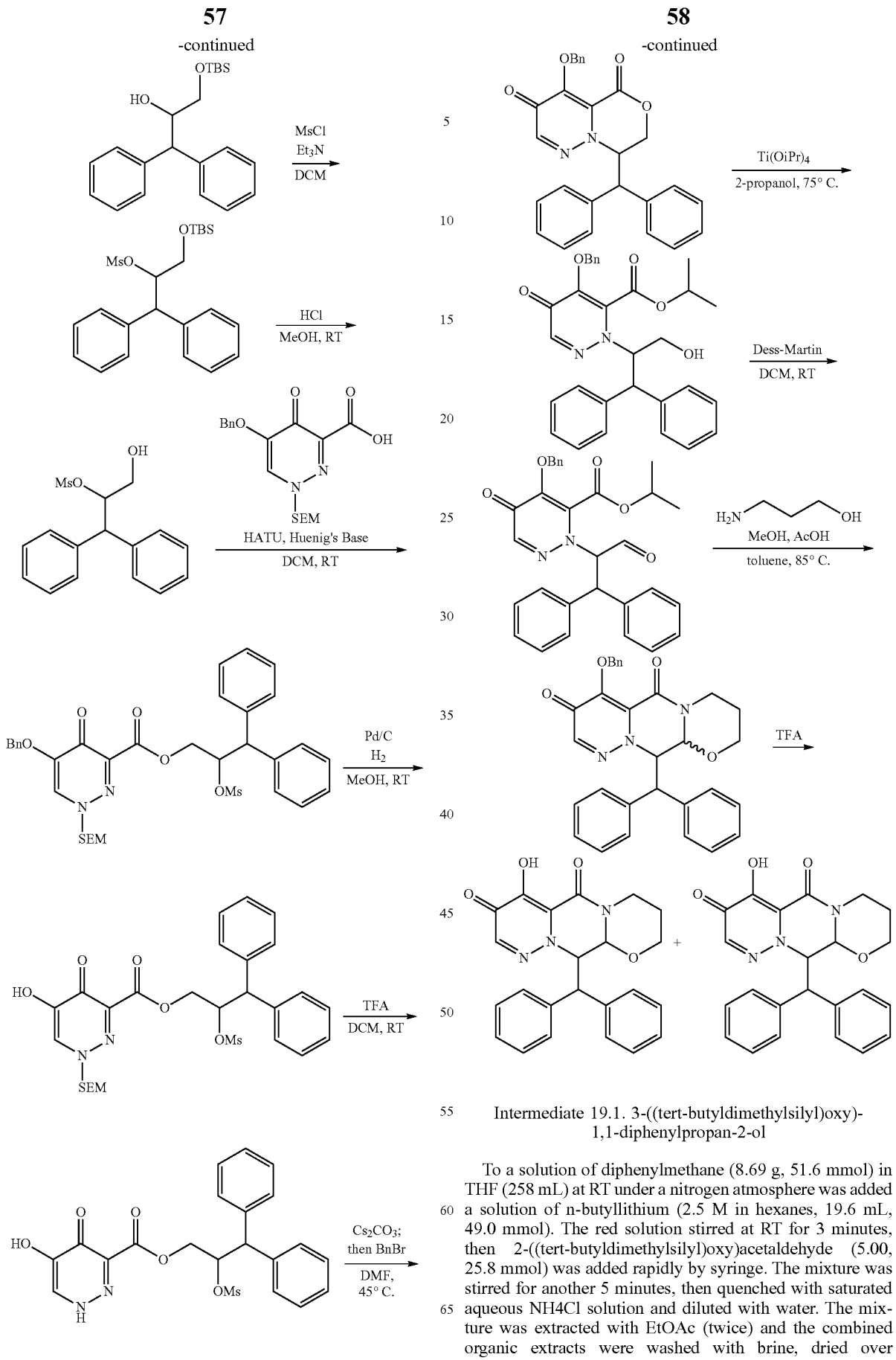

Intermediate 19.1. 3-((tert-butyldimethylsilyl)oxy)-1,1-diphenylpropan-2-ol

To a solution of diphenylmethane (8.69 g, 51.6 mmol) in THF (258 mL) at RT under a nitrogen atmosphere was added a solution of n-butyllithium (2.5 M in hexanes, 19.6 mL, 49.0 mmol). The red solution stirred at RT for 3 minutes, then 2-((tert-butyldimethylsilyl)oxy)acetaldehyde (5.00, 25.8 mmol) was added rapidly by syringe. The mixture was stirred for another 5 minutes, then quenched with saturated aqueous NH4Cl solution and diluted with water. The mixture was extracted with EtOAc (twice) and the combined organic extracts were washed with brine, dried over Na2SO4, filtered and concentrated in vacuo. Silica gel column chromatography (0-20% EtOAc in heptane) provided 3-((tert-butyldimethylsilyl)oxy)-1,1-diphenylpropan-2-ol (4.7 g, colorless oil) in 53% yield. 1H NMR (400 MHz, Chloroform-d) δ 7.42-7.37 (m, 2H), 7.34-7.17 (m, 8H), 4.42 (ddd, J=9.3, 6.2, 3.5 Hz, 1H), 4.04 (d, J=9.0 Hz, 1H), 3.58 (dd, J=10.1, 3.4 Hz, 1H), 3.44 (dd, J=10.1, 6.2 Hz, 1H), 2.51 (s, 1H), 0.90 (s, 9H), 0.03-0.01 (m, 6H).

Intermediate 19.2. 3-((tert-butyldimethylsilyl)oxy)-1,1-diphenylpropan-2-yl methanesulfonate Methanesulfonyl chloride (1.4 mL, 17.8 mmol) was added dropwise to a solution of 3-((tert-butyldimethylsilyl)oxy)-1,1-diphenylpropan-2-ol (4.70 g, 13.7 mmol) and triethylamine (3.8 mL, 27.4 mmol) in DCM (137 mL) at 0° C. The solution was stirred for 30 minutes, and then diluted with DCM and washed with water. The organic layer was dried over Na2SO4, filtered, and concentrated in vacuo to give crude 3-((tert-butyldimethylsilyl)oxy)-1,1-diphenylpropan-2-yl methanesulfonate as a colorless oil. Used without further purification. MS m/z 421.4 (M+1).

Intermediate 19.3. 3-hydroxy-1,1-diphenylpropan-2-yl methanesulfonate

A solution of hydrogen chloride (4.0 M in dioxane, 5.2 mL, 20.6 mmol) was added to a solution of crude 3-((tert-butyldimethylsilyl)oxy)-1,1-diphenylpropan-2-yl methanesulfonate (5.8 g, 13.7 mmol) in methanol (137 mL) at RT. The mixture was stirred for 1 h, and then concentrated in vacuo. Silica gel column chromatography (25-80% EtOAc in heptane) provided 3-hydroxy-1,1-diphenylpropan-2-yl methanesulfonate (3.81 g, colorless oil) in 91% yield. 1H NMR (400 MHz, Chloroform-d) δ 7.45-7.38 (m, 2H), 7.37-7.29 (m, 6H), 7.29-7.20 (m, 2H), 5.46 (ddd, J=10.2, 5.4, 2.6 Hz, 1H), 4.33 (d, J=10.2 Hz, 1H), 3.87 (dd, J=12.9, 2.6 Hz, 1H), 3.68 (dd, J=12.9, 5.5 Hz, 1H), 2.37 (s, 3H).

Intermediate 19.4. 2-((methylsulfonyl)oxy)-3,3-diphenylpropyl 5-(benzyloxy)-4-oxo-1-((2-(trimethylsilyl)ethoxy)methyl)-1,4-dihydropyridazine-3-carboxylate To a solution of 5-(benzyloxy)-4-oxo-1-((2-(trimethylsilyl)ethoxy)methyl)-1,4-dihydropyridazine-3-carboxylic acid (700 mg, 1.86 mmol) in DCM (6 ML) at 0° C. was added Huenig's Base (812 μl, 4.65 mmol) and HATU (848 mg, 2.23 mmol). Stirred for 15 min, then added a solution of 3-hydroxy-1,1-diphenylpropan-2-yl methanesulfonate (854 mg, 2.79 mmol) in DCM (3 mL). The mixture was stirred at RT overnight, diluted with DCM and washed with water. The organic layer was dried over $Na_2SO_4$, filtered and concentrated in vacuo. Silica gel column chromatography (5-80% EtOAc in heptane) provided 2-((methylsulfonyl)oxy)-3,3-diphenylpropyl 5-(benzyloxy)-4-oxo-1-((2-(trimethylsilyl)ethoxy)methyl)-1,4-dihydropyridazine-3-carboxylate (878 mg, white foam) in 71% yield. MS m/z 665.2 (M+1).

Intermediate 19.5. 2-((methylsulfonyl)oxy)-3,3-diphenylpropyl 5-hydroxy-4-oxo-1-((2-(trimethylsilyl)ethoxy)methyl)-1,4-dihydropyridazine-3-carboxylate A solution of 2-((methylsulfonyl)oxy)-3,3-diphenylpropyl 5-(benzyloxy)-4-oxo-1-((2-(trimethylsilyl)ethoxy) methyl)-1,4-dihydropyridazine-3-carboxylate (1.0 g, 1.5 mmol) in methanol (40 mL) was purged with nitrogen. 10% palladium on carbon (160 mg, 0.15 mmol) was added and the flask was evacuated and refilled with hydrogen from a balloon (3 times). The mixture was stirred vigorously under a hydrogen atmosphere for 30 minutes. The flask was then purged with nitrogen and the mixture was filtered through a plug of celite, using methanol to wash the filter cake. The filtrated was concentrated in vacuo to give crude 2-((methylsulfonyl)oxy)-3,3-diphenylpropyl 5-hydroxy-4-oxo-1-((2-(trimethylsilyl)ethoxy)methyl)-1,4-dihydropyridazine-3-carboxylate, which was used without further purification. MS m/z 575.4 (M+1).

Intermediate 19.6. 2-((methylsulfonyl)oxy)-3,3-diphenylpropyl 5-hydroxy-4-oxo-1,4-dihydropyridazine-3-carboxylate Trifluoroacetic acid (20 mL) was added to a solution of crude 2-((methylsulfonyl)oxy)-3,3-diphenylpropyl 5-hydroxy-4-oxo-1-((2-(trimethylsilyl)ethoxy)methyl)-1,4-dihydropyridazine-3-carboxylate (864 mg, 1.50 mmol) in DCM (5 mL) at RT. The mixture was stirred for 5 h and then concentrated in vacuo to give crude 2-((methylsulfonyl)oxy)-3,3-diphenylpropyl 5-hydroxy-4-oxo-1,4-dihydropyridazine-3-carboxylate, which was used without further purification. MS m/z 445.3 (M+1).

Intermediate 19.7. 8-benzhydryl-4-(benzyloxy)-7,8-dihydropyridazino[6,1-c][1,4]oxazine-3,5-dione Cesium carbonate (5.39 g, 16.5 mmol) was added to a solution of crude 2-((methylsulfonyl)oxy)-3,3-diphenylpropyl 5-hydroxy-4-oxo-1,4-dihydropyridazine-3-carboxylate (840 mg, 1.50 mmol) in DMF at RT. The mixture was then stirred at 45° C. for 3 h. Benzyl bromide (1 mL) was then added and the mixture was stirred for another hour at 45° C. The mixture was then cooled to RT and filtered to remove solids. The filtrate was concentrated in vacuo and the residue was purified in batches by reverse-phase prep HPLC (MeCN/H2O with 0.1% TFA eluent) to give, after lyophilization, 8-benzhydryl-4-(benzyloxy)-7,8-dihydropyridazino[6,1-c][1,4]oxazine-3,5-dione (91 mg, white solid) in 11% yield. 1H NMR (400 MHz, DMSO-d6) δ 7.61-7.07 (m, 16H), 5.63 (ddd, J=11.7, 2.4, 1.3 Hz, 1H), 5.46 (d, J=11.3 Hz, 1H), 5.33 (d, J=11.3 Hz, 1H), 4.92 (dd, J=12.1, 2.6 Hz, 1H), 4.40 (d, J=11.5 Hz, 1H), 4.23 (dd, J=12.2, 1.3 Hz, 1H). MS m/z 439.2 (M+1).

Intermediate 19.8. isopropyl 4-(benzyloxy)-2-(3-hydroxy-1,1-diphenylpropan-2-yl)-5-oxo-2,5-dihydropyridazine-3-carboxylate Titanium isopropoxide (0.11 mL, 0.37 mmol) was added to a suspension of 8-benzhydryl-4-(benzyloxy)-7,8-dihydropyridazino[6,1-c][1,4]oxazine-3,5-dione (34 mg, 0.062 mmol) in 2-propanol (6 mL). The mixture was heated at 75° C. for 3 h and then cooled to RT. The mixture was diluted with EtOAc and brine. The layers were separated and the aqueous layer was extracted with EtOAc (twice) and the combined organic extracts were dried over Na2SO4, filtered and concentrated in vacuo to give a white residue. The residue was triturated with DCM and the DCM layer was pipetted off and concentrated in vacuo to give a mixture of starting material and crude isopropyl 4-(benzyloxy)-2-(3-hydroxy-1,1-diphenylpropan-2-yl)-5-oxo-2,5-dihydropyridazine-3-carboxylate, which was used without further purification. MS m/z 499.3 (M+1).

Intermediate 19.9. isopropyl 4-(benzyloxy)-5-oxo-2-(3-oxo-1,1-diphenylpropan-2-yl)-2,5-dihydro-pyridazine-3-carboxylate Dess-Martin periodinane (37 mg, 0.087 mmol) was added to a solution of crude isopropyl 4-(benzyloxy)-2-(3-hydroxy-1,1-diphenylpropan-2-yl)-5-oxo-2,5-dihydropyridazine-3-carboxylate in DCM (1 mL) at RT. The mixture was stirred for 1 h, and then diluted with DCM and washed sequentially with saturated aqueous sodium thiosulfate solution and brine. The organic layer was dried over Na2SO4, filtered and concentrated in vacuo to give crude isopropyl 4-(benzyloxy)-5-oxo-2-(3-oxo-1,1-diphenylpropan-2-yl)-2,5-dihydropyridazine-3-carboxylate, which was used without further purification. MS m/z 497.2 (M+1).

Intermediate 19. 12-benzhydryl-7-(benzyloxy)-3,4,12,12a-tetrahydro-2H-pyridazino[1',6':4,5]pyrazino[2,1-b][1,3]oxazine-6,8-dione

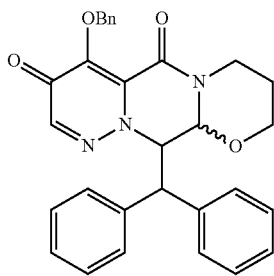

Methanol (2.4 mL, 60 mmol), 3-amino-1-propanol (1.8 mL, 24 mmol), and acetic acid (1.15 mL, 20.1 mmol) were carefully added to toluene (9 mL) at RT (exothermic). The mixture was agitated and 5 mL of the mixture was removed and added to crude isopropyl 4-(benzyloxy)-5-oxo-2-(3-oxo-1,1-diphenylpropan-2-yl)-2,5-dihydropyridazine-3-carboxylate (0.1 g, 0.2 mmol) in a vial. The vial was capped and the mixture was heated at 85° C. for 5 h. The reaction was cooled to RT and diluted with EtOAc and water. The layers were separated and the aqueous layer was extracted with EtOAc. The combined organic extracts were dried over Na2SO4, filtered and concentrated in vacuo. The residue was taken up in DMSO and purified by reverse-phase prep HPLC (MeCN/water with 0.1% TFA eluent) to give two diastereomers of 12-benzhydryl-7-(benzyloxy)-3,4,12,12a-tetrahydro-2H-pyridazino[1',6':4,5]pyrazino[2,1-b][1,3]oxazine-6,8-dione (white solid).

Diastereomer 1: LCMS Rt 0.91/1.50 min, m/z 494.2 (M+1). 1H NMR (400 MHz, DMSO-d6) δ 7.63-7.57 (m, 2H), 7.53-7.48 (m, 2H), 7.44-7.26 (m, 7H), 7.16 (dd, J=6.7, 3.0 Hz, 2H), 7.09 (dd, J=5.0, 1.9 Hz, 3H), 5.45 (dd, J=11.4, 1.3 Hz, 1H), 5.35 (d, J=11.2 Hz, 1H), 5.20 (d, J=11.1 Hz, 1H), 4.77 (d, J=1.4 Hz, 1H), 4.55-4.45 (m, 1H), 4.37 (d, J=11.3 Hz, 1H), 4.01 (dd, J=11.5, 4.7 Hz, 1H), 3.85-3.75 (m, 1H), 3.00 (td, J=12.8, 3.0 Hz, 1H), 1.66 (ddd, J=17.0, 8.4, 4.7 Hz, 1H), 1.44 (d, J=13.6 Hz, 1H).

Diastereomer 2: LCMS Rt 0.92/1.50 min, m/z 494.2 (M+1). 1H NMR (400 MHz, DMSO-d6) δ 7.70 (s, 1H), 7.51-7.44 (m, 4H), 7.40-7.28 (m, 5H), 7.27-7.20 (m, 1H), 7.16-7.03 (m, 5H), 5.61 (dd, J=7.2, 3.3 Hz, 1H), 5.07 (d, J=3.3 Hz, 1H), 4.96 (d, J=1.9 Hz, 2H), 4.88 (d, J=7.1 Hz, 1H), 4.26 (ddd, J=13.4, 5.1, 2.9 Hz, 1H), 3.94 (dd, J=11.1, 4.5 Hz, 1H), 3.45-3.39 (m, 1H), 3.13 (ddd, J=13.2, 11.7, 4.0 Hz, 1H), 1.93-1.79 (m, 1H), 1.66 (dt, J=13.8, 3.4 Hz, 1H).

Examples 19A and 19B. 12-benzhydryl-7-hydroxy-3,4,12,12a-tetrahydro-2H-pyridazino[1',6':4,5]pyrazino[2,1-b][1,3]oxazine-6,8-dione

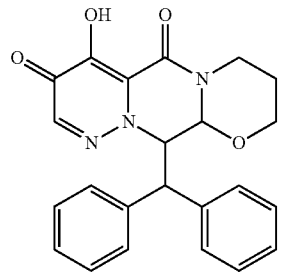 [SMILES: O=C1c2c(O)c(=O)cnn2C(C(c2ccccc2)c2ccccc2)C2OCCCN12]

Trifluoroacetic acid (5 mL) was added to crude 12-benzhydryl-7-(benzyloxy)-3,4,12,12a-tetrahydro-2H-pyridazino[1',6':4,5]pyrazino[2,1-b][1,3]oxazine-6,8-dione (mixture of diastereomers) at RT and the mixture was stirred for 20 minutes. The reaction was then concentrated in vacuo and the residue was taken up in DMSO. Purified by reverse-phase prep HPLC (MeCN/H2O with 0.1% TFA eluent) to give, after lyophilization the trifluoroacetate salts of two diastereomers of 12-benzhydryl-7-hydroxy-3,4,12,12a-tetrahydro-2H-pyridazino[1',6':4,5]pyrazino[2,1-b][1,3]oxazine-6,8-dione (white solid).

Example 19A

LCMS Rt 0.80/1.50 min, m/z 404.2 (M+1). 1H NMR (400 MHz, DMSO-d6) δ 7.62-7.57 (m, 2H), 7.42-7.25 (m, 7H), 7.13 (dd, J=4.9, 2.7 Hz, 2H), 5.50 (dd, J=11.2, 1.2 Hz, 1H), 4.87 (d, J=1.3 Hz, 1H), 4.48 (dd, J=11.9, 7.0 Hz, 2H), 4.04 (dd, J=11.4, 4.9 Hz, 1H), 3.91-3.79 (m, 1H), 3.12 (td, J=12.8, 3.1 Hz, 1H), 1.64 (dt, J=12.8, 6.6 Hz, 1H), 1.54-1.45 (m, 1H).

Example 19B

LCMS Rt 0.82/1.50 min, m/z 404.2 (M+1). 1H NMR (400 MHz, DMSO-d6) δ 7.53 (s, 1H), 7.50-7.44 (m, 2H), 7.38-7.02 (m, 8H), 5.64 (dd, J=7.0, 3.5 Hz, 1H), 5.11 (d, J=3.4 Hz, 1H), 4.90 (d, J=7.0 Hz, 1H), 4.28 (qd, J=7.1, 6.0, 3.7 Hz, 1H), 3.98 (dd, J=11.2, 4.7 Hz, 1H), 3.43 (td, J=11.8, 2.4 Hz, 1H), 3.19 (td, J=12.9, 3.8 Hz, 1H), 1.93 (dddd, J=12.5, 9.0, 7.1, 5.2 Hz, 1H), 1.68 (ddd, J=14.1, 4.0, 2.1 Hz, 1H).

Note that Examples 19A and 19B, and other example numbers that include A or B, were separated and tested as individual isomers, and biological activity is reported for each isolated isomer. However, since the absolute stereochemistry of the two isomers has not been determined, the structures shown for these Examples do not depict stereochemistry, so the A and B structures look the same, but each represents a single diastereomer.

TABLE 1a

| Compounds of the Preceding Examples. | | |
|---|---|---|
| Example No. | Structure | Name |
| 1 | | 12-benzhydryl-4-hydroxy-7,8,9,10-tetrahydro-12H-dipyridazino[1,2-a:1',6'-d][1,2,4]triazine-3,5-dione |
| 2 | | 12-(bis(3-fluorophenyl)methyl)-4-hydroxy-7,8,9,10-tetrahydro-12H-dipyridazino[1,2-a:1',6'-d][1,2,4]triazine-3,5-dione |
| 3 | | 12-(bis(4-chlorophenyl)methyl)-4-hydroxy-7,8,9,10-tetrahydro-12H-dipyridazino[1,2-a:1',6'-d][1,2,4]triazine-3,5-dione |
| 4 | | 12-(bis(3-chlorophenyl)methyl)-4-hydroxy-7,8,9,10-tetrahydro-12H-dipyridazino[1,2-a:1',6'-d][1,2,4]triazine-3,5-dione |
| 5 | | 12-(bis(4-fluorophenyl)methyl)-4-hydroxy-7,8,9,10-tetrahydro-12H-dipyridazino[1,2-a:1',6'-d][1,2,4]triazine-3,5-dione |

TABLE 1a-continued

Compounds of the Preceding Examples.

| Example No. | Structure | Name |
|---|---|---|
| 6 | 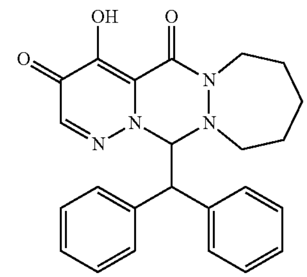 [SMILES: O=C1c2c(O)c(=O)cnn2C(C(c2ccccc2)c2ccccc2)N2CCCCCN12] | 13-benzhydryl-4-hydroxy-8,9,10,11-tetrahydro-7H,13H-pyridazino[1',6':4,5][1,2,4]triazino[1,2-a][1,2]diazepine-3,5-dione |
| 7 | 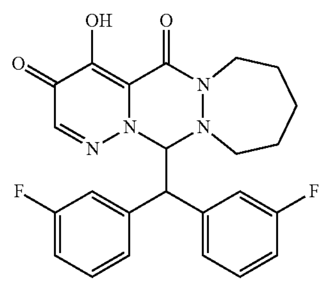 [SMILES: O=C1c2c(O)c(=O)cnn2C(C(c2cccc(F)c2)c2cccc(F)c2)N2CCCCCN12] | 13-(bis(3-fluorophenyl)methyl)-4-hydroxy-8,9,10,11-tetrahydro-7H,13H-pyridazino[1',6':4,5][1,2,4]triazino[1,2-a][1,2]diazepine-3,5-dione |
| 8 | 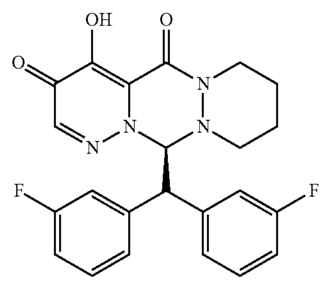 | (R)-12-(bis(3-fluorophenyl)methyl)-4-hydroxy-7,8,9,10-tetrahydro-12H-dipyridazino[1,2-a:1',6'-d][1,2,4]triazine-3,5-dione |
| 9 | 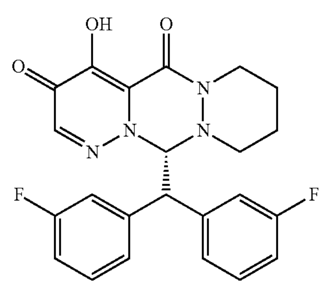 | (S)-12-(bis(3-fluorophenyl)methyl)-4-hydroxy-7,8,9,10-tetrahydro-12H-dipyridazino[1,2-a:1',6'-d][1,2,4]triazine-3,5-dione |
| 10 | 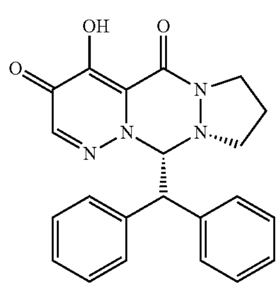 | (9aR,10S)-10-benzhydryl-4-hydroxy-8,9,9a,10-tetrahydro-7H-pyrrolo[1',2':4,5]pyrazino[1,2-b]pyridazine-3,5-dione |

TABLE 1a-continued

Compounds of the Preceding Examples.

| Example No. | Structure | Name |
| --- | --- | --- |
| 11 | 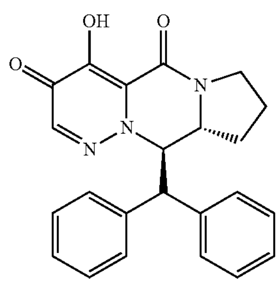 [SMILES: O=C1c2c(O)c(=O)cnn2[C@H](C(c2ccccc2)c2ccccc2)[C@H]2CCCN12] | (9aR,10R)-10-benzhydryl-4-hydroxy-8,9,9a,10-tetrahydro-7H-pyrrolo[1',2':4,5]pyrazino[1,2-b]pyridazine-3,5-dione |
| 12 | 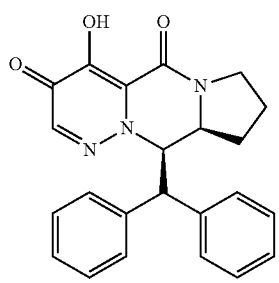 [SMILES: O=C1c2c(O)c(=O)cnn2[C@H](C(c2ccccc2)c2ccccc2)[C@@H]2CCCN12] | (9aS,10R)-10-benzhydryl-4-hydroxy-8,9,9a,10-tetrahydro-7H-pyrrolo[1',2':4,5]pyrazino[1,2-b]pyridazine-3,5-dione |
| 13 | 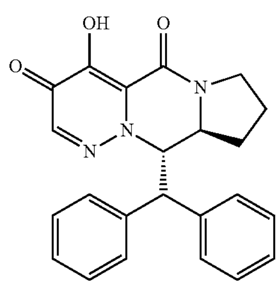 [SMILES: O=C1c2c(O)c(=O)cnn2[C@@H](C(c2ccccc2)c2ccccc2)[C@@H]2CCCN12] | (9aS,10S)-10-benzhydryl-4-hydroxy-8,9,9a,10-tetrahydro-7H-pyrrolo[1',2':4,5]pyrazino[1,2-b]pyridazine-3,5-dione |
| 14 | 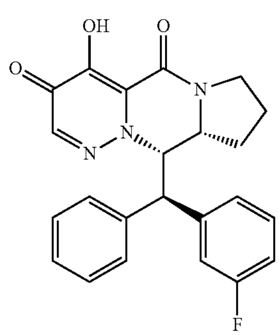 [SMILES: O=C1c2c(O)c(=O)cnn2[C@@H]([C@H](c2ccccc2)c2cccc(F)c2)[C@H]2CCCN12] | (9aR,10S)-10-((R)-(3-fluorophenyl)(phenyl)methyl)-4-hydroxy-8,9,9a,10-tetrahydro-7H-pyrrolo[1',2':4,5]pyrazino[1,2-b]pyridazine-3,5-dione |
| 15 | 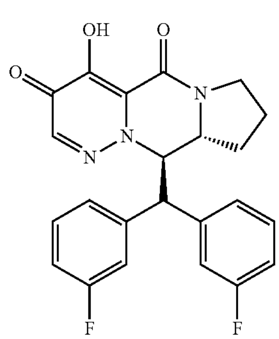 [SMILES: O=C1c2c(O)c(=O)cnn2[C@H](C(c2cccc(F)c2)c2cccc(F)c2)[C@H]2CCCN12] | (9aR,10R)-10-(bis(3-fluorophenyl)methyl)-4-hydroxy-8,9,9a,10-tetrahydro-7H-pyrrolo[1',2':4,5]pyrazino[1,2-b]pyridazine-3,5-dione |

TABLE 1a-continued

Compounds of the Preceding Examples.

| Example No. | Structure | Name |
|---|---|---|
| 16 | 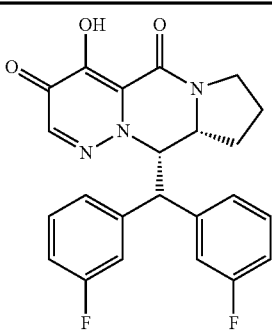 | (9aR,10S)-10-(bis(3-fluorophenyl)methyl)-4-hydroxy-8,9,9a,10-tetrahydro-7H-pyrrolo[1',2':4,5]pyrazino[1,2-b]pyridazine-3,5-dione |
| 17 | 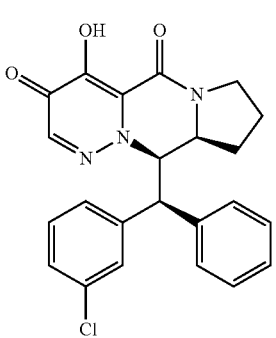 [SMILES: O=C1c2c(O)c(=O)cnn2[C@H]([C@@H](c2ccccc2)c2cccc(Cl)c2)[C@@H]2CCCN12] | (9aS,10R)-10-((S)-(3-chlorophenyl)(phenyl)methyl)-4-hydroxy-8,9,9a,10-tetrahydro-7H-pyrrolo[1',2':4,5]pyrazino[1,2-b]pyridazine-3,5-dione |
| 18 | 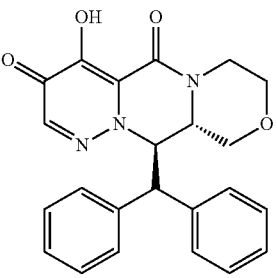 | (10aS,11R)-11-benzhydryl-4-hydroxy-7,8,10a,11-tetrahydro-10H-pyridazino[1',6':4,5]pyrazino[2,1-c][1,4]oxazine-3,5-dione |
| 19A | 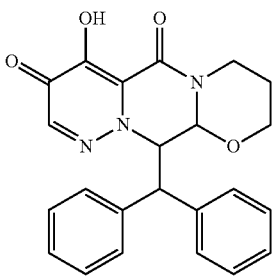 [SMILES: O=C1c2c(O)c(=O)cnn2C(C(c2ccccc2)c2ccccc2)C2OCCCN12] | 12-benzhydryl-7-hydroxy-3,4,12,12a-tetrahydro-2H-pyridazino[1',6':4,5]pyrazino[2,1-b][1,3]oxazine-6,8-dione |
| 19B | 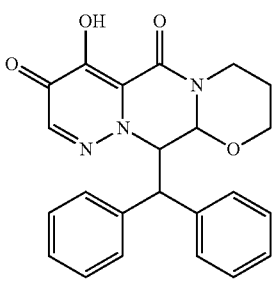 | 12-benzhydryl-7-hydroxy-3,4,12,12a-tetrahydro-2H-pyridazino[1',6':4,5]pyrazino[2,1-b][1,3]oxazine-6,8-dione |

TABLE 1b

| | Additional examples made by the method of Example 1. | |
|---|---|---|
| 20 | 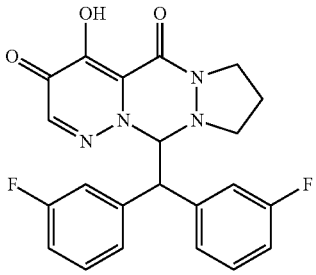 [SMILES: O=C1c2c(O)c(=O)cnn2C(C(c2cccc(F)c2)c2cccc(F)c2)N2CCCN12] | 425.2 (400 MHz, DMSO-d6) δ 7.49 (dt, J = 10.8, 1.9 Hz, 1H), 7.39-7.31 (m, 2H), 7.22-7.10 (m, 2H), 7.05 (dd, J = 10.0, 5.1 Hz, 2H), 6.95 (td, J = 8.6, 2.5 Hz, 1H), 6.75 (d, J = 10.2 Hz, 1H), 4.91 (d, J = 10.2 Hz, 1H), 4.03 (dt, J = 11.5, 6.7 Hz, 1H), 3.15-3.01 (m, 2H), 2.83 (q, J = 8.2 Hz, 1H), 2.04-1.85 (m, 3H) |
| 21 | 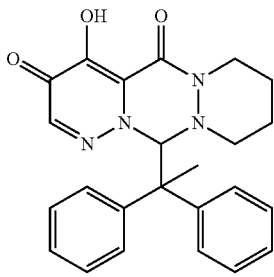 [SMILES: CC(c1ccccc1)(c1ccccc1)C1N2CCCCN2C(=O)c2c(O)c(=O)cnn21] | 417.2 (400 MHz, DMSO-d6) δ 7.67 (s, 1H), 7.31-7.11 (m, 8H), 7.10-7.01 (m, 2H), 6.30 (s, 1H), 3.88 (dd, J = 12.7, 4.6 Hz, 1H), 3.56 (d, J = 11.1 Hz, 1H), 2.89 (td, J = 11.5, 2.8 Hz, 1H), 2.66 (td, J = 12.7, 3.2 Hz, 1H), 1.81 (t, J = 12.6 Hz, 1H), 1.72 (d, J = 12.0 Hz, 1H), 1.61 (s, 4H), 1.44-1.24 (m, 1H) |
| 22 | 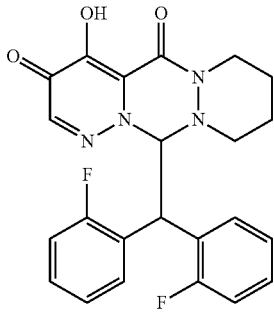 [SMILES: O=C1c2c(O)c(=O)cnn2C(C(c2ccccc2F)c2ccccc2F)N2CCCCN12] | 439.1 (400 MHz, DMSO-d6) δ 7.58-7.50 (m, 2H), 7.39-7.29 (m, 3H), 7.19-7.08 (m, 2H), 7.05-6.96 (m, 2H), 6.32 (d, J = 10.7 Hz, 1H), 4.73 (d, J = 10.7 Hz, 1H), 4.34-4.22 (m, 2H), 3.27-3.10 (m, 1H), 2.85 (dd, J = 12.1, 9.4 Hz, 1H), 2.41-2.29 (m, 1H), 1.64 (d, J = 12.0 Hz, 1H), 1.59-1.33 (m, 3H) |
| 23A | 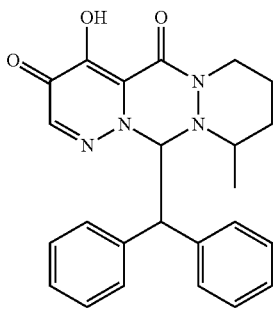 [SMILES: CC1CCCN2C(=O)c3c(O)c(=O)cnn3C(C(c3ccccc3)c3ccccc3)N12] | 417.1 (400 MHz, DMSO-d6) δ 7.55-7.46 (m, 2H), 7.34 (s, 1H), 7.30 (dt, J = 7.6, 4.1 Hz, 4H), 7.26-7.06 (m, 4H), 6.45 (d, J = 10.5 Hz, 1H), 4.57 (d, J = 10.5 Hz, 1H), 4.36-4.23 (m, 1H), 3.68 (m, 1H), 2.42-2.26 (m, 2H), 1.71-1.47 (m, 2H), 1.39 (t, J = 12.9 Hz, 2H), 0.69 (d, J = 6.5 Hz, 3H) |
| 23B | 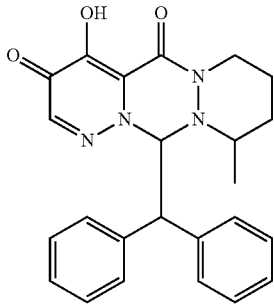 [SMILES: CC1CCCN2C(=O)c3c(O)c(=O)cnn3C(C(c3ccccc3)c3ccccc3)N12] | 417.1 (400 MHz, DMSO-d6) δ 7.57-7.50 (m, 2H), 7.40-7.28 (m, 5H), 7.21 (t, J = 7.3 Hz, 1H), 7.18-7.06 (m, 3H), 6.16 (d, J = 10.6 Hz, 1H), 4.66 (d, J = 10.6 Hz, 1H), 4.32 (dt, J = 12.8, 3.3 Hz, 1H), 2.91 (ddt, J = 12.4, 6.2, 3.1 Hz, 1H), 2.39 (ddd, J = 15.8, 8.3, 5.7 Hz, 1H), 1.70-1.59 (m, 1H), 1.54 (d, J = 9.3 Hz, 2H), 1.21-1.03 (m, 4H) |

TABLE 1b-continued

Additional examples made by the method of Example 1.

| 24 | 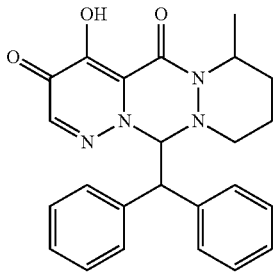 [SMILES: CC1CCCN2C(C(c3ccccc3)c3ccccc3)n3ncc(=O)c(O)c3C(=O)N12] | 417.3 | (400 MHz, DMSO-d6) δ 7.53-7.47 (m, 2H), 7.34-7.19 (m, 5H), 7.10 (dp, J = 30.0, 7.0 Hz, 5H), 6.34 (d, J = 11.1 Hz, 1H), 4.68-4.57 (m, 1H), 4.51 (d, J = 11.1 Hz, 1H), 3.35-3.13 (m, 1H), 2.80 (td, J = 11.1, 3.2 Hz, 1H), 1.71 (d. J = 9.8 Hz, 1H), 1.57 (tt, J = 12.8, 4.8 Hz, 1H), 1.43 (dt, J = 13.1, 3.4 Hz, 1H),1.31 (d, J = 13.0 Hz, 1H), 0.57 (d, J = 6.8 Hz, 3H) |
| --- | --- | --- | --- |
| 25A | 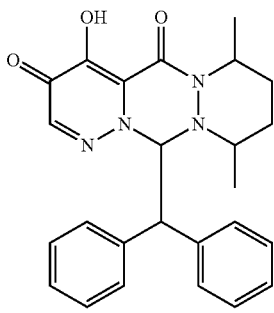 [SMILES: CC1CCC(C)N2C(C(c3ccccc3)c3ccccc3)n3ncc(=O)c(O)c3C(=O)N12] | 431.4 | (400 MHz, DMSO-d6) δ 7.58-7.47 (m, 2H), 7.38-7.27 (m, 2H), 7.25 (s, 1H), 7.22-7.05 (m, 6H), 6.52 (d, J = 11.2 Hz, 1H), 4.62-4.41 (m, 4H), 3.73 (q, J = 5.7 Hz, 2H), 1.95-1.67 (m, 2H), 1.33-1.02 (m, 2H), 0.69 (dd, J = 6.6, 4.3 Hz, 6H) |
| 25B | 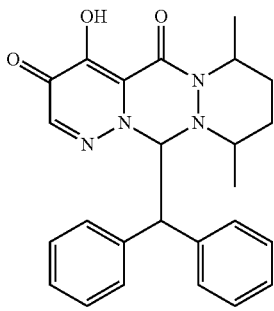 [SMILES: CC1CCC(C)N2C(C(c3ccccc3)c3ccccc3)n3ncc(=O)c(O)c3C(=O)N12] | 431.4 | (400 MHz, DMSO-d6) δ 7.59-7.52 (m, 2H), 7.43-7.37 (m, 2H), 7.36-7.27 (m, 3H), 7.23-7.09 (m, 4H), 6.08 (d, J = 10.4 Hz, 1H), 4.75 (d, J = 10.3 Hz, 1H), 2.86 (ddd, J = 11.2, 6.1, 2.6 Hz, 1H), 2.77-2.63 (m, 1H), 1.73 (s, 1H), 1.66 (ddd, J = 14.3, 9.0, 4.0 Hz, 1H), 1.57 (d, J = 7.1 Hz, 4H), 1.26-1.11 (m, 1H), 1.06 (d, J = 6.1 Hz, 3H) |
| 26A | 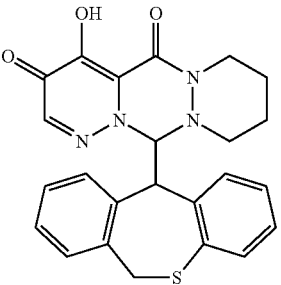 | 447.1 | (400 MHz, DMSO-d6) δ 7.43 (s, 1H), 7.34-7.12 (m, 4H), 7.08-7.00 (m, 2H), 6.75 (d, J = 7.7 Hz, 1H), 6.22 (d, J = 9.8 Hz, 1H), 4.80 (d, J = 15.0 Hz, 1H), 4.64 (d, J = 9.9 Hz, 1H), 4.22 (d, J = 12.4 Hz, 1H), 3.90 (dd, J = 15.4, 10.5 Hz, 1H), 3.30 (d, J = 11.0 Hz, 1H), 2.82 (t, J = 10.5 Hz, 1H), 2.18-2.00 (m, 2H), 1.67-1.55 (m, 2H), 1.45 (d, J = 14.7 Hz, 4H) |
| 26B | 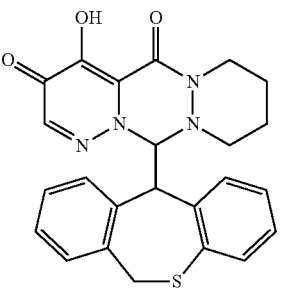 [SMILES: O=C1c2c(O)c(=O)cnn2C(C2c3ccccc3CSc3ccccc32)N2CCCCN12] | 447.1 | (400 MHz, DMSO-d6) δ 7.32-7.21 (m, 3H), 7.16 (q, J = 7.4, 6.8 Hz, 3H), 6.95 (td, J = 7.3, 2.1 Hz, 1H), 6.81 (d, J = 7.4 Hz, 1H), 6.45 (d, J = 10.5 Hz, 1H), 4.93 (d, J = 15.6 Hz, 1H), 4.66 (t, J = 10.3 Hz, 1H), 4.49-4.39 (m, 1H), 3.90 (dd, J = 15.3, 10.4 Hz, 3H), 3.11 (d, J = 11.7 Hz, 1H), 2.92-2.76 (m, 2H), 1.61 (d, J = 8.2 Hz, 2H), 1.48 (t, J = 9.2 Hz, 3H) |

TABLE 1b-continued

Additional examples made by the method of Example 1.

| | | | |
|---|---|---|---|
| 27A | 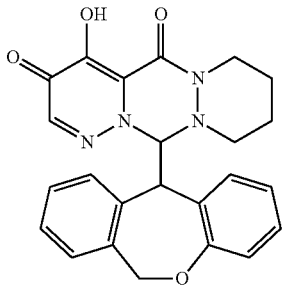 | 431.4 | (400 MHz, DMSO-d6) δ 7.32-7.25 (m, 4H), 7.21-7.12 (m, 2H), 6.94 (d, J = 7.9 Hz, 1H), 6.77-6.66 (m, 2H), 5.94 (d, J = 10.0 Hz, 1H), 5.70 (d, J = 15.2 Hz, 1H), 4.96 (d, J = 15.2 Hz, 1H), 4.50 (dd, J = 12.2, 8.4 Hz, 3H), 3.04 (d, J = 11.1 Hz, 1H), 2.94-2.75 (m, 2H), 1.72-1.39 (m, 4H) |
| 27B | 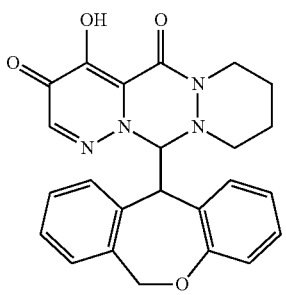 | 431.4 | (400 MHz, DMSO-d6) δ 7.27 (ddd, J = 7.5, 5.0, 2.6 Hz, 2H), 7.23 (s, 1H), 7.20-7.14 (m, 1H), 7.07 (dd, J = 19.1, 7.7 Hz, 3H), 6.95 (td, J = 7.5, 1.5 Hz, 1H), 6.68 (d, J = 7.6 Hz, 1H), 6.00 (d, J = 10.0 Hz, 1H), 5.69 (d, J = 15.3 Hz, 1H), 4.95 (d, J = 15.3 Hz, 1H), 4.54-4.39 (m, 3H) |
| 28A | 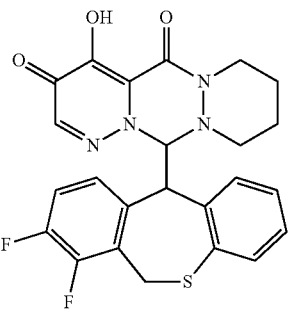 [SMILES: O=C1c2c(O)c(=O)cnn2C(C2c3ccccc3SCc3c2ccc(F)c3F)N2CCCCN12] | 483.1 | (400 MHz, DMSO-d6) δ 7.41 (s, 1H), 7.32 (td, J = 7.2, 3.1 Hz, 2H), 7.27-7.17 (m, 2H), 7.09 (q, J = 8.8 Hz, 1H), 6.76 (t, J = 7.1 Hz, 1H), 6.52 (d, J = 10.4 Hz, 1H), 4.89-4.70 (m, 2H), 4.39 (d, J = 12.5 Hz, 1H), 4.05 (d, J = 16.5 Hz, 1H), 3.08 (d, J = 10.9 Hz, 1H), 2.87 (t, J = 10.2 Hz, 1H), 2.67-2.52 (m, 2H), 1.68-1.54 (m, 2H), 1.46 (s, 2H) |
| 28B | 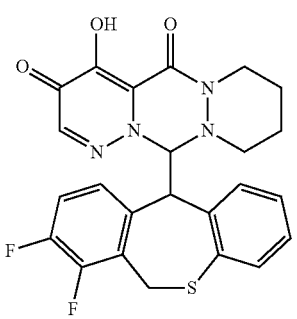 [SMILES: O=C1c2c(O)c(=O)cnn2C(C2c3ccccc3SCc3c2ccc(F)c3F)N2CCCCN12] | 483.1 | (400 MHz, DMSO-d6) δ 7.42 (s, 1H), 7.32 (q, J = 8.9 Hz, 1H), 7.19 (dd, J = 8.9, 5.0 Hz, 1H), 7.14-7.03 (m, 2H), 6.88 (td, J = 7.3, 6.9, 1.9 Hz, 1H), 6.77 (d, J = 7.7 Hz, 1H), 6.27 (d, J = 9.8 Hz, 1H), 4.82 (d, J = 9.8 Hz, 1H), 4.64 (dd, J = 15.8, 2.2 Hz, 1H), 4.30-4.20 (m, 1H), 4.09 (d, J = 15.8 Hz, 1H), 3.28 (d, J = 11.7 Hz, 1H), 2.88-2.75 (m, 1H), 2.33-2.17 (m, 1H), 1.67-1.34 (m, 4H) |

TABLE 1c

Additional compounds prepared by the method of Examples 8-9.

| Example No. | Structure | Mass M + H | 1H NMR |
|---|---|---|---|
| 29 | 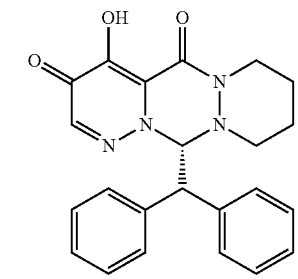 [SMILES: O=C1c2c(O)c(=O)cnn2[C@@H](C(c2ccccc2)c2ccccc2)N2CCCCN12] | 403.1 | (400 MHz, DMSO-d6) δ 7.49 (d, J = 7.3 Hz, 2H), 7.36-7.23 (m, 5H), 7.22-7.05 (m, 4H), 6.32 (d, J = 10.6 Hz, 1H), 4.60 (d, J = 10.5 Hz, 1H), 4.35-4.23 (m, 1H), 3.23 (d, J = 10.9 Hz, 2H), 2.84 (td, J = 10.9, 2.6 Hz, 1H), 2.40 (td, J = 12.4, 2.8 Hz, 1H), 1.64 (d, J = 11.7 Hz, 1H), 1.60-1.33 (m, 3H) |
| 30 | 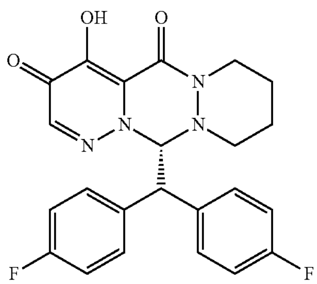 | 439.4 | (400 MHz, DMSO-d6) δ 7.58-7.50 (m, 2H), 7.39-7.29 (m, 3H), 7.13 (t, J = 8.9 Hz, 2H), 7.01 (t, J = 8.8 Hz, 2H), 6.32 (d, J = 10.7 Hz, 1H), 4.73 (d, J = 10.7 Hz, 1H), 4.40-4.13 (m, 1H), 3.20 (d, J = 10.5 Hz, 2H), 2.85 (dd, J = 12.3, 9.4 Hz, 1H), 2.45-2.29 (m, 1H), 1.64 (d, J = 11.7 Hz, 1H), 1.49 (dt, J = 37.6, 12.3 Hz, 3H) |
| 31 | 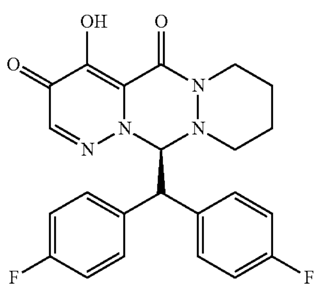 | 439.4 | (400 MHz, DMSO-d6) δ 7.54 (dd, J = 8.6, 5.6 Hz, 2H), 7.40-7.29 (m, 3H), 7.13 (t, J = 8.8 Hz, 2H), 7.01 (t, J = 8.8 Hz, 2H), 6.32 (d, J = 10.7 Hz, 1H), 4.73 (d, J = 10.7 Hz, 1H), 4.29 (dd, J = 11.9, 3.5 Hz, 1H), 3.20 (d, J = 10.8 Hz, 2H), 2.85 (dd, J = 12.3, 9.4 Hz, 1H), 2.45-2.28 (m, 1H), 1.64 (d, J = 12.2 Hz, 1H), 1.59-1.37 (m, 3H) |

General Synthesis of Chiral N-Boc Amino Alcohols

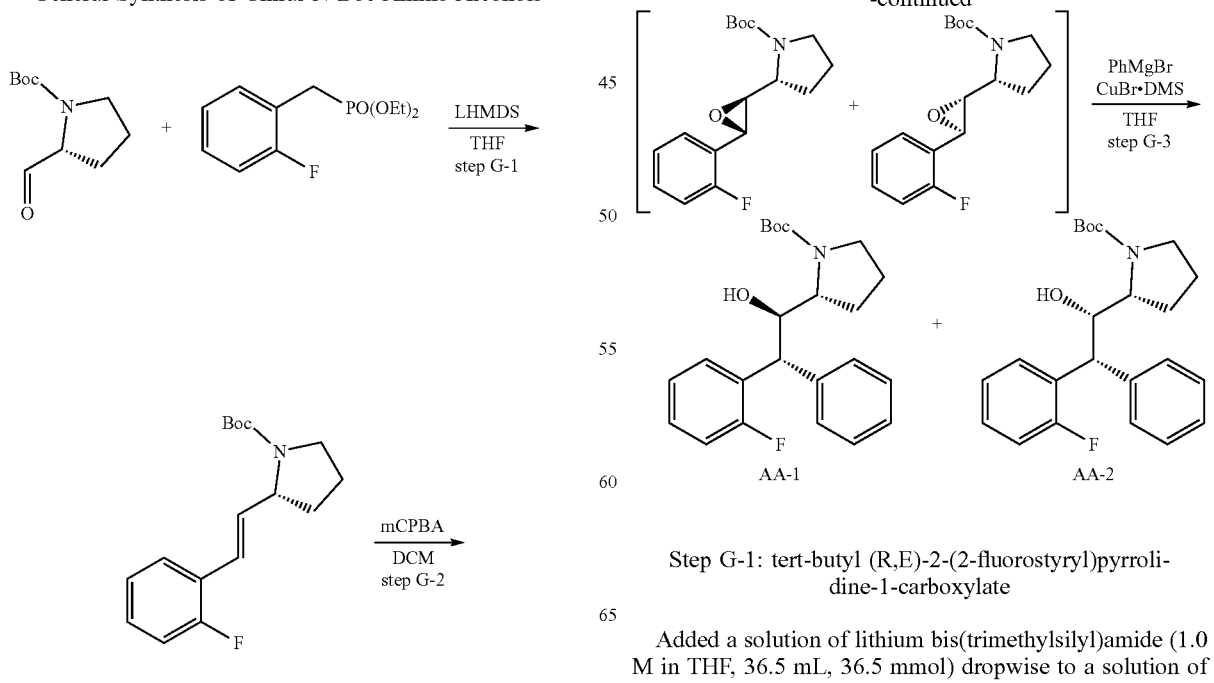

Step G-1: tert-butyl (R,E)-2-(2-fluorostyryl)pyrrolidine-1-carboxylate

Added a solution of lithium bis(trimethylsilyl)amide (1.0 M in THF, 36.5 mL, 36.5 mmol) dropwise to a solution of diethyl 2-fluorobenzylphosphonate (9.08 g, 36.9 mmol) in THF (80 mL) at 0° C. Stirred at 0° C. for 20 minutes, then added a solution of (R)-tert-butyl 2-formylpyrrolidine-1-carboxylate (7 g, 35.1 mmol) in THF (30 mL) dropwise. Reaction mixture was stirred in ice bath for 1 h and then slowly warmed to RT over 1 h and then stirred for an additional 1 h at RT. The reaction was quenched with water and extracted with EtOAc (twice). The combined organic extracts were washed with brine, dried over Na₂SO₄, filtered and concentrated. Silica gel column chromatography (EtOAc/heptane) provided tert-butyl (R,E)-2-(2-fluorostyryl)pyrrolidine-1-carboxylate (6.5 g, white solid) in 64% yield. MS m/z 236.3 (M-tBu+H).

Step G-2: tert-butyl (R)-2-((2S,3S)-3-(2-fluorophenyl)oxiran-2-yl)pyrrolidine-1-carboxylate and tert-butyl (R)-2-((2R,3R)-3-(2-fluorophenyl)oxiran-2-yl)pyrrolidine-1-carboxylate To tert-butyl (R,E)-2-(2-fluorostyryl)pyrrolidine-1-carboxylate (1.85 g, 6.35 mmol) in DCM (60 mL) was added mCPBA (7.83 g, 31.7 mmol). The reaction mixture was stirred at RT for 2H. The reaction was quenched with water and extracted with DCM (twice). The combined organic extracts were washed sequentially with saturated aqueous Na₂S₂O₃, saturated aqueous NaHCO₃ and brine. The organic layer was then dried over Na₂SO₄, filtered and concentrated. Silica gel column chromatography (EtOAc/heptane) provided an inseparable mixture of tert-butyl (R)-2-((2S,3S)-3-(2-fluorophenyl)oxiran-2-yl)pyrrolidine-1-carboxylate and tert-butyl (R)-2-((2R,3R)-3-(2-fluorophenyl)oxiran-2-yl)pyrrolidine-1-carboxylate (1.6 g, colorless oil) in 41% yield. The mixture was used in the next step without further purification.

Step G-3: tert-butyl (R)-2-((1R,2R)-2-(2-fluorophenyl)-1-hydroxy-2-phenylethyl)pyrrolidine-1-carboxylate and tert-butyl (R)-2-((1S,2S)-2-(2-fluorophenyl)-1-hydroxy-2-phenylethyl)pyrrolidine-1-carboxylate Added copper(I) bromide-dimethyl sulfide complex (0.495 g, 2.408 mmol) to a mixture of tert-butyl (R)-2-((2S,3S)-3-(2-fluorophenyl)oxiran-2-yl)pyrrolidine-1-carboxylate and tert-butyl (R)-2-((2R,3R)-3-(2-fluorophenyl)oxiran-2-yl)pyrrolidine-1-carboxylate (0.74 g, 2.41 mmol) in THF (30 mL) at RT. Cooled to between −20 and −30° C. in an acetone bath with periodic dry ice additions. A solution of phenylmagnesium bromide (1.0 M in THF, 9.63 mL, 9.63 mmol) was added dropwise. Stirred 15 min and allowed the temperature to warm to 0° C. Added 2 equiv more of phenylmagnesium bromide and stirred another 20 min. Added another 2 equiv of phenylmagnesium bromide and stirred another 20 min. The reaction was quenched with saturated aqueous NH₄Cl solution and extracted with EtOAc (2 times). The combined organic extracts were dried over Na₂SO₄, filtered and concentrated. Silica gel column chromatography (EtOAc/heptane) provided tert-butyl (R)-2-((1R,2R)-2-(2-fluorophenyl)-1-hydroxy-2-phenylethyl)pyrrolidine-1-carboxylate (353 mg, colorless oil, eluted first) in 38% yield and tert-butyl (R)-2-((1S,2S)-2-(2-fluorophenyl)-1-hydroxy-2-phenylethyl)pyrrolidine-1-carboxylate (300 mg, white foam, eluted second) in 32% yield. MS m/z 286.2 (MH+−Boc).

Example 32. (9aR,10S)-10-((R)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione

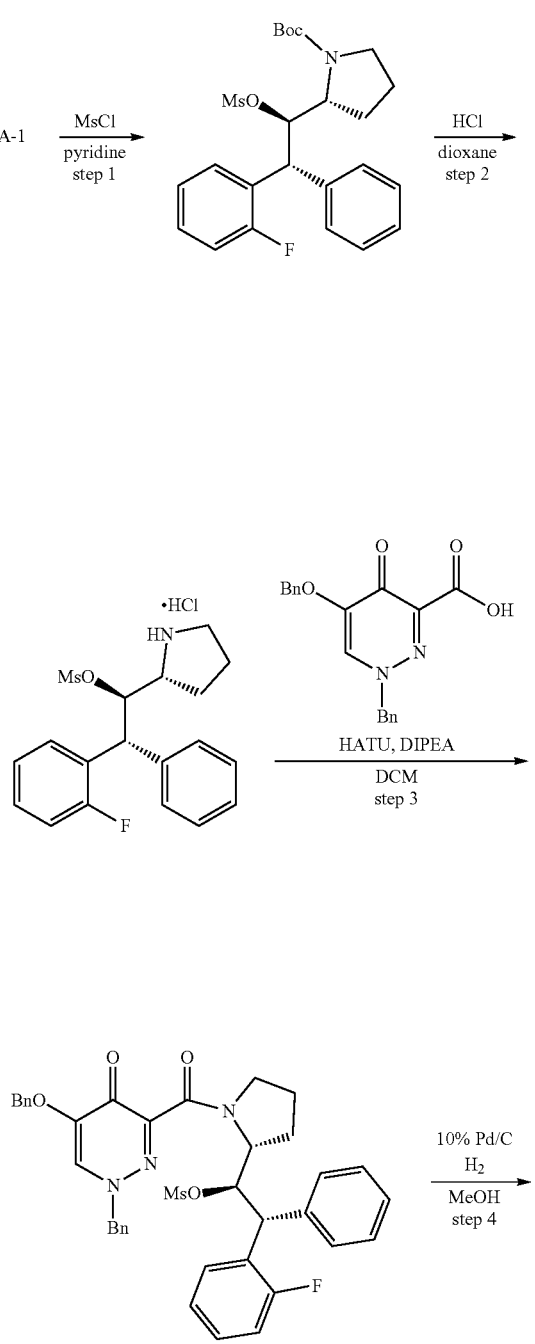

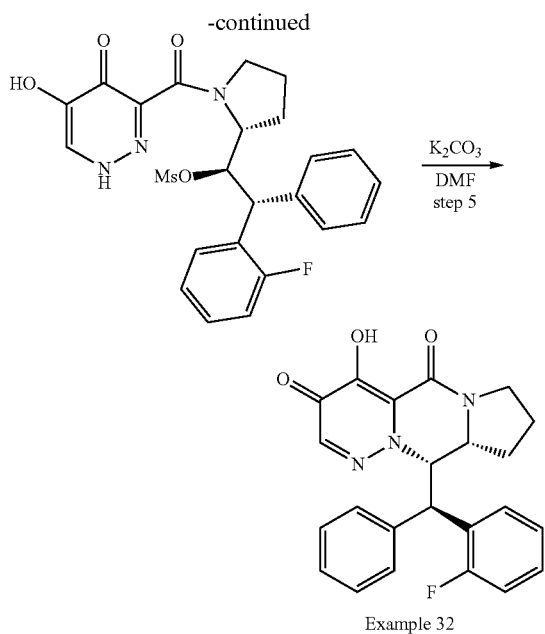

Example 32

Step 1: tert-butyl (R)-2-((1R,2R)-2-(2-fluorophenyl)-1-((methylsulfonyl)oxy)-2-phenylethyl)pyrrolidine-1-carboxylate To a solution of tert-butyl (R)-2-((1R,2R)-2-(2-fluorophenyl)-1-hydroxy-2-phenylethyl)pyrrolidine-1-carboxylate (470 mg, 0.914 mmol) in pyridine (9 mL) at 0° C. was added methanesulfonyl chloride (1.069 mL, 13.72 mmol). After 5 min the ice bath was removed and the reaction was stirred for 2 h at RT. The reaction mixture was then partitioned between DCM and water. The DCM layer was separated and washed with saturated aqueous NaHCO$_3$, then brine, dried over Na$_2$SO$_4$, filtered and concentrated. Silica gel column chromatography (EtOAc/heptane) provided tert-butyl (R)-2-((1R,2R)-2-(2-fluorophenyl)-1-((methylsulfonyl)oxy)-2-phenylethyl)pyrrolidine-1-carboxylate (350 mg, white foam) in 83% yield. MS m/z 408.4 (MH+−tBu).

Step 2: (1R,2R)-2-(2-fluorophenyl)-2-phenyl-1-((R)-pyrrolidin-2-yl)ethyl methanesulfonate hydrochloride Added HCl (4.0 M in dioxane, 5 ml, 20 mmol) to tert-butyl (R)-2-((1R,2R)-2-(2-fluorophenyl)-1-((methylsulfonyl)oxy)-2-phenylethyl)pyrrolidine-1-carboxylate (350 mg, 0.755 mmol). Stirred for 1 h at RT. The reaction was then concentrated to give (1R,2R)-2-(2-fluorophenyl)-2-phenyl-1-((R)-pyrrolidin-2-yl)ethyl methanesulfonate hydrochloride, which was used in the next step without further purification. MS m/z 364.5 (MH+).

Step 3: (1R,2R)-1-((R)-1-(1-benzyl-5-(benzyloxy)-4-oxo-1,4-dihydropyridazine-3-carbonyl)pyrrolidin-2-yl)-2-(2-fluorophenyl)-2-phenylethyl methanesulfonate Added Huenig's Base (0.519 mL, 2.97 mmol) and HATU (367 mg, 0.966 mmol) to a solution of 1-benzyl-5-(benzyloxy)-4-oxo-1,4-dihydropyridazine-3-carboxylic acid (275 mg, 0.817 mmol) in DCM (6 mL) at RT. Stirred at RT for 15 min, then added a solution of crude (1R,2R)-2-(2-fluorophenyl)-2-phenyl-1-((R)-pyrrolidin-2-yl)ethyl methanesulfonate hydrochloride (270 mg, 0.743 mmol) in DCM (4 mL) and 2 equiv of Huenig's base. The mixture was stirred at RT for 1H. The reaction was then diluted with DCM and washed with water and brine. The organic layer was dried over Na$_2$SO$_4$, filtered and concentrated. Silica gel column chromatography (EtOAc/EtOH/heptane) provided (1R,2R)-1-((R)-1-(1-benzyl-5-(benzyloxy)-4-oxo-1,4-dihydropyridazine-3-carbonyl)pyrrolidin-2-yl)-2-(2-fluorophenyl)-2-phenylethyl methanesulfonate (470 mg) in 93% yield. MS m/z 682.5 (MH+).

Step 4: (1R,2R)-2-(2-fluorophenyl)-1-((R)-1-(5-hydroxy-4-oxo-1,4-dihydropyridazine-3-carbonyl)pyrrolidin-2-yl)-2-phenylethyl methanesulfonate A solution of (1R,2R)-1-((R)-1-(1-benzyl-5-(benzyloxy)-4-oxo-1,4-dihydropyridazine-3-carbonyl)pyrrolidin-2-yl)-2-(2-fluorophenyl)-2-phenylethyl methanesulfonate (470 mg, 0.689 mmol) in methanol (12 mL) was purged with nitrogen. Added 10% palladium on carbon (220 mg, 0.207 mmol) and attached a hydrogen balloon. The flask was evacuated and refilled with hydrogen (3 times) and then stirred vigorously for 6 h at RT under a balloon of hydrogen. The reaction mixture was filtered through celite and the filter cake was washed with MeOH. The filtrate was concentrated to provide crude (1R,2R)-2-(2-fluorophenyl)-1-((R)-1-(5-hydroxy-4-oxo-1,4-dihydropyridazine-3-carbonyl)pyrrolidin-2-yl)-2-phenylethyl methanesulfonate which was used in the next step without further purification. MS m/z 502.4 (MH+).

Step 5: (9aR,10S)-10-((R)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione To a solution of crude (1R,2R)-2-(2-fluorophenyl)-1-((R)-1-(5-hydroxy-4-oxo-1,4-dihydropyridazine-3-carbonyl)pyrrolidin-2-yl)-2-phenylethyl methanesulfonate (345 mg, 0.619 mmol) in DMF (10 mL) was added potassium carbonate (342 mg, 2.476 mmol) and the mixture was stirred overnight at RT. The reaction was filtered through a 1 micron filter and purified by reverse phase HPLC. Product fractions were combined, frozen and lyophilized to afford a formate salt of (9aR,10S)-10-((R)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione (125 mg, 0.275 mmol, white solid) in 44% yield over two steps. $^1$H NMR (400 MHz, CD$_3$OD) δ ppm 7.91 (td, J=7.36, 2.01 Hz, 1H) 7.26-7.42 (m, 3H) 7.02-7.17 (m, 4H) 6.96 (dd, J=6.38, 2.96 Hz, 2H) 5.79 (dd, J=9.56, 3.59 Hz, 1H) 4.69 (d, J=9.63 Hz, 1H) 4.52 (dt, J=9.96, 5.12 Hz, 1H) 3.84-3.99 (m, 1H) 3.57-3.73 (m, 1H) 2.01-2.12 (m, 1H) 1.91-2.00 (m, 1H) 1.78-1.91 (m, 1H) 1.55 (qd, J=11.56, 6.80 Hz, 1H). MS m/z 406.4 (MH+).

TABLE 1d

Additional compounds prepared by the method of Example 32.

| Example No. | Structure | Mass M + H | 1H NMR |
|---|---|---|---|
| 33 | 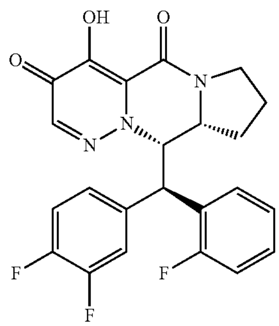 [SMILES: O=C1c2c(O)c(=O)cnn2[C@@H]([C@H](c2ccc(F)c(F)c2)c2ccccc2F)[C@H]2CCCN12] | 442.4 | (400 MHz, MeOD) δ ppm 7.84-7.96 (m, 1 H) 7.46 (S, 1 H) 7.29-7.43 (m, 2 H) 7.08-7.20 (m, 1 H) 6.90-7.06 (m, 2 H) 6.78 (br d, J = 8.46 Hz, 1 H) 5.81 (dd, J = 9.95, 3.64 Hz, 1 H) 4.72 (d, J = 9.98 Hz, 1 H) 4.52 (dt, J = 10.12, 5.11 Hz, 1 H) 3.82-3.96 (m, 1 H) 3.63 (td, J = 11.20, 7.43 Hz, 1 H) 1.98-2.09 (m, 1 H) 1.75-1.97 (m, 2 H) 1.47 (qd, J = 11.61, 6.70 Hz, 1 H) |
| 34 | 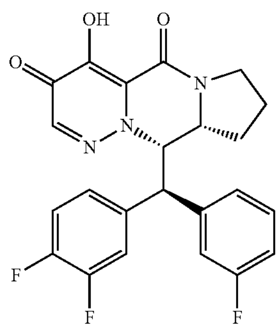 [SMILES: O=C1c2c(O)c(=O)cnn2[C@@H]([C@@H](c2cccc(F)c2)c2ccc(F)c(F)c2)[C@H]2CCCN12] | 442.3 | (400 MHz, MeOD) δ ppm 1.47-1.62 (m, 1 H) 1.74-1.95 (m, 2 H) 2.00-2.11 (m, 1 H) 3.67 (td, J = 11.08, 7.38 Hz, 1 H) 3.80-3.96 (m, 1H) 4.44-4.55 (m, 1 H) 4.62 (d, J = 9.83 Hz, 1 H) 5.76 (dd, J = 9.83, 3.57 Hz, 1 H) 6.70-6.84 (m, 1 H) 6.90-7.02 (m, 2 H) 7.03-7.11 (m, 1 H) 7.33-7.53 (m, 4 H) |
| 35 | 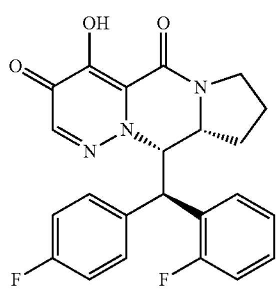 | 424.2 | (400 MHz, MeOD) δ ppm 7.84-7.94 (m, 1 H) 7.28-7.44 (m, 3 H) 7.07-7.17 (m, 1 H) 7.01 (dd, J = 8.58, 5.31 Hz, 2 H) 6.82 (t, J = 8.71 Hz, 2 H) 5.79 (dd, J = 9.78, 3.57 Hz, 1 H) 4.70 (d, J = 9.78 Hz, 1 H) 4.52 (dt, J = 10.20, 4.98 Hz, 1 H) 3.81-3.96 (m, 1 H) 3.63 (td, J = 11.19, 7.31 Hz, 1 H) 2.00-2.10 (m, 1 H) 1.77-1.99 (m, 2 H) 1.51 (qd, J = 11.52, 6.63 Hz, 1 H) |
| 36 | 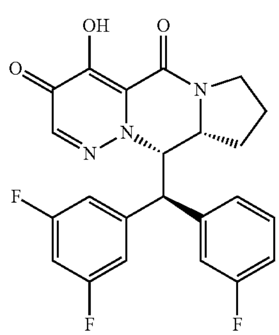 [SMILES: O=C1c2c(O)c(=O)cnn2[C@@H]([C@@H](c2cccc(F)c2)c2cc(F)cc(F)c2)[C@H]2CCCN12] | 442.5 | (400 MHz, MeOD) δ ppm 1.54 (qd, J = 11.62, 7.14 Hz, 1 H) 1.73-1.93 (m, 2 H) 1.99-2.11 (m, 1 H) 3.67 (td, J = 11.08, 7.53 Hz, 1 H) 3.81-3.94 (m, 1 H) 4.45-4.57 (m, 1 H) 4.66 (d, J = 9.88 Hz, 1 H) 5.78 (dd, J = 9.85, 3.55 Hz, 1 H) 6.57-6.79 (m, 3 H) 7.06-7.16 (m, 1 H) 7.35-7.54 (m, 4 H) |

TABLE 1d-continued

Additional compounds prepared by the method of Example 32.

| Example No. | Structure | Mass M + H | 1H NMR |
|---|---|---|---|
| 37 | 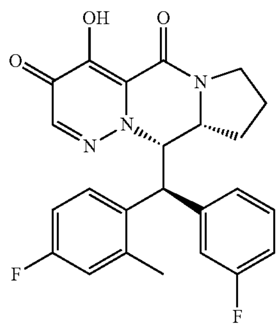 [SMILES: Cc1cc(F)ccc1[C@H](c1cccc(F)c1)[C@H]1[C@H]2CCCN2C(=O)c2c(O)c(=O)cnn21] | 438.3 | (400 MHz, MeOD) δ ppm 1.56 (qd, J = 11.84, 6.46 Hz, 1 H) 1.76-2.11 (m, 3 H) 2.13-2.40 (m, 3 H) 3.66 (td, J = 11.33, 7.36 Hz, 1 H) 3.82-3.99 (m, 1 H) 4.48-4.65 (m, 1 H) 5.88 (br s, 1 H) 6.60-6.82 (m, 2 H) 6.95-7.12 (m, 1 H) 7.21 (br s, 1 H) 7.30-7.45 (m, 3 H) |
| 38 | 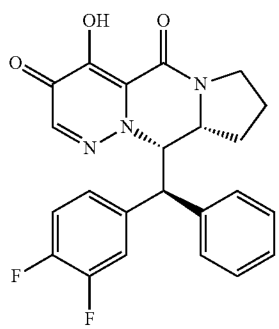 [SMILES: O=C1c2c(O)c(=O)cnn2[C@@H]([C@@H](c2ccccc2)c2ccc(F)c(F)c2)[C@H]2CCCN12] | 424.4 | (400 MHz, MeOD) δ ppm 7.56 (d, J = 7.58 Hz, 2 H) 7.37-7.48 (m, 3 H) 7.26-7.36 (m, 1 H) 6.85-7.05 (m, 2 H) 6.77 (dt, J = 4.36, 2.05 Hz, 1 H) 5.76 (dd, J = 9.93, 3.62 Hz, 1 H) 4.45-4.64 (m, 2 H) 3.87 (br dd, J = 12.86, 7.83 Hz, 1 H) 3.58-3.72 (m, 1 H) 1.94-2.10 (m, 1 H) 1.70-1.91 (m, 2 H) 1.46-1.64 (m, 1 H) |
| 39 | 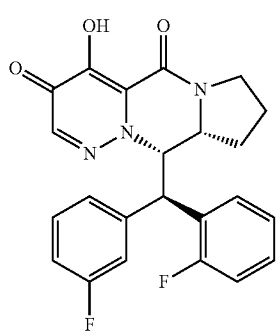 [SMILES: O=C1c2c(O)c(=O)cnn2[C@@H]([C@H](c2cccc(F)c2)c2ccccc2F)[C@H]2CCCN12] | 424.4 | (400 MHz, MeOD) δ ppm 7.82-7.99 (m, 1 H) 7.26-7.47 (m, 3 H) 7.01-7.20 (m, 2 H) 6.69-6.92 (m, 3 H) 5.81 (dd, J = 9.78, 3.57 Hz, 1H) 4.73 (d, J = 9.78 Hz, 1 H) 4.52 (dt, J = 10.04, 5.08 Hz, 1 H) 3.82-3.93 (m, 1 H) 3.64 (td, J = 11.16, 7.36 Hz, 1 H) 2.01-2.10 (m, 1 H) 1.76-1.99 (m, 2 H) 1.51 (qd, J = 11.53, 6.63 Hz, 1 H) |
| 40 | 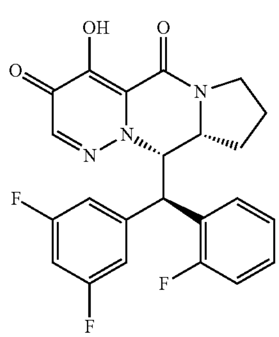 [SMILES: O=C1c2c(O)c(=O)cnn2[C@@H]([C@H](c2cc(F)cc(F)c2)c2ccccc2F)[C@H]2CCCN12] | 442.4 | (400 MHz, MeOD) δ ppm 7.81-7.96 (m, 1 H) 7.45 (s, 1 H) 7.31-7.44 (m, 2 H) 7.06-7.21 (m, 1 H) 6.52-6.79 (m, 3 H) 5.83 (dd, J = 9.98, 3.62 Hz, 1 H) 4.75 (d, J = 9.98 Hz, 1 H) 4.52 (dt, J = 10.36, 4.97 Hz, 1 H) 3.81-3.95 (m, 1 H) 3.63 (td, J = 11.21, 7.36 Hz, 1 H) 1.98-2.08 (m, 1 H) 1.89-1.97 (m, 1 H) 1.73-1.88 (m, 1 H) 1.47 (qd, J = 11.59, 6.70 Hz, 1 H) |

TABLE 1d-continued

Additional compounds prepared by the method of Example 32.

| Example No. | Structure | Mass M + H | 1H NMR |
|---|---|---|---|
| 41 | 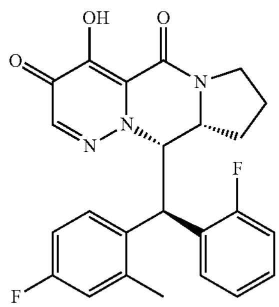 [SMILES: Cc1cc(F)ccc1[C@H](c1ccccc1F)[C@H]1[C@H]2CCCN2C(=O)c2c(O)c(=O)cnn21] | 438.4 | 1H NMR (400 MHz, MeOD) δ ppm 7.88-7.99 (m, 1 H) 7.40 (s. 1 H) 7.27-7.37 (m, 2 H) 7.24 (br s, 1 H) 7.05-7.14 (m, 1 H) 6.61-6.78 (m, 2 H) 5.89 (br d, J = 9.05 Hz, 1 H) 5.02 (br d, J = 10.17 Hz, 1 H) 4.51-4.61 (m, 1 H) 3.84-3.98 (m, 1 H) 3.60 (td, J = 11.25, 7.34 Hz, 1 H) 2.23 (s, 3 H) 2.00-2.07 (m, 1 H) 1.94 (dt, J = 11.99, 5.91 Hz, 1 H) 1.77-1.89 (m, 1 H) 1.36-1.54 (m, 1 H) |
| 42 | 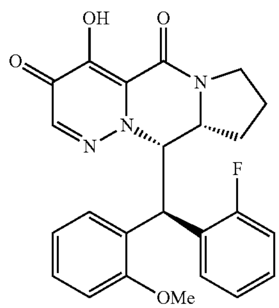 [SMILES: COc1ccccc1[C@H](c1ccccc1F)[C@H]1[C@H]2CCCN2C(=O)c2c(O)c(=O)cnn21] | 438.4 | (400 MHz, MeOD) δ ppm 7.83-7.96 (m, 1 H) 7.24-7.44 (m, 3 H) 6.98-7.15 (m, 2 H) 6.93 (dd, J = 7.65, 1.30 Hz, 1 H) 6.57-6.77 (m, 2 H) 5.71 (dd, J = 10.05, 3.59 Hz, 1 H) 5.46 (d, J = 10.03 Hz, 1 H) 4.49 (br dd, J = 10.07, 5.04 Hz, 1 H) 3.87-3.98 (m, 1 H) 3.54-3.69 (m, 4 H) 2.01-2.12 (m, 1 H) 1.80-1.96 (m, 2 H) 1.44-1.60 (m, 1 H) |
| 43 | 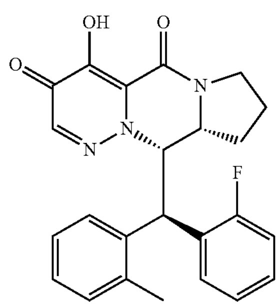 [SMILES: Cc1ccccc1[C@H](c1ccccc1F)[C@H]1[C@H]2CCCN2C(=O)c2c(O)c(=O)cnn21] | 420.4 | (400 MHz, MeOD) δ ppm 7.88-8.04 (m, 1 H) 7.29-7.41 (m, 3 H) 7.22 (br d, J = 6.60 Hz, 1 H) 7.02-7.12 (m, 1 H) 6.87-7.02 (m, 3 H) 5.90 (br d, J = 7.63 Hz, 1 H) 5.06 (br d, J = 10.51 Hz, 1 H) 4.55 (dt, J = 10.29, 5.07 Hz, 1 H) 3.86-3.99 (m, 1 H) 3.61 (td, J = 11.35, 7.43 Hz, 1 H) 2.22 (s, 3 H) 2.00-2.11 (m, 1 H) 1.76-1.99 (m, 2 H) 1.41-1.54 (m, 1 H) |
| 44 | 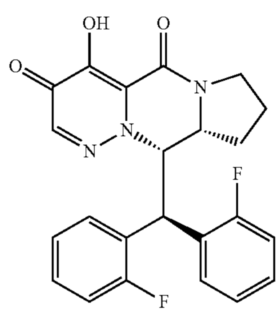 | 424.4 | (400 MHz, MeOD) δ ppm 7.95 (br t, J = 7.87 Hz, 1 H) 7.32-7.43 (m, 3 H) 7.04-7.15 (m, 3 H) 6.91-6.99 (m, 1 H) 6.80-6.88 (m, 1 H) 5.76-5.92 (m, 1 H) 5.17 (d, J = 9.88 Hz, 1 H) 4.50-4.59 (m, 1 H) 3.84-3.94 (m, 1 H) 3.57-3.68 (m, 1 H) 2.02-2.11 (m, 1 H) 1.80-1.99 (m, 2 H) 1.47-1.59 (m, 1 H) |
| 45 | 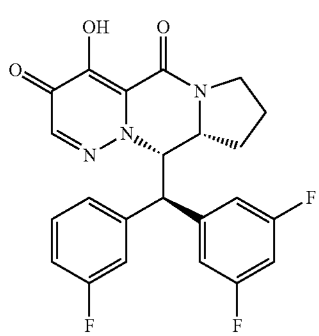 [SMILES: O=C1c2c(O)c(=O)cnn2[C@@H]([C@H](c2cccc(F)c2)c2cc(F)cc(F)c2)[C@H]2CCCN12] | 442.4 | (500 MHz, CHLOROFORM-d) δ ppm 7.38 (s, 1 H) 7.09 (td, J = 7.98, 5.91 Hz, 1 H) 6.97 (d, J = 6.52 Hz, 2 H) 6.80-6.88 (m, 2 H) 6.68 (d, J = 10.11 Hz, 1 H) 6.63 (d, J = 7.66 Hz, 1 H) 5.33 (dd, J = 9.52, 3.61 Hz, 1 H) 4.41-4.47 (m, 1 H) 4.28 (d, J = 9.46 Hz, 1 H) 3.94-4.01 (m, 1 H) 3.66 (td, J = 11.41, 7.21 Hz, 1 H) 2.09-2.29 (m, 1 H) 1.86-2.09 (m, 2 H) 1.58 (qd, J = 11.88, 6.80 Hz, 1 H) |

TABLE 1d-continued

Additional compounds prepared by the method of Example 32.

| Example No. | Structure | Mass M + H | 1H NMR |
|---|---|---|---|
| 46 | 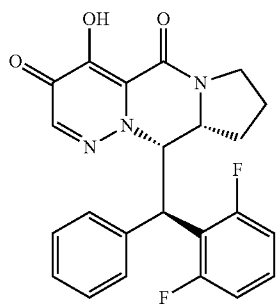 [SMILES: O=C1c2c(O)c(=O)cnn2[C@@H]([C@H](c2ccccc2)c2c(F)cccc2F)[C@H]2CCCN12] | 424.3 | (500 MHz, CD3OD) δ ppm 7.47-7.35 (m, 1H), 7.29 (s, 1H), 7.17-7.05 (m, 7H), 6.00 (d, J = 9.7 Hz, 1H), 4.69 (d, J = 10.0 Hz, 1H), 4.56 (s, 1H), 3.99-3.87 (m, 1H), 3.69-3.56 (m, 1H), 2.06 (s, 2H), 1.89 (s, 1H), 1.60-1.43 (m, 1H) |
| 47 | 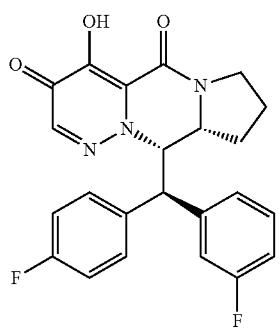 [SMILES: O=C1c2c(O)c(=O)cnn2[C@@H]([C@H](c2ccc(F)cc2)c2cccc(F)c2)[C@H]2CCCN12] | 423.4 | (500 MHz, CD3OD) δ ppm 7.43 (d, J = 7.3 Hz, 2H), 7.41-7.33 (m, 2H), 7.07-7.01 (m, 1H), 6.99 (dd, J = 8.6, 5.3 Hz, 2H), 6.81 (s, 2H), 5.75 (dd, J = 9.6, 3.6 Hz, 1H), 4.59 (d, J = 9.6 Hz, 1H), 4.51 (dt, J = 9.8, 4.7 Hz, 1H), 3.93-3.82 (m, 1H), 3.75-3.59 (m, 1H), 2.06 (dt, J = 12.8, 6.7 Hz, 1H), 1.96-1.89 (m, 1H), 1.89-1.77 (m, 1H), 1.67-1.55 (m, 1H) |
| 48 | 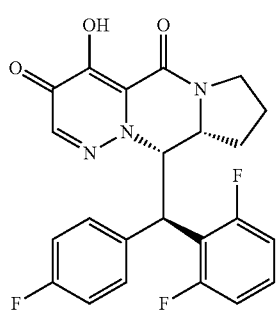 [SMILES: O=C1c2c(O)c(=O)cnn2[C@@H]([C@H](c2ccc(F)cc2)c2c(F)cccc2F)[C@H]2CCCN12] | 442.2 | (500 MHz, CD3OD) δ ppm 7.47-7.40 (m, 1H), 7.38 (s, 1H), 7.14 (d, J = 8.1 Hz, 2H), 7.11 (d, J = 9.0 Hz, 2H), 6.88 (t, J = 8.2 Hz, 2H), 5.99 (d, J = 10.6 Hz, 1H), 4.72 (d, J = 10.0 Hz, 1H), 4.56 (s, 1H), 3.99-3.86 (m, 1H), 3.63 (d, J = 7.1 Hz, 1H), 2.05 (s, 2H), 1.88 (s, 1H), 1.51 (d, J = 7.5 Hz, 1H) |
| 49 | 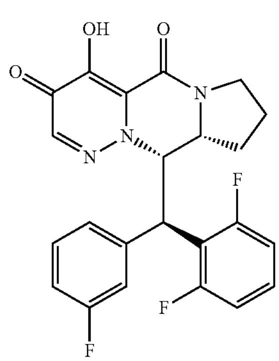 [SMILES: O=C1c2c(O)c(=O)cnn2[C@@H]([C@H](c2cccc(F)c2)c2c(F)cccc2F)[C@H]2CCCN12] | 442.4 | (500 MHz, CD3OD) δ ppm 7.49-7.41 (m, 1H), 7.37 (s, 1H), 7.13 (t, J = 9.5 Hz, 3H), 6.95 (d, J = 10.6 Hz, 1H), 6.89 (t, J = 9.9 Hz, 2H), 6.00 (d, J = 10.7 Hz, 1H), 4.74 (d, J = 10.1 Hz, 1H), 4.57 (s. 1H), 3.97-3.88 (m, 1H), 3.63 (d, J = 8.1 Hz, 1H), 2.05 (dd, J = 18.0, 11.8 Hz, 2H), 1.89 (s, 1H), 1.55-1.44 (m, 1H) |

TABLE 1d-continued
Additional compounds prepared by the method of Example 32.
| Example No. | Structure | Mass M + H | 1H NMR |
|---|---|---|---|
| 50 | 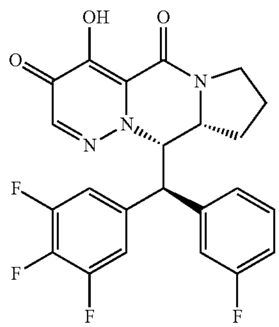 [SMILES: O=C1c2c(O)c(=O)cnn2[C@@H]([C@@H](c2cccc(F)c2)c2cc(F)c(F)c(F)c2)[C@H]2CCCN12] | 460.4 | (500 MHz, CD3OD) δ ppm 7.51 (s, 1H), 7.47 (q, J = 7.1, 6.6 Hz, 1H), 7.44-7.36 (m, 2H), 7.09 (t, J = 8.0 Hz, 1H), 6.86-6.79 (m, 2H), 5.77 (d, J = 9.8 Hz, 1H), 4.64 (d, J = 10.2 Hz, 1H), 4.51 (s, 1H), 3.92-3.81 (m, 1H), 3.71-3.61 (m, 1H), 2.02 (d, J = 10.7 Hz, 1H), 1.95-1.87 (m, 1H), 1.85 (d, J = 9.7 Hz, 1H), 1.50 (dd, J = 11.6, 6.9 Hz, 1H) |
Example 51. (9aR,10S)-10-((S)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione
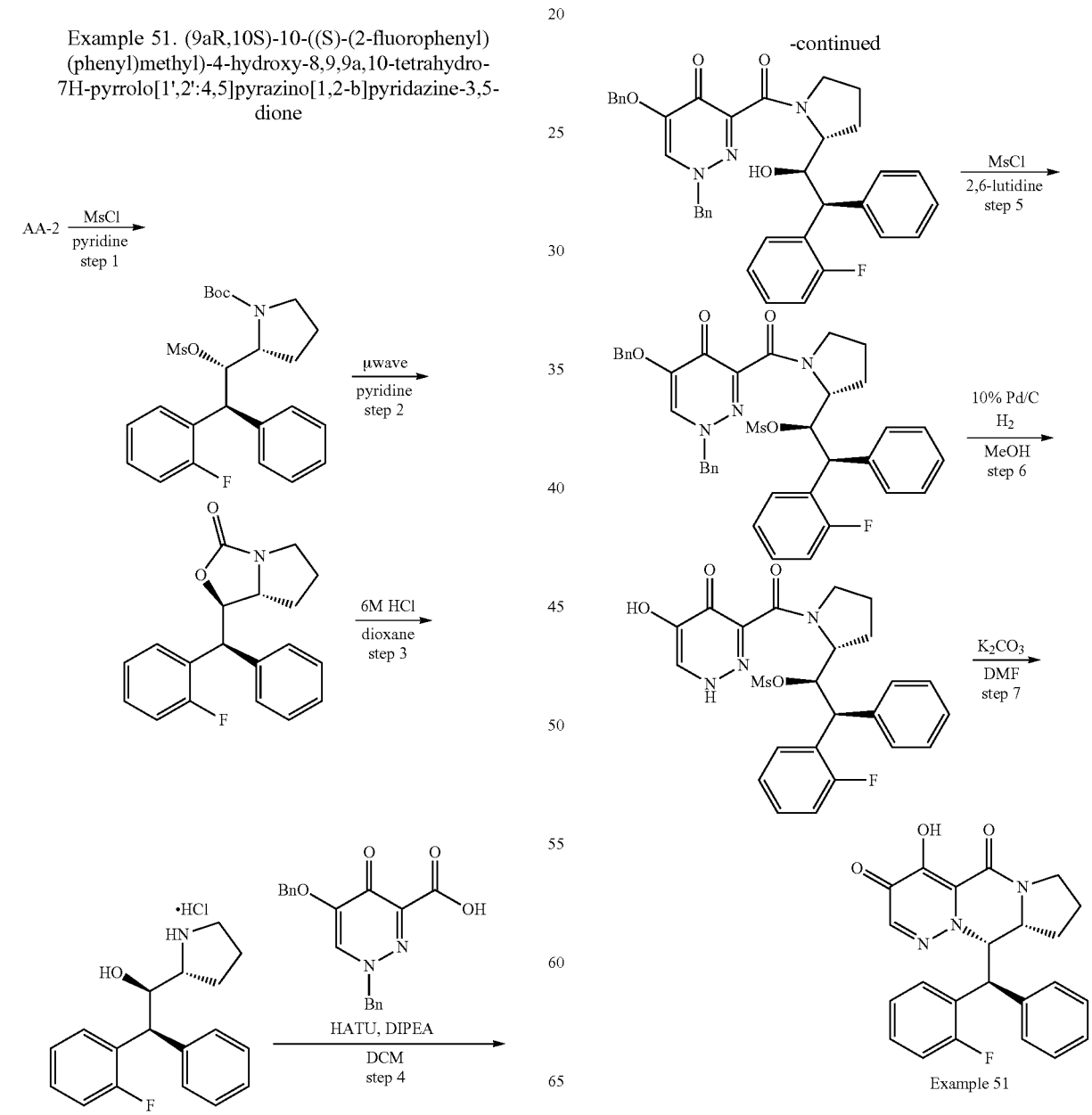

Step 1: tert-butyl (R)-2-((1S,2S)-2-(2-fluorophenyl)-1-((methylsulfonyl)oxy)-2-phenylethyl)pyrrolidine-1-carboxylate To a solution of tert-butyl (R)-2-((1S,2S)-2-(2-fluorophenyl)-1-hydroxy-2-phenylethyl)pyrrolidine-1-carboxylate (300 mg, 0.778 mmol) in pyridine (9 mL) at 0° C. was added methanesulfonyl chloride (0.910 mL, 11.67 mmol). After 5 min, the ice bath was removed and the reaction was stirred for 2 h at RT. The reaction mixture was partitioned between DCM and water. The DCM layer was separated and washed sequentially with 1N aqueous HCl, saturated aqueous NaHCO$_3$ and brine. The organic layer was dried over Na$_2$SO$_4$, filtered and concentrated. Silica gel column chromatography (EtOAc/heptane) provided tert-butyl (R)-2-((1S,2S)-2-(2-fluorophenyl)-1-((methylsulfonyl)oxy)-2-phenylethyl)pyrrolidine-1-carboxylate (325 mg, white foam) in 90% yield. MS m/z 408.3 (MH$^+$-tBu).

Step 2: (1R,7aR)-1-((S)-(2-fluorophenyl)(phenyl)methyl)tetrahydro-1H,3H-pyrrolo[1,2-c]oxazol-3-one A solution of tert-butyl (R)-2-((1S,2S)-2-(2-fluorophenyl)-1-((methylsulfonyl)oxy)-2-phenylethyl)pyrrolidine-1-carboxylate (325 mg, 0.701 mmol) in pyridine (4 mL) was heated at 120° C. for 2 h in a microwave reactor. Silica gel column chromatography (EtOAc/heptane) provided (1R,7aR)-1-((S)-(2-fluorophenyl)(phenyl)methyl)tetrahydro-1H,3H-pyrrolo[1,2-c]oxazol-3-one (150 mg) in 69% yield. MS m/z 312.4 (MH$^+$).

Step 3: (1R,2S)-2-(2-fluorophenyl)-2-phenyl-1-((R)-pyrrolidin-2-yl)ethan-1-ol hydrochloride Added 6N aqueous HCl solution to a solution of (1R,7aR)-1-((S)-(2-fluorophenyl)(phenyl)methyl)tetrahydro-1H,3H-pyrrolo[1,2-c]oxazol-3-one (150 mg, 0.482 mmol) in dioxane (2 mL) and the mixture was heated at 90° C. for 2 days in a sealed vial until the reaction was complete. The reaction was then concentrated to afford crude (1R,2S)-2-(2-fluorophenyl)-2-phenyl-1-((R)-pyrrolidin-2-yl)ethan-1-ol hydrochloride, which was used in the next step without further purification. MS m/z 286.4 (MH$^+$).

Step 4: 1-benzyl-5-(benzyloxy)-3-((R)-2-((1R,2S)-2-(2-fluorophenyl)-1-hydroxy-2-phenylethyl)pyrrolidine-1-carbonyl)pyridazin-4(1H)-one Added Huenig's Base (0.331 mL, 1.892 mmol) and HATU (234 mg, 0.615 mmol) to a solution of 1-benzyl-5-(benzyloxy)-4-oxo-1,4-dihydropyridazine-3-carboxylic acid (175 mg, 0.520 mmol) in DCM (2 mL) at RT. Stirred at RT for 15 min, then added a solution of crude (1R,2S)-2-(2-fluorophenyl)-2-phenyl-1-((R)-pyrrolidin-2-yl)ethan-1-ol hydrochloride (135 mg, 0.473 mmol) in DCM (2 mL) and Huenig's Base (0.331 mL, 1.892 mmol). The mixture was stirred at RT for 30 min. The mixture was then diluted with DCM and washed with water and brine. The organic layer was dried over Na$_2$SO$_4$, filtered and concentrated. Silica gel column chromatography (EtOAc/EtOH/heptane) provided 1-benzyl-5-(benzyloxy)-3-((R)-2-((1R,2S)-2-(2-fluorophenyl)-1-hydroxy-2-phenylethyl)pyrrolidine-1-carbonyl)pyridazin-4(1H)-one (270 mg, foamy solid) in 95% yield. MS m/z 604.7 (MH$^+$).

Step 5: (1R,2S)-1-((R)-1-(1-benzyl-5-(benzyloxy)-4-oxo-1,4-dihydropyridazine-3-carbonyl)pyrrolidin-2-yl)-2-(2-fluorophenyl)-2-phenylethyl methanesulfonate To a solution of 1-benzyl-5-(benzyloxy)-3-((R)-2-((1R,2S)-2-(2-fluorophenyl)-1-hydroxy-2-phenylethyl)pyrrolidine-1-carbonyl)pyridazin-4(1H)-one (270 mg, 0.447 mmol) in 2,6-lutidine (6 mL, 51.5 mmol) was added methanesulfonyl chloride (0.697 mL, 8.95 mmol) in an ice bath. After 5 min, the bath was removed and reaction mixture was stirred for 3 h at RT. LC-MS shows major, [M+H]+ 682.5/ 1.07 min corresponds to desired product. The reaction mixture was then partitioned between DCM and water. The DCM layer was separated and washed sequentially with 1N aqueous HCl, saturated aqueous NaHCO$_3$ and brine. The DCM layer was then dried over Na$_2$SO$_4$, filtered and concentrated. Silica gel column chromatography (EtOAc/heptane) provided (1R,2S)-1-((R)-1-(1-benzyl-5-(benzyloxy)-4-oxo-1,4-dihydropyridazine-3-carbonyl)pyrrolidin-2-yl)-2-(2-fluorophenyl)-2-phenylethyl methanesulfonate (245 mg, brown solid) in 80% yield. MS m/z 682.6 (MH$^+$).

Step 6: (1R,2S)-2-(2-fluorophenyl)-1-((R)-1-(5-hydroxy-4-oxo-1,4-dihydropyridazine-3-carbonyl)pyrrolidin-2-yl)-2-phenylethyl methanesulfonate To a solution of (1R,2S)-1-((R)-1-(1-benzyl-5-(benzyloxy)-4-oxo-1,4-dihydropyridazine-3-carbonyl)pyrrolidin-2-yl)-2-(2-fluorophenyl)-2-phenylethyl methanesulfonate (245 mg, 0.359 mmol) in methanol (6 mL) was added HCl (4.0 M in dioxane, 0.180 mL, 0.719 mmol) then the solution was purged with nitrogen. Added 10% palladium on carbon (115 mg, 0.108 mmol) and attached a hydrogen balloon. The flask was evacuated and refilled with hydrogen (3 times) and then stirred vigorously for 2 h at RT under a balloon of hydrogen. Added more palladium on carbon (115 mg, 0.108 mmol) and stirred for another 2 h at RT. The reaction mixture was filtered through celite, and the filter cake was washed with MeOH. The filtrate was concentrated to give crude (1R,2S)-2-(2-fluorophenyl)-1-((R)-1-(5-hydroxy-4-oxo-1,4-dihydropyridazine-3-carbonyl)pyrrolidin-2-yl)-2-phenylethyl methanesulfonate, which was used in the next step without further purification. MS m/z 502.3 (MH$^+$).

Step 7: (9aR,10S)-10-((S)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione To a solution of crude (1R,2S)-2-(2-fluorophenyl)-1-((R)-1-(5-hydroxy-4-oxo-1,4-dihydropyridazine-3-carbonyl)pyrrolidin-2-yl)-2-phenylethyl methanesulfonate (180 mg, 0.341 mmol) in DMF (5 mL) was added potassium carbonate (188 mg, 1.364 mmol) and the mixture was stirred overnight at RT. The reaction was filtered through a 1 micron filter and purified by reverse phase HPLC. Product fractions were combined, frozen and lyophilized to afford a formate salt of (9aR,10S)-10-((S)-(2-fluorophenyl)(phenyl)methyl)-4-hydroxy-8,9,9a,10-tetrahydro-7H-pyrrolo[1',2':4,5]pyrazino[1,2-b]pyridazine-3,5-dione (69 mg, 0.151 mmol, white solid) in 44% yield over two steps. $^1$H NMR (400 MHz, CD$_3$OD) δ ppm 7.55 (d, J=7.63 Hz, 2H) 7.42 (t, J=7.65 Hz, 2H) 7.37 (s, 1H) 7.27-7.34 (m, 1H) 7.03-7.13 (m, 2H) 6.88-6.95 (m, 1H) 6.83 (dd, J=10.37, 8.31 Hz, 1H) 5.82 (dd, J=9.88, 3.57 Hz, 1H) 4.92 (br d, J=9.98 Hz, 1H) 4.49-4.62 (m, 1H) 3.82-4.00 (m, 1H) 3.57-3.73 (m, 1H) 1.98-2.10 (m, 1H) 1.77-1.94 (m, 2H) 1.56-1.70 (m, 1H). MS m/z 406.4 (MH$^+$).

TABLE 1e

Additional compounds prepared by the method of Example 51.

| Example No. | Structure | Mass M + H | 1H NMR |
|---|---|---|---|
| 52 | 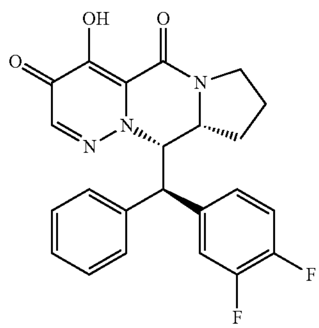 [SMILES: O=C1c2c(O)c(=O)cnn2[C@@H]([C@H](c2ccccc2)c2ccc(F)c(F)c2)[C@H]2CCCN12] | 424.4 | (400 MHz, MeOD) δ ppm 7.51-7.62 (m, 1 H) 7.25-7.47 (m, 3 H) 7.00-7.12 (m, 3 H) 6.90-6.96 (m, 2 H) 5.67-5.76 (m, 1 H) 4.56 (d, J = 9.24 Hz, 1 H) 4.46-4.53 (m, 1 H) 3.82-3.92 (m, 1 H) 3.67 (td, J = 11.05, 7.48 Hz, 1 H) 2.04-2.15 (m, 1 H) 1.92-2.02 (m, 1 H) 1.80-1.91 (m, 1 H) 1.57-1.73 (m, 1 H) |
| 53 | 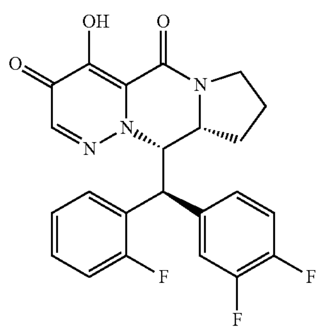 [SMILES: O=C1c2c(O)c(=O)cnn2[C@@H]([C@@H](c2ccc(F)c(F)c2)c2ccccc2F)[C@H]2CCCN12] | 442.3 | (400 MHz, MeOD) δ ppm 7.52-7.64 (m, 1 H) 7.37 (s, 2 H) 7.26-7.35 (m, 1 H) 7.08-7.17 (m, 1 H) 6.98-7.06 (m, 1 H) 6.90-6.97 (m, 1 H) 6.81-6.89 (m, 1 H) 5.81 (dd, J = 9.63, 3.57 Hz, 1 H) 4.91 (br s, 1 H) 4.52 (dt, J = 10.40, 5.04 Hz, 1 H) 3.83-3.94 (m, 1 H) 3.64 (td, J = 11.24, 7.26 Hz, 1 H) 2.03-2.14 (m, 1 H) 1.77-2.02 (m, 2 H) 1.60 (qd, J = 11.71, 6.68 Hz, 1 H) |
| 54 | 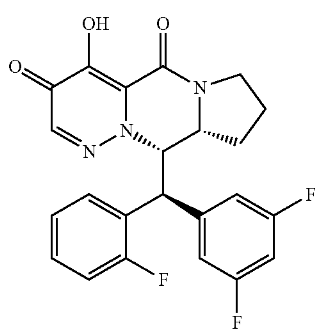 [SMILES: O=C1c2c(O)c(=O)cnn2[C@@H]([C@@H](c2cc(F)cc(F)c2)c2ccccc2F)[C@H]2CCCN12] | 442.4 | (400 MHz, MeOD) δ ppm 7.39 (s, 1 H) 7.26 (br d, J = 6.70 Hz, 2 H) 7.11-7.19 (m, 1 H) 7.00-7.07 (m, 1 H) 6.82-6.98 (m, 3 H) 5.84 (dd, J = 9.56, 3.55 Hz, 1 H) 4.94 (br d, J = 9.73 Hz, 1 H) 4.48-4.59 (m, 1 H) 3.83-3.93 (m, 1 H) 3.65 (td, J = 11.22, 7.29 Hz, 1 H) 1.97-2.13 (m, 2H) 1.80-1.92 (m, 1 H) 1.61 (qd, J = 11.79, 6.77 Hz, 1 H) |
| 55 | 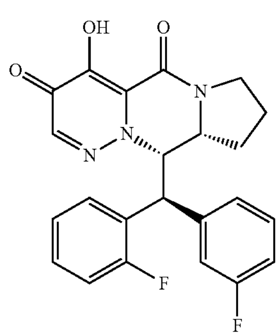 [SMILES: O=C1c2c(O)c(=O)cnn2[C@@H]([C@@H](c2cccc(F)c2)c2ccccc2F)[C@H]2CCCN12] | 424.4 | (400 MHz, MeOD) δ ppm 7.29-7.51 (m, 4 H) 7.00-7.18 (m, 3 H) 6.90-6.98 (m, 1 H) 6.80-6.89 (m, 1 H) 5.83 (dd, J = 9.73, 3.57 Hz, 1H) 4.94 (br d, J = 9.78 Hz, 1 H) 4.53 (dt, J = 10.37, 4.99 Hz, 1 H) 3.82-3.93 (m, 1 H) 3.65 (td, J = 11.30, 7.48 Hz, 1 H) 2.02-2.11 (m, 1 H) 1.78-2.00 (m, 2 H) 1.61 (qd, J = 11.65, 6.77 Hz, 1 H) |

TABLE 1e-continued

Additional compounds prepared by the method of Example 51.

| Example No. | Structure | Mass M + H | 1H NMR |
|---|---|---|---|
| 56 | 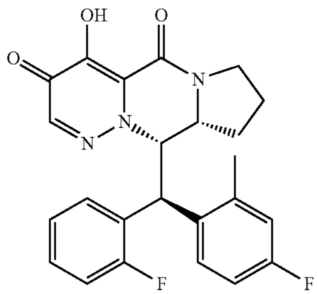 [SMILES: Cc1cc(F)ccc1[C@@H](c1ccccc1F)[C@H]1[C@H]2CCCN2C(=O)c2c(O)c(=O)cnn21] | 438.4 | (400 MHz, MeOD) δ ppm 7.93 (dd, J = 8.61, 5.58 Hz, 1 H) 7.33 (s, 1 H) 6.91-7.20 (m, 5 H) 6.79-6.88 (m, 1 H) 5.84 (dd, J = 9.93, 3.42 Hz, 1 H) 4.97 (br d, J = 9.98 Hz, 1 H) 4.47-4.60 (m, 1 H) 3.87-4.01 (m, 1 H) 3.54-3.67 (m, 1 H) 2.15 (s, 3 H) 2.01-2.09 (m, 1 H) 1.79-1.95 (m, 2 H) 1.30-1.43 (m, 1 H) |
| 57 | 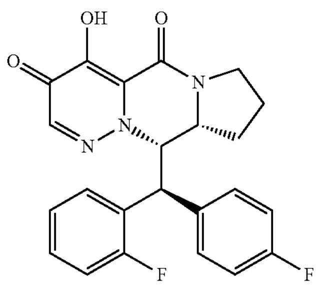 | 424.2 | (400 MHz, DMSO) δ ppm 7.62 (dd, J = 8.39, 5.50 Hz, 2 H) 7.14-7.24 (m, 3 H) 7.06-7.14 (m, 1 H) 6.98-7.05 (m, 1 H) 6.82-6.96 (m, 2H) 5.78 (dd, J = 10.15, 3.45 Hz, 1 H) 4.82 (d, J = 10.17 Hz, 1 H) 4.48 (dt, J = 9.99, 4.96 Hz, 1 H) 3.67-3.76 (m, 1 H) 3.55 (td, J = 10.92, 7.31 Hz, 1 H) 1.83-1.94 (m, 1 H) 1.72-1.80 (m, 1 H) 1.59-1.71 (m, 1 H) 1.33 (qd, J = 11.59, 6.80 Hz, 1 H) |
| 58 | 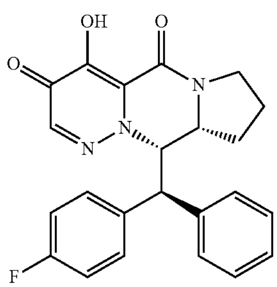 [SMILES: O=C1c2c(O)c(=O)cnn2[C@@H]([C@@H](c2ccccc2)c2ccc(F)cc2)[C@H]2CCCN12] | 406.4 | (400 MHz, d-DMSO) δ ppm 7.59 (d, J = 7.53 Hz, 2 H) 7.36 (t, J = 7.18 Hz, 2 H) 7.19-7.28 (m, 2 H) 6.94-7.03 (m, 2 H) 6.88 (t, J = 8.83 Hz, 2 H) 5.67 (dd, J = 9.76, 3.55 Hz, 1 H) 4.59 (d, J = 9.78 Hz, 1 H) 4.39-4.53 (m, 1 H) 3.65-3.89 (m, 1 H) 3.44-3.64 (m, 1 H) 1.80-1.96 (m, 1 H) 1.59-1.80 (m, 2 H) 1.30-1.46 (m, 1 H) |
| 59 | 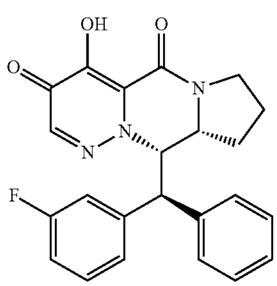 [SMILES: O=C1c2c(O)c(=O)cnn2[C@@H]([C@@H](c2ccccc2)c2cccc(F)c2)[C@H]2CCCN12] | 406.4 | (500 MHz, CHLOROFORM-d) δ ppm 7.34-7.49 (m, 5 H) 7.29 (s, 2 H) 7.02-7.08 (m, 1 H) 6.80 (br t, J = 8.28 Hz, 1 H) 6.73 (br d, J = 9.81 Hz, 1 H) 6.65 (br d, J = 7.68 Hz, 1 H) 5.42-5.46 (m, 1 H) 4.39-4.45 (m, 1 H) 4.31 (br d, J = 9.81 Hz, 1 H) 3.91-3.97 (m, 1 H) 3.60-3.68 (m, 1 H) 2.01-2.11 (m, 1 H) 1.79-1.92 (m, 2 H) 1.51-1.62 (m, 1 H) |
| 60 | 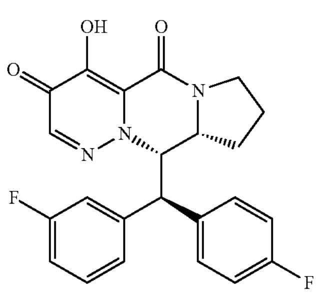 [SMILES: O=C1c2c(O)c(=O)cnn2[C@@H]([C@@H](c2ccc(F)cc2)c2cccc(F)c2)[C@H]2CCCN12] | 424.3 | (400 MHz, d-DMSO) δ ppm 7.81 (m, 1 H) 7.3-7.15 (m, 3 H) 7.1 (m, 1 H) 6.9 (m, 1 H) 6.9-6.8 (m, 2H) 5.75 (dd, J = 8, 4 Hz, 1 H) 4.75 (d, J = 8 Hz) 4.5 (m, 1H) 3.75 (m, 1H) 3.6 (m, 1H) 1.95 (m, 1H) 1.8 (m, 1H) 1.7 (m, 1H) 1.35 (m, 1H) |

TABLE 1e-continued

Additional compounds prepared by the method of Example 51.

| Example No. | Structure | Mass M + H | 1H NMR |
|---|---|---|---|
| 61 | 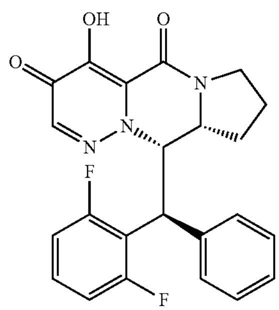 [SMILES: O=C1c2c(O)c(=O)cnn2[C@@H]([C@@H](c2ccccc2)c2c(F)cccc2F)[C@H]2CCCN12] | 424.3 | (500 MHz, CD3OD) δ ppm 7.51 (d, J = 7.5 Hz, 2H), 7.41 (s, 1H), 7.38 (t, J = 7.2 Hz, 2H), 7.29 (t, J = 7.1 Hz, 1H), 7.22-7.10 (m, 1H), 6.76 (t, J = 9.0 Hz, 2H), 6.07 (d, J = 10.6 Hz, 1H), 4.98 (d, J = 11.0 Hz, 1H), 4.59 (s, 1H), 3.93-3.82 (m, 1H), 3.64-3.53 (m, 1H), 1.97 (d, J = 6.2 Hz, 2H), 1.82 (s, 1H), 1.51-1.40 (m, 1H) |
| 62 | 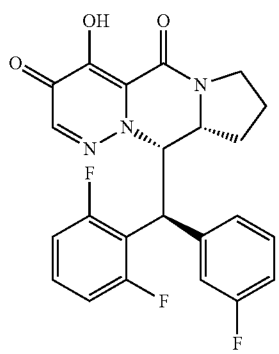 [SMILES: O=C1c2c(O)c(=O)cnn2[C@@H]([C@@H](c2cccc(F)c2)c2c(F)cccc2F)[C@H]2CCCN12] | 442.4 | (500 MHz, CD3OD) δ ppm 7.45-7.32 (m, 3H), 7.30 (d, J = 7.1 Hz, 1H), 7.21 (s, 1H), 7.05 (t, J = 7.9 Hz, 1H), 6.79 (s, 2H), 6.06 (s, 1H), 5.00 (d, J = 9.8 Hz, 1H), 4.59 (s, 1H), 3.88 (s, 1H), 3.59 (s, 1H), 2.01 (s, 2H), 1.84 (s, 1H), 1.46 (s, 1H) |
| 63 | 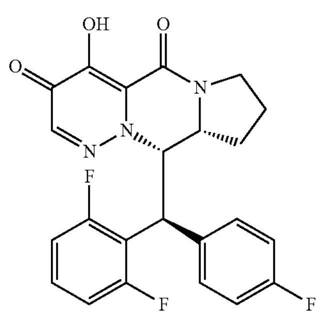 [SMILES: O=C1c2c(O)c(=O)cnn2[C@@H]([C@@H](c2ccc(F)cc2)c2c(F)cccc2F)[C@H]2CCCN12] | 442.4 | (500 MHz, CD3OD) δ ppm 7.53 (s, 2H), 7.39 (s, 1H), 7.10 (s, 3H), 6.76 (s, 2H), 6.02 (s, 1H), 4.98 (d, J = 11.6 Hz, 1H), 4.57 (s, 1H), 3.87 (s, 1H), 3.58 (s, 1H), 1.97 (s, 2H), 1.81 (s, 1H), 1.45 (s, 1H) |
| 64 | 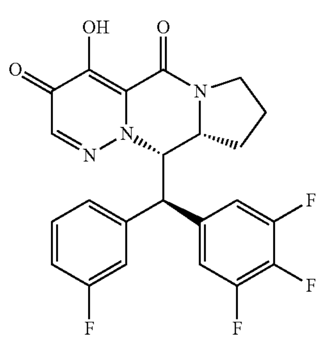 [SMILES: O=C1c2c(O)c(=O)cnn2[C@@H]([C@H](c2cccc(F)c2)c2cc(F)c(F)c(F)c2)[C@H]2CCCN12] | 460.9 | (500 MHz, CD3OD) δ ppm 7.47 (t, J = 7.2 Hz, 2H), 7.42 (s, 1H), 7.11 (d, J = 7.5 Hz, 1H), 6.85 (s, 1H), 6.74 (d, J = 8.5 Hz, 2H), 5.73 (d, J = 9.5 Hz, 1H), 4.64 (d, J = 9.7 Hz, 1H), 4.51 (s, 1H), 3.93-3.83 (m, 1H), 3.72-3.61 (m, 1H), 2.09 (s, 1H), 1.99 (s, 1H), 1.88 (s, 1H), 1.65-1.53 (m, 1H) |

General Synthesis of Chiral N-CBZ Amino Alcohols
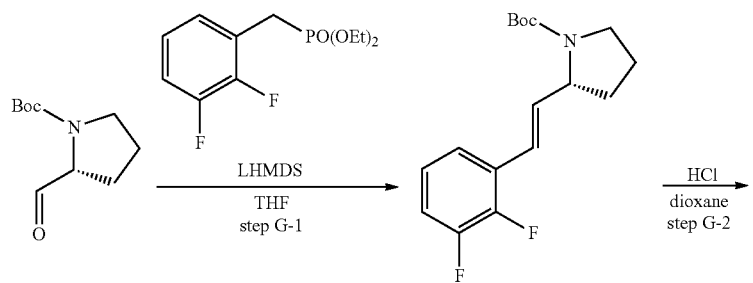
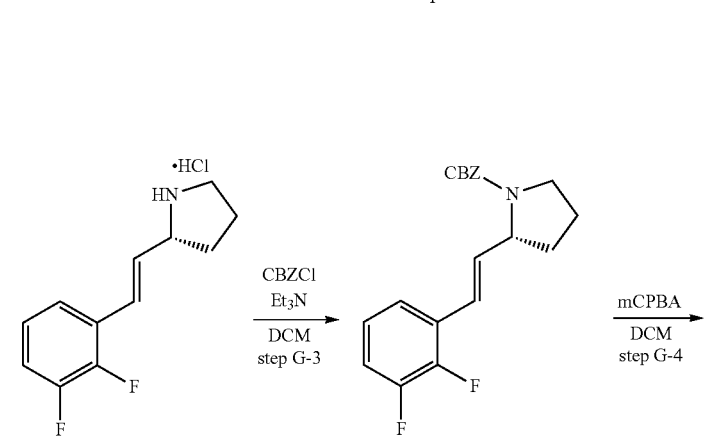
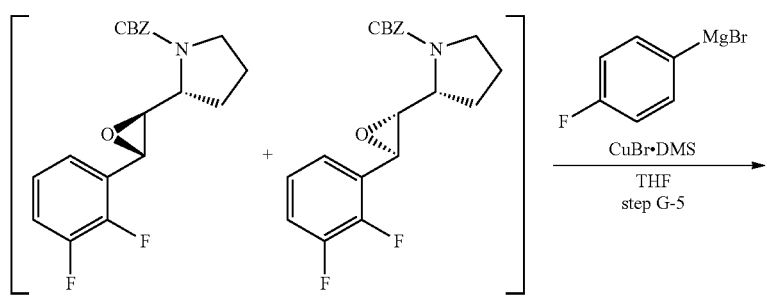
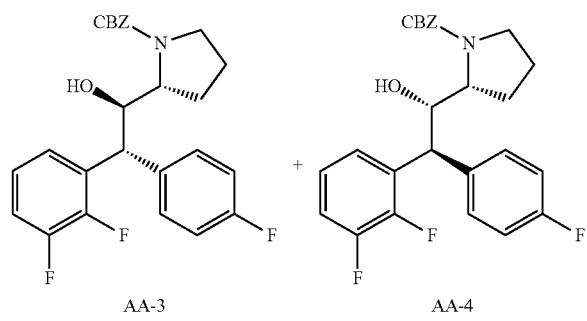

Step G-1: tert-butyl (R,E)-2-(2,3-difluorostyryl)pyrrolidine-1-carboxylate

Added a solution of lithium bis(trimethylsilyl)amide (1.0 M in THF, 26.3 mL, 26.3 mmol) dropwise to a solution of diethyl 2,3-difluorobenzylphosphonate (7.13 g, 25.1 mmol) in THF (84 mL) at 0° C. Stirred at 0° C. for 1 h, then added (R)-tert-butyl 2-formylpyrrolidine-1-carboxylate (5.0 g, 25.1 mmol) dropwise. Reaction mixture was stirred in ice bath for 1 h and then slowly warmed to RT over 1 h and then stirred for an additional 2 h at RT. The reaction was quenched with water and extracted with EtOAc (twice). The combined organic extracts were washed with brine, dried over $Na_2SO_4$, filtered and concentrated. Silica gel column chromatography (EtOAc/heptane) provided tert-butyl (R,E)-2-(2,3-difluorostyryl)pyrrolidine-1-carboxylate (6.87 g, white solid) in 88% yield. MS m/z 254.3 (M-tBu+H).

Step G-2: (R,E)-2-(2,3-difluorostyryl)pyrrolidine hydrochloride

Added a solution of HCl (4.0 M in dioxane, 19.6 ml, 78 mmol) to tert-butyl (R,E)-2-(2,3-difluorostyryl)pyrrolidine-1-carboxylate (6.07 g, 19.6 mmol) at RT and stirred for 1 h. The reaction mixture was then concentrated to give crude (R,E)-2-(2,3-difluorostyryl)pyrrolidine hydrochloride, which was used in the next step without further purification. MS m/z 210.2 (MH+).

Step G-3: benzyl (R,E)-2-(2,3-difluorostyryl)pyrrolidine-1-carboxylate

Benzylchloroformate (3.1 ml, 21.6 mmol) was added dropwise to a solution of triethylamine (6.84 ml, 49.1 mmol) and (R,E)-2-(2,3-difluorostyryl)pyrrolidine hydrochloride (4.11 g, 19.6 mmol) in DCM (98 ml) at 0° C. and the mixture was allowed to warm to RT and stirred overnight.

The reaction was then diluted with additional DCM, washed successively with water then brine, dried with $Na_2SO_4$, filtered and concentrated. Silica gel column chromatography (EtOAc/heptane) provided benzyl (R,E)-2-(2,3-difluorostyryl)pyrrolidine-1-carboxylate (6.67 g, colorless oil) in 99% yield over two steps. MS m/z 344.3 (MH+).

Step G-4: benzyl (R)-2-((2S,3S)-3-(2,3-difluorophenyl)oxiran-2-yl)pyrrolidine-1-carboxylate and benzyl (R)-2-((2R,3R)-3-(2,3-difluorophenyl)oxiran-2-yl)pyrrolidine-1-carboxylate To (R,E)-2-(2,3-difluorostyryl)pyrrolidine-1-carboxylate (5.9 g, 17.2 mmol) in DCM (286 mL) was added mCPBA (21.2 g, 86 mmol). The reaction mixture was stirred at RT overnight. The reaction was quenched with water and extracted with DCM (twice). The combined organic extracts were washed sequentially with saturated aqueous $Na_2S_2O_3$, saturated aqueous $NaHCO_3$ and brine. The organic layer was then dried over $Na_2SO_4$, filtered and concentrated. Silica gel column chromatography (EtOAc/heptane) provided an inseparable mixture of benzyl (R)-2-((2S,3S)-3-(2,3-difluorophenyl)oxiran-2-yl)pyrrolidine-1-carboxylate and benzyl (R)-2-((2R,3R)-3-(2,3-difluorophenyl)oxiran-2-yl)pyrrolidine-1-carboxylate (5.16 g, colorless oil) in 84% yield. The mixture was used in the next step without further purification.

Step G-5: benzyl (R)-2-((1R,2R)-2-(2,3-difluorophenyl)-2-(4-fluorophenyl)-1-hydroxyethyl)pyrrolidine-1-carboxylate and benzyl (R)-2-((1S,2S)-2-(2,3-difluorophenyl)-2-(4-fluorophenyl)-1-hydroxyethyl)pyrrolidine-1-carboxylate Added copper(I) bromide-dimethyl sulfide complex (286 mg, 1.39 mmol) to a mixture of benzyl (R)-2-((2S,3S)-3-(2,3-difluorophenyl)oxiran-2-yl)pyrrolidine-1-carboxylate and benzyl (R)-2-((2R,3R)-3-(2,3-difluorophenyl)oxiran-2-yl)pyrrolidine-1-carboxylate (500 mg, 1.39 mmol) in THF (8 mL) at RT. Cooled to between −20 and −30° C. in an acetone bath with periodic dry ice additions. A solution of (4-fluorophenyl)magnesium bromide (1.0 M in THF, 8.35 mL, 8.35 mmol) was added dropwise. Stirred 10 min and allowed the temperature to warm to 0° C. Added 2 equiv more of (4-fluorophenyl)magnesium bromide and stirred another 30 min. The reaction was quenched with saturated aqueous $NH_4Cl$ solution and extracted with EtOAc (2 times). The combined organic extracts were dried over $Na_2SO_4$, filtered and concentrated. Silica gel column chromatography (EtOAc/heptane) provided benzyl (R)-2-((1R,2R)-2-(2,3-difluorophenyl)-2-(4-fluorophenyl)-1-hydroxyethyl)pyrrolidine-1-carboxylate (88 mg, colorless oil, eluted first) in 14% yield and benzyl (R)-2-((1S,2S)-2-(2,3-difluorophenyl)-2-(4-fluorophenyl)-1-hydroxyethyl) pyrrolidine-1-carboxylate (350 mg, eluted second) in 55% yield. MS m/z 456.4 (MH+).

Example 65. (9aR,10S)-10-((R)-(2,3-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione

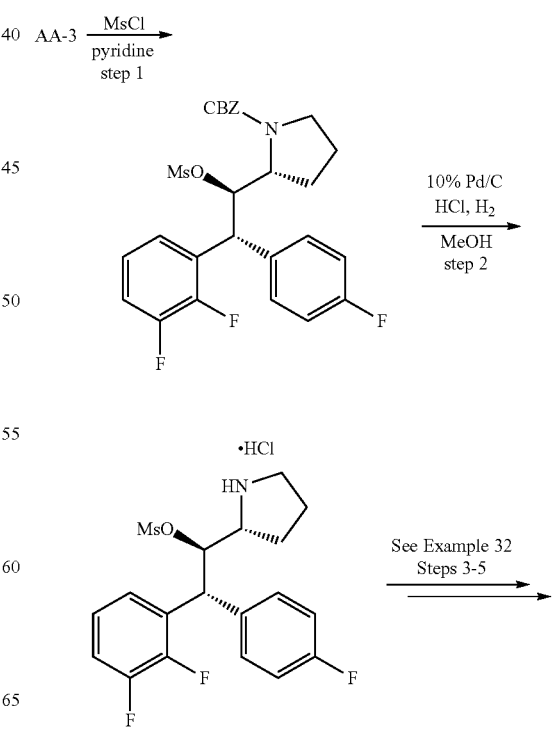

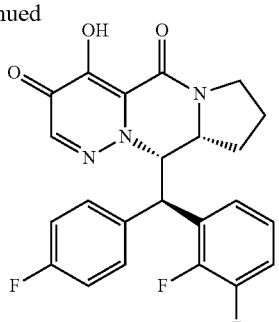

Example 65

Step 1: benzyl (R)-2-((1R,2R)-2-(2,3-difluorophenyl)-2-(4-fluorophenyl)-1-((methylsulfonyl)oxy)ethyl)pyrrolidine-1-carboxylate To a solution of benzyl (R)-2-((1R,2R)-2-(2,3-difluorophenyl)-2-(4-fluorophenyl)-1-hydroxyethyl)pyrrolidine-1-carboxylate (88 mg, 0.19 mmol) in pyridine (2.5 mL) at 0° C. was added methanesulfonyl chloride (0.23 mL, 2.9 mmol). After 5 min, the ice bath was removed and the reaction was stirred for 2 h at RT. The reaction mixture was partitioned between DCM and water. The DCM layer was separated and washed sequentially with 1N aqueous HCl, saturated aqueous NaHCO₃ and brine. The organic layer was dried over Na₂SO₄, filtered and concentrated. Silica gel column chromatography (EtOAc/heptane) provided benzyl (R)-2-((1R,2R)-2-(2,3-difluorophenyl)-2-(4-fluorophenyl)-1-((methylsulfonyl)oxy)ethyl)pyrrolidine-1-carboxylate (85 mg) in 82% yield. MS m/z 534.5 (MH⁺).

Step 2: (1R,2R)-2-(2,3-difluorophenyl)-2-(4-fluorophenyl)-1-((R)-pyrrolidin-2-yl)ethyl methanesulfonate hydrochloride A solution of benzyl (R)-2-((1R,2R)-2-(2,3-difluorophenyl)-2-(4-fluorophenyl)-1-((methylsulfonyl)oxy)ethyl)pyrrolidine-1-carboxylate (85 mg, 0.16 mmol) in methanol (4 mL) and HCl (4.0 M in dioxane, 0.080 mL, 0.32 mmol) was purged with nitrogen. Added 10% palladium on carbon (68 mg, 0.064 mmol) and attached a hydrogen balloon. The flask was evacuated and refilled with hydrogen (3 times) and then stirred vigorously at RT under a balloon of hydrogen. After 2H, the reaction mixture was filtered through celite, and the filter cake was washed with MeOH. The filtrate was concentrated to give crude (1R,2R)-2-(2,3-difluorophenyl)-2-(4-fluorophenyl)-1-((R)-pyrrolidin-2-yl)ethyl methanesulfonate hydrochloride, which was used in the next step without further purification. MS m/z 400.4 (MH⁺).

Example 65. (9aR,10S)-10-((R)-(2,3-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione Prepared from (1R,2R)-2-(2,3-difluorophenyl)-2-(4-fluorophenyl)-1-((R)-pyrrolidin-2-yl)ethyl methanesulfonate hydrochloride by the method of Example 32, steps 3-5. ¹H NMR (400 MHz, CD₃OD) δ ppm 7.79-7.65 (m, 1H), 7.42 (s, 1H), 7.37-7.21 (m, 2H), 7.02 (dd, J=8.6, 5.3 Hz, 2H), 6.85 (t, J=8.7 Hz, 2H), 5.79 (dd, J=9.6, 3.7 Hz, 1H), 4.74 (d, J=9.6 Hz, 1H), 4.62 (s, 1H), 4.53 (dt, J=10.2, 4.8 Hz, 1H), 3.90 (dd, J=12.7, 8.8 Hz, 1H), 3.65 (td, J=11.1, 7.0 Hz, 1H), 2.04 (ddt, J=38.5, 18.2, 6.4 Hz, 2H), 1.94 (s, 1H), 1.51 (qd, J=11.7, 6.7 Hz, 1H). MS m/z 442.4 (MH+).

TABLE 1f

Additional compounds prepared by the method of Example 65.

| Example No. | Structure | Mass M + H | 1H NMR |
|---|---|---|---|
| 66 | 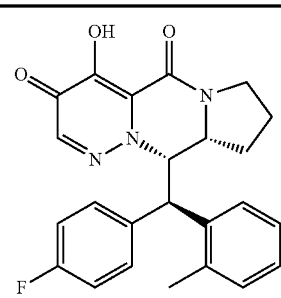 | 420.3 | (400 MHz, MeOD) δ ppm 7.84 (br dd, J = 13.01, 7.97 Hz, 1 H) 7.35 (br t, J = 12.79 Hz, 2 H) 7.07-7.26 (m, 2 H) 6.94 (br s, 2 H) 6.67-6.84 (m, 2 H) 5.79 (br t, J = 10.00 Hz, 1 H) 4.48 (br d, J = 10.07 Hz, 2 H) 3.90 (br d, J = 8.41 Hz, 1 H) 3.60 (br s, 1 H) 2.14 (br d, J = 13.60 Hz, 3 H) 1.73-2.04 (m, 3 H) 1.36-1.38 (m, 1 H) 1.31 (br s, 1 H) |
| 67 | 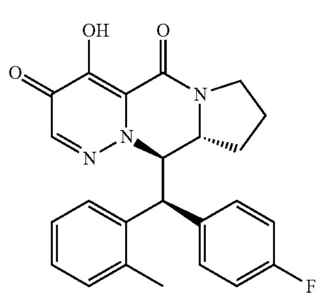 [SMILES: Cc1ccccc1[C@H](c1ccc(F)cc1)[C@@H]1[C@H]2CCCN2C(=O)c2c(O)c(=O)cnn21] | 420.3 | (400 MHz, MeOD) δ ppm 7.60 (br d, J = 16.24 Hz, 1 H) 7.05-7.35 (m, 6 H) 6.97 (dt, J = 16.93, 8.53 Hz, 2 H) 5.28-5.45 (m, 2 H) 4.30 (brs, 1 H) 3.53-3.73 (m, 2 H) 2.26 (br d, J = 16.77 Hz, 3 H) 1.91 (br d, J = 16.82 Hz, 1 H) 1.73 (br s, 1 H) 1.39 (ddd, J = 17.15, 11.11, 5.97 Hz, 2 H) |

TABLE 1f-continued

Additional compounds prepared by the method of Example 65.

| Example No. | Structure | Mass M + H | 1H NMR |
|---|---|---|---|
| 68 | 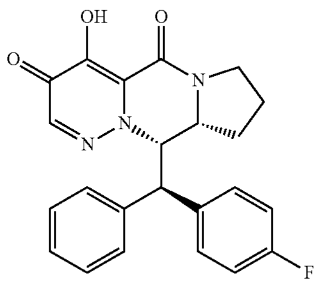 [SMILES: O=C1c2c(O)c(=O)cnn2[C@@H]([C@H](c2ccccc2)c2ccc(F)cc2)[C@H]2CCCN12] | 406.2 | (400 MHz, MeOD) δ ppm 7.59 (dd, J = 8.63, 5.26 Hz, 2 H) 7.36 (s, 1 H) 7.14 (t, J = 8.71 Hz, 2 H) 7.02-7.09 (m, 3 H) 6.93 (dd, J = 6.55, 2.84 Hz, 2 H) 5.72 (dd, J = 9.39, 3.62 Hz, 1 H) 4.42-4.60 (m, 2 H) 3.80-3.93 (m, 1 H) 3.68 (td, J = 10.99, 7.46 Hz, 1 H) 2.02-2.11 (m, 1 H) 1.77-1.96 (m, 2 H) 1.57-1.72 (m, 1 H) |
| 69 | 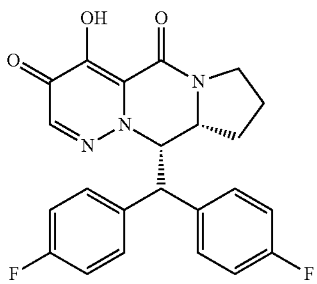 [SMILES: O=C1c2c(O)c(=O)cnn2[C@@H](C(c2ccc(F)cc2)c2ccc(F)cc2)[C@H]2CCCN12] | 424.3 | (400 MHz, MeOD) δ ppm 1.54-1.68 (m, 1 H) 1.77-1.96 (m, 2 H) 2.00-2.10 (m, 1 H) 3.59-3.76 (m, 1 H) 3.80-3.95 (m, 1 H) 4.44-4.65 (m, 2 H) 5.72 (dd, J = 9.59, 3.62 Hz, 1 H) 6.80 (t, J = 8.71 Hz, 2 H) 6.97 (dd, J = 8.61, 5.33 Hz, 2 H) 7.15 (t, J = 8.71 Hz, 2 H) 7.42 (s, 1 H) 7.58 (dd, J = 8.63, 5.26 Hz, 2 H) |
| 70 | 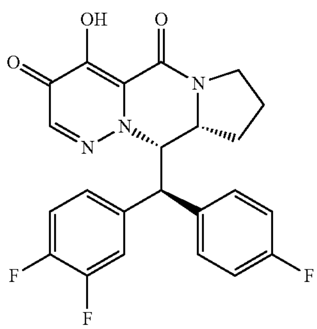 [SMILES: O=C1c2c(O)c(=O)cnn2[C@@H]([C@@H](c2ccc(F)cc2)c2ccc(F)c(F)c2)[C@H]2CCCN12] | 442.2 | (400 MHz, MeOD) δ ppm 7.59 (dd, J = 8.63, 5.21 Hz, 2 H) 7.45 (s, 1 H) 7.16 (t, J = 8.68 Hz, 2 H) 6.88-7.03 (m, 2 H) 6.71-6.80 (m, 1 H) 5.73 (dd, J = 9.81, 3.55 Hz, 1 H) 4.59 (d, J = 9.83 Hz, 1 H) 4.49 (br dd, J = 10.25, 5.01 Hz, 1 H) 3.81-3.95 (m, 1 H) 3.58-3.73 (m, 1 H) 1.98-2.10 (m, 1 H) 1.73-1.94 (m, 2 H) 1.46-1.65 (m, 1 H) |
| 71 | 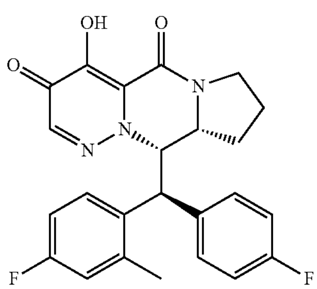 [SMILES: Cc1cc(F)ccc1[C@H](c1ccc(F)cc1)[C@H]1[C@H]2CCCN2C(=O)c2c(O)c(=O)cnn21] | 438.2 | (400 MHz, MeOD) δ ppm 7.54 (br s, 2 H) 7.43 (s, 1 H) 7.00-7.29 (m, 3 H) 6.54-6.83 (m, 2 H) 5.86 (br s, 1 H) 4.82 (br s, 1 H) 4.44-4.65 (m, 1 H) 3.76-3.99 (m, 1 H) 3.65 (td, J = 11.29, 7.36 Hz, 1 H) 2.23 (br s, 3 H) 1.99-2.09 (m, 1 H) 1.71-1.99 (m, 2 H) 1.45-1.67 (m, 1 H) |
| 72 | 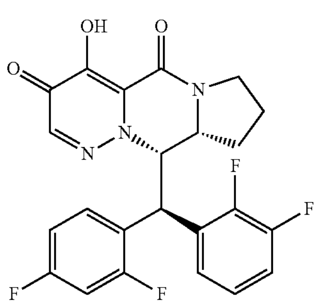 [SMILES: O=C1c2c(O)c(=O)cnn2[C@@H]([C@H](c2ccc(F)cc2F)c2cccc(F)c2F)[C@H]2CCCN12] | 460.4 | (400 MHz, MeOD) δ ppm 7.76 (br t, J = 6.92 Hz, 1 H) 7.46 (s, 1 H) 7.21-7.41 (m, 2 H) 7.04-7.18 (m, 1 H) 6.65-6.87 (m, 2 H) 5.86 (dd, J = 9.81, 3.55 Hz, 1 H) 5.11 (d, J = 9.88 Hz, 1 H) 4.54 (dt, J = 10.39, 4.98 Hz, 1 H) 3.84-3.97 (m, 1 H) 3.61 (td, J = 11.29, 7.26 Hz, 1 H) 2.04-2.13 (m, 1 H) 1.96-2.03 (m, 1 H) 1.80-1.92 (m, 1 H) 1.48 (qd, J = 11.83, 6.72 Hz, 1 H) |

TABLE 1f-continued

Additional compounds prepared by the method of Example 65.

| Example No. | Structure | Mass M + H | 1H NMR |
|---|---|---|---|
| 73 | 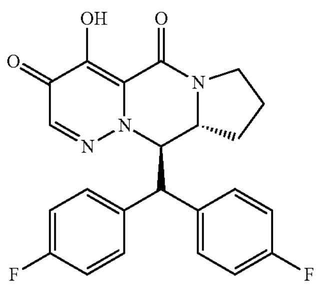 [SMILES: O=C1c2c(O)c(=O)cnn2[C@H](C(c2ccc(F)cc2)c2ccc(F)cc2)[C@H]2CCCN12] | 424.4 | 1H NMR (400 MHz, MeOD) δ ppm δ ppm 1.61-1.88 (m, 3 H) 1.98-2.10 (m, 1 H) 3.55-3.80 (m, 2 H) 4.10 (td, J = 10.59, 5.72 Hz, 1H) 5.17 (d, J = 5.53 Hz, 1 H) 5.34 (dd, J = 10.78, 5.60 Hz, 1 H) 7.04 (td, J = 8.64, 6.43 Hz, 4 H) 7.23-7.43 (m, 4 H) 7.67 (s, 1 H) |
| 74 | 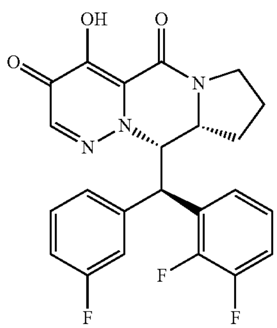 [SMILES: O=C1c2c(O)c(=O)cnn2[C@@H]([C@H](c2cccc(F)c2)c2cccc(F)c2F)[C@H]2CCCN12] | 442.4 | (400 MHz, MeOD) δ ppm 7.74 (br t, J = 6.99 Hz, 1 H) 7.40 (s, 1 H) 7.37 (br s, 1 H) 7.23-7.36 (m, 1 H) 7.06-7.16 (m, 1 H) 6.82-6.91 (m, 1 H) 6.72-6.81 (m, 2 H) 5.81 (dd, J = 9.61, 3.59 Hz, 1 H) 4.76 (d, J = 9.63 Hz, 1 H) 4.61 (br s, 1 H) 4.48-4.55 (m, 1 H) 3.84-3.94 (m, 1 H) 3.65 (td, J = 11.25, 7.38 Hz, 1 H) 2.04-2.14 (m, 1 H) 1.95-2.03 (m, 1 H) 1.80-1.92 (m, 1 H) 1.50 (qd, J = 11.67, 6.80 Hz, 1 H) |
| 75 | 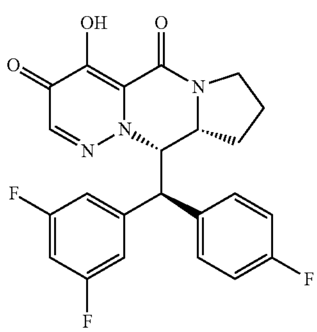 [SMILES: O=C1c2c(O)c(=O)cnn2[C@@H]([C@@H](c2ccc(F)cc2)c2cc(F)cc(F)c2)[C@H]2CCCN12] | 442.3 | (400 MHz, DMSO-d6) δ 7.67 (dd, J = 8.6, 5.5 Hz, 2H), 7.32 (s, 1H), 7.21 (t, J = 8.8 Hz, 2H), 6.95 (tt, J = 9.2, 2.4 Hz, 1H), 6.72 (dd, J = 8.8, 2.5 Hz, 2H), 5.72 (d, J = 3.6 Hz, 1H), 4.75 (d, J = 10.1 Hz, 1H), 4.53-4.39 (m, 1H), 3.79-3.64 (m, 1H), 3.61-3.49 (m, 1H), 1.86 (dd, J = 12.8, 6.8 Hz, 1H), 1.77-1.57 (m, 2H), 1.27 (qd, J = 11.3, 6.7 Hz, 1H) |
| 76 | 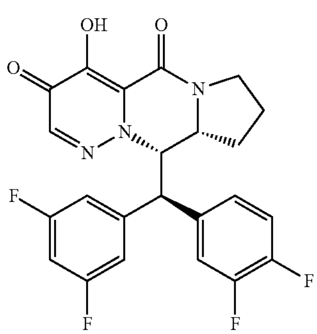 [SMILES: O=C1c2c(O)c(=O)cnn2[C@@H]([C@H](c2cc(F)cc(F)c2)c2ccc(F)c(F)c2)[C@H]2CCCN12] | 460.3 | (400 MHz, DMSO-d6) δ 7.88-7.77 (m, 1H), 7.53-7.39 (m, 2H), 7.31 (s, 1H), 6.97 (tt, J = 9.3, 2.4 Hz, 1H), 6.73 (dd, J = 8.7, 2.4 Hz, 2H), 5.73 (dd, J = 10.2, 3.6 Hz, 1H), 4.77 (d, J = 10.2 Hz, 1H), 4.46 (dt, J = 10.3, 5.2 Hz, 1H), 3.76-3.65 (m, 1H), 3.53 (td, J = 11.1, 7.0 Hz, 1H), 1.88 (dt, J = 12.9, 6.6 Hz, 1H), 1.78 (dt, J = 12.2, 6.1 Hz, 1H), 1.72-1.58 (m, 1H), 1.24 (qd, J = 11.5, 6.6 Hz, 1H) |

TABLE 1f-continued

Additional compounds prepared by the method of Example 65.

| Example No. | Structure | Mass M + H | 1H NMR |
|---|---|---|---|
| 77 | 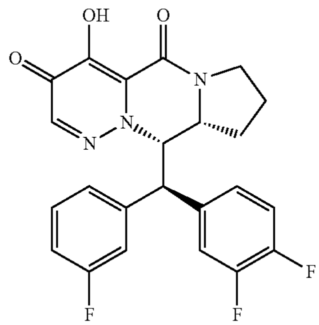 [SMILES: O=C1c2c(O)c(=O)cnn2[C@@H]([C@H](c2cccc(F)c2)c2ccc(F)c(F)c2)[C@H]2CCCN12] | 442.5 | (400 MHz, DMSO-d6) δ 7.87-7.72 (m, 1H), 7.53-7.36 (m, 2H), 7.24 (s, 1H), 7.16-7.04 (m, 1H), 6.89 (td, J = 8.6, 2.5 Hz, 1H), 6.85-6.72 (m, 2H), 5.71 (dd, J = 10.0, 3.6 Hz, 1H), 4.71 (d, J = 10.0 Hz, 1H), 4.46 (dd, J = 10.7, 5.2 Hz, 1H), 3.75-3.64 (m, 1H), 3.62-3.50 (m, 1H), 1.89 (dd, J = 12.6, 6.4 Hz, 1H), 1.79 (dt, J = 12.3, 5.9 Hz, 1H), 1.73-1.59 (m, 1H), 1.31 (qd, J = 11.5, 6.6 Hz, 1H). |
| 78 | 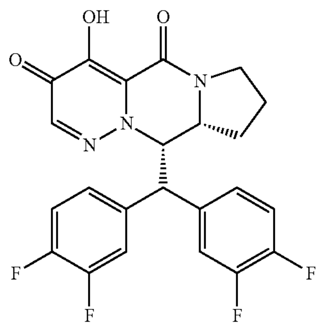 [SMILES: O=C1c2c(O)c(=O)cnn2[C@@H](C(c2ccc(F)c(F)c2)c2ccc(F)c(F)c2)[C@H]2CCCN12] | 460.5 | (400 MHz, DMSO-d6) δ 7.86-7.72 (m, 1H), 7.44 (dd, J = 9.6, 6.8 Hz, 2H), 7.30 (d, J = 4.0 Hz, 1H), 7.16 (q, J = 9.1 Hz, 1H), 7.11-7.03 (m, 1H), 6.80 (d, J = 10.0 Hz, 1H), 5.71 (dd, J = 10.1, 3.7 Hz, 1H), 4.73 (d, J = 10.0 Hz, 1H), 4.45 (s, 1H), 3.70 (t, J = 10.3 Hz, 1H), 3.54 (td, J = 10.5, 6.8 Hz, 1H), 1.88 (s, 1H), 1.77 (dt, J = 12.3, 6.0 Hz, 1H), 1.71-1.59 (m, 1H), 1.33-1.18 (m, 1H). |
| 79 | 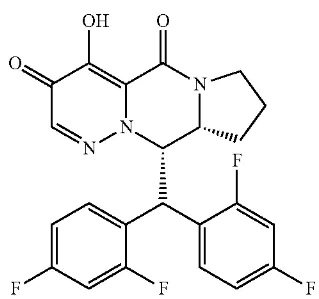 [SMILES: O=C1c2c(O)c(=O)cnn2[C@@H](C(c2ccc(F)cc2F)c2ccc(F)cc2F)[C@H]2CCCN12] | 460.4 | (400 MHz, DMSO-d6) δ 8.09 (q, J = 8.3 Hz, 1H), 7.33-7.13 (m, 3H), 7.10-6.96 (m, 2H), 6.87 (td, J = 8.5, 2.5 Hz, 1H), 5.85 (dd, J = 10.5, 3.5 Hz, 1H), 4.86 (d, J = 10.2 Hz, 1H), 4.55-4.43 (m, 1H), 3.77-3.65 (m, 1H), 3.56-3.42 (m, 2H), 1.96-1.79 (m, 2H), 1.70 (s, 1H), 1.31-1.11 (m, 1H) |
| 80 | 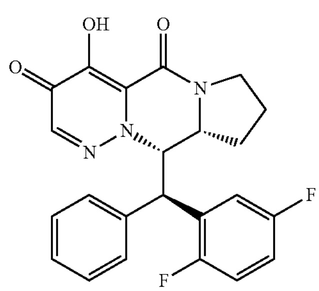 [SMILES: O=C1c2c(O)c(=O)cnn2[C@@H]([C@H](c2ccccc2)c2cc(F)ccc2F)[C@H]2CCCN12] | 424.4 | (400 MHz, CDCl3) δ ppm 7.29-7.42 (m, 2 H) 6.90-7.13 (m, 8 H) 5.34 (dd, J = 9.17, 3.55 Hz, 1 H) 4.57 (d, J = 9.15 Hz, 1 H) 4.32-4.50 (m, 1 H) 3.81-4.02 (m, 1 H) 3.57-3.81 (m, 1 H) 2.08-2.22 (m, 1 H) 1.82-2.07 (m, 3 H) 1.59 (qd, J = 11.72, 6.85 Hz, 1 H) |
| 81 | 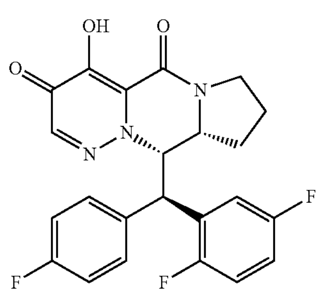 [SMILES: O=C1c2c(O)c(=O)cnn2[C@@H]([C@H](c2ccc(F)cc2)c2cc(F)ccc2F)[C@H]2CCCN12] | 442.4 | (400 MHz, CDCl3) δ ppm 7.30-7.41 (m, 2 H) 6.88-7.14 (m, 4 H) 6.80-6.91 (m, 2 H) 5.34 (dd, J = 9.49, 3.52 Hz, 1 H) 4.55 (d, J = 9.54 Hz, 1 H) 4.23-4.49 (m, 1 H) 3.79-4.03 (m, 1 H) 3.54-3.79 (m, 1 H) 2.07-2.18 (m, 1 H) 1.81-2.07 (m, 1 H) 1.53 (qd, J = 11.76, 6.77 Hz, 1 H) |

TABLE 1f-continued

Additional compounds prepared by the method of Example 65.

| Example No. | Structure | Mass M + H | 1H NMR |
|---|---|---|---|
| 82 | 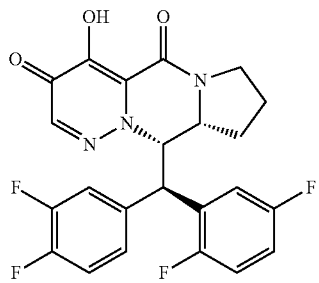 [SMILES: O=C1c2c(O)c(=O)cnn2[C@@H]([C@H](c2ccc(F)c(F)c2)c2cc(F)ccc2F)[C@H]2CCCN12] | 460.4 | (400 MHz, CDCl3) δ ppm 7.43 (s, 1 H) 7.29-7.42 (m, 1 H) 7.03-7.13 (m, 2 H) 7.0-6.95 (m, 2H) 6.94 (m, 1H) 5.35 (dd, J = 9.81, 3.43 Hz, 1 H) 4.53 (d, J = 10.17 Hz, 3 H) 4.42 (m, 1H) 3.95 (m, 1H) 3.63 (m, 1H 2.13 (m, 1H) 1.99 (s, 3 H) 1.88 (m, 1H) 1.48 (m, 1H) |
| 83 | 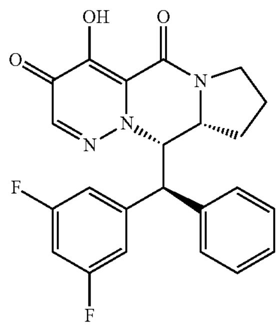 [SMILES: O=C1c2c(O)c(=O)cnn2[C@@H]([C@@H](c2ccccc2)c2cc(F)cc(F)c2)[C@H]2CCCN12] | 424.4 | (500 MHz, Methanol-d4) δ 7.60 (s, 1H), 7.58 (s, 1H), 7.51-7.42 (m, 3H), 7.36 (t, J = 7.4 Hz, 1H), 6.73-6.60 (m, 3H), 5.79 (d, J = 9.8 Hz, 1H), 4.61 (d, J = 9.9 Hz, 1H), 4.57-4.47 (m, 1H), 3.95-3.83 (m, 1H), 3.70 (t, J = 9.6 Hz, 1 H), 2.02 (d, J = 11.0 Hz, 1H), 1.95-1.77 (m, 2H), 1.65-1.50 (m, 1H). |
| 84 | 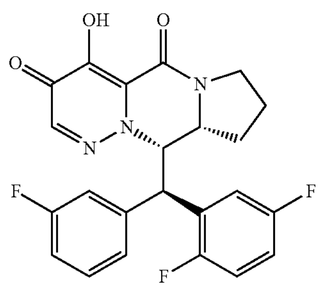 [SMILES: O=C1c2c(O)c(=O)cnn2[C@@H]([C@H](c2cccc(F)c2)c2cc(F)ccc2F)[C@H]2CCCN12] | 443.4 | (500 MHz, Chloroform-d) δ 7.40-7.32 (m, 2H), 7.13-7.03 (m, 3H), 6.83 (t, J = 8.3 Hz, 1H), 6.74 (d, J = 9.7 Hz, 1H), 6.67 (d, J = 7.7 Hz, 1H), 5.35 (dd, J = 9.5, 3.6 Hz, 1H), 4.57 (d, J = 9.5 Hz, 1H), 4.46-4.37 (m, 1H), 3.99-3.89 (m, 1H), 3.70-3.59 (m, 1H), 2.13 (dd, J = 13.2, 6.8 Hz, 1H), 2.01 (dt, J = 12.4, 6.0 Hz, 1H), 1.96-1.85 (m, 1H), 1.60-1.47 (m, 1H). |
| 85 | 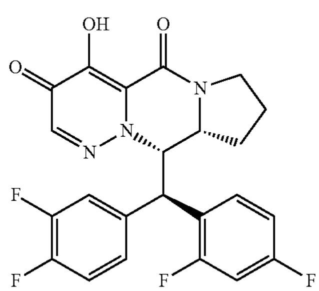 [SMILES: O=C1c2c(O)c(=O)cnn2[C@@H]([C@H](c2ccc(F)c(F)c2)c2ccc(F)cc2F)[C@H]2CCCN12] | 460.4 | (500 MHz, Chloroform-d) δ 7.65-7.56 (m, 1H), 7.44 (s, 1H), 7.07 (t, J = 7.8 Hz, 1H), 6.96-6.82 (m, 3H), 6.64 (d, J = 8.4 Hz, 1H), 5.41 (dd, J = 9.8, 3.5 Hz, 1H), 4.54 (d, J = 9.7 Hz, 1H), 4.43 (dd, J = 10.5, 5.5 Hz, 1H), 4.01-3.91 (m, 1H), 3.66 (td, J = 11.3, 7.1 Hz, 1H), 2.14 (dt, J = 13.5, 6.9 Hz, 1H), 1.98 (dt, J = 12.2, 5.9 Hz, 1H), 1.91 (d, J = 13.2 Hz, 1H), 1.50 (qd, J = 11.6, 6.6 Hz, 1H). |
| 86 | 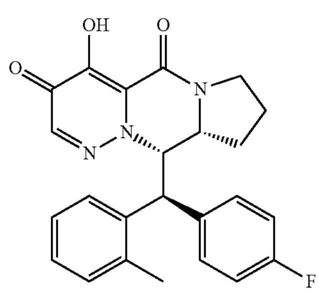 [SMILES: Cc1ccccc1[C@H](c1ccc(F)cc1)[C@H]1[C@H]2CCCN2C(=O)c2c(O)c(=O)cnn21] | 420.4 | (500 MHz, DMSO-d6) δ 7.63 (s, 2H), 7.21 (d, J = 1.5 Hz, 1H), 7.18 (t, J = 8.5 Hz, 2H), 7.13 (s, 1H), 6.96 (s, 1H), 6.91 (s, 2H), 5.83 (s, 1H), 4.78 (s, 1H), 4.52 (s, 1H), 3.74 (t, J = 10.4 Hz, 1H), 3.62 (q, J = 10.7, 10.2 Hz, 2H), 2.21 (s, 3H), 1.91 (d, J = 8.0 Hz, 1H), 1.80 (s, 1H), 1.71 (s, 1H), 1.38 (dd, J = 11.7, 6.8 Hz, 1H). |

TABLE 1f-continued

Additional compounds prepared by the method of Example 65.

| Example No. | Structure | Mass M + H | 1H NMR |
|---|---|---|---|
| 87 | 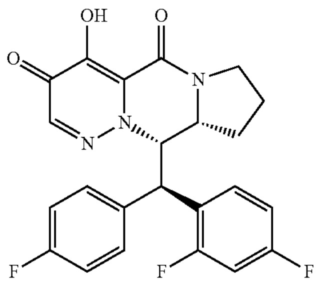 [SMILES: O=C1c2c(O)c(=O)cnn2[C@@H]([C@H](c2ccc(F)cc2)c2ccc(F)cc2F)[C@H]2CCCN12] | 442.4 | (500 MHz, Methanol-d4) δ 7.97 (q, J = 8.2 Hz, 1H), 7.44 (s, 1H), 7.15 (t, J = 8.4 Hz, 1H), 7.02 (dd, J = 8.5, 4.5 Hz, 3H), 6.85 (t, J = 8.5 Hz, 2H), 5.78 (dd, J = 9.5, 3.6 Hz, 1H), 4.70 (d, J = 9.4 Hz, 1H), 4.53 (d, J = 8.5 Hz, 1H), 3.97-3.87 (m, 1H), 3.65 (dd, J = 19.2, 10.7 Hz, 1H), 2.10 (d, J = 8.0 Hz, 1H), 2.00 (dd, J = 12.3, 6.2 Hz, 1H), 1.90 (s, 1H), 1.55 (dd, J = 11.7, 6.9 Hz, 1H). |
| 88 | 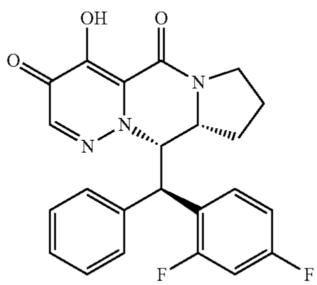 [SMILES: O=C1c2c(O)c(=O)cnn2[C@@H]([C@H](c2ccccc2)c2ccc(F)cc2F)[C@H]2CCCN12] | 424.4 | (500 MHz, Methanol-d4) δ 7.98 (q, J = 8.0 Hz, 1H), 7.37 (d, J = 1.3 Hz, 1H), 7.17-7.12 (m, 1H), 7.12-7.08 (m, 3H), 7.01 (t, J = 9.9 Hz, 1H), 6.97 (d, J = 5.4 Hz, 2H), 5.86-5.74 (m, 1H), 4.68 (d, J = 9.3 Hz, 1H), 4.60-4.50 (m, 1H), 3.99-3.87 (m, 1H), 3.73-3.61 (m, 1H), 2.11 (dd, J = 12.5, 6.4 Hz, 1H), 2.02 (dt, J = 12.6, 6.3 Hz, 1H), 1.92 (d, J = 12.6 Hz, 1H), 1.69-1.55 (m, 1H). |
| 89 | 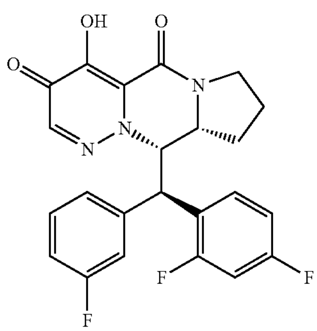 [SMILES: O=C1c2c(O)c(=O)cnn2[C@@H]([C@H](c2cccc(F)c2)c2ccc(F)cc2F)[C@H]2CCCN12] | 442.3 | (500 MHz, Methanol-d4) δ 7.98 (q, J = 8.3 Hz, 1H), 7.43 (d, J = 1.5 Hz, 1H), 7.14 (dt, J = 21.3, 7.8 Hz, 2H), 7.04 (t, J = 9.8 Hz, 1H), 6.87 (t, J = 8.6 Hz, 1H), 6.78 (d, J = 8.6 Hz, 2H), 5.81 (d, J = 7.4 Hz, 1H), 4.72 (d, J = 9.6 Hz, 1H), 4.53 (d, J = 6.7 Hz, 1H), 3.97-3.88 (m, 1H), 3.66 (q, J = 11.0, 10.4 Hz, 1H), 2.10 (s, 1H), 2.05-1.98 (m, 1H), 1.90 (s, 1H), 1.55 (dd, J = 11.8, 6.8 Hz, 1H). |
| 90 | 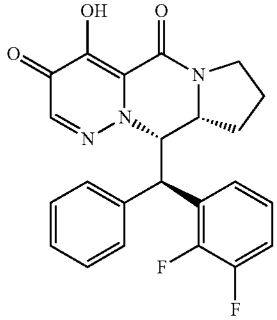 [SMILES: O=C1c2c(O)c(=O)cnn2[C@@H]([C@H](c2ccccc2)c2cccc(F)c2F)[C@H]2CCCN12] | 424.4 | (400 MHz, DMSO-d6) δ 7.84 (t, J = 7.1 Hz, 1H), 7.37 (ddt, J = 16.0, 13.4, 8.1 Hz, 2H), 7.21 (s, 1H), 7.14-7.03 (m, 3H), 6.98-6.85 (m, 2H), 5.77 (dd, J = 9.6, 3.7 Hz, 1H), 4.64 (d, J = 9.6 Hz, 1H), 4.50 (dt, J = 10.0, 5.1 Hz, 1H), 3.73 (dd, J = 12.0, 8.4 Hz, 2H), 1.92 (ddt, J = 30.6, 12.3, 6.1 Hz, 2H), 1.74 (q, J = 8.3, 6.0 Hz, 1H), 1.34 (qd, J = 11.6, 6.6 Hz, 1H). |

Example 91. (9aR,10S)-10-((S)-(2,3-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione

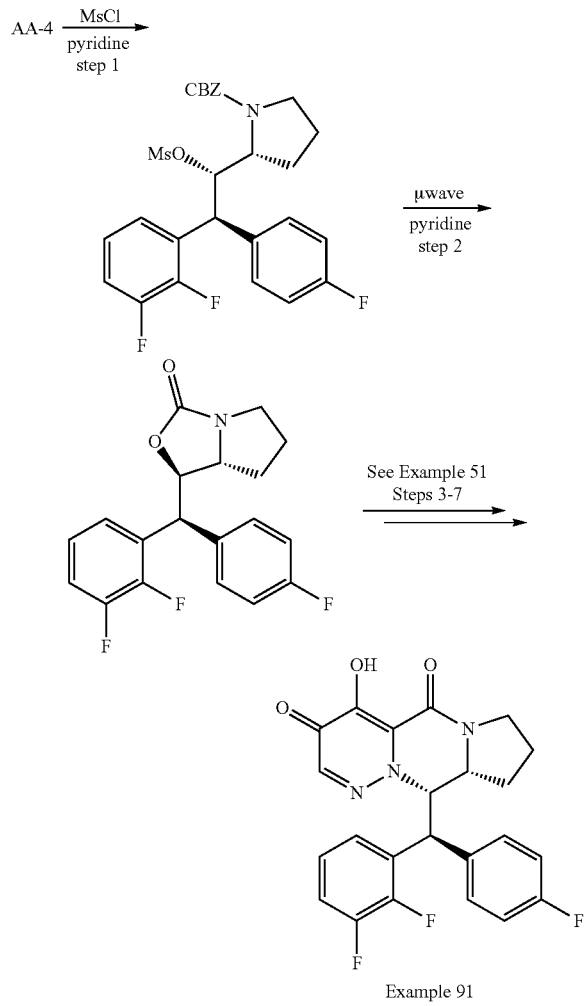

Example 91

Step 1: benzyl (R)-2-((1S,2S)-2-(2,3-difluorophenyl)-2-(4-fluorophenyl)-1-((methylsulfonyl)oxy)ethyl)pyrrolidine-1-carboxylate To a solution of benzyl (R)-2-((1S,2S)-2-(2,3-difluorophenyl)-2-(4-fluorophenyl)-1-hydroxyethyl)pyrrolidine-1-carboxylate (350 mg, 0.77 mmol) in pyridine (2.5 mL) at 0° C. was added methanesulfonyl chloride (0.90 mL, 11.5 mmol). After 5 min, the ice bath was removed and the reaction was stirred for 2 h at RT. The reaction mixture was partitioned between DCM and water. The DCM layer was separated and washed sequentially with 1N aqueous HCl, saturated aqueous $NaHCO_3$ and brine. The organic layer was dried over $Na_2SO_4$, filtered and concentrated. Silica gel column chromatography (EtOAc/heptane) provided benzyl (R)-2-((1S,2S)-2-(2,3-difluorophenyl)-2-(4-fluorophenyl)-1-((methylsulfonyl)oxy)ethyl)pyrrolidine-1-carboxylate (370 mg) in 90% yield. MS m/z 534.5 ($MH^+$).

Step 2: (1R,7aR)-1-((S)-(2,3-difluorophenyl)(4-fluorophenyl)methyl)tetrahydro-1H,3H-pyrrolo[1,2-c]oxazol-3-one A solution of benzyl (R)-2-((1S,2S)-2-(2,3-difluorophenyl)-2-(4-fluorophenyl)-1-((methylsulfonyl)oxy)ethyl)pyrrolidine-1-carboxylate (370 mg, 0.693 mmol) in pyridine (2 mL) was heated at 150° C. for 3 h in a microwave reactor. Silica gel column chromatography (EtOAc/heptane) provided (1R,7aR)-1-((S)-(2,3-difluorophenyl)(4-fluorophenyl)methyl)tetrahydro-1H,3H-pyrrolo[1,2-c]oxazol-3-one (200 mg) in 83% yield. MS m/z 348.4 (MH+).

Example 91. (9aR,10S)-10-((S)-(2,3-difluorophenyl)(4-fluorophenyl)methyl)-4-hydroxy-8,9,9a,10-tetrahydro-7H-pyrrolo[1',2':4,5]pyrazino[1,2-b]pyridazine-3,5-dione Prepared from (1R,7aR)-1-((S)-(2,3-difluorophenyl)(4-fluorophenyl)methyl)tetrahydro-1H,3H-pyrrolo[1,2-c]oxazol-3-one by the method of Example 51, steps 3-7. $^1$H NMR (400 MHz, CD3OD) δ ppm 7.61 (dd, J=8.6, 5.2 Hz, 2H), 7.42 (s, 1H), 7.16 (t, J=8.7 Hz, 2H), 7.01 (dtd, J=9.9, 7.9, 1.7 Hz, 1H), 6.96-6.80 (m, 2H), 5.85 (dd, J=10.0, 3.6 Hz, 1H), 4.95-4.90 (m, 1H), 4.54 (dt, J=10.6, 4.9 Hz, 1H), 3.89 (dd, J=12.5, 8.7 Hz, 1H), 3.72-3.60 (m, 1H), 2.04 (qd, J=7.3, 3.2 Hz, 1H), 1.98-1.78 (m, 2H), 1.57 (qd, J=11.5, 6.6 Hz, 1H). MS m/z 442.4 (MH+).

TABLE 1g

Additional compounds prepared by the method of Example 91.

| Example No. | Structure | Mass M + H | 1H NMR |
|---|---|---|---|
| 92 | 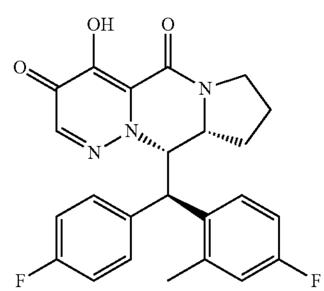 [SMILES: Cc1cc(F)ccc1[C@@H](c1ccc(F)cc1)[C@H]1[C@H]2CCCN2C(=O)c2c(O)c(=O)cnn21] | 438.3 | (400 MHz, MeOD) δ ppm 7.90 (dd, J = 8.63, 5.60 Hz, 1 H) 7.36 (s, 1 H) 7.12 (td, J = 8.46, 2.64 Hz, 1 H) 6.89-7.04 (m, 3 H) 6.82 (t,J = 8.68 Hz, 2 H) 5.79 (dd, J = 9.90, 3.59 Hz, 1 H) 4.40-4.56 (m, 2 H) 3.87-4.00 (m, 1 H) 3.57-3.72 (m, 1 H) 2.17 (s, 3 H) 2.01-2.07 (m, 1 H) 1.75-1.94 (m, 2H) 1.25-1.38 (m,1 H) |

TABLE 1g-continued

Additional compounds prepared by the method of Example 91.

| Example No. | Structure | Mass M + H | 1H NMR |
|---|---|---|---|
| 93 | 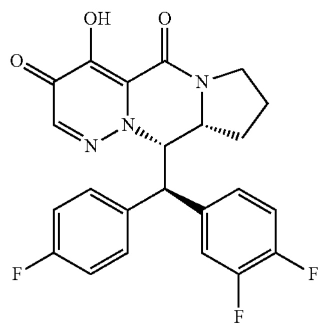 [SMILES: O=C1c2c(O)c(=O)cnn2[C@@H]([C@H](c2ccc(F)cc2)c2ccc(F)c(F)c2)[C@H]2CCCN12] | 442.4 | (400 MHz, MeOD) δ ppm 7.52-7.62 (m, 1 H) 7.36-7.45 (m, 2 H) 7.27-7.35 (m, 1 H) 6.97 (br dd, J = 8.46, 5.23 Hz, 2 H) 6.77-6.90 (m, 2 H) 5.65-5.76 (m, 1 H) 4.59 (br d, J = 9.39 Hz, 1 H) 4.46-4.53 (m, 1 H) 3.83-3.94 (m, 1 H) 3.62-3.73 (m, 1 H) 2.02-2.14 (m, 1 H) 1.79-1.99 (m, 2 H) 1.53-1.68 (m, 1 H) |
| 94 *isolated during purification of Example 93 | 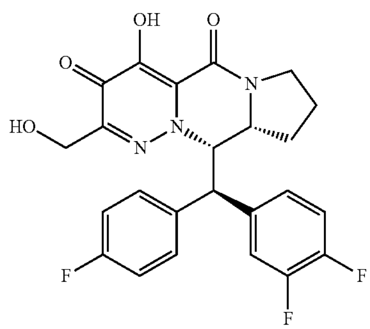 [SMILES: O=C1c2c(O)c(=O)c(CO)nn2[C@@H]([C@H](c2ccc(F)cc2)c2ccc(F)c(F)c2)[C@H]2CCCN12] | 472.2 | (400 MHz, MeOD) δ ppm 7.57-7.68 (m, 1 H) 7.42 (br d, J = 8.31 Hz, 1 H) 7.25-7.37 (m, 1 H) 6.98 (dd, J = 8.44, 5.31 Hz, 2 H) 6.78 (t, J = 8.66 Hz, 2H) 5.67 (dd, J = 9.29, 3.37 Hz, 1 H) 4.44-4.61 (m, 3 H) 4.17 (d, J = 14.18 Hz, 1 H) 3.80-3.93 (m, 1 H) 3.63-3.75 (m, 1 H) 3.34 (s, 1 H) 2.02-2.15 (m, 1 H) 1.78-1.98 (m, 2 H) 1.54-1.70 (m, 1 H) |
| 95 | 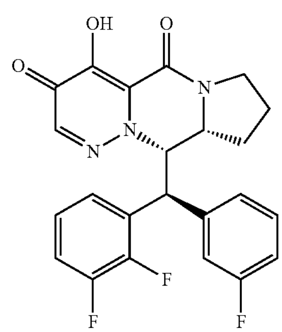 [SMILES: O=C1c2c(O)c(=O)cnn2[C@@H]([C@@H](c2cccc(F)c2)c2cccc(F)c2F)[C@H]2CCCN12] | 442.4 | 1H NMR (400 MHz, MeOD) δ ppm 7.26-7.48 (m, 4 H) 6.98-7.13 (m, 2 H) 6.82-6.96 (m, 2 H) 5.88 (dd, J = 9.83, 3.57 Hz, 1 H) 4.93 (br d, J = 9.98 Hz, 1 H) 4.49-4.58 (m, 1 H) 3.85-3.96 (m, 1 H) 3.60-3.70 (m, 1 H) 2.01-2.09 (m, 1 H) 1.95 (dt, J = 12.20, 5.98 Hz, 1 H) 1.77-1.89 (m, 1 H) 1.57 (qd, J = 11.69, 6.60 Hz, 1 H) |
| 96 | 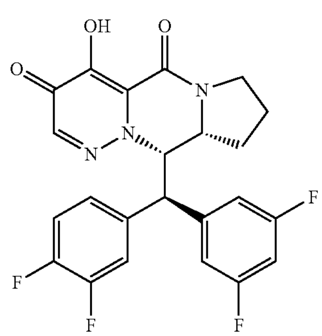 [SMILES: O=C1c2c(O)c(=O)cnn2[C@@H]([C@@H](c2cc(F)cc(F)c2)c2ccc(F)c(F)c2)[C@H]2CCCN12] | 460.4 | (400 MHz, DMSO-d6) δ 7.51-7.39 (m, 2H), 7.31 (d, J = 2.8 Hz, 1H), 7.24-7.04 (m, 3H), 6.84 (s, 1H), 5.75 (dd, J = 10.2, 3.7 Hz, 1H), 4.75 (d, J = 10.0 Hz, 1H), 4.53-4.40 (m, 1H), 3.70 (dd, J = 11.4, 9.0 Hz, 1H), 3.54 (q, J = 10.5 Hz, 1H), 1.90 (q, J = 6.7 Hz, 1H), 1.85-1.74 (m, 1H), 1.67 (s, 1H), 1.25 (tq, J = 11.5, 6.2 Hz, 1H) |

TABLE 1g-continued

Additional compounds prepared by the method of Example 91.

| Example No. | Structure | Mass M + H | 1H NMR |
|---|---|---|---|
| 97 | 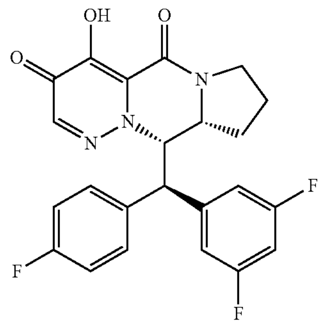 [SMILES: O=C1c2c(O)c(=O)cnn2[C@@H]([C@H](c2ccc(F)cc2)c2cc(F)cc(F)c2)[C@H]2CCCN12] | 442.4 | (500 MHz, CHLOROFORM-d) δ ppm 7.38 (br s, 1 H) 7.24-7.34 (m, 1 H) 7.16 (br s, 1 H) 6.97 (br s, 1 H) 6.77-6.92 (m, 3 H) 6.48 (br s, 1 H) 5.37 (br 1 H) 4.44 (br s, 1 H) 4.21-4.36 (m, 1 H) 3.96 (br s, 1 H) 3.65 (br s, 1 H) 2.15 (br s, 1 H) 1.97-2.06 (m, 1 H) 1.90 (br s, 1 H) 1.47-1.67 (m, 1 H) |
| 98 | 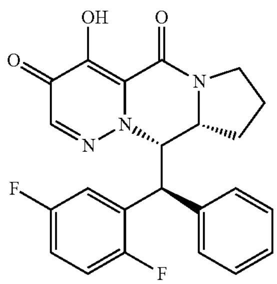 [SMILES: O=C1c2c(O)c(=O)cnn2[C@@H]([C@@H](c2ccccc2)c2cc(F)ccc2F)[C@H]2CCCN12] | 424.4 | (400 MHz, CDCl3) δ ppm 7.31-7.51 (m, 6 H) 6.66-6.84 (m, 3 H) 5.44 (dd, J = 9.71, 3.40 Hz, 1 H) 4.80 (d, J = 9.73 Hz, 1 H) 4.39 (br dd, J = 10.10, 4.96 Hz, 1 H) 3.80-4.01 (m, 1 H) 3.56-3.78 (m, 1 H) 1.96-2.20 (m, 1 H) 1.72-1.96 (m, 2 H) 1.48-1.72 (m, 1 H) |
| 99 | 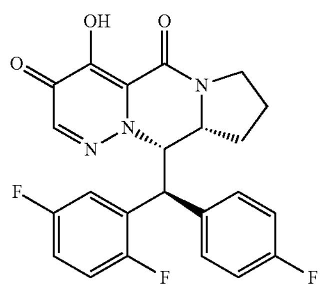 [SMILES: O=C1c2c(O)c(=O)cnn2[C@@H]([C@@H](c2ccc(F)cc2)c2cc(F)ccc2F)[C@H]2CCCN12] | 442.4 | (400 MHz, CDCl3) δ ppm 7.37-7.45 (m, 3 H) 7.14 (t, J = 8.49 Hz, 2 H) 6.70-6.86 (m, 2 H) 6.66 (ddd, J = 8.75, 5.80, 2.86 Hz, 1 H) 5.39 (dd, J = 9.56, 3.50 Hz, 1 H) 4.78 (d, J = 9.54 Hz, 1 H) 4.40 (br dd, J = 10.07, 4.99 Hz, 1 H) 3.82-4.02 (m, 1 H) 3.56-3.75 (m, 1 H) 2.04-2.27 (m, 1 H) 1.74-1.97 (m, 2 H) 1.48-1.71 (m, 1 H) |
| 100 | 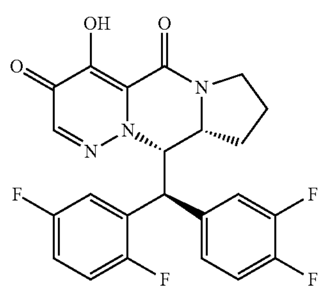 [SMILES: O=C1c2c(O)c(=O)cnn2[C@@H]([C@@H](c2ccc(F)c(F)c2)c2cc(F)ccc2F)[C@H]2CCCN12] | 460.4 | (400 MHz, d-DMSO) δ ppm 7.80 (br dd, J = 11.98, 7.73 Hz, 1 H) 7.28-7.47 (m, 3 H) 6.89-7.06 (m, 3H) 5.82 (dd, J = 10.42, 3.37 Hz, 1 H) 4.86 (d, J = 10.42 Hz, 1 H) 4.48 (dt, J = 10.14, 4.93 Hz, 1 H) 3.63-3.88 (m, 1 H) 3.54 (td, J = 11.03, 7.19 Hz, 1 H) 1.75-1.92 (m, 2 H) 1.51-1.75 (m, 1 H) 1.25 (qd, J = 11.64, 6.75 Hz, 1 H) |
| 101 | 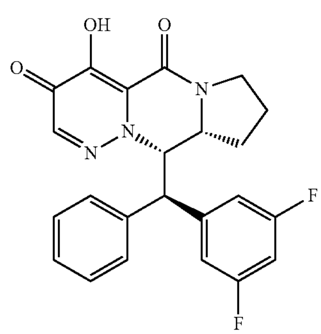 [SMILES: O=C1c2c(O)c(=O)cnn2[C@@H]([C@H](c2ccccc2)c2cc(F)cc(F)c2)[C@H]2CCCN12] | 424.4 | (500 MHz, Methanol-d4) δ 7.38 (d, J = 3.1 Hz, 1H), 7.29 (d, J = 7.8 Hz, 2H), 7.16-7.05 (m, 3H), 6.97 (d, J = 5.4 Hz, 2H), 6.92 (t, J = 9.2 Hz, 1H), 5.76 (dd, J = 9.2, 4.1 Hz, 1H), 4.62 (d, J = 8.7 Hz, 1H), 4.57-4.49 (m, 1H), 3.90 (t, J = 10.7 Hz, 1H), 3.71 (t, J = 10.3 Hz, 1H), 2.13 (s, 1H), 2.02 (d, J = 10.2 Hz, 1H), 1.90 (s, 1H), 1.69 (d, J = 11.9 Hz, 1H). |

TABLE 1g-continued

Additional compounds prepared by the method of Example 91.

| Example No. | Structure | Mass M + H | 1H NMR |
|---|---|---|---|
| 102 | 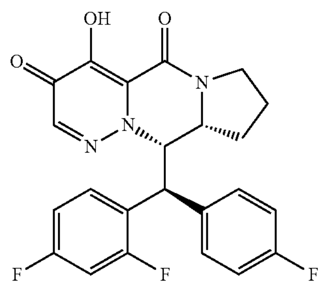 | 442.2 | (500 MHz, Methanol-d4) δ 7.65-7.57 (m, 2H), 7.47 (d, J = 1.2 Hz, 1H), 7.18 (t, J = 8.4 Hz, 2H), 7.11 (q, J = 8.1 Hz, 1H), 6.75 (q, J = 10.5, 9.4 Hz, 2H), 5.88-5.78 (m, 1H), 4.90 (d, J = 9.8 Hz, 1H), 4.61-4.51 (m, 1H), 3.96-3.84 (m, 1H), 3.66 (q, J = 10.5 Hz, 1H), 2.10-2.01 (m, 1H), 1.93 (dd, J = 12.3, 6.1 Hz, 1H), 1.86 (s, 1H), 1.71-1.56 (m, 1H). |
| 103 | 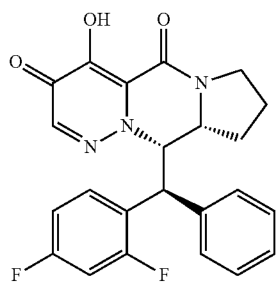 [SMILES: O=C1c2c(O)c(=O)cnn2[C@@H]([C@@H](c2ccccc2)c2ccc(F)cc2F)[C@H]2CCCN12] | 424.4 | (500 MHz, Methanol-d4) δ 7.57 (d, J = 7.8 Hz, 2H), 7.47-7.43 (m, 3H), 7.35 (d, J = 7.3 Hz, 1H), 7.14 (d, J = 7.8 Hz, 1H), 6.74 (d, J = 9.7 Hz, 2H), 5.84 (d, J = 9.6 Hz, 1H), 4.90 (s, 1H), 4.55 (s, 1H), 3.90 (s, 1H), 3.66 (d, J = 10.4 Hz, 1H), 2.04 (s, 1H), 1.89 (s, 2H), 1.62 (s, 1H). |
| 104 | 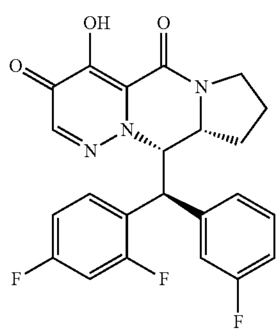 [SMILES: O=C1c2c(O)c(=O)cnn2[C@@H]([C@@H](c2cccc(F)c2)c2ccc(F)cc2F)[C@H]2CCCN12] | 442.3 | (500 MHz, Methanol-d4) δ 7.49-7.43 (m, 2H), 7.39 (d, J = 6.5 Hz, 2H), 7.10 (dt, J = 16.5, 8.0 Hz, 2H), 6.77 (q, J = 9.6, 8.8 Hz, 2H), 5.85 (d, J = 10.0 Hz, 1H), 4.92 (d, J = 10.0 Hz, 1H), 4.55 (s, 1H), 3.90 (t, J = 10.5 Hz, 1H), 3.66 (d, J = 9.0 Hz, 1H), 2.06 (s, 1H), 1.96 (d, J = 12.0 Hz, 1H), 1.87 (s, 1H), 1.61 (d, J = 12.2 Hz, 1H). |
| 105 | 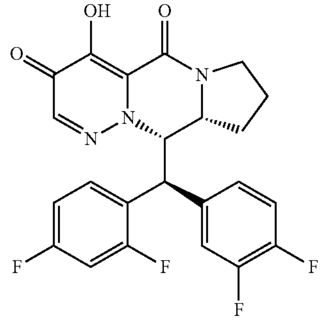 [SMILES: O=C1c2c(O)c(=O)cnn2[C@@H]([C@@H](c2ccc(F)c(F)c2)c2ccc(F)cc2F)[C@H]2CCCN12] | 460.3 | 1H NMR (500 MHz, DMSO-d6) δ 7.85-7.74 (m, 1H), 7.51-7.40 (m, 2H), 7.32 (s, 1H), 7.14 (td, J = 8.7, 6.5 Hz, 1H), 7.01 (ddd, J = 11.7, 9.3, 2.7 Hz, 1H), 6.90 (td, J = 8.4, 2.7 Hz, 1H), 5.85 (dd, J = 10.3, 3.6 Hz, 1H), 4.86 (d, J = 10.4 Hz, 1H), 4.51 (dt, J = 10.4, 4.9 Hz, 1H), 3.78-3.69 (m, 1H), 3.62-3.53 (m, 1H), 1.92 (dt, J = 13.0, 6.9 Hz, 1H), 1.84 (dt, J = 11.8, 6.0 Hz, 1H), 1.70 (h, J = 11.6 Hz, 1H), 1.31 (qd, J = 11.8, 6.6 Hz, 1H). |

Example 106. 10-(bis(3-fluorophenyl)methyl)-4-hydroxy-8,9,9a,10-tetrahydro-7H-pyrrolo[1',2':4,5]pyrazino[1,2-b]pyridazine-3,5-dione

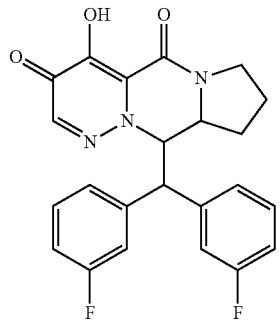 [SMILES: O=C1c2c(O)c(=O)cnn2C(C(c2cccc(F)c2)c2cccc(F)c2)C2CCCN12]

Prepared from tert-butyl 2-formylpyrrolidine-1-carboxylate by the method of Example 32. LCMS (m/z): 424.3 (MH+), $^1$H NMR (400 MHz, DMSO-d6) δ 7.59-7.52 (m, 1H), 7.51-7.37 (m, 2H), 7.27 (s, 1H), 7.12 (td, J=8.2, 6.1 Hz, 2H), 6.96-6.87 (m, 1H), 6.86-6.76 (m, 2H), 5.75 (dd, J=10.0, 3.6 Hz, 1H), 4.72 (d, J=10.0 Hz, 1H), 4.48 (dd, J=10.3, 5.3 Hz, 1H), 3.79-3.68 (m, 1H), 3.66-3.54 (m, 1H), 1.96-1.86 (m, 1H), 1.85-1.61 (m, 2H), 1.36 (td, J=11.3, 6.5 Hz, 1H).

Example 107. 4-((R)-(3-fluorophenyl)((9aR,10S)-4-hydroxy-3,5-dioxo-3,5,8,9,9a,10-hexahydro-7H-pyrrolo[1',2':4,5]pyrazino[1,2-b]pyridazin-10-yl)methyl)benzonitrile

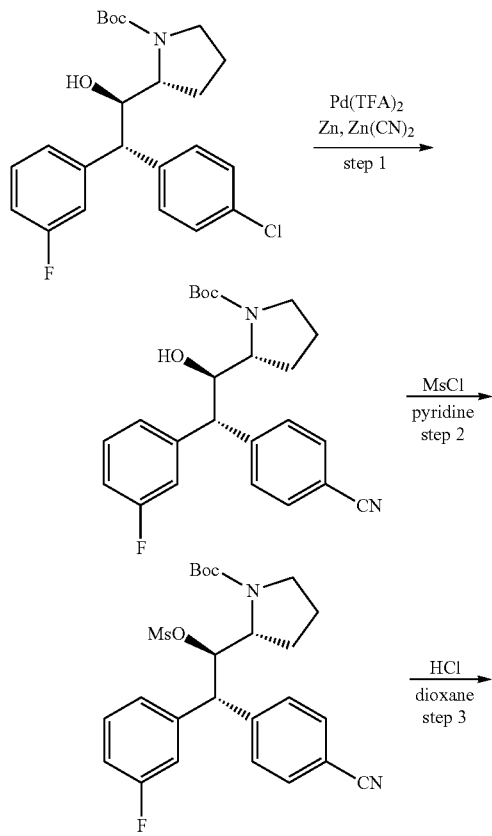

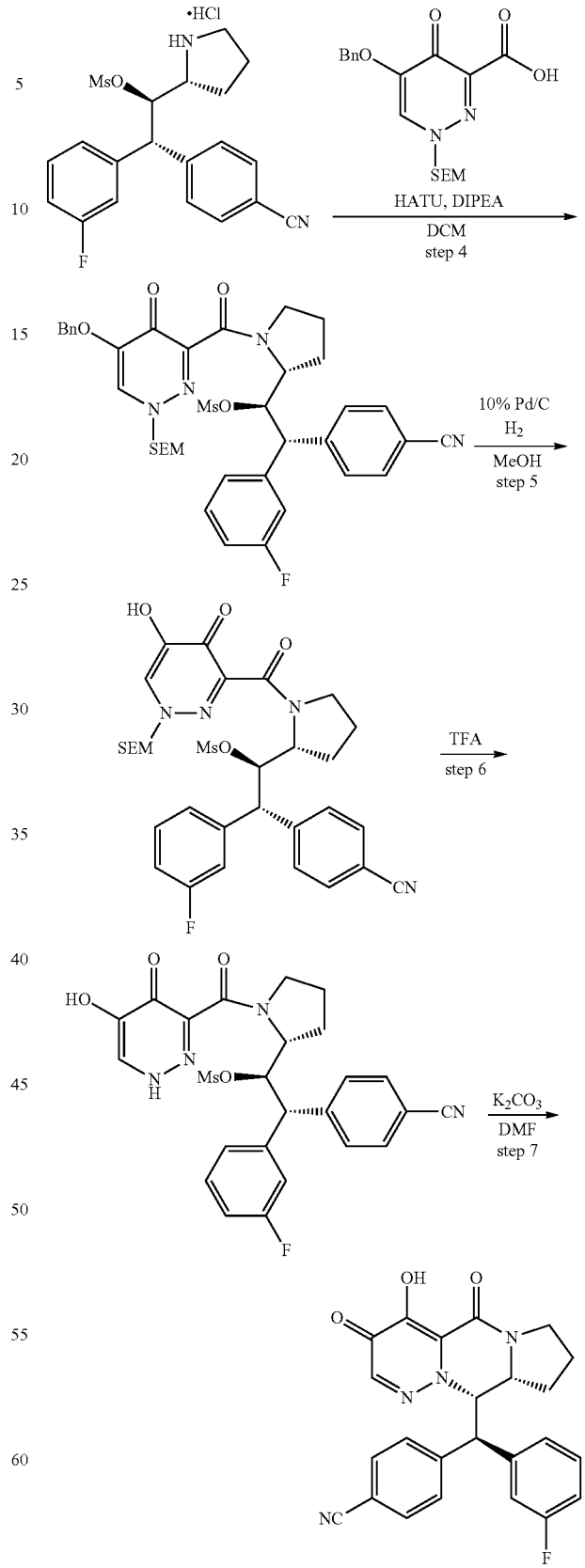

Example 107

Step 1: (R)-tert-butyl 2-((1R,2R)-2-(4-cyanophenyl)-2-(3-fluorophenyl)-1-hydroxyethyl)pyrrolidine-1-carboxylate Added (R)-tert-butyl 2-((1R,2R)-2-(4-chlorophenyl)-2-(3-fluorophenyl)-1-hydroxyethyl) pyrrolidine-1-carboxylate (190 mg, 0.362 mmol, prepared by the general method of AA-1), Zn powder (23.67 mg, 0.362 mmol), zinc cyanide (85 mg, 0.724 mmol), rac-2-(di-t-butylphosphino)-1,1'-binapthyl (28.8 mg, 0.072 mmol) and bis(2,2,2-trifluoroacetyl)palladium (10.88 mg, 0.036 mmol) at RT to a microwave vial equipped with a stir bar. Cap was sealed and $N_2$ was passed through for 5 min. DMA (Volume: 4 mL) was added through the syringe and $N_2$ was passed through for an additional 5 min. The microwave vial was placed in a heating block and heated at 95° C. for 1H. The reaction mixture was diluted with DCM and filtered through celite. The celite was washed with DCM and the filtrate was concentrated. Silica gel column chromatography (EtOAc/heptane) provided (R)-tert-butyl 2-((1R,2R)-2-(4-cyanophenyl)-2-(3-fluorophenyl)-1-hydroxyethyl)pyrrolidine-1-carboxylate, (110 mg) in 74% yield. MS m/z 411.2 (MH+).

Step 2: (R)-tert-butyl 2-((1R,2R)-2-(4-cyanophenyl)-2-(3-fluorophenyl)-1-((methylsulfonyl)oxy)ethyl)pyrrolidine-1-carboxylate To a solution of (R)-tert-butyl 2-((1R,2R)-2-(4-cyanophenyl)-2-(3-fluorophenyl)-1-hydroxyethyl)pyrrolidine-1-carboxylate (110 mg, 0.268 mmol) in pyridine (4 mL) at 0° C. was added methanesulfonyl chloride (0.251 mL, 3.22 mmol). After 5 min the ice bath was removed and the reaction was stirred for 2 h at RT. The reaction mixture was then partitioned between DCM and water. The DCM layer was washed with sat'd aq. $NaHCO_3$ then brine, dried over $Na_2SO_4$, filtered and concentrated. Silica gel column chromatography (EtOAc/heptane) provided (R)-tert-butyl 2-((1R,2R)-2-(4-cyanophenyl)-2-(3-fluorophenyl)-1-((methylsulfonyl) oxy)ethyl)pyrrolidine-1-carboxylate (105 mg) in 80% yield. MS m/z 489.3 (MH+).

Step 3: (1R,2R)-2-(4-cyanophenyl)-2-(3-fluorophenyl)-1-((R)-pyrrolidin-2-yl)ethyl methanesulfonate hydrochloride Added HCl (4.0 M in dioxane, 2 ml, 8 mmol) to (R)-tert-butyl 2-((1R,2R)-2-(4-cyanophenyl)-2-(3-fluorophenyl)-1-((methylsulfonyl)oxy)ethyl)pyrrolidine-1-carboxylate (105 mg, 0.215 mmol). Stirred for 1H at RT. The reaction was then concentrated to give (1R, 2R)-2-(4-cyanophenyl)-2-(3-fluorophenyl)-1-((R)-pyrrolidin-2-yl)ethyl methanesulfonate hydrochloride, which was used in the next step without further purification. MS m/z 389.3 (MH+).

Step 4: (1R,2R)-1-((R)-1-(5-(benzyloxy)-4-oxo-1-((2-(trimethylsilyl)ethoxy)methyl)-1,4-dihydropyridazine-3-carbonyl)pyrrolidin-2-yl)-2-(4-cyanophenyl)-2-(3-fluorophenyl)ethyl methanesulfonate Added Huenig's base (0.142 mL, 0.812 mmol) and HATU (100 mg, 0.264 mmol) to a solution of 5-(benzyloxy)-4-oxo-1-((2-(trimethylsilyl)ethoxy)methyl)-1,4-dihydropyridazine-3-carboxylic acid (84 mg, 0.223 mmol: see US 2015/0072982 A1) in DCM (1 mL) at RT. Stirred at RT for 15 min, then added a solution of crude (1R, 2R)-2-(4-cyanophenyl)-2-(3-fluorophenyl)-1-((R)-pyrrolidin-2-yl) ethyl methanesulfonate hydrochloride (83 mg, 0.203 mmol) in DCM (1 mL) and 2 equiv of Huenig's base. The mixture was stirred at RT for 1H. The reaction was then diluted with DCM and washed with water and brine. The organic layer was dried over $Na_2SO_4$, filtered and concentrated. Silica gel column chromatography (EtOAc/EtOH/heptane) provided (1R,2R)-1-((R)-1-(5-(benzyloxy)-4-oxo-1-((2-(trimethylsilyl)ethoxy)methyl)-1,4-dihydropyridazine-3-carbonyl) pyrrolidin-2-yl)-2-(4-cyanophenyl)-2-(3-fluorophenyl)ethyl methanesulfonate (130 mg) in 86% yield. MS m/z 747.4 (MH+).

Step 5: (1R,2R)-2-(4-cyanophenyl)-2-(3-fluorophenyl)-1-((R)-1-(5-hydroxy-4-oxo-1-((2-(trimethylsilyl)ethoxy)methyl)-1,4-dihydropyridazine-3-carbonyl)pyrrolidin-2-yl)ethyl methanesulfonate A solution of (1R,2R)-1-((R)-1-(5-(benzyloxy)-4-oxo-1-((2-(trimethylsilyl)ethoxy)methyl)-1,4-dihydropyridazine-3-carbonyl) pyrrolidin-2-yl)-2-(4-cyanophenyl)-2-(3-fluorophenyl)ethyl methanesulfonate (70 mg, 0.094 mmol) in methanol (5 mL) was purged with nitrogen. Added 10% palladium on carbon (29.9 mg, 0.028 mmol) and attached a hydrogen balloon. The flask was evacuated and refilled with hydrogen (3 times) and then stirred vigorously for 1 h at RT under a balloon of hydrogen. The reaction mixture was filtered through celite and the filter cake was washed with MeOH. The filtrate was concentrated to provide crude (1R,2R)-2-(4-cyanophenyl)-2-(3-fluorophenyl)-1-((R)-1-(5-hydroxy-4-oxo-1-((2-(trimethylsilyl)ethoxy)methyl)-1,4-dihydropyridazine-3-carbonyl)pyrrolidin-2-yl)ethyl methanesulfonate which was used in the next step without further purification. MS m/z 657.4 (MH+).

Step 6: (1R,2R)-2-(4-cyanophenyl)-2-(3-fluorophenyl)-1-((R)-1-(5-hydroxy-4-oxo-1,4-dihydropyridazine-3-carbonyl)pyrrolidin-2-yl)ethyl methanesulfonate To crude (1R,2R)-2-(4-cyanophenyl)-2-(3-fluorophenyl)-1-((R)-1-(5-hydroxy-4-oxo-1-((2-(trimethylsilyl)ethoxy)methyl)-1,4-dihydropyridazine-3-carbonyl)pyrrolidin-2-yl) ethyl methanesulfonate (61 mg, 0.088 mmol) was added TFA (1.2 ml, 15.58 mmol). The reaction mixture was stirred 2H at RT. The solvent was concentrated and the residue was azeotroped with toluene to provide crude (1R,2R)-2-(4-cyanophenyl)-2-(3-fluorophenyl)-1-((R)-1-(5-hydroxy-4-oxo-1,4-dihydropyridazine-3-carbonyl)pyrrolidin-2-yl) ethyl methanesulfonate which was used in the next step without further purification. MS m/z 527.3 (MH+).

Step 7: 4-((R)-(3-fluorophenyl)((9aR,10S)-4-hydroxy-3,5-dioxo-3,5,8,9,9a,10-hexahydro-7H-pyrrolo[1',2':4,5]pyrazino[1,2-b]pyridazin-10-yl)methyl)benzonitrile To a solution of crude (1R,2R)-2-(4-cyanophenyl)-2-(3-fluorophenyl)-1-((R)-1-(5-hydroxy-4-oxo-1,4-dihydropyridazine-3-carbonyl)pyrrolidin-2-yl)ethyl methanesulfonate (49 mg, 0.084 mmol) in DMF (2 mL) was added potassium carbonate (46.3 mg, 0.335 mmol) and the mixture was stirred overnight at RT. The reaction was filtered through a 1 micron filter and purified by reverse phase HPLC. Product fractions were combined, frozen and lyophilized to afford a TFA salt of 4-((R)-(3-fluorophenyl)((9aR,10S)-4-hydroxy-3,5-dioxo-3,5,8,9,9a,10-hexahydro-7H-pyrrolo[1',2':4,5]pyrazino[1,2-b]pyridazin-10-yl)methyl)benzonitrile (15.2 mg, 0.027 mmol, white solid) in 32.7% yield over three steps. $^1$H NMR (400 MHz, CD$_3$OD) δ ppm 7.36-7.53 (m, 5H) 7.22 (d, J=8.27 Hz, 2H) 7.00-7.14 (m, 1H) 5.83 (dd, J=9.93, 3.62 Hz, 1H) 4.72 (d, J=9.93 Hz, 1H) 4.46-4.59 (m, 1H) 3.78-3.94 (m, 1H) 3.68 (td, J=11.09, 7.51 Hz, 1H) 1.99-2.11 (m, 1H) 1.73-1.96 (m, 2H) 1.49-1.65 (m, 1H). MS m/z 431.2 (MH+).

Example 108. (9aR,10S)-10-((S)-(4-chlorophenyl)(3-fluorophenyl)methyl)-4-hydroxy-8,9,9a,10-tetrahydro-7H-pyrrolo[1',2':4,5]pyrazino[1,2-b]pyridazine-3,5-dione

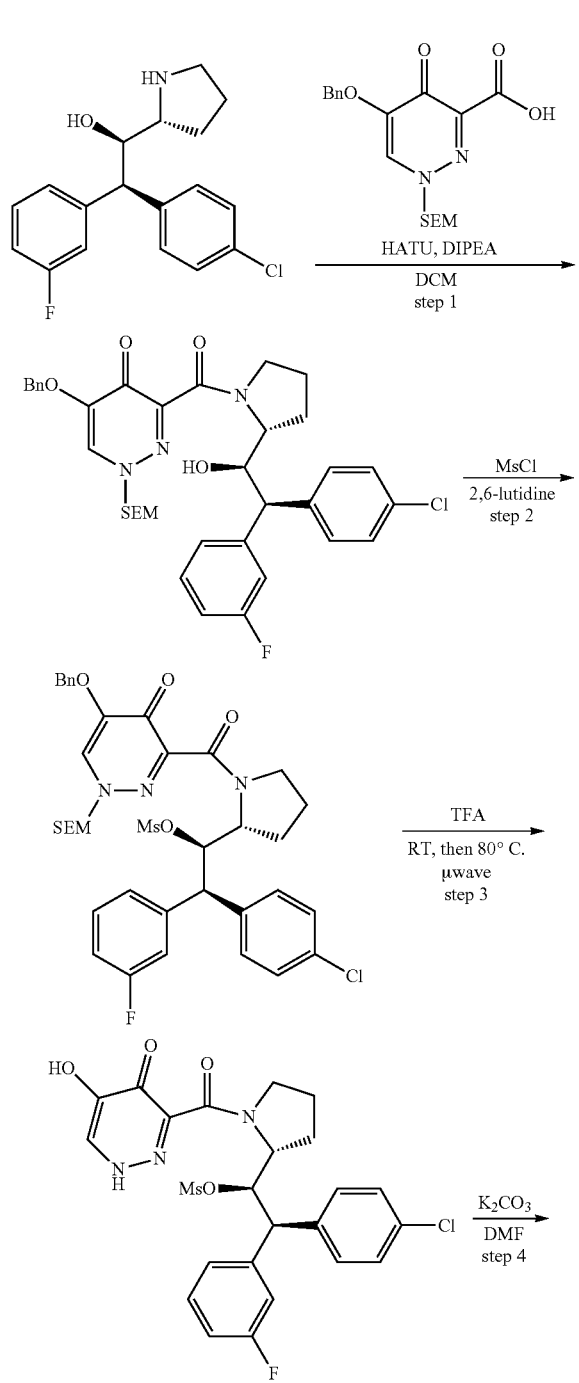

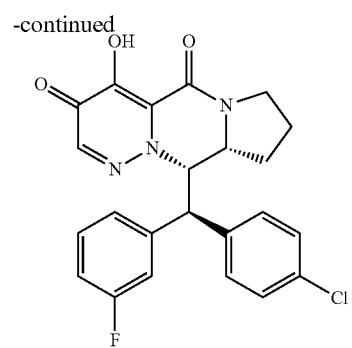

Example 108

Step 1: 5-(benzyloxy)-3-((R)-2-((1R,2R)-2-(4-chlorophenyl)-2-(3-fluorophenyl)-1-hydroxyethyl)pyrrolidine-1-carbonyl)-1-((2-(trimethylsilyl)ethoxy)methyl)pyridazin-4(1H)-one Added Huenig's base (0.360 mL, 2.064 mmol) and HATU (255 mg, 0.671 mmol) to a solution of 5-(benzyloxy)-4-oxo-1-((2-(trimethylsilyl)ethoxy)methyl)-1,4-dihydropyridazine-3-carboxylic acid (214 mg, 0.568 mmol: see US 2015/0072982 A1) in DCM (3 mL) at RT. Stirred at RT for 15 min, then added a solution of crude (1R,2R)-2-(4-chlorophenyl)-2-(3-fluorophenyl)-1-((R)-pyrrolidin-2-yl)ethanol (165 mg, 0.516 mmol, prepared by the method of Example 51, steps 1-3) in DCM (3 mL) and 2 equiv of Huenig's base. The mixture was stirred at RT for 1 h. The reaction was then diluted with DCM and washed with water and brine. The organic layer was dried over Na$_2$SO$_4$, filtered and concentrated. Silica gel column chromatography (EtOAc/EtOH/heptane) provided 5-(benzyloxy)-3-((R)-2-((1R,2R)-2-(4-chlorophenyl)-2-(3-fluorophenyl)-1-hydroxyethyl)pyrrolidine-1-carbonyl)-1-((2-(trimethylsilyl)ethoxy)methyl)pyridazin-4(1H)-one (280 mg) in 80% yield. MS m/z 678.6 (MH+).

Step 2: (1R,2S)-1-((R)-1-(5-(benzyloxy)-4-oxo-1-((2-(trimethylsilyl)ethoxy)methyl)-1,4-dihydropyridazine-3-carbonyl)pyrrolidin-2-yl)-2-(4-chlorophenyl)-2-(3-fluorophenyl)ethyl methanesulfonate To a solution of 5-(benzyloxy)-3-((R)-2-((1R,2R)-2-(4-chlorophenyl)-2-(3-fluorophenyl)-1-hydroxyethyl)pyrrolidine-1-carbonyl)-1-((2-(trimethylsilyl)ethoxy)methyl)pyridazin-4(1H)-one (280 mg, 0.413 mmol) in 2,6-lutidine (4 mL) at 0° C. was added methanesulfonyl chloride (0.643 mL, 8.26 mmol). After 5 min the ice bath was removed and the reaction was stirred for 3 h at RT. The reaction mixture was then partitioned between DCM and water. The DCM layer was separated and washed with 1 NHCl, saturated aqueous NaHCO$_3$, brine, dried over Na$_2$SO$_4$, filtered and concentrated. Silica gel column chromatography (EtOAc/EtOH/heptane) provided (1R,2S)-1-((R)-1-(5-(benzyloxy)-4-oxo-1-((2-(trimethylsilyl)ethoxy)methyl)-1,4-dihydropyridazine-3-carbonyl)pyrrolidin-2-yl)-2-(4-chlorophenyl)-2-(3-fluorophenyl)ethyl methanesulfonate (280 mg) in 90% yield. MS m/z 756.6 (MH+).

Step 3: (1R,2S)-2-(4-chlorophenyl)-2-(3-fluorophenyl)-1-((R)-1-(5-hydroxy-4-oxo-1,4-dihydropyridazine-3-carbonyl)pyrrolidin-2-yl)ethyl methanesulfonate To (1R,2S)-1-((R)-1-(5-(benzyloxy)-4-oxo-1-((2-(trimethylsilyl)ethoxy)methyl)-1,4-dihydropyridazine-3-carbonyl)pyrrolidin-2-yl)-2-(4-chlorophenyl)-2-(3-fluorophenyl) ethyl methanesulfonate (240 mg, 0.286 mmol) was added TFA (4 mL, 51.9 mmol). The reaction mixture was stirred 1 h at RT then heated for 20 min at 80° C. in a microwave reactor. The solvent was concentrated and the residue was azeotroped with toluene to provide crude (1R,2S)-2-(4-chlorophenyl)-2-(3-fluorophenyl)-1-((R)-1-(5-hydroxy-4-oxo-1,4-dihydropyridazine-3-carbonyl)pyrrolidin-2-yl) ethyl methanesulfonate which was used in the next step without further purification. MS m/z 536.2 (MH+).

Step 4: (9aR,10S)-10-((S)-(4-chlorophenyl)(3-fluorophenyl)methyl)-4-hydroxy-8,9,9a,10-tetrahydro-7H-pyrrolo[1',2':4,5]pyrazino[1,2-b]pyridazine-3,5-dione To a solution of crude (1R,2S)-2-(4-chlorophenyl)-2-(3-fluorophenyl)-1-((R)-1-(5-hydroxy-4-oxo-1,4-dihydropyridazine-3-carbonyl)pyrrolidin-2-yl)ethyl methanesulfonate (175 mg, 0.327 mmol) in DMF (6 mL) was added potassium carbonate (181 mg, 1.306 mmol) and the mixture was stirred overnight at RT. The reaction was filtered through a 1 micron filter and purified by reverse phase HPLC. Product fractions were combined, frozen and lyophilized to afford a formate salt of (9aR,10S)-10-((S)-(4-chlorophenyl)(3-fluorophenyl)methyl)-4-hydroxy-8,9,9a,10-tetrahydro-7H-pyrrolo[1',2':4,5]pyrazino[1,2-b]pyridazine-3,5-dione (33.5 mg, 0.068 mmol, white solid) in 29% yield. $^1$H NMR (400 MHz, CD$_3$OD) δ ppm 7.57 (d, J=8.46 Hz, 2H) 7.35-7.48 (m, 3H) 7.02-7.13 (m, 1H) 6.78-6.86 (m, 1H) 6.68-6.77 (m, 2H) 5.74 (dd, J=9.59, 3.52 Hz, 1H) 4.60 (d, J=9.59 Hz, 1H) 4.50 (br dd, J=10.47, 5.18 Hz, 1H) 3.82-3.94 (m, 1H) 3.67 (td, J=11.00, 7.58 Hz, 1H) 2.01-2.13 (m, 1H) 1.75-1.97 (m, 2H) 1.51-1.64 (m, 1H)

MS m/z 440.3 (MH+).

TABLE 1h

Additional compounds prepared by the method of Example 108.

| Example No. | Structure | Mass M + H | 1H NMR |
|---|---|---|---|
| 109 | 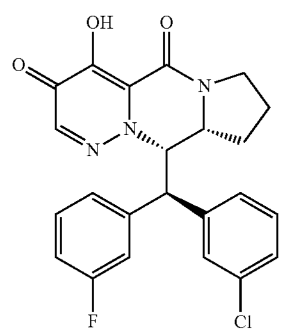 [SMILES: O=C1c2c(O)c(=O)cnn2[C@@H]([C@H](c2cccc(F)c2)c2cccc(Cl)c2)[C@H]2CCCN12] | 440.4 | (400 MHz, MeOD) δ ppm 7.62 (s, 1 H) 7.55 (d, J = 7.78 Hz, 1 H) 7.37-7.46 (m, 2 H) 7.30-7.37 (m, 1 H) 7.03-7.17 (m, 1 H) 6.64-6.91 (m, 3 H) 5.78 (dd, J = 9.54, 3.62 Hz, 1 H) 4.61 (d, J = 9.54 Hz, 1 H) 4.51 (dt, J = 10.26, 4.97 Hz, 1 H) 3.78-3.95 (m, 1 H) 3.68 (td, J = 11.09, 7.51 Hz, 1H) 2.00-2.11 (m, 1 H) 1.79-1.97 (m, 2H) 1.50-1.70 (m, 1 H) |
| 110 | 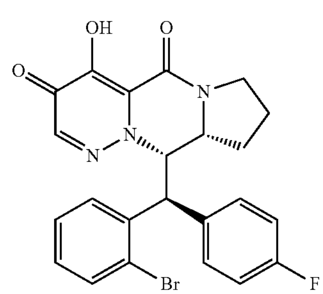 [SMILES: O=C1c2c(O)c(=O)cnn2[C@@H]([C@@H](c2ccc(F)cc2)c2ccccc2Br)[C@H]2CCCN12] | 484.1 | (500 MHz, CD3OD) δ ppm 7.58 (s, 2H), 7.33 (s, 3H), 7.15 (t, J = 7.6 Hz, 3H), 6.98 (d, J = 6.6 Hz, 1H),5.85 (d, J = 10.0 Hz, 1H), 5.33 (d, J = 10.3 Hz, 1H), 4.54 (s, 1H),3.90 (t, J = 9.9 Hz, 1H), 3.69-3.57 (m, 1H), 2.02 (s, 1H), 1.91 (d, J = 6.0 Hz, 1H), 1.85 (d, J = 9.3 Hz, 1H), 1.60-1.48 (m, 1H) |

Example 111. (9aR,10S)-10-((R)-(2-bromophenyl)(4-fluorophenyl)methyl)-4-hydroxy-8,9,9a,10-tetrahydro-3H-pyrrolo[1',2':4,5]pyrazino[1,2-b]pyridazine-3,5(7H)-dione

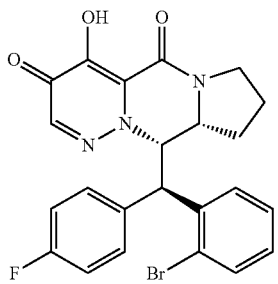 [SMILES: O=C1c2c(O)c(=O)cnn2[C@@H]([C@H](c2ccc(F)cc2)c2ccccc2Br)[C@H]2CCCN12]

Prepared by the method of Example 107 (steps 2-4) and Example 108 (steps 3-4). LCMS (m/z): 484.1 (MH+), 1H NMR (500 MHz, CD3OD) δ ppm 8.07 (d, J=7.7 Hz, 1H), 7.64 (d, J=8.1 Hz, 1H), 7.57 (s, 1H), 7.41 (s, 1H), 7.27 (d, J=7.7 Hz, 1H), 7.03 (s, 2H), 6.83 (t, J=8.3 Hz, 2H), 5.78 (d, J=9.4 Hz, 1H), 4.90 (d, J=9.6 Hz, 1H), 4.52 (s, 1H), 3.94 (s, 1H), 3.67 (s, 1H), 2.07 (s, 1H), 1.89 (s, 2H), 1.38 (s, 1H).

Example 112. (9aR,10S)-10-((S)-(3-fluorophenyl)(o-tolyl)methyl)-4-hydroxy-8,9,9a,10-tetrahydro-7H-pyrrolo[1',2':4,5]pyrazino[1,2-b]pyridazine-3,5-dione

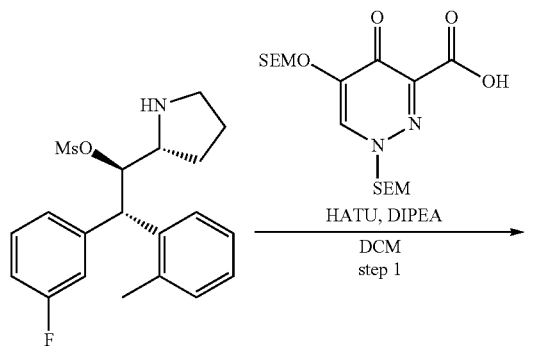

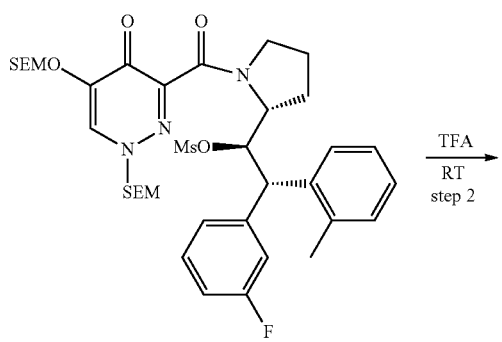

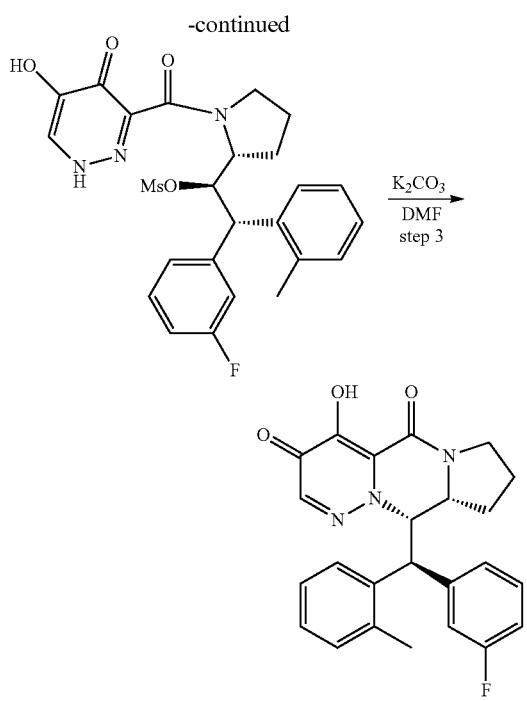

Example 112

Step 1: (1R,2S)-2-(3-fluorophenyl)-1-((R)-1-(4-oxo-5-((2-(trimethylsilyl)ethoxy)methoxy)-1-((2-(trimethylsilyl)ethoxy)methyl)-1,4-dihydropyridazine-3-carbonyl)pyrrolidin-2-yl)-2-(o-tolyl)ethyl methanesulfonate Added Huenig's base (0.102 mL, 0.583 mmol) and HATU (72 mg, 0.189 mmol) to a solution of 4-oxo-5-((2-(trimethylsilyl)ethoxy)methoxy)-1-((2-(trimethylsilyl)ethoxy)methyl)-1,4-dihydropyridazine-3-carboxylic acid (66.8 mg, 0.160 mmol: see US 2015/0072982 A1) in DCM (1 mL) at RT. Stirred at RT for 15 min, then added a solution of crude (1R,2S)-2-(3-fluorophenyl)-1-((R)-pyrrolidin-2-yl)-2-(o-tolyl)ethyl methanesulfonate (55 mg, 0.146 mmol, prepared by the method of Example 32, steps 1-2) in DCM (1 mL) and 2 equiv of Huenig's base. The mixture was stirred at RT for 1 h. The reaction was then diluted with DCM and washed with water and brine. The organic layer was dried over Na₂SO₄, filtered and concentrated. Silica gel column chromatography (EtOAc/EtOH/heptane) provided (1R,2S)-2-(3-fluorophenyl)-1-((R)-1-(4-oxo-5-((2-(trimethylsilyl)ethoxy)methoxy)-1-((2-(trimethylsilyl)ethoxy)methyl)-1,4-dihydropyridazine-3-carbonyl)pyrrolidin-2-yl)-2-(o-tolyl)ethyl methanesulfonate (48 mg) in 42% yield. MS m/z 776.5 (MH+).

Step 2: (1R,2S)-2-(3-fluorophenyl)-1-((R)-1-(5-hydroxy-4-oxo-1,4-dihydropyridazine-3-carbonyl)pyrrolidin-2-yl)-2-(o-tolyl)ethyl methanesulfonate To (1R,2S)-2-(3-fluorophenyl)-1-((R)-1-(4-oxo-5-((2-(trimethylsilyl)ethoxy)methoxy)-1-((2-(trimethylsilyl)ethoxy)methyl)-1,4-dihydropyridazine-3-carbonyl)pyrrolidin-2-yl)-2-(o-tolyl)ethyl methanesulfonate (48 mg, 0.062 mmol) was added TFA (1.2 mL, 15.6 mmol). The reaction mixture was stirred 1.5 hr at RT. The solvent was concentrated and the residue was azeotroped with toluene to provide crude (1R,2S)-2-(3-fluorophenyl)-1-((R)-1-(5-hydroxy-4-oxo-1,4-dihydropyridazine-3-carbonyl)pyrrolidin-2-yl)-2-(o-tolyl)ethyl methanesulfonate which was used in the next step without further purification. MS m/z 516.3 (MH+).

Step 3: (9aR,10S)-10-((S)-(3-fluorophenyl)(o-tolyl)methyl)-4-hydroxy-8,9,9a,10-tetrahydro-7H-pyrrolo[1',2':4,5]pyrazino[1,2-b]pyridazine-3,5-dione To a solution of crude (1R,2S)-2-(3-fluorophenyl)-1-((R)-1-(5-hydroxy-4-oxo-1,4-dihydropyridazine-3-carbonyl)pyrrolidin-2-yl)-2-(o-tolyl)ethyl methanesulfonate (32 mg, 0.062 mmol) in DMF (1 mL) was added potassium carbonate (30 mg, 0.217 mmol) and the mixture was stirred overnight at RT. The reaction was filtered through a 1 micron filter and purified by reverse phase HPLC. Product fractions were combined, frozen and lyophilized to afford a TFA salt of (9aR,10S)-10-((S)-(3-fluorophenyl)(o-tolyl)methyl)-4-hydroxy-8,9,9a,10-tetrahydro-7H-pyrrolo[1',2':4,5]pyrazino[1,2-b]pyridazine-3,5-dione (3 mg, 0.005 mmol, white solid) in 21% yield over two steps. 1H NMR (400 MHz, MeOD) δ ppm 1.49-1.68 (m, 1H) 1.76-2.11 (m, 4H) 2.14-2.39 (m, 3H) 3.66 (td, J=11.36, 7.12 Hz, 1H) 3.80-3.96 (m, 1H) 4.46-4.64 (m, 1H) 5.74-6.02 (m, 1H) 6.84-7.09 (m, 4H) 7.16 (br s, 1H) 7.25-7.55 (m, 4H), MS m/z 420.3 (MH+).

Example 115. (9aR,10S)-10-((R)-(3-fluorophenyl)(4-fluorophenyl)methyl)-4-hydroxy-7,7-dimethyl-8,9,9a,10-tetrahydro-7H-pyrrolo[1',2':4,5]pyrazino[1,2-b]pyridazine-3,5-dione

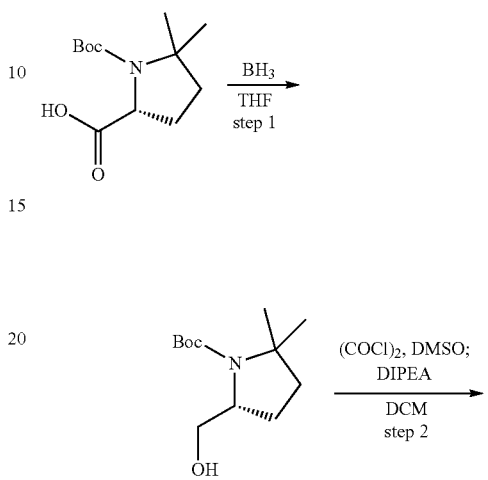

Table 1i

Additional compounds prepared by the method of Example 112.

| Example No. | Structure | Mass M + H | 1H NMR |
|---|---|---|---|
| 113 | OH, O, O, N, N, Cl, F | 440.3 | (400 MHz, MeOD) δ ppm 1.53-1.68 (m, 1 H) 1.75-1.97 (m, 2 H) 2.03-2.12 (m, 1 H) 3.68 (td, J = 11.11, 7.46 Hz, 1 H) 3.81-3.95 (m, 1H) 4.44-4.55 (m, 1 H) 4.61 (d, J = 9.54 Hz, 1 H) 5.76 (dd, J = 9.54, 3.62 Hz, 1 H) 6.90 (br d, J = 6.99 Hz, 1 H) 6.99 (s, 1 H) 7.01-7.14 (m, 3 H) 7.30-7.53 (m, 4 H) |
| 114 | OH, O, O, N, N, F, Cl | 440.3 | (400 MHz, MeOD) δ ppm 1.55-1.68 (m, 1 H) 1.80-1.99 (m, 2 H) 2.02-2.12 (m, 1 H) 3.62-3.75 (m, 1 H) 3.82-3.92 (m, 1 H) 4.46-4.64 (m, 2 H) 5.76 (dd, J = 9.49, 3.57 Hz, 1 H) 6.82 (t, J = 8.68 Hz, 2 H) 6.98 (dd, J = 8.53, 5.31 Hz, 2 H) 7.29-7.35 (m, 1 H) 7.37-7.46 (m, 2 H) 7.54(br d, J = 7.68 Hz, 1 H) 7.61 (s, 1 H) |

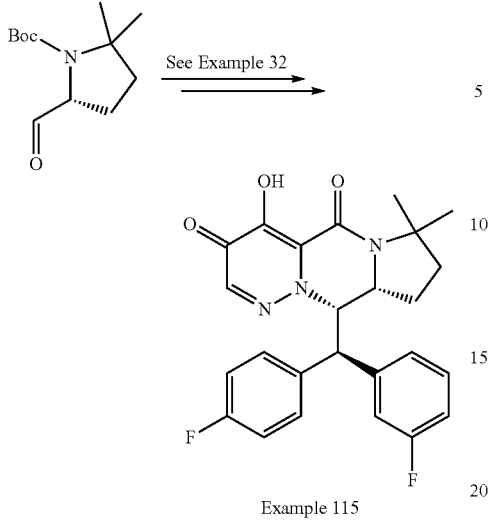

Step 1: tert-butyl (R)-5-(hydroxymethyl)-2,2-dimethylpyrrolidine-1-carboxylate

Borane tetrahydrofuran complex (1M in THF) (15.41 ml, 15.41 mmol) was added dropwise to a 0° C. solution of (R)-1-(tert-butoxycarbonyl)-5,5-dimethylpyrrolidine-2-carboxylic acid (2.2 g, 9.04 mmol) in THF under an atmosphere of nitrogen, and the mixture was stirred at RT for 3 hours. The solution was cooled, 2.5 mL of water was added, then sodium carbonate (1.960 g, 18.50 mmol), and the mixture stirred vigorously at RT for 30 minutes. The mixture was extracted with ethyl acetate, washed with brine, dried with $Na_2SO_4$, and concentrated to provide tert-butyl (R)-5-(hydroxymethyl)-2,2-dimethylpyrrolidine-1-carboxylate (2.1 g, >99% yield) as a colorless oil, which was used in the next step without further purification. LCMS [MH+] 230.1/0.91 min.

Step 2: tert-butyl (R)-5-formyl-2,2-dimethylpyrrolidine-1-carboxylate

DMSO (1.431 ml, 20.15 mmol) was added dropwise to a −78° C. solution of oxalyl chloride (0.942 ml, 10.99 mmol) in DCM (Volume: 41.6 ml, Ratio: 10), and the solution was stirred for 15 minutes. A solution of tert-butyl (R)-5-(hydroxymethyl)-2,2-dimethylpyrrolidine-1-carboxylate in DCM (Volume: 4.16 ml, Ratio: 1.000) was then added, and the solution stirred for 1 hour at −78° C. DIPEA (6.40 ml, 36.6 mmol) was then added, and the solution was warmed to room temperature. The mixture was then washed sequentially with 1M HCl, water, then brine, dried with $Na_2SO_4$, and concentrated to give tert-butyl (R)-5-formyl-2,2-dimethylpyrrolidine-1-carboxylate (1.9 g, 91% yield) as a yellow oil, which was used in the next step without further purification. LCMS [MH+] 228.2/0.82 min.

Example 115: (9aR,10S)-10-((R)-(3-fluorophenyl)(4-fluorophenyl)methyl)-4-hydroxy-7,7-dimethyl-8,9,9a,10-tetrahydro-7H-pyrrolo[1',2':4,5]pyrazino[1,2-b]pyridazine-3,5-dione Prepared from tert-butyl (R)-5-formyl-2,2-dimethylpyrrolidine-1-carboxylate by the method of Example 32. LCMS (m/z): 452.3 (MH+), 1H NMR (500 MHz, CD3OD) δ ppm 7.45 (q, J=7.8 Hz, 1H), 7.41-7.34 (m, 3H), 7.06 (t, J=8.1 Hz, 1H), 7.04-6.98 (m, 2H), 6.82 (t, J=8.5 Hz, 2H), 5.70 (d, J=10.1 Hz, 1H), 4.67-4.58 (m, 1H), 4.42 (d, J=9.9 Hz, 1H), 1.89-1.79 (m, 2H), 1.75 (d, J=12.3 Hz, 1H), 1.69 (s, 3H), 1.63 (s, 3H), 1.60-1.50 (m, 1H).

Example 116. (9aR,10R)-10-((S)-(3-fluorophenyl)(4-fluorophenyl)methyl)-4-hydroxy-7,7-dimethyl-8,9,9a,10-tetrahydro-7H-pyrrolo[1',2':4,5]pyrazino[1,2-b]pyridazine-3,5-dione

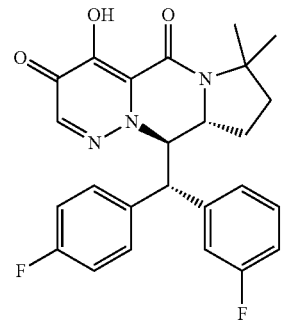 [SMILES: CC1(C)CC[C@@H]2[C@@H]([C@@H](c3ccc(F)cc3)c3cccc(F)c3)n3ncc(=O)c(O)c3C(=O)N21]

Prepared from tert-butyl (R)-5-formyl-2,2-dimethylpyrrolidine-1-carboxylate by the method of Example 32. LCMS (m/z): 452.3 (MH+), $^1$H NMR (500 MHz, CD$_3$OD) δ ppm 7.66 (s, 1H), 7.41-7.35 (m, 2H), 7.29 (d, J=6.8 Hz, 1H), 7.08 (t, J=8.5 Hz, 3H), 6.99 (d, J=10.7 Hz, 1H), 6.95 (s, 1H), 5.32 (dd, J=11.3, 3.9 Hz, 1H), 5.09 (d, J=3.8 Hz, 1H), 4.13 (d, J=6.5 Hz, 1H), 1.93 (q, J=9.9, 8.9 Hz, 1H), 1.86 (d, J=6.4 Hz, 2H), 1.82 (s, 1H), 1.63 (s, 3H), 1.56 (s, 3H).

Example 117. (7S,9aR,10S)-10-((R)-(3-fluorophenyl)(4-fluorophenyl)methyl)-4-hydroxy-7-methyl-8,9,9a,10-tetrahydro-7H-pyrrolo[1',2':4,5]pyrazino[1,2-b]pyridazine-3,5-dione tert-butyl (2R,5S)-2-formyl-5-methylpyrrolidine-1-carboxylate -continued

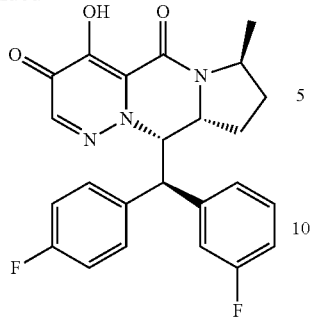

Example 117

Prepared from tert-butyl (2R,5S)-2-(hydroxymethyl)-5-methylpyrrolidine-1-carboxylate by the method of Example 115, Step 2. LCMS [M+Na]+236.2/0.70 min.

Example 117: (7S,9aR,10S)-10-((R)-(3-fluorophenyl)(4-fluorophenyl)methyl)-4-hydroxy-7-methyl-8,9,9a,10-tetrahydro-7H-pyrrolo[1',2':4,5]pyrazino[1,2-b]pyridazine-3,5-dione Prepared from tert-butyl (2R,5S)-2-formyl-5-methylpyrrolidine-1-carboxylate by the method of Example 32. LCMS (m/z): 438.5 (MH+), 1H NMR (500 MHz, CD$_3$OD) δ ppm 7.47-7.37 (m, 4H), 7.07-7.02 (m, 1H), 7.00 (dd, J=8.7, 5.3 Hz, 2H), 6.81 (t, J=8.7 Hz, 2H), 5.70 (dd, J=9.5, 3.9 Hz, 1H), 4.69-4.63 (m, 1H), 4.56 (d, J=9.5 Hz, 1H), 4.41 (q, J=6.4 Hz, 1H), 2.26-2.18 (m, 1H), 1.95-1.88 (m, 1H), 1.63-1.55 (m, 2H), 1.48 (d, J=6.3 Hz, 3H).

Example 118. (7S,9aR,10R)-10-((S)-(3-fluorophenyl)(4-fluorophenyl)methyl)-4-hydroxy-7-methyl-8,9,9a,10-tetrahydro-3H-pyrrolo[1',2':4,5]pyrazino[1,2-b]pyridazine-3,5(7H)-dione

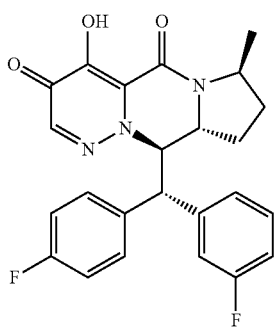 [SMILES: C[C@H]1CC[C@@H]2[C@@H]([C@@H](c3ccc(F)cc3)c3cccc(F)c3)n3ncc(=O)c(O)c3C(=O)N21]

Prepared from tert-butyl (2R,5S)-2-formyl-5-methylpyrrolidine-1-carboxylate by the method of Example 32. LCMS (m/z): 438.4 (MH+), 1H NMR (500 MHz, CD$_3$OD) δ ppm 7.61 (s, 1H), 7.37 (dd, J=8.0, 5.5 Hz, 2H), 7.31 (d, J=6.8 Hz, 1H), 7.10 (d, J=7.8 Hz, 1H), 7.07 (t, J=8.6 Hz, 2H), 7.04-6.94 (m, 2H), 5.37 (dd, J=9.8, 5.8 Hz, 1H), 5.05 (d, J=5.7 Hz, 1H), 4.29 (h, J=6.5 Hz, 1H), 4.10 (td, J=10.1, 5.6 Hz, 1H), 2.27 (dd, J=13.1, 7.2 Hz, 1H), 1.78-1.71 (m, 1H), 1.68 (dd, J=11.2, 8.0 Hz, 1H), 1.51 (ddd, J=19.7, 11.8, 7.8 Hz, 1H), 1.39 (d, J=6.3 Hz, 3H).

Example 119. (7R,9aR,10S)-10-((R)-(3-fluorophenyl)(4-fluorophenyl)methyl)-4-hydroxy-7-methyl-8,9,9a,10-tetrahydro-3H-pyrrolo[1',2':4,5]pyrazino[1,2-b]pyridazine-3,5(7H)-dione

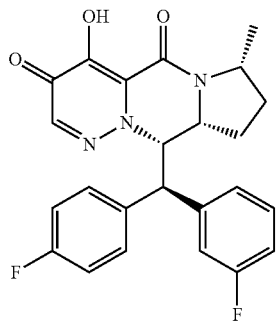 [SMILES: C[C@@H]1CC[C@@H]2[C@H]([C@H](c3ccc(F)cc3)c3cccc(F)c3)n3ncc(=O)c(O)c3C(=O)N12]

Prepared from tert-butyl (2R,5R)-2-formyl-5-methylpyrrolidine-1-carboxylate (For synthesis see US 20120195857, using tert-butyl (2R,5R)-2-(hydroxymethyl)-5-methylpyrrolidine-1-carboxylate) by the method of Example 32. LCMS (m/z): 438.4 (MH+), 1H NMR (500 MHz, CD$_3$OD) δ ppm 7.46 (q, J=7.7 Hz, 1H), 7.40 (d, J=8.7 Hz, 2H), 7.38 (s, 1H), 7.08 (s, 1H), 7.05-6.95 (m, 2H), 6.84 (t, J=8.5 Hz, 2H), 5.74 (dd, J=10.2, 3.1 Hz, 1H), 4.51 (dd, J=7.4, 4.6 Hz, 1H), 4.47-4.36 (m, 2H), 2.01 (dd, J=13.3, 6.4 Hz, 1H), 1.86-1.75 (m, 1H), 1.68 (dd, J=12.5, 6.3 Hz, 1H), 1.57 (dd, J=12.6, 6.3 Hz, 1H), 1.46 (d, J=6.5 Hz, 3H).

Example 120. (7R,9aR,10R)-10-((S)-(3-fluorophenyl)(4-fluorophenyl)methyl)-4-hydroxy-7-methyl-8,9,9a,10-tetrahydro-3H-pyrrolo[1',2':4,5]pyrazino[1,2-b]pyridazine-3,5(7H)-dione

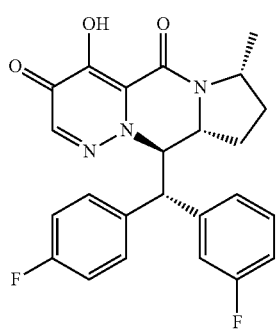 [SMILES: C[C@@H]1CC[C@@H]2[C@@H]([C@@H](c3ccc(F)cc3)c3cccc(F)c3)n3ncc(=O)c(O)c3C(=O)N12]

Prepared from tert-butyl (2R,5R)-2-formyl-5-methylpyrrolidine-1-carboxylate (For synthesis see US 20120195857, using tert-butyl (2R,5R)-2-(hydroxymethyl)-5-methylpyrrolidine-1-carboxylate) by the method of Example 32. LCMS (m/z): 438.4 (MH+), 1H NMR (500 MHz, CD$_3$OD) δ ppm 7.70 (s, 1H), 7.37 (dd, J=8.7, 5.3 Hz, 2H), 7.30 (td, J=8.0, 6.2 Hz, 1H), 7.12 (d, J=7.8 Hz, 1H), 7.08 (t, J=8.7 Hz, 2H), 7.03 (d, J=10.6 Hz, 1H), 6.96 (td, J=8.4, 2.3 Hz, 1H), 5.36 (dd, J=11.4, 4.6 Hz, 1H), 5.15 (d, J=4.5 Hz, 1H), 4.37-4.26 (m, 1H), 4.08 (d, J=5.4 Hz, 1H), 2.07-1.96 (m, 1H), 1.91 (dd, J=11.6, 6.2 Hz, 1H), 1.87-1.80 (m, 1H), 1.73 (dd, J=12.3, 6.0 Hz, 1H), 1.38 (d, J=6.5 Hz, 3H).

Example 121. (8S,9aR,10S)-10-(bis(3-fluorophenyl)methyl)-4-hydroxy-8-methoxy-8,9,9a,10-tetrahydro-3H-pyrrolo[1',2':4,5]pyrazino[1,2-b]pyridazine-3,5(7H)-dione

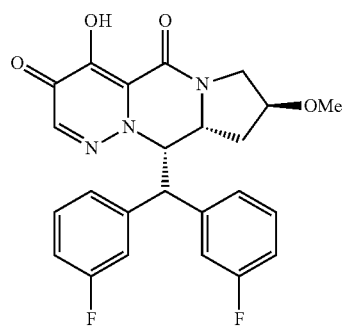 [SMILES: CO[C@H]1C[C@@H]2[C@H](C(c3cccc(F)c3)c3cccc(F)c3)n3ncc(=O)c(O)c3C(=O)N2C1]

Prepared from tert-butyl (2R,4S)-2-formyl-4-methoxypyrrolidine-1-carboxylate (For synthesis see WO 2014046441 A1, using tert-butyl (2R,4S)-2-(hydroxymethyl)-4-methoxypyrrolidine-1-carboxylate) by the method of Example 32. LCMS (m/z): 454.3 (MH+), $^1$H NMR (500 MHz, CD$_3$OD) δ ppm 7.49-7.43 (m, 1H), 7.43-7.34 (m, 3H), 7.12-7.04 (m, 2H), 6.82 (td, J=8.5, 2.2 Hz, 1H), 6.80-6.73 (m, 2H), 5.78 (dd, J=9.8, 3.6 Hz, 1H), 4.71 (dt, J=11.9, 4.6 Hz, 1H), 4.62 (d, J=9.8 Hz, 1H), 4.06 (t, J=3.8 Hz, 1H), 3.90 (d, J=13.5 Hz, 1H), 3.83 (dd, J=13.5, 3.9 Hz, 1H), 3.30 (s, 3H), 2.08 (dd, J=13.3, 5.3 Hz, 1H), 1.62 (td, J=12.9, 4.0 Hz, 1H).

Example 122. (8R,9aR,10S)-10-(bis(3-fluorophenyl)methyl)-4-hydroxy-8-methoxy-8,9,9a,10-tetrahydro-7H-pyrrolo[1',2':4,5]pyrazino[1,2-b]pyridazine-3,5-dione

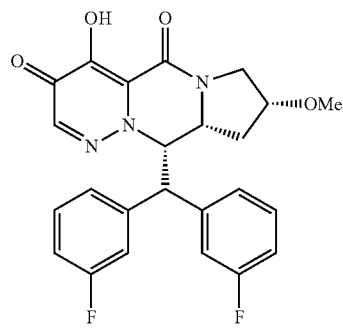 [SMILES: CO[C@@H]1C[C@@H]2[C@H](C(c3cccc(F)c3)c3cccc(F)c3)n3ncc(=O)c(O)c3C(=O)N2C1]

Prepared from tert-butyl (2R,4R)-2-formyl-4-methoxypyrrolidine-1-carboxylate (For synthesis see WO 2014046441 A1, using tert-butyl (2R,4R)-2-(hydroxymethyl)-4-methoxypyrrolidine-1-carboxylate) by the method of Example 32. LCMS (m/z): 454.3 (MH+), 1H NMR (500 MHz, CD3OD) δ ppm 7.53 (s, 1H), 7.48-7.35 (m, 3H), 7.06 (t, J=7.1 Hz, 2H), 6.79 (dd, J=15.8, 8.3 Hz, 2H), 6.72 (d, J=10.1 Hz, 1H), 5.67 (s, 1H), 4.91 (d, J=8.0 Hz, 1H), 4.60 (s, 1H), 4.13 (d, J=5.3 Hz, 1H), 3.87 (s, 1H), 3.85-3.79 (m, 1H), 3.37 (s, 3H), 2.42-2.31 (m, 1H), 1.80 (s, 1H).

Example 123. (10aR,11S)-11-benzhydryl-4-hydroxy-7,8,10a,11-tetrahydro-10H-pyridazino[1',6':4,5]pyrazino[2,1-c][1,4]oxazine-3,5-dione

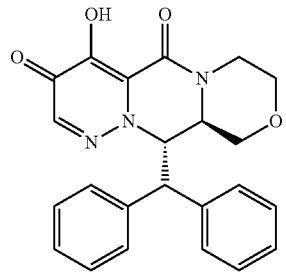 [SMILES: O=C1c2c(O)c(=O)cnn2[C@@H](C(c2ccccc2)c2ccccc2)[C@@H]2COCCN12]

Prepared from tert-butyl (S)-3-formylmorpholine-4-carboxylate by the method of Example 32. LCMS (m/z): 404.2 (MH+), 1H NMR (500 MHz, DMSO-d6) δ 7.61-7.55 (m, 2H), 7.39 (t, J=7.7 Hz, 2H), 7.29 (t, J=7.5 Hz, 1H), 7.21 (dd, J=7.8, 1.8 Hz, 2H), 7.17 (s, 1H), 7.17-7.10 (m, 3H), 5.50 (d, J=11.1 Hz, 1H), 4.58 (d, J=11.1 Hz, 1H), 4.37 (s, 1H), 3.98 (d, J=9.0 Hz, 1H), 3.75-3.66 (m, 3H), 3.48 (s, 1H), 3.02-2.95 (m, 1H).

Examples 124A and 124B

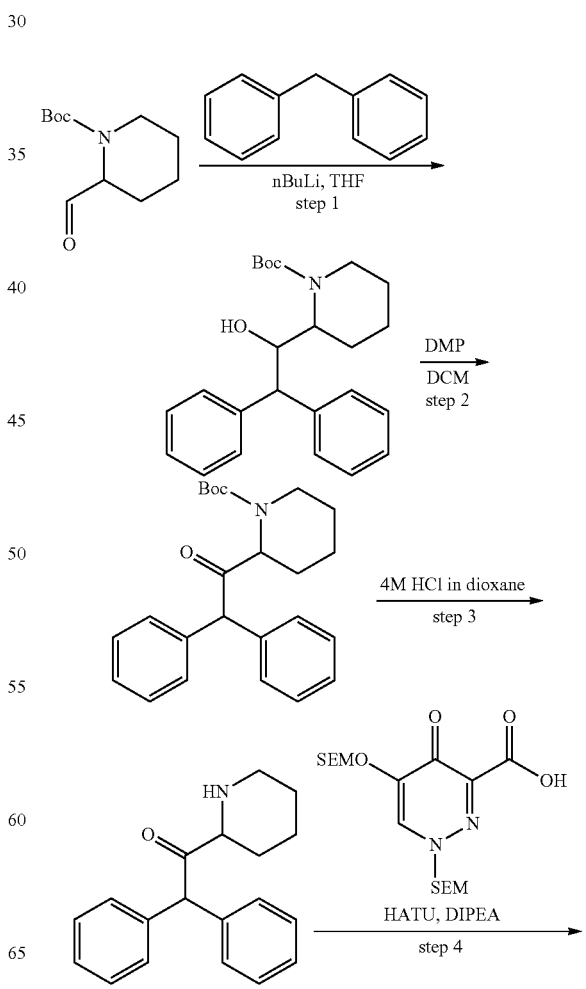

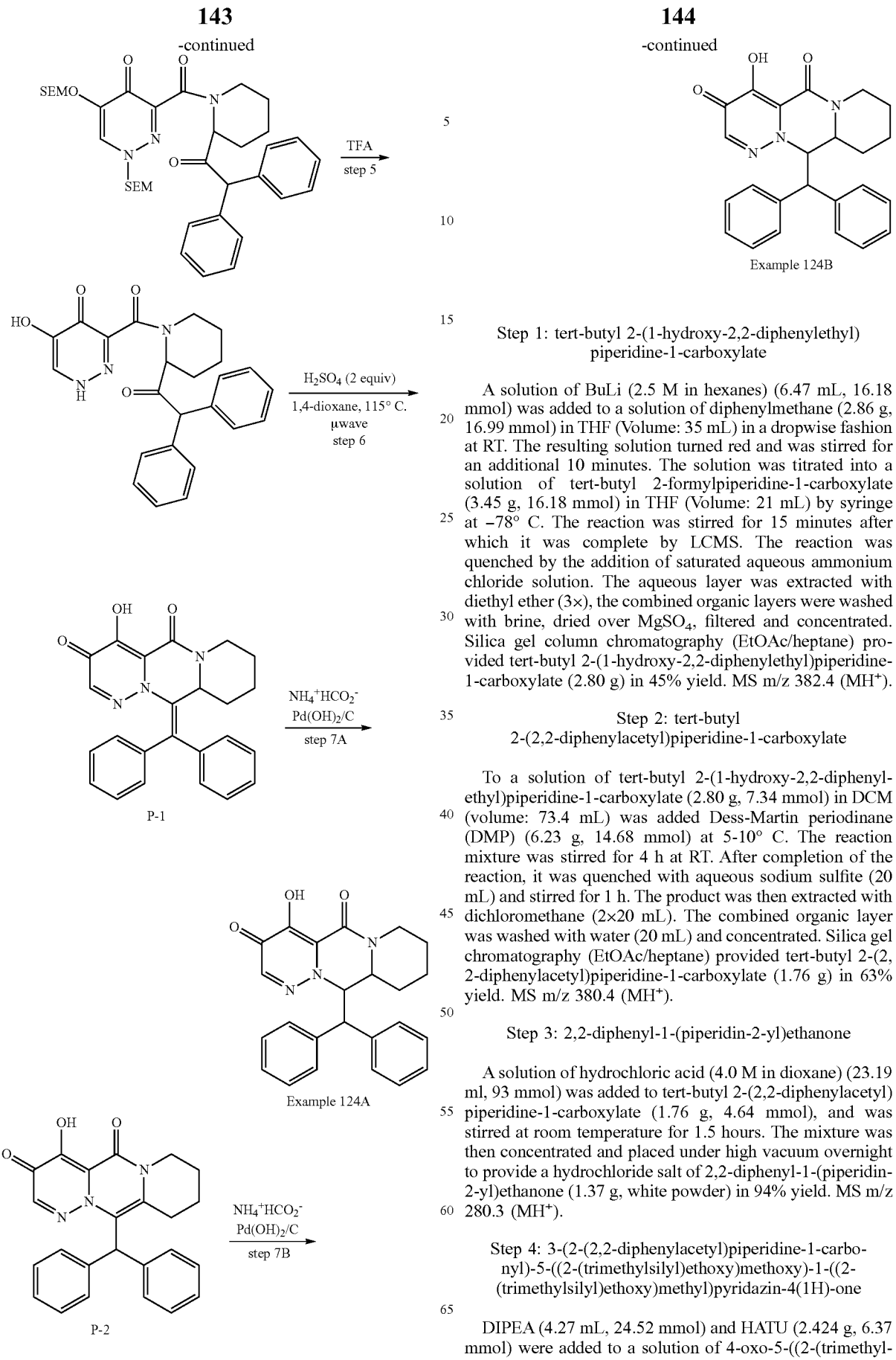

Example 124B

Step 1: tert-butyl 2-(1-hydroxy-2,2-diphenylethyl)piperidine-1-carboxylate

A solution of BuLi (2.5 M in hexanes) (6.47 mL, 16.18 mmol) was added to a solution of diphenylmethane (2.86 g, 16.99 mmol) in THF (Volume: 35 mL) in a dropwise fashion at RT. The resulting solution turned red and was stirred for an additional 10 minutes. The solution was titrated into a solution of tert-butyl 2-formylpiperidine-1-carboxylate (3.45 g, 16.18 mmol) in THF (Volume: 21 mL) by syringe at −78° C. The reaction was stirred for 15 minutes after which it was complete by LCMS. The reaction was quenched by the addition of saturated aqueous ammonium chloride solution. The aqueous layer was extracted with diethyl ether (3×), the combined organic layers were washed with brine, dried over $MgSO_4$, filtered and concentrated. Silica gel column chromatography (EtOAc/heptane) provided tert-butyl 2-(1-hydroxy-2,2-diphenylethyl)piperidine-1-carboxylate (2.80 g) in 45% yield. MS m/z 382.4 ($MH^+$).

Step 2: tert-butyl 2-(2,2-diphenylacetyl)piperidine-1-carboxylate

To a solution of tert-butyl 2-(1-hydroxy-2,2-diphenylethyl)piperidine-1-carboxylate (2.80 g, 7.34 mmol) in DCM (volume: 73.4 mL) was added Dess-Martin periodinane (DMP) (6.23 g, 14.68 mmol) at 5-10° C. The reaction mixture was stirred for 4 h at RT. After completion of the reaction, it was quenched with aqueous sodium sulfite (20 mL) and stirred for 1 h. The product was then extracted with dichloromethane (2×20 mL). The combined organic layer was washed with water (20 mL) and concentrated. Silica gel chromatography (EtOAc/heptane) provided tert-butyl 2-(2,2-diphenylacetyl)piperidine-1-carboxylate (1.76 g) in 63% yield. MS m/z 380.4 ($MH^+$).

Step 3: 2,2-diphenyl-1-(piperidin-2-yl)ethanone

A solution of hydrochloric acid (4.0 M in dioxane) (23.19 ml, 93 mmol) was added to tert-butyl 2-(2,2-diphenylacetyl)piperidine-1-carboxylate (1.76 g, 4.64 mmol), and was stirred at room temperature for 1.5 hours. The mixture was then concentrated and placed under high vacuum overnight to provide a hydrochloride salt of 2,2-diphenyl-1-(piperidin-2-yl)ethanone (1.37 g, white powder) in 94% yield. MS m/z 280.3 ($MH^+$).

Step 4: 3-(2-(2,2-diphenylacetyl)piperidine-1-carbonyl)-5-((2-(trimethylsilyl)ethoxy)methoxy)-1-((2-(trimethylsilyl)ethoxy)methyl)pyridazin-4(1H)-one DIPEA (4.27 mL, 24.52 mmol) and HATU (2.424 g, 6.37 mmol) were added to a solution of 4-oxo-5-((2-(trimethylsilyl)ethoxy)methoxy)-1-((2-(trimethylsilyl)ethoxy) methyl)-1,4-dihydropyridazine-3-carboxylic acid (2.247 g, 5.39 mmol: see US 2015/0072982 A1) in DCM (volume: 50 mL) at RT. The mixture was stirred at RT for 15 min, then added a solution of crude 2,2-diphenyl-1-(piperidin-2-yl) ethanone hydrochloride (1.37 g, 4.90 mmol) and DIPEA (2 mL) in DCM (Volume: 25). The mixture was stirred at RT overnight before it was diluted with DCM and washed with water and brine. The organic layer was dried over Na$_2$SO$_4$, filtered and concentrated. Silica gel column chromatography (EtOAc/heptane/MeOH) provided 3-(2-(2,2-diphenylacetyl) piperidine-1-carbonyl)-5-((2-(trimethylsilyl)ethoxy) methoxy)-1-((2-(trimethylsilyl)ethoxy)methyl)pyridazin-4 (1H)-one (1.85 g) in 56% yield. MS m/z 678.5 (MH$^+$).

Step 5: 3-(2-(2,2-diphenylacetyl)piperidine-1-carbonyl)-5-hydroxypyridazin-4(1H)-one A solution of 3-(2-(2,2-diphenylacetyl)piperidine-1-carbonyl)-5-((2-(trimethylsilyl)ethoxy) methoxy)-1-((2-(trimethylsilyl)ethoxy)methyl)pyridazin-4(1H)-one (83.4 mg, 0.123 mmol) in TFA (1.5 ml, 19.47 mmol) was stirred at rt for 2 days. The reaction was concentrated and the residue was azeotroped from benzene (3×) to provide crude 3-(2-(2,2-diphenylacetyl)piperidine-1-carbonyl)-5-hydroxypyridazin-4(1H)-one yield (51 mg) that was used in the next step without purification. MS m/z 418.3 (MH$^+$).

Step 6: 11-(diphenylmethylene)-4-hydroxy-7,8,9,10, 10a,11-hexahydropyrido[1',2':4,5]pyrazino [1,2-b] pyridazine-3,5-dione and 11-benzhydryl-4-hydroxy-7,8,9,10-tetrahydropyrido[1',2':4,5]pyrazino[1,2-b] pyridazine-3,5-dione To a solution of 3-(2-(2,2-diphenylacetyl)piperidine-1-carbonyl)-5-hydroxypyridazin-4(1H)-one (867 mg, 2.077 mmol) in 1,4-dioxane (Volume: 29.7 ml) was added concentrated sulfuric acid (221 µl, 4.15 mmol). The mixture was heated to 115° C. for 90 min in a microwave reactor. The reaction was filtered and the filtrate was purified by reverse phase HPLC. Product fractions were combined, frozen and lyophilized to afford 11-(diphenylmethylene)-4-hydroxy-7,8,9,10,10a,11-hexahydropyrido[1',2':4,5]pyrazino[1,2-b] pyridazine-3,5-dione (Peak 1, MS m/z 400.3 (MH$^+$)) and 11-benzhydryl-4-hydroxy-7,8,9,10-tetrahydropyrido[1',2':4, 5]pyrazino[1,2-b]pyridazine-3,5-dione (Peak 2, MS m/z 400.3 (MH$^+$)).

Step 7A: 11-benzhydryl-4-hydroxy-7,8,9,10,10a,11-hexahydropyrido[1',2':4,5]pyrazino[1,2-b] pyridazine-3,5-dione To a solution of 11-(diphenylmethylene)-4-hydroxy-7,8, 9,10,10a,11-hexahydropyrido[1',2':4,5] pyrazino[1,2-b] pyridazine-3,5-dione (22.8 mg, 0.044 mmol) in MeOH (Volume: 1 mL) were added palladium hydroxide on carbon (20%) (31.2 mg, 0.044 mmol) and ammonium formate (28.0 mg, 0.444 mmol). The vial was sealed and the reaction was heated to 70° C. for 2 h. The reaction was filtered through celite and the filtrate was concentrated. The residue was dissolved in DMF and purified by reverse phase HLPC. Product fractions were combined, frozen and lyophilized to afford a TFA salt of 11-benzhydryl-4-hydroxy-7,8,9,10,10a, 11-hexahydropyrido[1',2':4,5]pyrazino[1,2-b]pyridazine-3, 5-dione (4.1 mg, white solid) in 17% yield.

$^1$H NMR (500 MHz, Methanol-d$_4$) δ 7.65-7.55 (m, 2H), 7.51 (s, 1H), 7.40 (t, J=7.8 Hz, 2H), 7.33-7.26 (m, 1H), 7.05 (s, 6H), 5.58 (dd, J=8.0, 3.1 Hz, 1H), 4.79 (d, J=8.0 Hz, 1H), 4.40 (d, J=13.8 Hz, 1H), 4.18 (d, J=9.6 Hz, 1H), 3.15-3.06 (m, 1H), 1.89 (d, J=13.6 Hz, 1H), 1.83-1.75 (m, 1H), 1.70-1.61 (m, 2H), 1.51 (qd, J=12.9, 3.9 Hz, 1H), 1.37 (tt, J=12.2, 3.6 Hz, 1H). MS m/z 402.2 (MH$^+$).

Step 7B: 11-benzhydryl-4-hydroxy-7,8,9,10,10a,11-hexahydropyrido[1',2':4,5]pyrazino[1,2-b] pyridazine-3,5-dione To a solution of 11-benzhydryl-4-hydroxy-7,8,9,10-tetrahydropyrido[1',2':4,5]pyrazino[1,2-b]pyridazine-3,5-dione (8.3 mg, 0.016 mmol) in MeOH (1 mL) were added palladium hydroxide on carbon (20%) (11.35 mg, 0.016 mmol) and ammonium formate (10.19 mg, 0.162 mmol). The vial was sealed and the reaction was heated to 70° C. for 2 h. The reaction was filtered through celite and the filtrate was concentrated. The residue was dissolved in DMF and purified by reverse phase HLPC. Product fractions were combined, frozen and lyophilized to afford a TFA salt of 11-benzhydryl-4-hydroxy-7,8,9,10,10a,11-hexahydropyrido[1',2': 4,5]pyrazino[1,2-b]pyridazine-3,5-dione (1.5 mg) in 17% yield. $^1$H NMR (500 MHz, Methanol-d$_4$) δ 7.53-7.49 (m, 2H), 7.41 (t, J=7.7 Hz, 2H), 7.35 (s, 1H), 7.34-7.30 (m, 1H), 7.15 (tt, J=5.5, 2.6 Hz, 5H), 5.37-5.27 (m, 1H), 4.62 (s, 1H), 4.48 (d, J=11.1 Hz, 1H), 3.69 (d, J=11.4 Hz, 1H), 2.81-2.67 (m, 1H), 1.92 (d, J=18.0 Hz, 2H), 1.70-1.49 (m, 4H). MS m/z 402.1 (MH+).

Example 125A. 11-(bis(3-fluorophenyl)methyl)-4-hydroxy-7,8,9,10,10a,11-hexahydropyrido[1',2':4,5] pyrazino[1,2-b]pyridazine-3,5-dione

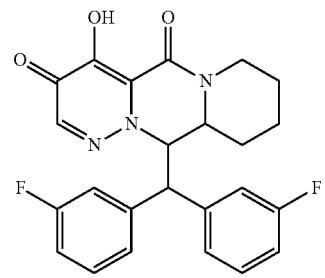

Prepared from bis(3-fluorophenyl)methane by the method of Example 124A. LCMS (m/z): 438.0 (MH+), 1H NMR (500 MHz, Methanol-d4) δ 7.51-7.44 (m, 1H), 7.42 (s, 1H), 7.38 (d, J=7.7 Hz, 2H), 7.22-7.15 (m, 1H), 7.11 (d, J=7.9 Hz, 1H), 7.05 (d, J=10.2 Hz, 1H), 6.99 (d, J=7.9 Hz, 1H), 6.95-6.89 (m, 1H), 5.39 (d, J=11.3 Hz, 1H), 4.67 (s, 1H), 4.62 (d, J=11.2 Hz, 1H), 3.67 (d, J=10.2 Hz, 1H), 2.75 (d, J=12.2 Hz, 1H), 1.94 (s, 1H), 1.67 (q, J=11.7, 10.0 Hz, 4H).

Example 125B. 11-(bis(3-fluorophenyl)methyl)-4-hydroxy-7,8,9,10,10a,11-hexahydropyrido[1',2':4,5]pyrazino[1,2-b]pyridazine-3,5-dione

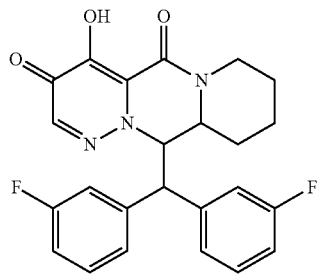

Prepared from bis(3-fluorophenyl)methane by the method of Example 124B. LCMS (m/z): 438.0 (MH+), 1H NMR (500 MHz, Methanol-d4) δ 8.22 (d, J=20.2 Hz, 1H), 7.58 (s, 1H), 7.48-7.40 (m, 2H), 7.38-7.33 (m, 2H), 7.32-7.23 (m, 3H), 5.63 (d, J=7.7 Hz, 1H), 4.91 (d, J=8.2 Hz, 1H), 4.42 (d, J=14.3 Hz, 1H), 4.13 (t, J=6.4 Hz, 2H), 3.15-3.06 (m, 1H), 7.38-7.33 (m, 1H), 1.76-1.60 (m, 4H).

Example 126. 11-benzhydryl-4-hydroxy-7,8,10a,11-tetrahydro-10H-pyridazino[1',6':4,5]pyrazino[2,1-c][1,4]oxazine-3,5-dione

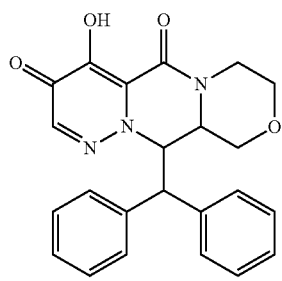

Prepared from tert-butyl 3-formylmorpholine-4-carboxylate by the method of Example 124A. LCMS (m/z): 404.2 (MH+), 1H NMR (500 MHz, Methanol-d4) δ 7.58 (d, J=7.4 Hz, 2H), 7.43 (t, J=7.7 Hz, 2H), 7.37 (s, 1H), 7.31 (t, J=7.4 Hz, 1H), 7.06-7.01 (m, 3H), 6.99 (dd, J=6.8, 3.0 Hz, 2H), 5.61 (dd, J=8.9, 3.4 Hz, 1H), 4.81 (d, J=8.9 Hz, 1H), 4.47 (dt, J=11.2, 3.9 Hz, 1H), 4.24 (dd, J=13.9, 3.0 Hz, 1H), 4.04 (dd, J=11.9, 4.7 Hz, 1H), 3.63 (td, J=11.9, 3.6 Hz, 2H), 3.25 (d, J=11.5 Hz, 1H), 3.23-3.17 (m, 1H).

Example 127. 11-benzhydryl-4-hydroxy-7-methyl-7,8,9,10,10a,11-hexahydropyrido[1',2':4,5]pyrazino[1,2-b]pyridazine-3,5-dione

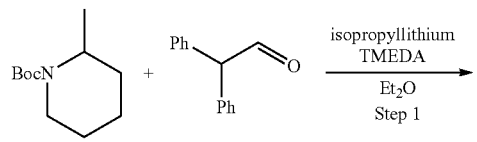

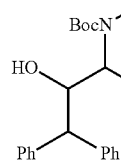

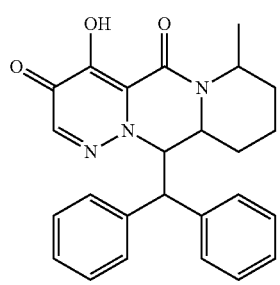

Example 127

Step 1: tert-butyl 2-(1-hydroxy-2,2-diphenylethyl)-6-methylpiperidine-1-carboxylate To a solution of tert-butyl 2-methylpiperidine-1-carboxylate (1 mL, 4.70 mmol) and TMEDA (0.745 mL, 4.94 mmol) in anhydrous Et₂O (10 mL) cooled to −78° C., was added, dropwise, isopropyllithium (0.7 M in pentane) (8.06 mL, 5.64 mmol). The reaction mixture was stirred for 15 min, gradually warmed to −20° C., stirred at this temperature for 60 min and then cooled to −72° C. 2,2-Diphenylacetaldehyde (1.251 mL, 7.05 mmol) was added to the reaction mixture which was subsequently stirred for 30 min and then quenched by addition of saturated aqueous ammonium chloride (40 mL). The mixture was allowed to warm to room temperature, and diluted with ether (100 ml) and water (50 ml). The aqueous phase was extracted with ether (2×25 ml). The combined organic phase was dried over Na2SO4 and concentrated. Silica gel column chromatography (EtOAc/heptane) provided tert-butyl 2-(1-hydroxy-2,2-diphenylethyl)-6-methylpiperidine-1-carboxylate (711 mg) in 38% yield. MS m/z 396.4 (MH+).

149

Example 127. 11-benzhydryl-4-hydroxy-7-methyl-7,8,9,10,10a,11-hexahydropyrido[1',2':4,5]pyrazino[1,2-b]pyridazine-3,5-dione Prepared from tert-butyl 2-(1-hydroxy-2,2-diphenylethyl)-6-methylpiperidine-1-carboxylate by the method of Example 124A, steps 2-7A. LCMS (m/z): 416.4 (MH+), 1H NMR (500 MHz, Methanol-d4) δ 7.57-7.53 (m, 2H), 7.42 (t, J=7.6 Hz, 2H), 7.33 (d, J=8.4 Hz, 2H), 7.19-7.15 (m, 2H), 7.13 (dd, J=5.2, 2.1 Hz, 4H), 5.35-5.25 (m, 1H), 4.35 (d, J=11.5 Hz, 1H), 3.84 (d, J=10.1 Hz, 1H), 1.88-1.81 (m, 1H), 1.79-1.69 (m, 2H), 1.65-1.58 (m, 2H), 1.50-1.32 (m, 1H), 1.06 (d, J=7.0 Hz, 3H).

150

-continued

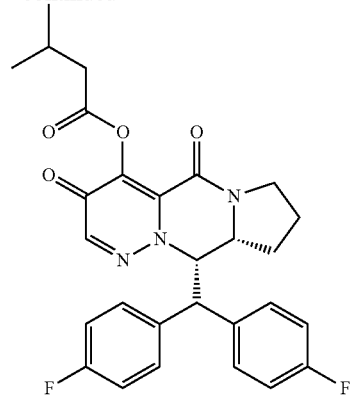

Example 128

Example 128. (9aR,10S)-10-(bis(4-fluorophenyl)methyl)-3,5-dioxo-5,7,8,9,9a,10-hexahydro-3H-pyrrolo[1',2':4,5]pyrazino[1,2-b]pyridazin-4-yl 3-methylbutanoate

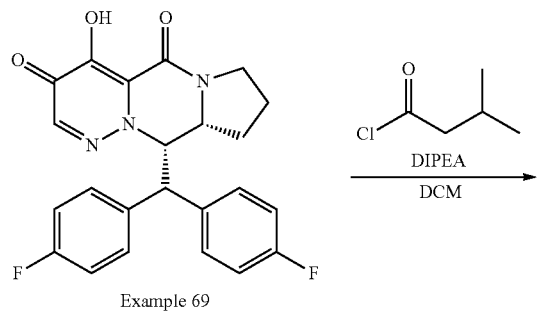

To a solution of (9aR,10S)-10-(bis(4-fluorophenyl)methyl)-4-hydroxy-8,9,9a,10-tetrahydro-3H-pyrrolo[1',2':4,5]pyrazino[1,2-b]pyridazine-3,5(7H)-dione (60 mg, 0.128 mmol) in DCM (3 mL) was added Hunig's base (0.054 mL, 0.307 mmol) followed by 3-methylbutanoyl chloride (0.019 mL, 0.160 mmol). The reaction mixture was stirred for 1 h at RT, Diluted with DCM and washed with aqueous NaHCO₃ solution. The organic layer was dried over Na₂SO₄, filtered and concentrated. The residue was dissolved in DMSO and purified by reverse phase HPLC. Product fractions were combined, frozen and lyophilized to afford a formate salt of (9aR,10S)-10-(bis(4-fluorophenyl)methyl)-3,5-dioxo-5,7,8,9,9a,10-hexahydro-3H-pyrrolo[1',2':4,5]pyrazino [1,2-b]pyridazin-4-yl 3-methylbutanoate (55.5 mg, 0.099 mmol, white solid) in 76% yield.

¹H NMR (400 MHz, CD₃OD) δ ppm 7.44-7.66 (m, 3H) 7.16 (t, J=8.68 Hz, 2H) 6.88-7.01 (m, 2H) 6.77-6.90 (m, 2H) 5.71 (br dd, J=9.85, 2.91 Hz, 1H) 4.43-4.58 (m, 2H) 3.70-3.81 (m, 1H) 3.64 (td, J=11.14, 7.02 Hz, 1H) 2.54 (d, J=6.94 Hz, 2H) 2.21 (dquin, J=13.39, 6.65, 6.65, 6.65, 6.65 Hz, 1H) 1.94-2.05 (m, 1H) 1.85-1.93 (m, 1H) 1.71-1.84 (m, 1H) 1.48-1.63 (m, 1H) 0.98-1.18 (m, 6H). MS m/z 508.3 (MH⁺).

TABLE 1j

Additional compounds prepared by the method of Example 128.

| Example No. | Structure | Mass M + H | ¹H NMR |
|---|---|---|---|
| 129 | 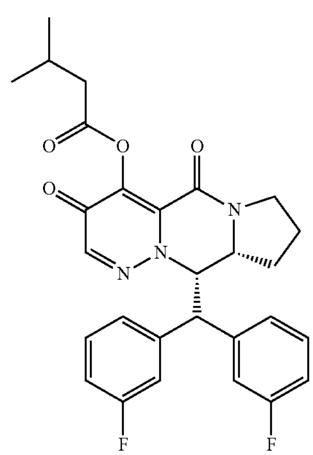 [SMILES: CC(C)CC(=O)Oc1c2n(ncc1=O)[C@@H](C(c1cccc(F)c1)c1cccc(F)c1)[C@H]1CCCN1C2=O] | 508.3 | (400 MHz, MeOD) δ ppm 0.96-1.18 (m, 6 H) 1.48-1.65 (m, 1 H) 1.73-1.85 (m, 1 H) 1.86-1.94 (m, 1 H) 1.94-2.01 (m, 1 H) 2.20 (tt, J = 13.43, 6.74 Hz, 1 H) 2.52 (d, J = 6.99 Hz, 2 H) 3.64 (td, J = 11.21, 6.92 Hz, 1 H) 3.71-3.81 (m, 1 H) 4.43-4.60 (m, 2 H) 5.77 (br dd, J = 9.93, 3.03 Hz, 1 H) 6.75 (br d, J = 7.92 Hz, 2 H) 6.78-6.86 (m, 1 H) 7.10 (td, J = 14.44, 7.90 Hz, 2 H) 7.35-7.49 (m, 1 H) 7.35-7.49 (m, 2 H) 7.54 (s, 1 H) |

TABLE 1j-continued

Additional compounds prepared by the method of Example 128.

| Example No. | Structure | Mass M + H | ¹H NMR |
|---|---|---|---|
| 130 | 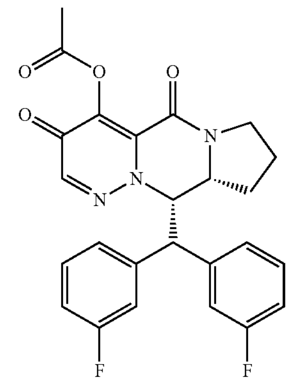 [SMILES: CC(=O)Oc1c2n(ncc1=O)[C@@H](C(c1cccc(F)c1)c1cccc(F)c1)[C@H]1CCCN1C2=O] | 466.3 | (400 MHz, DMSO-d6) δ 7.61-7.48 (m, 2H), 7.44 (td, J = 7.9, 6.1 Hz, 1H), 7.12 (tt, J = 10.2, 5.1 Hz, 2H), 6.90 (td, J = 8.9, 2.1 Hz, 1H), 6.77 (d, J = 8.3 Hz, 2H), 6.69 (s, 1H), 5.77 (dd, J = 10.2, 3.5 Hz, 1H), 4.64 (d, J = 10.2 Hz, 1H), 4.50 (ddd, J = 9.9, 6.1, 3.5 Hz, 1H), 3.67-3.54 (m, 2H), 2.24 (s, 3H), 1.92-1.73 (m, 2H), 1.67 (d, J = 13.3 Hz, 1H), 1.41-1.25 (m, 1H). |
| 131 | 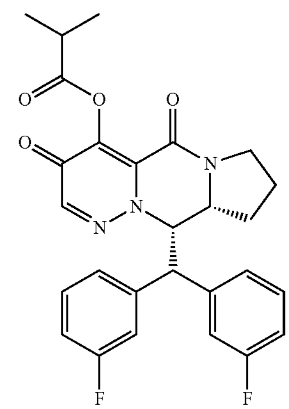 [SMILES: CC(C)C(=O)Oc1c2n(ncc1=O)[C@@H](C(c1cccc(F)c1)c1cccc(F)c1)[C@H]1CCCN1C2=O] | 494.3 | (400 MHz, DMSO-d6) δ 7.58 (d, J = 10.5 Hz, 1H), 7.54-7.39 (m, 3H), 7.18-7.04 (m, 2H), 6.90 (t, J = 8.1 Hz, 1H), 6.79 (d, J = 7.9 Hz, 2H), 5.77 (d, J = 8.9 Hz, 1H), 4.65 (d, J = 10.4 Hz, 1H), 4.50 (dt, J = 9.7, 5.8 Hz, 1H), 3.59 (p, J = 12.3, 11.7 Hz, 2H), 2.79 (p, J = 7.0 Hz, 1H), 1.90-1.71 (m, 2H), 1.65 (s, 1H), 1.24 (dd, J = 6.6, 3.4 Hz, 7H). |
| 132 | 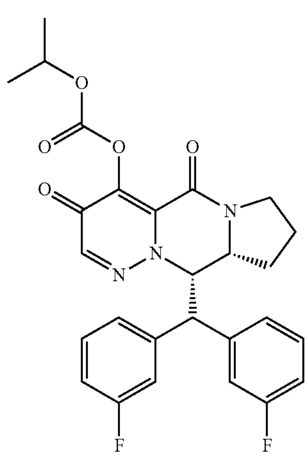 [SMILES: CC(C)OC(=O)Oc1c2n(ncc1=O)[C@@H](C(c1cccc(F)c1)c1cccc(F)c1)[C@H]1CCCN1C2=O] | 510.4 | (500 MHz, DMSO-d6) δ 7.72-7.63 (m, 2H), 7.55 (s, 1H), 7.26-7.18 (m, 2H), 6.97-6.84 (m, 4H), 5.69 (dd, J = 10.1, 3.5 Hz, 1H), 4.86 (p, J = 6.2 Hz, 1H), 4.61 (d, J = 10.1 Hz, 1H), 4.50 (ddd, J = 10.0, 6.2, 3.5 Hz, 1H), 3.60 (dd, J = 9.9, 6.5 Hz, 2H), 1.89-1.80 (m, 1H), 1.77 (dt, J = 13.3, 6.2 Hz, 1H), 1.72-1.60 (m, 1H), 1.32 (t, J = 6.5 Hz, 7H). |

Example 133. 1-(((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy) ethyl ethyl carbonate

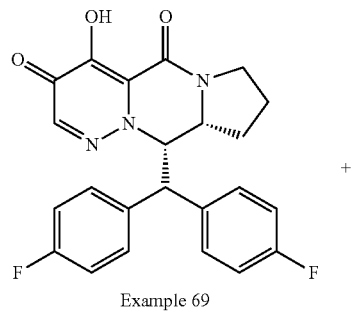

Example 69

+

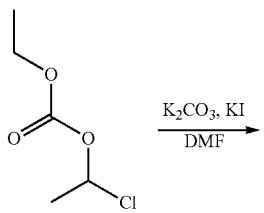

$\xrightarrow{K_2CO_3, KI}_{DMF}$

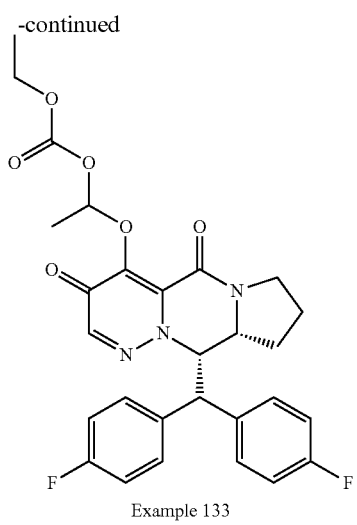

Example 133

Added $K_2CO_3$ (93 mg, 0.670 mmol), KI (111 mg, 0.670 mmol) and 1-chloroethyl ethyl carbonate (90 µl, 0.670 mmol) to a solution of (9aR,10S)-10-(bis(4-fluorophenyl)methyl)-4-hydroxy-8,9,9a,10-tetrahydro-7H-pyrrolo[1',2':4,5]pyrazino[1,2-b]pyridazine-3,5-dione (90 mg, 0.167 mmol) in DMF (Volume: 3.3 mL) at RT. Stirred at 60° C. for 4 hours, by which time the reaction was complete. The reaction mixture was then filtered through a fritted funnel and purified by SFC ($CO_2$/MeOH) to provide 1-(((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)ethyl ethyl carbonate (17 mg) in 19% yield. $^1H$ NMR (400 MHz, DMSO-$d_6$) δ 7.75 (d, J=2.9 Hz, 1H), 7.68 (dd, J=8.6, 5.4 Hz, 2H), 7.28-7.13 (m, 2H), 6.90 (ddt, J=27.1, 8.7, 4.6 Hz, 3H), 6.68 (dq, J=15.4, 5.2 Hz, 1H), 5.71 (ddd, J=9.4, 8.0, 3.3 Hz, 1H), 4.56 (dd, J=9.5, 2.5 Hz, 1H), 4.46 (t, J=7.8 Hz, 1H), 4.09 (dqd, J=14.3, 7.1, 2.6 Hz, 2H), 3.67-3.52 (m, 2H), 1.91-1.58 (m, 3H), 1.46 (d, J=5.2 Hz, 3H), 1.37 (t, J=10.1 Hz, 2H), 1.18 (dt, J=11.7, 7.1 Hz, 3H). MS m/z 540.6 (M+1).

TABLE 1k

Additional compounds prepared by the method of Example 133.

| Example No. | Structure | Mass M + H | 1H NMR |
|---|---|---|---|
| 134 | 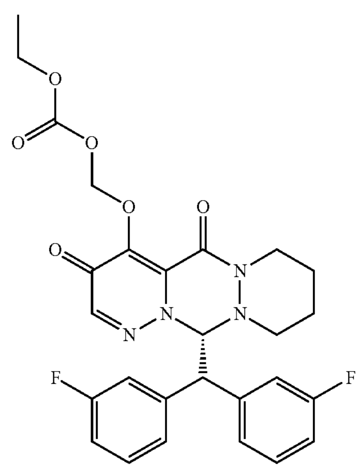 [SMILES: CCOC(=O)OCOc1c2n(ncc1=O)[C@@H](C(c1cccc(F)c1)c1cccc(F)c1)N1CCCCN1C2=O] | 541.2 | (400 MHz, DMSO-d6) δ 7.64 (s, 1H), 7.47 (dt, J = 10.5, 1.9 Hz, 1H), 7.40-7.12 (m, 5H), 7.09-6.95 (m, 2H), 6.44 (d, J = 10.7 Hz, 1H), 5.74 (d, J = 6.6 Hz, 1H), 5.64 (d, J = 6.6 Hz, 1H), 4.74 (d, J = 10.7 Hz, 1H), 4.25 (td, J = 11.5, 10.2, 6.0 Hz, 1H), 4.10 (qd, J = 7.1, 1.9 Hz, 2H), 3.22 (d, J = 10.9 Hz, 1H), 2.65 (td, J = 11.2, 2.7 Hz, 1H), 2.28 (td, J = 12.5, 11.3, 3.7 Hz, 1H), 1.66 (d, J = 12.2 Hz, 1H), 1.52 (d, J = 11.5 Hz, 2H), 1.40-1.25 (m, 1H), 1.19 (t, J = 7.1 Hz, 3H) |

TABLE 1k-continued
Additional compounds prepared by the method of Example 133.
| Example No. | Structure | Mass M + H | 1H NMR |
|---|---|---|---|
| 135 | 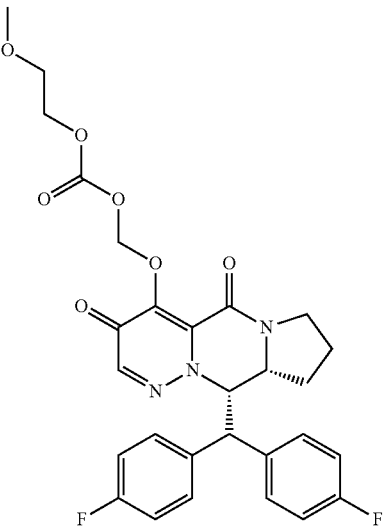 [SMILES: COCCOC(=O)OCOc1c2n(ncc1=O)[C@@H](C(c1ccc(F)cc1)c1ccc(F)cc1)[C@H]1CCCN1C2=O] | 556.3 | (400 MHz, DMSO-d6) δ 7.65 (dd, J = 8.5, 5.3 Hz, 2H), 7.51 (s, 1H), 7.21 (t, J = 8.6 Hz, 2H), 7.00-6.83 (m, 4H), 5.74 (d, J = 6.5 Hz, 1H), 5.63 (dd, J = 9.7, 3.4 Hz, 1H), 5.58 (d, J = 6.5 Hz, 1H), 4.45 (dd, J = 27.0, 9.6 Hz, 2H), 4.22 (q, J = 4.7 Hz, 2H), 3.58 (dt, J = 11.9, 4.7 Hz, 4H), 3.26 (s, 3H), 1.91-1.72 (m, 2H), 1.67 (dd, J = 18.0, 8.7 Hz, 1H), 1.36 (p, J = 10.6 Hz, 1H) |
| 136 | 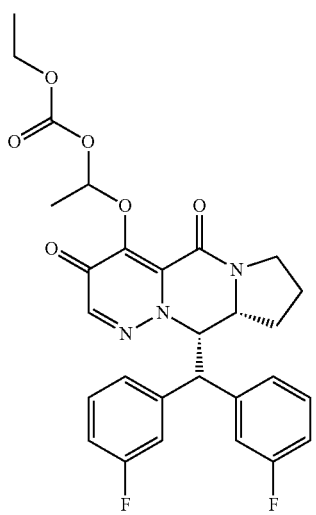 [SMILES: CCOC(=O)OC(C)Oc1c2n(ncc1=O)[C@@H](C(c1cccc(F)c1)c1cccc(F)c1)[C@H]1CCCN1C2=O] | 540.5 | (400 MHz, DMSO-d6) δ 7.78 (s, 1H), 7.75 (s, 1H), 7.58 (d, J = 10.5 Hz, 2H), 7.51 (d, J = 7.9 Hz, 2H), 7.47-7.38 (m, 2H), 7.09 (dt, J = 14.1,7.4 Hz, 4H), 6.85 (q, J = 8.3, 7.6 Hz, 2H), 6.77 (t, J = 7.8 Hz, 3H), 6.71 (q, J = 5.2 Hz, 1H), 6.62 (q, J = 5.2 Hz, 1H), 5.78 (dt, J = 8.4, 3.9 Hz, 3H), 4.68-4.57 (m, 2H), 4.48 (d, J = 5.7 Hz, 3H), 4.19-4.00 (m, 4H), 3.73-3.51 (m, 5H), 3.31 (s, 50H), 1.82 (dd, J = 11.4, 5.1 Hz, 4H), 1.66 (s,3H), 1.46 (t, J = 4.7 Hz, 5H), 1.37 (d, J = 8.9 Hz, 2H), 1.19 (dt, J = 11.2, 7.1 Hz, 7H). |

Example 137. (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl methyl carbonate

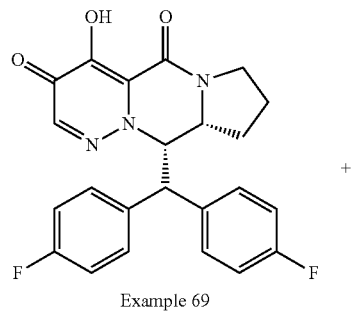

Example 69

+

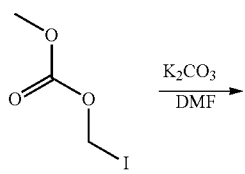

K₂CO₃ / DMF →

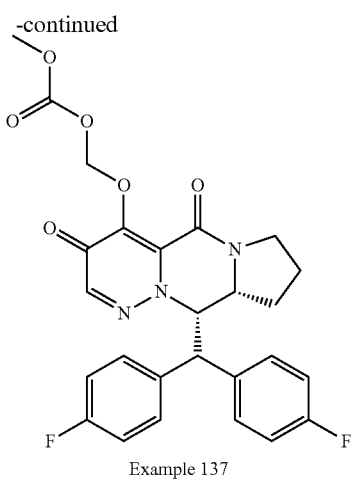

Example 137

Added potassium carbonate (48.6 mg, 0.351 mmol) and iodomethyl methyl carbonate (50.6 mg, 0.234 mmol) to a solution of (9aR,10S)-10-(bis(4-fluorophenyl)methyl)-4-hydroxy-8,9,9a,10-tetrahydro-7H-pyrrolo[1',2':4,5]pyrazino[1,2-b]pyridazine-3,5-dione (55 mg, 0.117 mmol) in DMF (Volume: 586 µl) at 0° C. Stirred at 0° C. for 1 hour and then RT for another hour. The reaction was filtered to remove solids and purified by SFC (CO₂/MeOH) to provide (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl methyl carbonate (41 mg, white solid) in 68% yield. $^1$H NMR (500 MHz, DMSO-d6) δ 7.71-7.62 (m, 2H), 7.52 (s, 1H), 7.27-7.14 (m, 2H), 6.98-6.85 (m, 4H), 5.76 (d, J=6.5 Hz, 1H), 5.64 (dd, J=9.7, 3.4 Hz, 1H), 5.57 (d, J=6.5 Hz, 1H), 4.53 (d, J=9.7 Hz, 1H), 4.44 (ddd, J=10.0, 6.4, 3.4 Hz, 1H), 3.75 (s, 3H), 3.68-3.54 (m, 2H), 1.93-1.75 (m, 2H), 1.68 (p, J=9.5, 8.8 Hz, 1H), 1.45-1.33 (m, 1H). MS m/z 512.3 (M+1).

TABLE 11

Additional compounds prepared by the method of Example 137.

| Example No. | Structure | Mass M + H | 1H NMR |
|---|---|---|---|
| 138 | 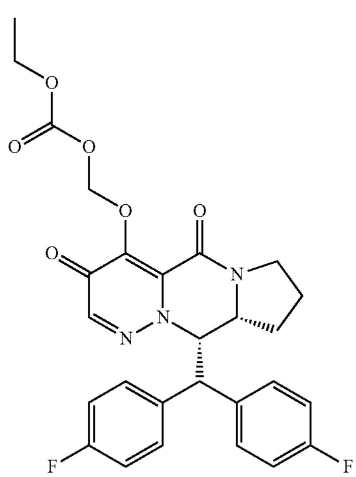 [SMILES: CCOC(=O)OCOc1c2n(ncc1=O)[C@@H](C(c1ccc(F)cc1)c1ccc(F)cc1)[C@H]1CCCN1C2=O] | 526.4 | (500 MHz, DMSO-d6) δ 7.71-7.63 (m, 2H), 7.52 (s, 1H), 7.22 (t, J = 8.8 Hz, 2H), 6.98-6.86 (m, 4H), 5.74 (d, J = 6.5 Hz, 1H), 5.64 (dd, J = 9.6, 3.4 Hz, 1H), 5.58 (d, J = 6.4 Hz, 1H), 4.51 (d, J = 9.7 Hz, 1H), 4.44 (ddd, J = 10.0, 6.3, 3.4 Hz, 1H), 4.17 (qq, J = 6.9, 3.5 Hz, 2H), 3.67-3.54 (m, 2H), 1.91-1.84 (m, 1H), 1.84-1.76 (m, 1H), 1.67 (p, J = 9.1, 8.4 Hz, 1H), 1.39 (qd, J = 11.2, 6.7 Hz, 1H), 1.25 (t, J = 7.1 Hz, 3H). |

TABLE 11-continued

Additional compounds prepared by the method of Example 137.

| Example No. | Structure | Mass M + H | 1H NMR |
|---|---|---|---|
| 139 | 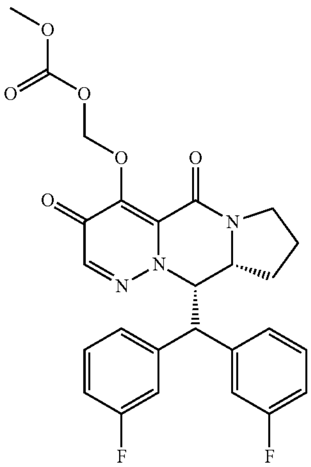 [SMILES: COC(=O)OCOc1c2n(ncc1=O)[C@@H](C(c1cccc(F)c1)c1cccc(F)c1)[C@H]1CCCN1C2=O] | 512.2 | (400 MHz, DMSO-d6) δ 7.58 (dt, J = 10.6, 2.1 Hz, 1H), 7.52 (d, J = 12.4 Hz, 2H), 7.44 (td, J = 7.9, 6.2 Hz, 1H), 7.18-7.07 (m, 2H), 6.91 (td, J = 8.8, 2.1 Hz, 1H), 6.82-6.74 (m, 2H), 5.76-5.68 (m, 2H), 5.54 (d, J = 6.5 Hz, 1H), 4.59 (d, J = 9.8 Hz, 1H), 4.45 (ddd, J = 10.1, 6.2, 3.3 Hz, 1H), 3.74 (s, 3H), 3.68-3.56 (m, 2H), 1.93-1.76 (m, 2H), 1.69 (d, J = 8.2 Hz, 1H), 1.36 (qd, J = 11.2, 6.6 Hz, 1H). |
| 140 | 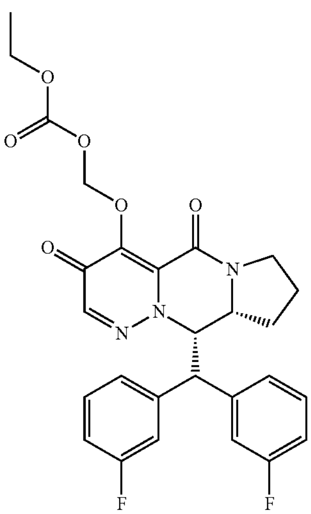 [SMILES: CCOC(=O)OCOc1c2n(ncc1=O)[C@@H](C(c1cccc(F)c1)c1cccc(F)c1)[C@H]1CCCN1C2=O] | 526.4 | (400 MHz, DMSO-d6) δ 7.58 (dt, J = 10.6, 2.2 Hz, 1H), 7.53 (s, 1H), 7.52-7.40 (m, 2H), 7.18-7.07 (m, 2H), 6.91 (td, J = 7.9, 7.3, 2.2 Hz, 1H), 6.82-6.74 (m, 2H), 5.76-5.68 (m, 2H), 5.54 (d, J = 6.5 Hz, 1H), 4.57 (d, J = 9.8 Hz, 1H), 4.49-4.38 (m, 1H), 4.22-4.08 (m, 2H), 3.60 (dt, J = 9.2, 4.8 Hz, 2H), 1.94-1.75 (m, 2H), 1.66 (q, J = 10.2, 9.6 Hz, 1H), 1.36 (dt, J = 11.6, 5.6 Hz, 1H), 1.24 (t, J = 7.1 Hz, 3H). |
| 141 | 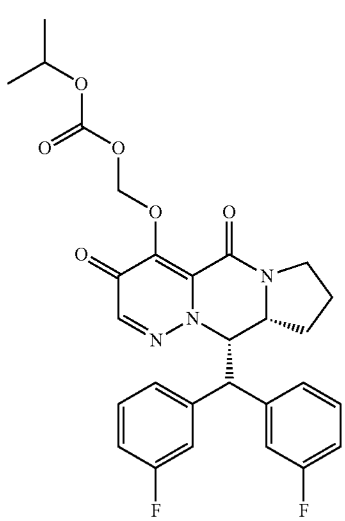 [SMILES: CC(C)OC(=O)OCOc1c2n(ncc1=O)[C@@H](C(c1cccc(F)c1)c1cccc(F)c1)[C@H]1CCCN1C2=O] | 540.5 | (400 MHz, DMSO-d6) δ 7.57 (dt, J = 10.6, 2.1 Hz, 1H), 7.52 (s, 1H), 7.51-7.39 (m, 2H), 7.13 (td, J = 7.8, 5.9 Hz, 2H), 6.95-6.87 (m, 1H), 6.82-6.73 (m, 2H), 5.73 (dd, J = 9.8, 3.4 Hz, 1H), 5.68 (d, J = 6.4 Hz, 1H), 5.56 (d, J = 6.4 Hz, 1H), 4.79 (p, J = 6.2 Hz, 1H), 4.55 (d, J = 9.8 Hz, 1H), 4.44 (ddd, J = 10.0, 6.4, 3.5 Hz, 1H), 3.65-3.53 (m, 2H), 1.94-1.76 (m, 2H), 1.74-1.57 (m, 1H), 1.36 (qd, J = 11.3, 6.7 Hz, 1H), 1.25 (d, J = 6.2 Hz, 6H). |

TABLE 1l-continued

Additional compounds prepared by the method of Example 137.

| Example No. | Structure | Mass M + H | 1H NMR |
|---|---|---|---|
| 142 | 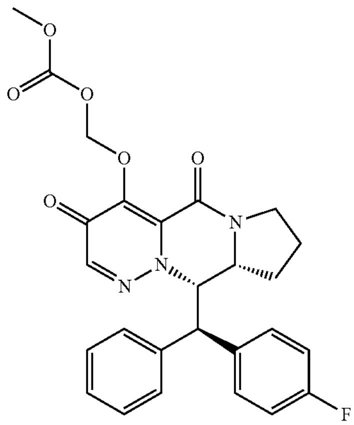 [SMILES: COC(=O)OCOc1c2n(ncc1=O)[C@@H]([C@H](c1ccccc1)c1ccc(F)cc1)[C@H]1CCCN1C2=O] | 494.4 | (400 MHz, DMSO-d6) δ 7.75-7.59 (m, 2H), 7.44 (s, 1H), 7.22 (t, J = 8.8 Hz, 2H), 7.07 (qd, J = 7.7, 6.7, 3.6 Hz, 3H), 6.96-6.84 (m, 2H), 5.73 (d, J = 6.5 Hz, 1H), 5.65 (dd, J = 9.8, 3.4 Hz, 1H), 5.54 (d, J = 6.5 Hz, 1H), 4.45 (dd, J = 17.5, 9.8 Hz, 2H), 3.75 (s, 3H), 3.67-3.53 (m, 2H), 1.94-1.75 (m, 2H), 1.68 (s, 1H), 1.51-1.32 (m, 1H). |
| 143 | 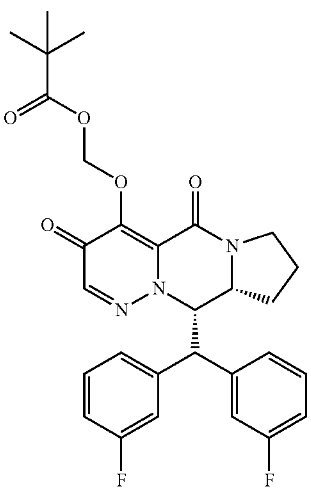 [SMILES: CC(C)(C)C(=O)OCOc1c2n(ncc1=O)[C@@H](C(c1cccc(F)c1)c1cccc(F)c1)[C@H]1CCCN1C2=O] | 538.5 | (400 MHz, DMSO-d6) δ 7.58 (dd, J = 10.6, 2.4 Hz, 1H), 7.53 (s, 1H), 7.51 (d, J = 8.0 Hz, 1H), 7.43 (td, J = 8.0, 6.2 Hz, 1H), 7.18-7.08 (m, 2H), 6.90 (td, J = 8.8, 2.2 Hz, 1H), 6.84-6.74 (m, 2H), 5.77-5.69 (m, 2H), 5.63 (d, J = 6.3 Hz, 1H), 4.57 (d, J = 9.9 Hz, 1H), 4.46-4.35 (m, 1H), 3.59 (ddd, J = 21.1, 11.8, 8.2 Hz, 2H), 1.82 (dq, J = 19.5, 6.4 Hz, 2H), 1.63 (dd, J = 11.9, 6.4 Hz, 1H), 1.43-1.27 (m, 1H), 1.11 (s, 9H). |
| 144 | 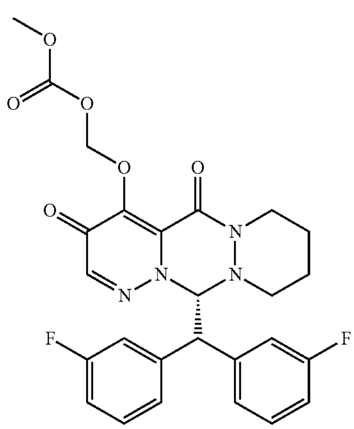 [SMILES: COC(=O)OCOc1c2n(ncc1=O)[C@@H](C(c1cccc(F)c1)c1cccc(F)c1)N1CCCCN1C2=O] | 527.1 | (400 MHz, DMSO-d6) δ 7.64 (s, 1H), 7.47 (d, J = 10.3 Hz, 1H), 7.38-7.30 (m, 2H), 7.30-7.20 (m, 2H), 7.17 (d, J = 7.7 Hz, 1H), 7.10-6.94 (m, 2H), 6.44 (d, J = 10.7 Hz, 1H), 5.76 (d, J = 6.6 Hz, 1H), 5.64 (d, J = 6.6 Hz, 1H), 4.75 (d, J = 10.6 Hz, 2H), 4.27 (d, J = 11.9 Hz, 2H), 3.69 (s, 3H), 2.70-2.59 (m, 2H), 2.36-2.22 (m, 2H), 1.66 (d, J = 13.1 Hz, 1H), 1.51 (s, 2H) |

Example 145. (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl L-valinate

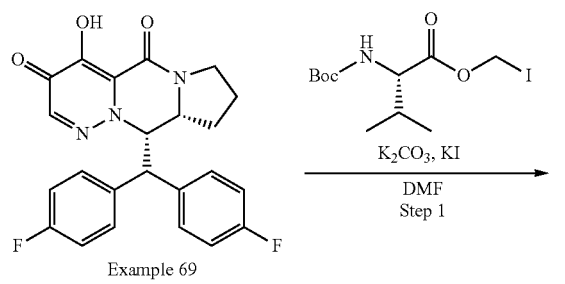

Example 69

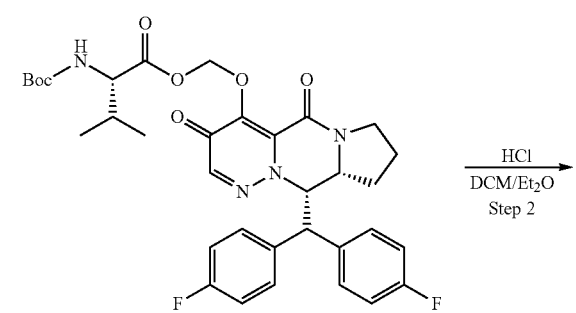

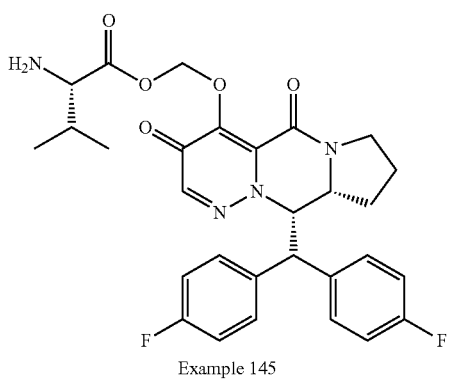

Example 145

Step 1. (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl (tert-butoxycarbonyl)-L-valinate To a solution of (9aR,10S)-10-(bis(4-fluorophenyl)methyl)-4-hydroxy-8,9,9a,10-tetrahydro-7H-pyrrolo[1',2':4,5]pyrazino[1,2-b]pyridazine-3,5-dione (50 mg, 0.093 mmol) in DMF (1.8 mL) were added K₂CO₃ (51.4 mg, 0.372 mmol), and KI (15.44 mg, 0.093 mmol). The mixture was cooled to 0° C. and iodomethyl (tert-butoxycarbonyl)-L-valinate (133 mg, 0.372 mmol) was added. The reaction was stirred at rt for 2 h and then diluted with EtOAc. The organic layer was washed with water, dried over Na₂SO₄, filtered and concentrated. Silica gel column chromatography (DCM/MeOH) provided (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl (tert-butoxycarbonyl)-L-valinate (38 mg) in 63% yield. MS m/z 653.7 (MH⁺).

Step 2. (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl L-valinate To a solution of (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl (tert-butoxycarbonyl)-L-valinate (38 mg, 0.058 mmol) in DCM (Volume: 582 μl) at 0° C. was added HCl (1.0 M in Et₂O, 2.9 mL, 2.9 mmol) dropwise. The mixture was stirred for 5 h at 0° C. and maintained at 0° C. overnight. The reaction was concentrated and the residue was triturated with Et₂O. The solid was filtered and dried under high vacuum to provide a hydrochloride salt of (((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)methyl L-valinate (15 mg) in 46% yield. ¹H NMR (400 MHz, DMSO-d6) δ 7.66 (dd, J=8.6, 5.4 Hz, 2H), 7.50 (s, 1H), 7.20 (t, J=8.7 Hz, 2H), 6.99-6.82 (m, 4H), 5.77 (d, J=6.3 Hz, 1H), 5.69 (d, J=6.2 Hz, 1H), 5.64 (dd, J=9.8, 3.4 Hz, 1H), 4.52 (d, J=9.7 Hz, 1H), 4.39 (t, J=9.6 Hz, 1H), 3.66-3.50 (m, 2H), 3.14 (d, J=5.1 Hz, 1H), 1.92-1.72 (m, 1H), 1.60 (d, J=33.1 Hz, 1H), 1.35 (dd, J=19.1, 8.7 Hz, 1H), 1.21 (d, J=4.2 Hz, 2H), 0.86 (d, J=6.8 Hz, 3H), 0.80 (t, J=7.3 Hz, 3H). MS m/z 553.4 (M+1).

Example 146. (9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl dimethylcarbamate

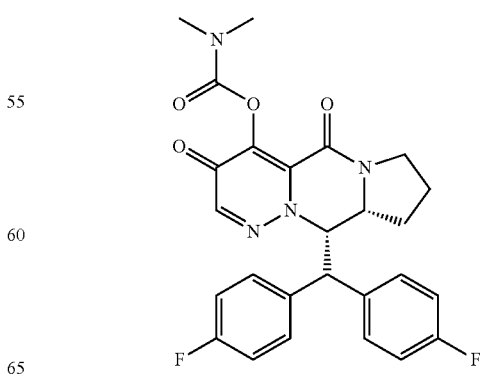

To a solution of (9aR,10S)-10-(bis(4-fluorophenyl)methyl)-4-hydroxy-8,9,9a,10-tetrahydro-3H-pyrrolo[1',2':4,5]pyrazino[1,2-b]pyridazine-3,5(7H)-dione (25 mg, 0.047 mmol) 1.5 ml of dry $CH_2Cl_2$ at 0° C. was added trimethylamine (0.1 mL), 2 drops of N, N-dimethylcarbamoyl chloride and a catalytic amount of DMAP. The mixture was stirred at rt overnight. Added another 0.1 ml $Et_3N$ and 3 drops of N, N-dimethylcarbamoyl chloride (×3) and stirred until completion. The reaction was quenched with 5% aqueous $NaHCO_3$ and washed with brine. The organic layer was dried over sodium sulfate and concentrated. SFC purification ($CO_2$/MeOH) provided (9aR,10S)-10-(bis(4-fluorophenyl)methyl)-3,5-dioxo-5,7,8,9,9a,10-hexahydro-3H-pyrrolo[1',2':4,5]pyrazino[1,2-b]pyridazin-4-yl dimethylcarbamate (12 mg) in 50% yield. $^1$H NMR (400 MHz, Chloroform-d) δ 7.50 (d, J=18.0 Hz, 1H), 7.34 (s, 2H), 7.12 (t, J=8.4 Hz, 2H), 6.97-6.71 (m, 4H), 5.32 (s, 1H), 4.36 (d, J=58.5 Hz, 2H), 3.89-3.77 (m, 1H), 3.59 (dq, J=11.8, 7.2 Hz, 1H), 3.08 (d, J=73.7 Hz, 6H), 1.89 (d, J=50.3 Hz, 3H), 1.48 (s, 1H). MS m/z 495.1 (MH+).

Example 147. (((9aR,10S)-10-(bis(4-fluorophenyl)methyl)-3,5-dioxo-5,7,8,9,9a,10-hexahydro-3H-pyrrolo[1',2':4,5]pyrazino[1,2-b]pyridazin-4-yl)oxy)methyl ethyl(methyl)carbamate

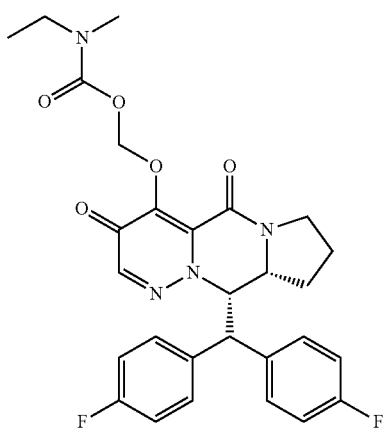 [SMILES: CCN(C)C(=O)OCOc1c2n(ncc1=O)[C@@H](C(c1ccc(F)cc1)c1ccc(F)cc1)[C@H]1CCCN1C2=O]

To a solution of (9aR,10S)-10-(bis(4-fluorophenyl)methyl)-4-hydroxy-8,9,9a,10-tetrahydro-3H-pyrrolo[1',2':4,5]pyrazino[1,2-b]pyridazine-3,5(7H)-dione (50 mg, 0.093 mmol) in DMF (Volume: 0.5 mL) at RT was added $K_2CO_3$ (77 mg, 0.558 mmol), KI (61.8 mg, 0.372 mmol) and chloromethyl ethyl(methyl)carbamate (56.4 mg, 0.372 mmol). The mixture was stirred at rt for 4 hours. The reaction was diluted with 2.5 ml DMSO and filtered to remove solids. SFC purification ($CO_2$/MeOH) and silica gel column chromatography (DCM/MeOH) provided (((9aR,10S)-10-(bis(4-fluorophenyl)methyl)-3,5-dioxo-5,7,8,9,9a,10-hexahydro-3H-pyrrolo[1',2':4,5]pyrazino[1,2-b]pyridazin-4-yl)oxy)methyl ethyl(methyl)carbamate (9 mg) in 17% yield. 1H NMR (400 MHz, Chloroform-d) δ 7.39 (d, J=25.3 Hz, 3H), 7.11 (t, J=7.1 Hz, 2H), 6.95-6.71 (m, 4H), 5.92 (s, 1H), 5.80 (d, J=3.9 Hz, 1H), 5.28 (d, J=10.2 Hz, 1H), 4.38 (s, 1H), 4.25 (d, J=9.7 Hz, 1H), 3.78 (s, 1H), 3.63 (s, 1H), 3.33 (s, 2H), 2.91 (d, J=14.0 Hz, 3H), 1.96 (s, 1H), 1.80 (d, J=29.9 Hz, 2H), 1.49 (s, 1H), 1.27-1.06 (m, 3H). MS m/z 539.2 (MH+).

Example 148. methyl 2-(((((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)(ethoxy)phosphoryl)oxy)acetate

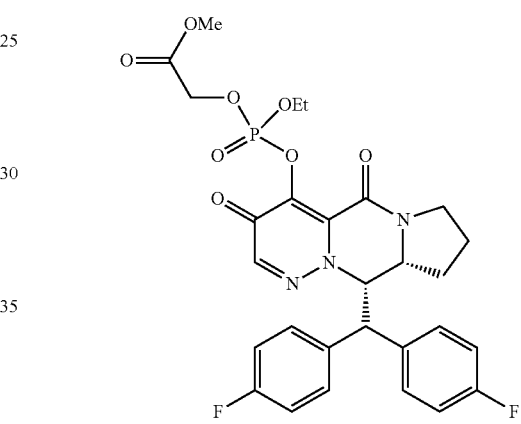

To a solution of ethyl phosphorodichloridate (45 mg, 0.279 mmol) in dichloromethane (1 mL) at −78° C. was added triethylamine (0.078 ml, 0.558 mmol) and a solution of methyl 2-hydroxyacetate (35 mg, 0.279 mmol) in dichloromethane (2 mL) dropwise. After the reaction mixture was stirred at room temperature for 2 hours, a solution of (9aR,10S)-10-(bis(4-fluorophenyl)methyl)-4-hydroxy-8,9,9a,10-tetrahydro-3H-pyrrolo[1',2':4,5]pyrazino[1,2-b]pyridazine-3,5(7H)-dione (50 mg, 0.093 mmol) and triethylamine (3 equiv) in DCM (1 mL) was added. The mixture was stirred at RT for 3 h, filtered and concentrated. SFC purification ($CO_2$/MeOH) provided methyl 2-(((((9aR,10S)-10-(bis(4-fluorophenyl)methyl)-3,5-dioxo-3,5,8,9,9a,10-hexahydro-7H-pyrrolo[1',2':4,5]pyrazino[1,2-b]pyridazin-4-yl)oxy)(ethoxy)phosphoryl)oxy)acetate (27 mg) in 46% yield. $^1$H NMR (400 MHz, Chloroform-d) δ 7.45 (d, J=5.2 Hz, 1H), 7.39-7.31 (m, 2H), 7.12 (t, J=8.5 Hz, 2H), 6.87 (q, J=7.2 Hz, 2H), 6.80 (t, J=8.4 Hz, 2H), 5.33 (dt, J=10.0, 3.1 Hz, 1H), 5.01-4.90 (m, 2H), 4.60-4.40 (m, 3H), 4.27 (dd, J=10.1, 2.3 Hz, 1H), 3.80 (d, J=7.1 Hz, 4H), 3.62 (dq, J=12.0, 6.9 Hz, 1H), 1.99 (d, J=13.6 Hz, 1H), 1.92-1.78 (m, 2H), 1.56-1.34 (m, 4H). MS m/z 604.2 (MH+).

Example 149. methyl 2-((((((9aR,10S)-10-(bis(4-fluorophenyl)methyl)-3,5-dioxo-5,7,8,9,9a,10-hexahydro-3H-pyrrolo[1',2':4,5]pyrazino[1,2-b]pyridazin-4-yl)oxy)methoxy)carbonyl)oxy)-2-methylpropanoate

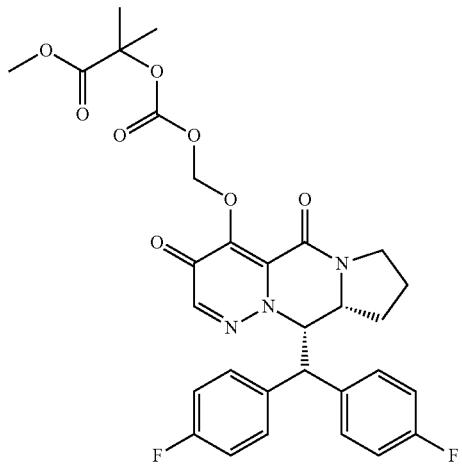 [SMILES: COC(=O)C(C)(C)OC(=O)OCOc1c2n(ncc1=O)[C@@H](C(c1ccc(F)cc1)c1ccc(F)cc1)[C@H]1CCCN1C2=O]

To a solution of (9aR,10S)-10-(bis(4-fluorophenyl)methyl)-4-hydroxy-8,9,9a,10-tetrahydro-3H-pyrrolo[1',2':4,5]pyrazino[1,2-b]pyridazine-3,5(7H)-dione (50 mg, 0.093 mmol) in DMF (Volume: 0.5 mL) at RT was added $K_2CO_3$ (77 mg, 0.558 mmol), KI (61.8 mg, 0.372 mmol) and methyl 2-(((chloromethoxy)carbonyl)oxy)-2-methylpropanoate (78 mg, 0.372 mmol). The mixture was stirred at rt for 4 hours. The reaction was diluted with 2.5 ml DMSO and filtered to remove solids. SFC purification ($CO_2$/MeOH) and silica gel column chromatography (heptane/EtOAc) provided methyl 2-((((((9aR,10S)-10-(bis(4-fluorophenyl)methyl)-3,5-dioxo-5,7,8,9,9a,10-hexahydro-3H-pyrrolo[1',2':4,5]pyrazino[1,2-b]pyridazin-4-yl)oxy)methoxy)carbonyl)oxy)-2-methylpropanoate (12 mg) in 20% yield. $^1$H NMR (400 MHz, Chloroform-d) δ 7.42 (s, 1H), 7.37 (dd, J=8.3, 5.2 Hz, 2H), 7.12 (t, J=8.4 Hz, 2H), 6.91-6.77 (m, 4H), 6.01-5.80 (m, 2H), 5.30 (dd, J=10.1, 3.2 Hz, 1H), 4.40 (d, J=4.0 Hz, 1H), 4.24 (d, J=10.0 Hz, 1H), 3.76 (s, 4H), 3.61 (dq, J=11.6, 7.0 Hz, 1H), 2.02-1.92 (m, 1H), 1.85 (dd, J=12.5, 6.2 Hz, 1H), 1.81-1.72 (m, 1H), 1.67 (d, J=5.8 Hz, 6H), 1.53-1.45 (m, 1H). MS m/z 598.3 (MH+).

Biological Assays and Data

The activity of a compound according to the present invention can be assessed by the following in vitro and in vivo methods. Using the test assays described herein, compounds of the invention exhibit inhibitory efficacy in accordance with Tables 2 and 3.

Influenza Virus Neuraminidase Assay (NA Assay)

For influenza NA assays, MDCK cells were plated in Phenol Red-free DMEM (Gibco) supplemented with 2 mM L-Glutamine, 1% sodium pyruvate (Cellgro, Manassas, Va.) and 0.1% BSA at cell densities of $1.8 \times 10^4$ cells/well in 384-well format. Compounds were added to the cells 2 hours pre-infection. Infections were performed at MOI 0.005 and the plates were incubated at 37° C., 5% $CO_2$ for 48 hours. Following incubation, neuraminidase activity was evaluated with the NA assay kit (ThermoFisher, Carlsbad, Calif.). For cell toxicity measurement, CellTiter-Glo® (Promega, Madison, Wis.) was added to treated cells according to manufacturer's instructions.

Influenza Virus Minigenome Assays (RNP Assay)

For influenza A virus minigenome reporter assays, 293T cells were transfected with expression vectors encoding PB2, PB1, PA, NP proteins and an influenza A Luciferase reporter plasmid. Cells were harvested in Dulbecco's modified Eagle's medium (DMEM) minus phenol red, supplemented with 10% heat inactivated FBS (fetal bovine serum), 1% sodium pyruvate and 1% L-glutamine (Cellgro, Manassas, Va.). The five plasmids were co-transfected with Fugene 6 transfection reagent (Promega, Madison, Wis.) with a 1:3 ratio DNA (μg):Fugene 6 (μl), in OptiMEM® (Gibco, Carlsbad, Calif.). Transfections were performed at cell densities of $1.8 \times 10^4$ cells/well in 384-well format. Compounds were added 2 hours post-transfection, and plates were incubated at 37° C., 5% $CO_2$ for 48 hours. Following incubation, cells were lysed and luciferase production quantified by addition of Britelite Plus® (Perkin-Elmer, Waltham, Mass.). For cell toxicity measurement, CellTiter-Glo® (Promega, Madison, Wis.) was added to treated cells following manufacturer's instructions.

TABLE 2

Activity of Selected Compounds on multiple flu strains in the NA assay.

| Example # | NA_VIR_H1N1 $EC_{50}$ (μM) | NA_VIR_H3N2 $EC_{50}$ (μM) | NA_Hubei $EC_{50}$ (μM) |
|---|---|---|---|
| 1 | 0.22 | 1.0 | 0.61 |
| 2 | 0.085 | 0.55 | 0.27 |
| 3 | 0.66 | 1.5 | 0.57 |
| 4 | 0.084 | 0.38 | 0.15 |
| 5 | 0.19 | 0.79 | 0.27 |
| 6 | 0.82 | 2.1 | 0.77 |
| 7 | 0.59 | 1.6 | 0.42 |
| 8 | 0.27 | 1.6 | 0.66 |
| 9 | 0.033 | 0.17 | 0.057 |
| 10 | 0.091 | 0.47 | 0.082 |
| 11 | 7.3 | 35 | 1.6 |
| 12 | >50 | >50 | >50 |
| 13 | 0.35 | 1.1 | 0.34 |
| 14 | 0.084 | 0.45 | 0.092 |
| 15 | 17 | 30 | 0.88 |
| 16 | 0.11 | 0.44 | 0.067 |
| 17 | 0.25 | 1.5 | 0.29 |
| 18 | 4.4 | 21 | 9.1 |
| 19B | 0.40 | 1.9 | 0.49 |

TABLE 3

Activity of Selected Compounds on multiple flu strains using the RNP assay

| Example No. | RNP_Alaska $EC_{50}$ (μM) | RNP_CAL_$EC_{50}$ (μM) | RNP_Hubei $EC_{50}$ (μM) |
|---|---|---|---|
| 1 | 0.42 | 0.13 | 0.20 |
| 2 | 0.22 | 0.087 | 0.094 |
| 3 | 1.4 | 1.1 | 0.79 |
| 4 | 0.16 | 0.27 | 0.10 |
| 5 | 0.086 | 0.18 | 0.030 |
| 6 | 1.3 | 0.56 | 0.51 |
| 7 | 1.3 | 0.50 | 0.30 |
| 8 | 0.65 | 2.2 | 0.58 |
| 9 | 0.051 | 0.045 | 0.026 |
| 10 | 0.13 | 0.13 | 0.035 |
| 11 | 7.3 | 9.3 | 3.5 |
| 12 | 3.5 | 6.9 | 26 |
| 13 | 0.32 | 0.47 | 0.18 |
| 14 | 0.15 | 0.13 | 0.048 |
| 15 | 7.0 | 3.5 | 1.2 |
| 16 | 0.12 | 0.059 | 0.038 |
| 17 | 0.16 | 0.32 | 0.036 |
| 18 | 7.8 | 2.6 | 10 |
| 19A | 0.24 | 0.22 | 0.33 |

TABLE 3-continued

Activity of Selected Compounds on multiple flu strains using the RNP assay

| Example No. | RNP_Alaska EC$_{50}$ (μM) | RNP_CAL_EC$_{50}$ (μM) | RNP_Hubei EC$_{50}$ (μM) |
|---|---|---|---|
| 19B | 0.98 | 0.63 | 0.40 |
| 20 | 0.22 | 0.18 | 0.11 |
| 21 | 0.89 | 0.49 | 0.36 |
| 22 | 0.14 | 0.12 | 0.21 |
| 23A | 0.28 | 0.25 | 0.29 |
| 23B | 0.34 | 0.093 | 0.76 |
| 24 | 0.37 | 0.17 | 0.51 |
| 25A | 0.35 | 0.14 | 0.39 |
| 25B | 0.91 | 0.44 | 2.6 |
| 26A | 0.075 | 0.026 | 0.16 |
| 26B | 0.13 | 0.058 | 0.15 |
| 27A | 0.24 | 0.052 | 0.12 |
| 27B | 0.082 | 0.063 | 0.14 |
| 28A | 0.30 | 0.25 | 0.27 |
| 28B | 0.086 | 0.046 | 0.35 |
| 29 | 0.11 | 0.093 | 0.18 |
| 30 | 0.068 | 0.034 | 0.089 |
| 31 | 5.3 | 1.8 | 8 |
| 32 | 0.11 | 0.093 | 0.061 |
| 33 | 0.10 | 0.097 | 0.046 |
| 34 | 0.098 | 0.079 | 0.043 |
| 35 | 0.098 | 0.088 | 0.066 |
| 36 | 0.29 | 0.12 | 0.033 |
| 37 | 0.093 | 0.035 | 0.028 |
| 38 | 0.024 | 0.30 | 0.11 |
| 39 | 0.091 | 0.074 | 0.049 |
| 40 | 0.30 | 0.25 | 0.12 |
| 41 | 0.073 | 0.088 | 0.043 |
| 42 | 0.28 | 0.31 | 0.10 |
| 43 | 0.082 | 0.075 | 0.035 |
| 44 | 0.15 | 0.16 | 0.10 |
| 45 | 0.13 | 0.12 | 0.043 |
| 46 | 0.068 | 0.069 | 0.061 |
| 47 | 0.093 | 0.068 | 0.032 |
| 48 | 0.095 | 0.094 | 0.078 |
| 49 | 0.065 | 0.058 | 0.044 |
| 50 | 0.43 | 0.36 | 0.081 |
| 51 | 0.30 | 0.33 | 0.13 |
| 52 | 0.087 | 0.072 | 0.046 |
| 53 | 0.078 | 0.051 | 0.033 |
| 54 | 0.14 | 0.15 | 0.067 |
| 55 | 0.15 | 0.16 | 0.073 |
| 56 | 0.059 | 0.048 | 0.064 |
| 57 | 0.092 | 0.11 | 0.080 |
| 58 | 0.20 | 0.21 | 0.099 |
| 59 | 0.18 | 0.18 | 0.069 |
| 60 | 0.080 | 0.052 | 0.032 |
| 61 | 0.34 | 0.37 | 0.23 |
| 62 | 0.17 | 0.21 | 0.079 |
| 63 | 0.17 | 0.20 | 0.16 |
| 64 | 0.071 | 0.096 | 0.033 |
| 65 | 0.031 | 0.034 | 0.022 |
| 66 | 0.038 | 0.030 | 0.052 |
| 67 | 3.8 | 2.5 | 3.8 |
| 68 | 0.062 | 0.044 | 0.046 |
| 69 | 0.084 | 0.058 | 0.052 |
| 70 | 0.082 | 0.077 | 0.049 |
| 71 | 0.085 | 0.060 | 0.033 |
| 72 | 0.037 | 0.046 | 0.025 |
| 73 | 2.7 | 1.1 | 1.2 |
| 74 | 0.030 | 0.034 | 0.016 |
| 75 | 0.24 | 0.28 | 0.11 |
| 76 | 0.11 | 0.14 | 0.046 |
| 77 | 0.038 | 0.049 | 0.030 |
| 78 | 0.045 | 0.059 | 0.031 |
| 79 | 0.083 | 0.079 | 0.079 |
| 80 | 0.087 | 0.097 | 0.065 |
| 81 | 0.098 | 0.099 | 0.057 |
| 82 | 0.092 | 0.15 | 0.061 |
| 83 | 0.36 | 0.47 | 0.21 |
| 84 | 0.093 | 0.069 | 0.036 |
| 85 | 0.054 | 0.047 | 0.041 |
| 86 | 0.072 | 0.066 | 0.034 |
| 87 | 0.058 | 0.052 | 0.061 |
| 88 | 0.042 | 0.053 | 0.050 |
| 89 | 0.039 | 0.061 | 0.042 |
| 90 | 0.037 | 0.041 | 0.020 |
| 91 | 0.079 | 0.090 | 0.058 |
| 92 | 0.040 | 0.031 | 0.036 |
| 93 | 0.073 | 0.070 | 0.045 |
| 94 | 0.52 | 0.50 | 0.12 |
| 95 | 0.13 | 0.12 | 0.055 |
| 96 | 0.14 | 0.15 | 0.06 |
| 97 | 0.15 | 0.18 | 0.074 |
| 98 | 0.28 | 0.29 | 0.12 |
| 99 | 0.10 | 0.13 | 0.067 |
| 100 | 0.085 | 0.11 | 0.034 |
| 101 | 0.099 | 0.097 | 0.050 |
| 102 | 0.14 | 0.14 | 0.16 |
| 103 | 0.30 | 0.32 | 0.22 |
| 104 | 0.14 | 0.15 | 0.075 |
| 105 | 0.095 | 0.12 | 0.081 |
| 106 | 0.27 | 0.19 | 0.076 |
| 107 | 0.81 | 0.16 | 0.42 |
| 108 | 0.16 | 0.089 | 0.045 |
| 109 | 0.12 | 0.11 | 0.045 |
| 110 | 0.075 | 0.059 | 0.032 |
| 111 | 0.073 | 0.050 | 0.072 |
| 112 | 0.17 | 0.081 | 0.022 |
| 113 | 0.052 | 0.030 | 0.032 |
| 114 | 0.094 | 0.077 | 0.028 |
| 115 | 0.12 | 0.064 | 0.14 |
| 116 | 4.7 | 3.6 | 2.9 |
| 117 | 0.10 | 0.068 | 0.081 |
| 118 | 5.5 | 6.2 | 2.6 |
| 119 | 0.12 | 0.068 | 0.076 |
| 120 | 4.6 | 4.5 | 6.2 |
| 121 | 0.15 | 0.20 | 0.098 |
| 122 | 0.88 | 2.1 | 0.17 |
| 123 | 0.34 | 0.27 | 0.45 |
| 124A | 0.18 | 0.077 | 0.16 |
| 124B | 0.071 | <0.016 | 0.18 |
| 125B | 0.53 | 0.19 | 0.19 |
| 126 | 0.47 | 0.23 | 0.25 |
| 127 | 0.41 | 0.19 | 0.66 |
| 128 | 0.085 | 0.060 | 0.048 |
| 129 | 0.095 | 0.021 | 0.026 |
| 130 | 0.10 | 0.021 | 0.031 |
| 131 | 0.077 | 0.066 | 0.025 |
| 132 | 0.15 | 0.15 | 0.079 |
| 133 | 0.097 | 0.070 | 0.068 |
| 134 | 0.076 | 0.062 | 0.071 |
| 135 | 0.11 | 0.16 | 0.11 |
| 136 | 0.18 | 0.11 | 0.052 |
| 137 | 0.076 | 0.042 | 0.071 |
| 138 | 0.11 | 0.18 | 0.11 |
| 139 | 0.18 | 0.051 | 0.065 |
| 140 | 0.11 | 0.096 | 0.050 |
| 141 | 0.10 | 0.060 | 0.038 |
| 142 | 0.14 | 0.17 | 0.061 |
| 143 | 0.12 | 0.19 | 0.045 |
| 144 | 0.084 | 0.036 | 0.083 |
| 145 | 0.12 | 0.083 | 0.14 |
| 146 | >5 | >5 | >5 |
| 147 | >5 | >5 | >5 |
| 148 | 0.093 | 0.098 | 0.13 |
| 149 | 0.49 | 0.49 | 0.70 |

The invention claimed is:

1. A compound of Formula (A):

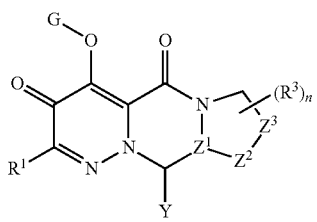

or a pharmaceutically acceptable salt thereof, wherein:
Y is a group of the formula

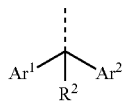

wherein the dashed line represents a bond connecting this group to Formula (A);

G is H or a group selected from —C(O)R$^O$, —C(O)—OR$^O$, —C(R$^G$)$_2$—O—C(O)R$^O$, —C(R$^G$)$_2$O—C(O)—OR$^O$, —P(=O)(OR$^O$)$_2$, —(CR$^G$)$_2$—O—P(=O)(OR$^O$)$_2$, —C(O)—N(R$^O$)$_2$, and —C(R$^G$)$_2$—O—C(O)N(R$^O$)$_2$, where each R$^O$ is independently H or a group selected from C$_1$-C$_6$ alkyl, phenyl, pyridyl, C$_3$-C$_7$ cycloalkyl, and a 3-6 membered heterocyclic ring containing one or two heteroatoms selected from N, O and S as ring members; and each R$^O$ that is not H is optionally substituted with one or two groups selected from halo, CN, —OH, amino, C$_{1-4}$ alkyl, COOR, phenyl, C$_{1-4}$ alkoxy, C$_{1-4}$ haloalkyl, and C$_{1-4}$ haloalkoxy;

and each R$^G$ is independently selected from H and C$_{1-4}$ alkyl;

R$^1$ is H, halo, CN, COOR*, —CONR*$_2$, or C$_1$-C$_6$ alkyl that is optionally substituted with one or two groups selected from halo, —OR*, and —NR*$_2$;

R* is independently at each occurrence H or C$_1$-C$_6$ alkyl optionally substituted with —OR or —NR$_2$;

Z$^1$ is N, and Z$^2$ is C(R)$_2$;
or Z$^1$ is CH, and Z$^2$ is NR, O, S, or CH$_2$;

Z$^3$ is CH$_2$, Q, —CH$_2$—CH$_2$—, -Q-CH$_2$—, —CH$_2$-Q-, —CH$_2$-Q-CH$_2$— or —CH$_2$—CH$_2$—CH$_2$—;

Q is selected from —NR—, O, S, SO, and SO$_2$;

R$^2$ is selected from H, halo, CN, C$_{1-4}$ alkyl optionally substituted with up to three groups independently selected from halo, CN, C$_{1-4}$ alkyl, —OR, C$_{1-4}$ haloalkoxy, —NR$_2$, and C$_{1-4}$ haloalkyl, OR, and C$_1$-C$_4$ haloalkyl;

each R$^3$ is a substituent optionally present on any carbon atom of the ring containing Z$^2$ and Z$^3$, and is independently selected from halo, —OR, C$_{1-4}$ haloalkyl, C$_{1-4}$ haloalkoxy, oxo, CN, —NR$_2$, and C$_{1-4}$ alkyl optionally substituted with up to three groups independently selected from halo, CN, C$_{1-4}$ alkyl, —OR, C$_{1-4}$ haloalkoxy, —NR$_2$, and C$_{1-4}$ haloalkyl;

n is 0-2;

Ar$^1$ and Ar$^2$ each independently represent phenyl or a 5-6 membered heteroaryl ring containing 1-3 heteroatoms selected from N, O and S as ring members, and Ar$^1$ and Ar$^2$ are each independently substituted with up to three groups selected from halo, C$_{1-4}$ alkyl, C$_{1-4}$ haloalkyl, C$_{1-4}$ alkoxy, C$_{1-4}$ haloalkoxy, C$_{2-4}$alkyne, and CN;

and Ar$^1$ and Ar$^2$ are optionally linked together by a bridge of the formula —C(R$^L$)$_2$L- to form a tricyclic group, wherein Ar$^1$ and Ar$^2$ are each optionally substituted by up to two groups independently selected from halo, C$_{1-4}$ alkyl, C$_{1-4}$ haloalkyl, C$_{1-4}$ alkoxy, C$_{1-4}$ haloalkoxy, C$_{2-4}$ alkyne, and CN;

R is independently at each occurrence H or C$_1$-C$_4$ alkyl optionally substituted with up to three groups independently selected from halo, OH, oxo, C$_{1-4}$ alkyl, C$_{1-4}$ alkoxy, C$_{1-4}$ haloalkoxy, and C$_{1-4}$ haloalkyl;

L is selected from S, S=O, SO$_2$, O, NR, C(R$^L$)$_2$ and CF$_2$; and and each R$^L$ is independently H or C$_{1-2}$ alkyl.

2. The compound of claim 1, wherein G is H, or a pharmaceutically acceptable salt thereof.

3. The compound of claim 1, wherein G is selected from —C(O)R$^O$, —C(O)—OR$^O$, —C(R$^G$)$_2$—O—C(O)R$^O$, —C(R$^G$)$_2$—O—C(O)—OR$^O$, —C(O)—N(R$^O$)$_2$, and —C(R$^G$)$_2$—O—C(O)N(R$^O$)$_2$, where each R$^O$ is independently H or C$_1$-C$_4$ alkyl that is optionally substituted with one or two groups selected from halo, CN, —OH, amino, C$_{1-4}$ alkyl, phenyl, C$_{1-4}$ alkoxy, C$_{1-4}$ haloalkyl, and C$_{1-4}$ haloalkoxy, or a pharmaceutically acceptable salt thereof.

4. The compound of claim 3, wherein G is selected from —C(O)R$^O$, —C(O)—OR$^O$, —C(R$^G$)$_2$—O—C(O)R$^O$, and —C(R$^G$)$_2$—O—C(O)—OR$^O$, where each R$^O$ is independently H or a group selected from C$_1$-C$_4$ alkyl, and each R$^G$ is H or C$_1$-C$_4$ alkyl;

or a pharmaceutically acceptable salt thereof.

5. The compound of claim 1, wherein G is selected from —C(O)R$^O$, —C(O)—OR$^O$, —CH$_2$—C(O)R$^O$, and —CH$_2$—C(O)—OR$^O$, wherein each R$^O$ is C$_1$-C$_4$ alkyl; or a pharmaceutically acceptable salt thereof.

6. The compound of claim 1, which is of the formula:

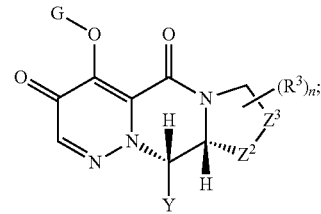

or a pharmaceutically acceptable salt thereof.

7. The compound of claim 6, wherein Z$^2$ is CH$_2$, Z$^3$ is CH$_2$, n is 0, 1 or 2, and each R$^3$ is Me; or a pharmaceutically acceptable salt thereof.

8. The compound of claim 1, which is of the formula (I):

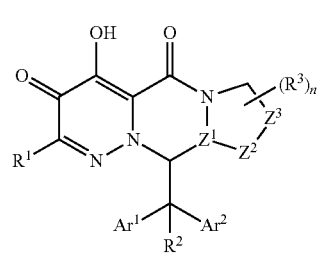

or a pharmaceutically acceptable salt thereof, wherein:
R¹ is H, halo, CN, COOR*, —CONR*₂, or $C_1$-$C_6$ alkyl optionally substituted with one or two groups selected from —OR* and —NR*₂, $C_1$-$C_4$ haloalkyl;
R* is independently at each occurrence H or $C_1$-$C_6$ alkyl optionally substituted with —OR or —NR₂;
Z¹ is N, and Z² is C(R)₂;
or Z¹ is CH, and Z² is NR, O, S, or CH₂;
Z³ is CH₂, Q, —CH₂—CH₂—, -Q-CH₂—, —CH₂-Q-, —CH₂-Q-CH₂— or —CH₂—CH₂—CH₂—;
Q is selected from —NR—, O, S, SO, and SO₂;
R² is selected from H, halo, CN, $C_{1-4}$ alkyl optionally substituted with up to three groups independently selected from halo, CN, $C_{1-4}$ alkyl, —OR, $C_{1-4}$ haloalkoxy, —NR₂, and $C_{1-4}$ haloalkyl, OR, and $C_1$-$C_4$ haloalkyl;
each R³ is a substituent optionally present on any carbon atom of the ring containing Z² and Z³, and is independently selected from —OR, $C_{1-4}$ haloalkyl, $C_{1-4}$ haloalkoxy, oxo, CN, —NR₂, and $C_{1-4}$ alkyl optionally substituted with up to three groups independently selected from halo, CN, $C_{1-4}$ alkyl, —OR, $C_{1-4}$ haloalkoxy, —NR₂, and $C_{1-4}$ haloalkyl;
n is 0-2;
Ar¹ and Ar² each independently represent phenyl or a 5-6 membered heteroaryl ring containing 1-3 heteroatoms selected from N, O and S as ring members, and are each independently substituted with up to three groups selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;
and Ar¹ and Ar² are optionally linked together by a bridge of the formula —C(R$^L$)₂L- to form a tricyclic group, wherein Ar¹ and Ar² are each optionally substituted by up to two groups independently selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN;
R is independently at each occurrence H or $C_1$-$C_4$ alkyl optionally substituted with up to three groups independently selected from halo, OH, oxo, $C_{1-4}$ alkyl, $C_{1-4}$ alkoxy, $C_{1-4}$ haloalkoxy, and $C_{1-4}$ haloalkyl;
L is selected from S, S=O, SO₂, O, NR, C(R$^L$)₂ and CF₂; and
and each R$^L$ is independently H or $C_{1-2}$ alkyl.

9. The compound according to claim 1, or a pharmaceutically acceptable salt thereof, wherein Z is CH.

10. The compound according to claim 1, or a pharmaceutically acceptable salt thereof, wherein Z¹ is N.

11. The compound according to claim 1, or a pharmaceutically acceptable salt thereof, wherein Z² is CH₂.

12. The compound according to claim 1, or a pharmaceutically acceptable salt thereof, wherein Z³ is CH₂, —CH₂—CH₂—, —CH₂—CH₂—CH₂—, —CH₂—O—, or O.

13. The compound of claim 12 or a pharmaceutically acceptable salt thereof, wherein Z³ is CH₂.

14. The compound according to claim 1 or a pharmaceutically acceptable salt thereof, wherein R¹ is H.

15. The compound of claim 1, which is of the formula:

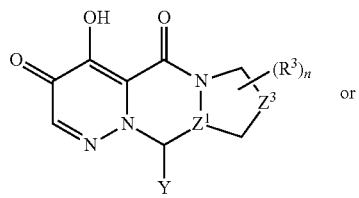

or

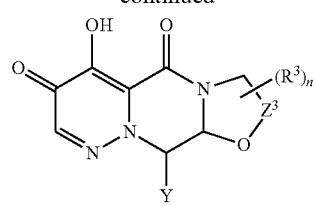

wherein Y represents a group selected from

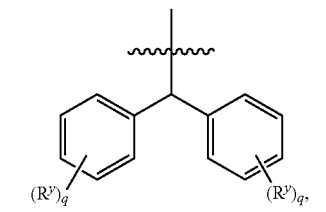

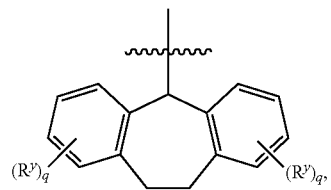

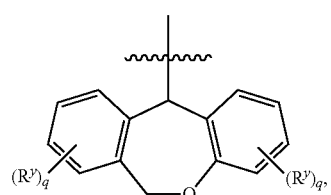

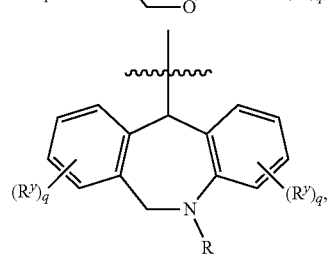

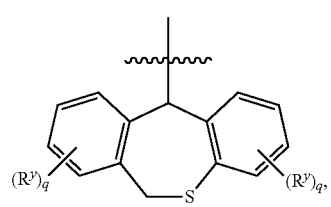

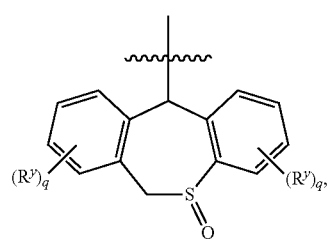

-continued

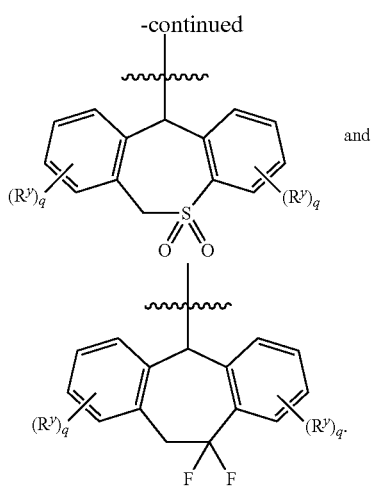

wherein each R is independently selected from halo, $C_{1-4}$ alkyl, $C_{1-4}$ haloalkyl, $C_{1-4}$ alkoxy, $C_{1-4}$ haloalkoxy, $C_{2-4}$ alkyne, and CN; and each q is independently 0, 1 or 2;

or a pharmaceutically acceptable salt thereof.

16. The compound of claim 15, or a pharmaceutically acceptable salt thereof, wherein $Z^1$ is N or CH; and $Z^3$ is $CH_2$ or —$CH_2$—$CH_2$—.

17. A pharmaceutical composition comprising a compound of claim 1, or a pharmaceutically acceptable salt thereof, and one or more pharmaceutically acceptable carriers.

18. A combination comprising a therapeutically effective amount of a compound according to claim 1, or a pharmaceutically acceptable salt thereof, and one or more therapeutically active co-agents.

19. A method of treating influenza, comprising administering to a subject in need thereof a therapeutically effective amount of a compound of claim 1 or a pharmaceutically acceptable salt thereof.

* * * * *